(12) United States Patent
Doronina et al.

(10) Patent No.: US 7,745,394 B2
(45) Date of Patent: Jun. 29, 2010

(54) MONOMETHYLVALINE COMPOUNDS CAPABLE OF CONJUGATION TO LIGANDS

(75) Inventors: Svetlana O. Doronina, Snohomish, WA (US); Peter D. Senter, Seattle, WA (US); Brian E. Toki, Shoreline, WA (US); Allen J. Ebens, San Carlos, CA (US); Toni Beth Kline, Seattle, WA (US); Paul Polakis, Burlingame, CA (US); Mark X. Sliwkowski, San Carlos, CA (US); Susan D. Spencer, Tiburon, CA (US)

(73) Assignee: Seattle Genetics, Inc., Bothell, WA (US)

( * ) Notice: Subject to any disclaimer, the term of this patent is extended or adjusted under 35 U.S.C. 154(b) by 276 days.

(21) Appl. No.: 11/833,964

(22) Filed: Aug. 3, 2007

(65) Prior Publication Data

US 2008/0226657 A1 Sep. 18, 2008

Related U.S. Application Data

(62) Division of application No. 10/983,340, filed on Nov. 5, 2004, now Pat. No. 7,498,298.

(60) Provisional application No. 60/622,455, filed on Oct. 27, 2004, provisional application No. 60/598,899, filed on Aug. 4, 2004, provisional application No. 60/557,116, filed on Mar. 26, 2004, provisional application No. 60/518,534, filed on Nov. 6, 2003.

(51) Int. Cl.
*A61K 38/00* (2006.01)
(52) U.S. Cl. .......................................................... 514/2
(58) Field of Classification Search ............. 435/299.1; 424/178.1, 179.1, 181.1; 530/391.9
See application file for complete search history.

(56) References Cited

U.S. PATENT DOCUMENTS

| 3,445,518 | A | 5/1969 | Shavel, Jr. et al. |
|---|---|---|---|
| 4,414,205 | A | 11/1983 | Pettit |
| 4,753,894 | A | 6/1988 | Frankel et al. |
| 4,764,368 | A | 8/1988 | Blatter et al. |
| 4,816,444 | A | 3/1989 | Pettit et al. |
| 4,879,278 | A | 11/1989 | Pettit et al. |
| 4,943,628 | A | 7/1990 | Rosen et al. |
| 4,978,744 | A | 12/1990 | Petit et al. |
| 5,122,368 | A | 6/1992 | Greenfield et al. |
| 5,165,923 | A | 11/1992 | Thorpe et al. |
| 5,169,774 | A | 12/1992 | Frankel et al. |
| 5,286,637 | A | 2/1994 | Veronese et al. |
| 5,410,024 | A | 4/1995 | Petit et al. |
| 5,521,284 | A | 5/1996 | Pettit et al. |
| 5,530,097 | A | 6/1996 | Pettit et al. |
| 5,554,725 | A | 9/1996 | Pettit |
| 5,585,089 | A | 12/1996 | Queen et al. |
| 5,599,902 | A | 2/1997 | Pettit et al. |
| 5,629,197 | A | 5/1997 | Ring et al. |
| 5,635,483 | A | 6/1997 | Pettit et al. |
| 5,654,399 | A | 8/1997 | Sakakibara et al. |
| 5,663,149 | A | 9/1997 | Pettit et al. |
| 5,665,860 | A | 9/1997 | Pettit et al. |
| 5,708,146 | A | 1/1998 | Willner et al. |
| 5,714,586 | A | 2/1998 | Kunstmann et al. |
| 5,741,892 | A | 4/1998 | Barlozzari et al. |
| 5,767,236 | A | 6/1998 | Kim et al. |
| 5,767,237 | A | 6/1998 | Sakakibara et al. |
| 5,780,588 | A | 7/1998 | Pettit et al. |
| 5,821,337 | A | 10/1998 | Carter et al. |
| 5,840,699 | A | 11/1998 | Sakakibara et al. |
| 5,965,537 | A | 10/1999 | Ritter et al. |
| 6,004,934 | A | 12/1999 | Sakakibara et al. |
| 6,033,876 | A | 3/2000 | Lemke et al. |
| 6,034,065 | A | 3/2000 | Pettit et al. |
| 6,048,720 | A | 4/2000 | Dalborg et al. |
| 6,054,297 | A | 4/2000 | Carter et al. |
| 6,054,561 | A | 4/2000 | Ring |
| 6,124,431 | A | 9/2000 | Sakakibara et al. |
| 6,143,721 | A | 11/2000 | Janssen et al. |
| 6,162,930 | A | 12/2000 | Pinney et al. |
| 6,214,345 | B1 | 4/2001 | Firestone et al. |
| 6,239,104 | B1 | 5/2001 | Pettit et al. |
| 6,323,315 | B1 | 11/2001 | Pettit et al. |
| 6,342,219 | B1 | 1/2002 | Thorpe et al. |
| 6,342,221 | B1 | 1/2002 | Thorpe et al. |
| 6,407,213 | B1 | 6/2002 | Carter et al. |
| 6,569,834 | B1 | 5/2003 | Pettit et al. |
| 6,620,911 | B1 | 9/2003 | Petit et al. |
| 6,639,055 | B1 | 10/2003 | Carter et al. |
| 6,884,869 | B2 | 4/2005 | Senter et al. |
| 6,913,748 | B2 | 7/2005 | Widdison |
| 7,090,843 | B1 | 8/2006 | Francisco et al. |
| 7,091,186 | B2 | 8/2006 | Senter et al. |
| 7,097,840 | B2 | 8/2006 | Erickson et al. |
| 7,098,305 | B2 | 8/2006 | Deghenghi et al. |
| 7,098,308 | B2 | 8/2006 | Senter et al. |
| 7,498,298 | B2 | 3/2009 | Doronina et al. |
| 2001/0018422 | A1 | 8/2001 | Ritter et al. |
| 2002/0001587 | A1 | 1/2002 | Erickson et al. |
| 2003/0083263 | A1 | 5/2003 | Doronina et al. |
| 2003/0096743 | A1 | 5/2003 | Senter et al. |
| 2003/0130189 | A1 | 7/2003 | Senter et al. |

(Continued)

FOREIGN PATENT DOCUMENTS

CA 2114156 A1 7/1994

(Continued)

OTHER PUBLICATIONS

S.R. Vippagunta, et al Adv. Drug Delivery Rev. (2001)48, pp. 3-26.*

(Continued)

*Primary Examiner*—Andrew D Kosar
(74) *Attorney, Agent, or Firm*—Townsend and Townsend and Crew LLP

(57) ABSTRACT

Auristatin peptides, including MeVal-Val-Dil-Dap-Norephedrine (MMAE) and MeVal-Val-Dil-Dap-Phe (MMAF), were prepared and attached to Ligands through various linkers, including maleimidocaproyl-val-cit-PAB. The resulting ligand drug conjugates were active in vitro and in vivo.

44 Claims, 40 Drawing Sheets

U.S. PATENT DOCUMENTS

| | | |
|---|---|---|
| 2004/0018194 A1 | 1/2004 | Francisco et al. |
| 2004/0096392 A1 | 5/2004 | Bhaskar et al. |
| 2004/0141983 A1 | 7/2004 | Law et al. |
| 2004/0197325 A1 | 10/2004 | Law et al. |
| 2004/0235068 A1 | 11/2004 | Levinson |
| 2005/0009751 A1 | 1/2005 | Senter et al. |
| 2005/0014687 A1 | 1/2005 | Anderson et al. |
| 2005/0084449 A1 | 4/2005 | Landes et al. |
| 2005/0106644 A1 | 5/2005 | Cairns et al. |
| 2005/0107595 A1 | 5/2005 | Cairns et al. |
| 2005/0113308 A1 | 5/2005 | Senter et al. |
| 2005/0123536 A1 | 6/2005 | Law et al. |
| 2005/0180972 A1 | 8/2005 | Wahl et al. |
| 2005/0232929 A1 | 10/2005 | Kadkhodayan et al. |
| 2005/0238649 A1 | 10/2005 | Doronina et al. |
| 2005/0238650 A1 | 10/2005 | Crowley et al. |
| 2005/0256030 A1 | 11/2005 | Feng |
| 2005/0260212 A1 | 11/2005 | Zhang et al. |
| 2005/0272665 A1 | 12/2005 | Schmid et al. |
| 2006/0073152 A1 | 4/2006 | Dennis |
| 2006/0074008 A1 | 4/2006 | Senter et al. |
| 2006/0128970 A1 | 6/2006 | Bliss et al. |
| 2006/0182751 A1 | 8/2006 | Gazzard et al. |
| 2006/0233794 A1 | 10/2006 | Law et al. |
| 2007/0092520 A1 | 4/2007 | Dennis et al. |
| 2007/0098715 A1 | 5/2007 | Ettenberg et al. |
| 2007/0134243 A1 | 6/2007 | Gazzard et al. |
| 2007/0160617 A1 | 7/2007 | Ma et al. |
| 2007/0212356 A1 | 9/2007 | Chen et al. |
| 2007/0258987 A1 | 11/2007 | Francisco et al. |

FOREIGN PATENT DOCUMENTS

| | | |
|---|---|---|
| EP | 0 598 129 A1 | 5/1994 |
| EP | 0 695 757 A2 | 2/1996 |
| EP | 0 695 758 A2 | 2/1996 |
| EP | 0 695 759 A2 | 2/1996 |
| JP | 06-234790 A | 8/1994 |
| JP | 09-77791 A | 3/1997 |
| WO | WO 93/03054 A1 | 2/1993 |
| WO | WO 95/09864 A1 | 4/1995 |
| WO | WO 96/14856 A1 | 5/1996 |
| WO | WO 96/22384 A1 | 7/1996 |
| WO | WO 96/33212 A1 | 10/1996 |
| WO | WO 99/35164 A1 | 7/1999 |
| WO | WO 01/18032 A2 | 3/2001 |
| WO | WO 02/43661 A2 | 6/2002 |
| WO | WO 02/43661 A3 | 6/2002 |
| WO | WO 02/088172 A | 11/2002 |
| WO | WO 02/088172 A2 | 11/2002 |
| WO | WO 03/008378 A1 | 1/2003 |
| WO | WO 03/034903 A2 | 5/2003 |
| WO | WO 03/043583 A2 | 5/2003 |
| WO | WO 2004/010957 A2 | 3/2004 |
| WO | WO 2004/032828 A2 | 4/2004 |
| WO | WO 2005/084390 A2 | 9/2005 |
| WO | WO 2006/034488 A3 | 3/2006 |
| WO | WO 2006/071441 A2 | 7/2006 |
| WO | WO 2006/083936 A3 | 8/2006 |
| WO | WO 2007/001851 A3 | 1/2007 |
| WO | WO 2007/030642 A2 | 3/2007 |
| WO | WO 2007/059082 A1 | 5/2007 |
| WO | WO 2007/062138 A2 | 5/2007 |
| WO | WO 2007/070538 A2 | 6/2007 |
| WO | WO 2007/109567 A1 | 9/2007 |

OTHER PUBLICATIONS

Alley et al., "Controlling the location of drug attachment in antibody-drug conjugates," *Proceedings of the AACR*, vol. 45, abstract # 627 (2004).

Afar et al., "Preclinical validation of anti-TMEFF2-auristatin E-conjugated antibodies in the treatment of prostate cancer," *Molecular Cancer Therapeutics*, 3(8):921-932 (2004).

Bhaskar et al., "E-Selectin Up-Regulation Allows for Targeted Drug Delivery in Prostate Cancer," *Cancer Research*, 63:6387-6394 (2003).

Carter, "Improving the Efficacy of Antibody-Based Cancer Therapies," *Nature Reviews* 1:118-129 (2001).

Dillman, "Monoclonal Antibodies for Treating Cancer, " *Annals of Internal Medicine* 111:592-603 (1989).

Doronina et al., "Development of potent monoclonal antibody auristatin conjugates for cancer therapy," *Nature Biotechnology*, 21(7):778-784 (2003) + Erratum, *Nature Biotechnology*, 21(8):941 (2003).

Emery et al., "Humanized monoclonal antibodies for therapeutic applications," *Exp. Opin. Invest. Drugs* 3(3):241-251 (1994).

Francisco et al., "cAC10-vcMMAE, an anti-CD30-monomethyl auristatin E conjugate with potent and selective antitumor activity," *Blood*, 102(4):1458-1465 (2003).

Hamblett et al., "Effect of drug loading on the pharmacology, pharmacokinetics, and toxicity of an anti-CD30 antibody-drug conjugate," *Proceedings of the AACR*, vol. 45, abstract # 624 (2004).

Kline et al., "Novel Antitumor Prodrugs Designed for Activation by Matrix Metalloproteinases-2 and -9," *Molecular Pharmaceutics*, 1(1):9-22 (2004).

Klussman et al., "Secondary mAb—vcMMAE conjugates are highly sensitive reporters of antibody internalization via the lysosome pathway," *Bioconjug Chem.*, 15(4):765-773 (2004).

Law et al., "CD70 is expressed on renal cell carcinoma and is a potential target for tumor cell elimination by antibody-drug conjugates," *Proceedings of the AACR*, vol. 45, abstract # 625 (2004).

Mao et al., "EphB2 as a Therapeutic Antibody Drug Target for the Treatment of Colorectal Cancer," *Cancer Research*, 64:781-788 (2004).

Meyer et al., "Recent Advances in Antibody Drug Conjugates for Cancer Therapy," *Annual Reports in Medical Chemistry*, 38(chapter 23):229-237 (2003).

Pettit et al., "The Absolute Configuration and Synthesis of Natural (−)-Dolastatin 10," *J. Am. Chem. Soc.*, 111:5463-5465 (1989).

Pettit et al., "Dolastatins 24. Synthesis of (−) -dolastatin 10. X-Ray molecular structure of N,N-dimethylvalyl-valyl-dolaisoleuine *tert*-butyl ester," *J. Chem. Soc. Perkin Trans.1*, 5:859-863 (1996).

Pettit et al., "Antineoplastic agents 365. Dolastatin 10 SAR probes," *Anticancer Drug Des.*, 13(4):243-277 (1998).

Press Release, "Seattle Genetics, Inc. (SGEN) To Present Advances In Preclinical Research At American Cancer Research Annual Meeting," Mar. 24, 2004, downloaded from internet on Aug. 31, 2004.

Schoffski et al., "Phase I and pharmacokinetic study of TZT-1027, a novel synthetic dolastatin 10 derivative, administered as a 1-hour intravenous infusion every 3 weeks in patients with advanced refractory cancer," *Annals of Oncology*, 15:671-679 (2004).

Senter et al., "Immunoconjugates comprised of drugs with impaired cellular permeability: A new approach to targeted therapy," *Proceedings of the AACR*, vol. 45, abstract # 623 (2004).

Toki et al., "Protease-Mediated Fragmentation of *p*-Amidobenzyl Ethers: A New Strategy for the Activation of Anticancer Prodrugs," *J. Org. Chem.*, 67:1866-1872 (2002).

Woyke et al., "In Vitro Activities and Postantifungal Effects of the Potent Dolastatin 10 Derivative Auristatin PHE," *Antimicrobial Agents and Chemotherapy*, 45(12):3580-3584 (2001).

Doronina et al., "Enhanced Activity of Monomethylauristatin F through Monoclonal Antibody Delivery: Effects of Linker Technology on Efficacy and Toxicity," *Bioconjugate Chem.*, 17:114-124 (2006).

Doronina et al., "Immunoconjugates comprised of drugs with impaired cellular permeability: A new approach to targeted therapy," SciFinder search result, abstract of paper from 228th ACS National Meeting held in Philadelphia, PA, Aug. 22-26, 2004.

Gaertner & Offord, "Site-specific attachment of functionalized poly-(ethylene glycol) to the amino terminus of proteins." *Bioconj. Chem.* 7(1): 38-44 (1996).

Genet, J. P., "Recent studies on asymmetric hydrogenation. New catalysts and synthetic applications in organic synthesis," *Pure Appl. Chem.*, 74(1):77-83 (2002).

Inada et al., "Modification of proteins with polyethylene glycol derivatives." *Methods Enzymol.* 242: 65-90 (1994).

Miyazaki et al., "Synthesis and Antitumor Activity of Novel Dolastatin 10 Analogs," *Chem. Pharm. Bull.*, 43(10):1706-1718 (1995).

Natsume et al., "Characterization of the Interaction of TZT-1027, a Potent Antitumor Agent, with Tubulin," *Jpn. J. Cancer*, 91:737-747 (2000).

Petit et al., "Antineoplastic agents 337. Synthesis of dolastatin 10 structural modifications," *Anti-Cancer Drug Design*, 10:529-544 (1995).

Petit et al., "Specific Activities of Dolastatin 10 and Peptide Derivatives against *Cryptococcus neoformans*," *Antimicrobial Agents and Chemotherapy*, 42(11):2961-2965 (1998).

Petit et al., "A Cobalt—Phosphine Complex Directed Reformatsky Approach to a Stereospecific Synthesis of the Dolastatin 10 Unit Dolaproine (Dap)[1]," *J. Org. Chem.*, 66:8640-8642 (2001).

Thornber, "Isosterism and molecular modification in drug design." *Chem. Soc. Rev.* 8(4): 563-580 (1979).

Vippagunta et al., "Crystalline solids." *Adv. Drug Delivery Rev.* 48: 3-26 (2001).

Woyke et al., "Effect of auristatin PHE on microtube integrity and nuclear localization in *Cryptococcus neoformans*," *Antimicrobial Agents and Chemotherapy*, 46(12):3802-3808 (2003).

International Search Report of Oct. 2, 2006 for PCT application PCT/US04/38392, which corresponds to the parent application, U.S. Appl. No. 10/983,340.

Written Opinion of Oct. 2, 2006 for PCT application PCT/US04/38392, which corresponds to the parent application, U.S. Appl. No. 10/983,340.

Aherne et al., "Antitumour evaluation of dolastatins 10 and 15 and their measurements in plasma by radioimmunoassay," *Cancer Chemother. Pharmacol.*, 1996, 38, 225-323.

Bowman et al. 1950, "N-substituted amino-acids. Part I. A new method of preparation of dimethylamino-acids,". J. Chem. Soc. :1342-1351.

Bradley, C.M. et al., "Limits of Cooperativity in a Structurally Modular Protein: Response of the Notch Ankyrin Domain to analogous Alanine Substitutions in Each Request," *J. Mol. Biol.*, 2002, vol. 324, pp. 373-386.

Carter, P.J. at al., "Antibody-Drug Conjugates for Cancer Therapy," *The Cancer Journal*, May/Jun. 2008, vol. 14, No. 3, pp. 154-169.

Dermer, G.B., "Another Anniversary for the War on Cancer," *Bio/Technology*, Mar. 12, 1994, vol. 12, p. 320.

Doronina et al., "Errata and Corrigenda," *Nature Biotechnology*, 2003, 21(8), 941.

Doronina, S.O. et al., "Potent Monoclonal Antibody-Drug Conjugates: The Role of Linker Stability in Efficacy, Toxicity and Specificity," poster #6425 at the annual meeting of the American Association for Cancer Research, AACR, Toronto, Ontario, CA, Apr. 5-9, 2003.

Dubowchik, G.M. et al., "Cathepsin B-Sensitive Dipeptide Prodrugs. 2. Models of Anticancer Drugs Paclitaxel (Taxol®), Mitomycin C and Doxorubicin," *Bioorganic & Medicinal Chemistry Letters*, 1998, vol. 8, pp. 3347-3352.

Engert et al., "Evaluation of Ricin A Chain-containing Immunotoxins Directed against the CD30 Antigen as Potential Reagents for the Treatment of Hodgkin's Disease," *Cancer Research*, 1990, 50, 84-88.

Falini et al., "Responses of refractory Hodgkin's disease to monoclonal anti-CD30 immunotoxin," *The Lancet*, 1992, 339, 1195-1196.

Francisco, J.A. et al., "SGN-35, an Anti-CD30 Antibody-Drug Conjugate with Potent Antitumor Activity," poster #770 at the annual meeting of the American Association for Cancer Research, AACR, Toronto, Ontario, CA, Apr. 5-9, 2003.

Frisch et al., "Synthesis of Short Polyoxyethylene-Based Heterobifunctional Cross-Linking Reagents. Application to the Coupling o Peptides to Liposomes," *Bioconjugate Chem.*, 1996, 7, 180-186.

Garteiz, D.A. et al., "Quantitation of dolastatin-10 using HPLC/electrospray ionization mass spectrometry: application in a phase 1 clinical trial," *Cancer Chemother. Pharmacol.*, 1998, vol. 41, pp. 299-306.

Golden, F., "Of mice and men: Don't blame the rodents," *Time Australia*, May 18, 1998, 2 pages.

Gura, T., "Systems for Identifying New Drugs Are Often Faulty," *Science*, Nov. 7, 1997, vol. 278, pp. 1041-1042.

Hamann, P.R. et al., "Gemtuzumab Ozogamicin, A Potent and Selective Anti-CD33 Antibody-Calicheamicin Conjugate for Treatment of Acute Myeloid Leukemia," *Bioconjugate Chem.*, 2002, vol. 13, No. 1, pp. 47-58.

International search report of International Application No. PCT/US03/24209, Apr. 16, 2004.

King et al., "Monoclonal Antibody Conjugates of Doxorubicin Prepared with Branched Linkers: A Novel Method for Increasing the Potency of Doxorubicin Immunoconjugates," *Bioconjugate Chem.*, 1999, 10, 279-288.

King et al., "Monoclonal Antibody Conjugates of Doxorubicin with Branched Peptide Linkers: Inhibition of Aggregation by Methoxytriethyleneglycol Chains," *J. Med. Chem.*, 2002, 45, 4336-4343.

May et al., "Evaluation of Ricin a Chain- Containing Immunotoxins Directed Against Different Epitopes On the δ-Chain of Cell Surface-Associated IgD on Murine B Cells," *The Journal of Immunology*, 1990, 144(9), 3637-3642.

Meyer, D. et al., "Proteolytic vs. Hydrolytic Released Drug from Anti-Tumor Immunochemotherapeutic Agents." poster presentation at Gordon Research Conference on Drug Carriers in Medicine & Biology, Feb. 24-Mar. 1, 2002, Ventura, California, USA.

Mohammad et al., "An Orthotopic Model of Human Pancreatic Cancer in Severe Combined Immunodeficient Mice: Potential Application for Preclinical Studies[1]," *Clinical Cancer Research*, 1998, 4, 887-894.

Office Action mailed on Mar. 26, 2008, for U.S. Appl. No. 10/496,628, filed Dec. 17, 2004, 19 pages.

Pettit et al., 1994, "The Dolastatins. 17. Synthesis of dolaproine and related diastereoisomers," J. Org. Chem., 59(21):6287-6295.

Pettit et al., 1994, "The Dolastatins. 19. Synthesis of dolaisoleuine," J. Org. Chem. 59(7):1796-1800.

Pettit et al., 1996, "Dolastatins. 23: Stereospecific synthesis of dolaisoleuine," J. Chem Soc. Perkin. Trans. 1:853-858.

Pettit et al., 1996, "The Dolastatins. 18. Stereospecific synthesis of dolaproine," Synthesis 6:719-725.

Pettit, 1997, "The Dolastatins," (reprint) Springer-Verlag, New York 70:1-79.

Press et al., "Ricin A-Chain Containing Immunotoxins directed Against Different Epitopes on the CD2 Molecule Differ In Their Ability to Kill Normal and Malignant T Cells," *The Journal of Immunology*, 1988, 141(12), 4410-4417.

Restriction Requirement mailed on Mar. 3, 2009, for U.S. Appl. No. 10/558,811, filed Feb. 5, 2007 8 pages.

Rudinger, J., "Characteristics of the amino acids as components of a peptide hormone sequence," *Peptide Hormones*, Jun. 1976, pp. 1-6.

Schnell et al., "Development of New Ricin A-Chain Immunotoxins With Potent Anti-Tumor effects Against human Hodgkin Cells In Vitro And Disseminated Hodgkin Tumors in Scid Mice Using High-Affinity Monoclonal Antibodies Directed Against The CD30 Antigen," *Int. J. Cancer*, 1995, 63, 238-244.

Senter, P. et al., "Cures and Regressions of Established Tumors with Monoclonal Antibody-Auristatin E Conjugates." poster presentation at the annual meeting of the American Association for Cancer Research, Apr. 6-10, 2002, San Francisco, California, USA.

Shioiri et al., 1993, "Stereoselective synthesis of dolastatin 10 and its congeners," Tetrahedron 49(9):1913-1924.

Supplementary European Search Report for EP Application No. 03772186.7, filed on Jul. 31, 2003, 2 pages.

Toki et al., "Cures and regressions of established tumor xenografts with monoclonal antibody," 223rd ACS Metting, Orlando FL, Apr. 7-11, 2002, Abstract 147.

Tomioka et al., 1991, "An expeditious synthesis of dolastatin 10," Tetrahedron Letters 32(21):2395-2398.

Trail et al., "Cure of Xenografted Human Carcinomas by BR-96-Doxorubicin Immunoconjugates," *Science*, 1993, 261, 212-215.

Trail et al., "Effects of Linker Variation on the Stability, Potency, and Efficacy of Carcinoma-reactive BR64-Doxorubicin Immunoconjugates," *Cancer Research*, 1997, 57, 100-105.

Tsutsumi et al., "Site-specific chemical modification with polyethylene glycol of recombinant immunotoxin anti-Tac(Fv)-PE38(LMB-2) improves Antitumor activity and reduces animal toxicity and immunogenicity," *PNAS*, 2000, 97(15), 8548-8553.

Verdier-Pinard, P. et al., "Sustained Intracellular Retention of Dolastatin 10 Causes Its Potent Antimitotic Activity," *Molecular Pharmacology*, 2000, vol. 57, pp. 180-187.

Wahl, A.F. et al., "Anti-Cancer Activity of High Potency Anti-CD20 Antibody-Drug Conjugates," poster #769 at the annual meeting of the American Association for Cancer Research, AACR, Toronto, Ontario, CA, Apr. 5-9, 2003.

* cited by examiner

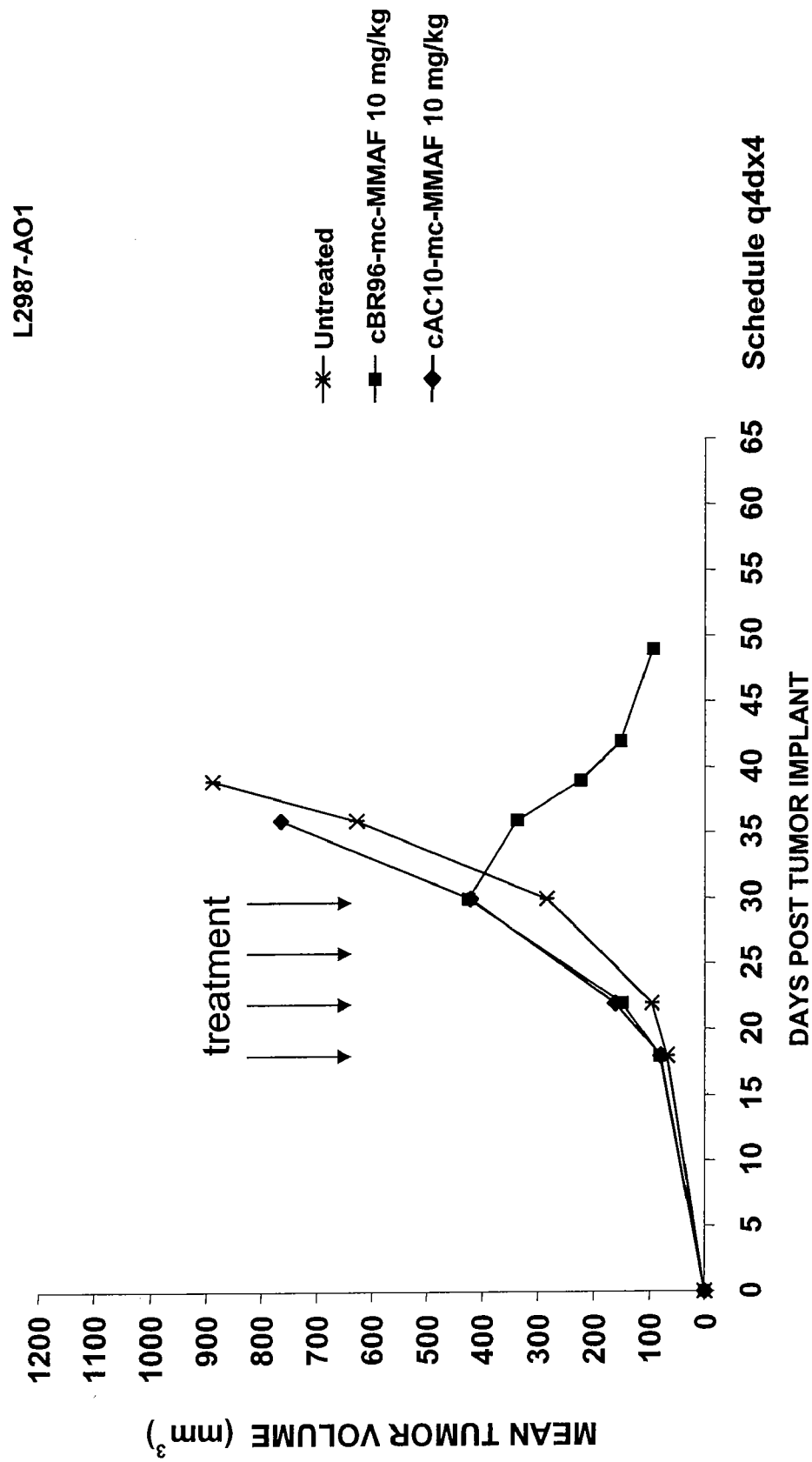

↓ enzymatic cleavage

↓ 1,6-elimination

+ Drug enzymatic cleavage 2 drugs (Ib) where Z is -O- and R$^{11}$ is t-butyl (Ib) where Z is -O- and R$^{11}$ is -H

SEQUENCE LISTING

```
<160> NUMBER OF SEQ ID NOS: 35

<210> SEQ ID NO 1
<211> LENGTH: 502
<212> TYPE: PRT
<213> ORGANISM: Homo sapiens
<220> FEATURE:
<223> OTHER INFORMATION: BMPR1B

<400> SEQUENCE: 1

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140
```

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
            165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
            195                 200                 205

Gln Ile Gly Lys Gly Arg Tyr Gly Glu Val Trp Met Gly Lys Trp Arg
210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
            245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
            275                 280                 285

Asp Tyr Leu Lys Ser Thr Thr Leu Asp Ala Lys Ser Met Leu Lys Leu
            290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
            325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
            405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
            435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
            485                 490                 495

Ser Gln Asp Ile Lys Leu
            500

<210> SEQ ID NO 2
<211> LENGTH: 507
<212> TYPE: PRT
<213> ORGANISM: Homo sapiens
<220> FEATURE:
<223> OTHER INFORMATION: SLC7A5

<400> SEQUENCE: 2

-continued

```
Met Ala Gly Ala Gly Pro Lys Arg Arg Ala Leu Ala Ala Pro Ala Ala
 1               5                  10                  15
Glu Glu Lys Glu Glu Ala Arg Glu Lys Met Leu Ala Ala Lys Ser Ala
                20                  25                  30
Asp Gly Ser Ala Pro Ala Gly Glu Gly Glu Gly Val Thr Leu Gln Arg
             35                  40                  45
Asn Ile Thr Leu Leu Asn Gly Val Ala Ile Ile Val Gly Thr Ile Ile
 50                  55                  60
Gly Ser Gly Ile Phe Val Thr Pro Thr Gly Val Leu Lys Glu Ala Gly
 65                  70                  75                  80
Ser Pro Gly Leu Ala Leu Val Val Trp Ala Ala Cys Gly Val Phe Ser
                 85                  90                  95
Ile Val Gly Ala Leu Cys Tyr Ala Glu Leu Gly Thr Thr Ile Ser Lys
                100                 105                 110
Ser Gly Gly Asp Tyr Ala Tyr Met Leu Glu Val Tyr Gly Ser Leu Pro
                115                 120                 125
Ala Phe Leu Lys Leu Trp Ile Glu Leu Leu Ile Ile Arg Pro Ser Ser
130                 135                 140
Gln Tyr Ile Val Ala Leu Val Phe Ala Thr Tyr Leu Leu Lys Pro Leu
145                 150                 155                 160
Phe Pro Thr Cys Pro Val Pro Glu Glu Ala Ala Lys Leu Val Ala Cys
                165                 170                 175
Leu Cys Val Leu Leu Leu Thr Ala Val Asn Cys Tyr Ser Val Lys Ala
                180                 185                 190
Ala Thr Arg Val Gln Asp Ala Phe Ala Ala Lys Leu Leu Ala Leu
                195                 200                 205
Ala Leu Ile Ile Leu Leu Gly Phe Val Gln Ile Gly Lys Gly Val Val
210                 215                 220
Ser Asn Leu Asp Pro Asn Phe Ser Phe Glu Gly Thr Lys Leu Asp Val
225                 230                 235                 240
Gly Asn Ile Val Leu Ala Leu Tyr Ser Gly Leu Phe Ala Tyr Gly Gly
                245                 250                 255
Trp Asn Tyr Leu Asn Phe Val Thr Glu Glu Met Ile Asn Pro Tyr Arg
                260                 265                 270
Asn Leu Pro Leu Ala Ile Ile Ser Leu Pro Ile Val Thr Leu Val
                275                 280                 285
Tyr Val Leu Thr Asn Leu Ala Tyr Phe Thr Thr Leu Ser Thr Glu Gln
                290                 295                 300
Met Leu Ser Ser Glu Ala Val Ala Val Asp Phe Gly Asn Tyr His Leu
305                 310                 315                 320
Gly Val Met Ser Trp Ile Ile Pro Val Phe Val Gly Leu Ser Cys Phe
                325                 330                 335
Gly Ser Val Asn Gly Ser Leu Phe Thr Ser Ser Arg Leu Phe Phe Val
                340                 345                 350
Gly Ser Arg Glu Gly His Leu Pro Ser Ile Leu Ser Met Ile His Pro
                355                 360                 365
Gln Leu Leu Thr Pro Val Pro Ser Leu Val Phe Thr Cys Val Met Thr
370                 375                 380
Leu Leu Tyr Ala Phe Ser Lys Asp Ile Phe Ser Val Ile Asn Phe Phe
385                 390                 395                 400
Ser Phe Phe Asn Trp Leu Cys Val Ala Leu Ala Ile Ile Gly Met Ile
                405                 410                 415
```

-continued

```
Trp Leu Arg His Arg Lys Pro Glu Leu Glu Arg Pro Ile Lys Val Asn
            420                 425                 430

Leu Ala Leu Pro Val Phe Phe Ile Leu Ala Cys Leu Phe Leu Ile Ala
            435                 440                 445

Val Ser Phe Trp Lys Thr Pro Val Glu Cys Gly Ile Gly Phe Thr Ile
450                 455                 460

Ile Leu Ser Gly Leu Pro Val Tyr Phe Phe Gly Val Trp Trp Lys Asn
465                 470                 475                 480

Lys Pro Lys Trp Leu Leu Gln Gly Ile Phe Ser Thr Thr Val Leu Cys
                485                 490                 495

Gln Lys Leu Met Gln Val Val Pro Gln Glu Thr
            500                 505

<210> SEQ ID NO 3
<211> LENGTH: 339
<212> TYPE: PRT
<213> ORGANISM: Homo sapiens
<220> FEATURE:
<223> OTHER INFORMATION: STEAP1

<400> SEQUENCE: 3

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His Pro
                85                  90                  95

Leu Ala Thr Ser His Gln Gln Tyr Phe Tyr Lys Ile Pro Ile Leu Val
            100                 105                 110

Ile Asn Lys Val Leu Pro Met Val Ser Ile Thr Leu Leu Ala Leu Val
        115                 120                 125

Tyr Leu Pro Gly Val Ile Ala Ala Ile Val Gln Leu His Asn Gly Thr
    130                 135                 140

Lys Tyr Lys Lys Phe Pro His Trp Leu Asp Lys Trp Met Leu Thr Arg
145                 150                 155                 160

Lys Gln Phe Gly Leu Leu Ser Phe Phe Phe Ala Val Leu His Ala Ile
                165                 170                 175

Tyr Ser Leu Ser Tyr Pro Met Arg Arg Ser Tyr Arg Tyr Lys Leu Leu
            180                 185                 190

Asn Trp Ala Tyr Gln Gln Val Gln Gln Asn Lys Glu Asp Ala Trp Ile
        195                 200                 205

Glu His Asp Val Trp Arg Met Glu Ile Tyr Val Ser Leu Gly Ile Val
    210                 215                 220

Gly Leu Ala Ile Leu Ala Leu Leu Ala Val Thr Ser Ile Pro Ser Val
225                 230                 235                 240

Ser Asp Ser Leu Thr Trp Arg Glu Phe His Tyr Ile Gln Ser Lys Leu
                245                 250                 255

Gly Ile Val Ser Leu Leu Leu Gly Thr Ile His Ala Leu Ile Phe
            260                 265                 270
```

```
Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
        290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 4
<211> LENGTH: 6995
<212> TYPE: PRT
<213> ORGANISM: Homo sapiens
<220> FEATURE:
<223> OTHER INFORMATION: MUC16

<400> SEQUENCE: 4

Pro Val Thr Ser Leu Leu Thr Pro Gly Leu Val Ile Thr Thr Asp Arg
1               5                   10                  15

Met Gly Ile Ser Arg Glu Pro Gly Thr Ser Ser Thr Ser Asn Leu Ser
            20                  25                  30

Ser Thr Ser His Glu Arg Leu Thr Thr Leu Glu Asp Thr Val Asp Thr
        35                  40                  45

Glu Ala Met Gln Pro Ser Thr His Thr Ala Val Thr Asn Val Arg Thr
    50                  55                  60

Ser Ile Ser Gly His Glu Ser Gln Ser Ser Val Leu Ser Asp Ser Glu
65                  70                  75                  80

Thr Pro Lys Ala Thr Ser Pro Met Gly Thr Thr Tyr Thr Met Gly Glu
                85                  90                  95

Thr Ser Val Ser Ile Ser Thr Ser Asp Phe Phe Glu Thr Ser Arg Ile
            100                 105                 110

Gln Ile Glu Pro Thr Ser Ser Leu Thr Ser Gly Leu Arg Glu Thr Ser
        115                 120                 125

Ser Ser Glu Arg Ile Ser Ser Ala Thr Glu Gly Ser Thr Val Leu Ser
    130                 135                 140

Glu Val Pro Ser Gly Ala Thr Thr Glu Val Ser Arg Thr Glu Val Ile
145                 150                 155                 160

Ser Ser Arg Gly Thr Ser Met Ser Gly Pro Asp Gln Phe Thr Ile Ser
                165                 170                 175

Pro Asp Ile Ser Thr Glu Ala Ile Thr Arg Leu Ser Thr Ser Pro Ile
            180                 185                 190

Met Thr Glu Ser Ala Glu Ser Ala Ile Thr Ile Glu Thr Gly Ser Pro
        195                 200                 205

Gly Ala Thr Ser Glu Gly Thr Leu Thr Leu Asp Thr Ser Thr Thr Thr
    210                 215                 220

Phe Trp Ser Gly Thr His Ser Thr Ala Ser Pro Gly Phe Ser His Ser
225                 230                 235                 240

Glu Met Thr Thr Leu Met Ser Arg Thr Pro Gly Asp Val Pro Trp Pro
                245                 250                 255

Ser Leu Pro Ser Val Glu Glu Ala Ser Ser Val Ser Ser Ser Leu Ser
            260                 265                 270

Ser Pro Ala Met Thr Ser Thr Ser Phe Phe Ser Thr Leu Pro Glu Ser
        275                 280                 285

Ile Ser Ser Ser Pro His Pro Val Thr Ala Leu Leu Thr Leu Gly Pro
```

```
                290                     295                     300
Val Lys Thr Thr Asp Met Leu Arg Thr Ser Ser Glu Pro Glu Thr Ser
305                     310                     315                     320

Ser Pro Pro Asn Leu Ser Ser Thr Ser Ala Glu Ile Leu Ala Thr Ser
                325                     330                     335

Glu Val Thr Lys Asp Arg Glu Lys Ile His Pro Ser Ser Asn Thr Pro
                340                     345                     350

Val Val Asn Val Gly Thr Val Ile Tyr Lys His Leu Ser Pro Ser Ser
                355                     360                     365

Val Leu Ala Asp Leu Val Thr Thr Lys Pro Thr Ser Pro Met Ala Thr
370                     375                     380

Thr Ser Thr Leu Gly Asn Thr Ser Val Ser Thr Ser Thr Pro Ala Phe
385                     390                     395                     400

Pro Glu Thr Met Met Thr Gln Pro Thr Ser Ser Leu Thr Ser Gly Leu
                405                     410                     415

Arg Glu Ile Ser Thr Ser Gln Glu Thr Ser Ser Ala Thr Glu Arg Ser
                420                     425                     430

Ala Ser Leu Ser Gly Met Pro Thr Gly Ala Thr Thr Lys Val Ser Arg
                435                     440                     445

Thr Glu Ala Leu Ser Leu Gly Arg Thr Ser Thr Pro Gly Pro Ala Gln
                450                     455                     460

Ser Thr Ile Ser Pro Glu Ile Ser Thr Glu Thr Ile Thr Arg Ile Ser
465                     470                     475                     480

Thr Pro Leu Thr Thr Thr Gly Ser Ala Glu Met Thr Ile Thr Pro Lys
                485                     490                     495

Thr Gly His Ser Gly Ala Ser Ser Gln Gly Thr Phe Thr Leu Asp Thr
                500                     505                     510

Ser Ser Arg Ala Ser Trp Pro Gly Thr His Ser Ala Ala Thr His Arg
                515                     520                     525

Ser Pro His Ser Gly Met Thr Thr Pro Met Ser Arg Gly Pro Glu Asp
                530                     535                     540

Val Ser Trp Pro Ser Arg Pro Ser Val Glu Lys Thr Ser Pro Pro Ser
545                     550                     555                     560

Ser Leu Val Ser Leu Ser Ala Val Thr Ser Pro Ser Pro Leu Tyr Ser
                565                     570                     575

Thr Pro Ser Glu Ser Ser His Ser Ser Pro Leu Arg Val Thr Ser Leu
                580                     585                     590

Phe Thr Pro Val Met Met Lys Thr Thr Asp Met Leu Asp Thr Ser Leu
                595                     600                     605

Glu Pro Val Thr Thr Ser Pro Pro Ser Met Asn Ile Thr Ser Asp Glu
                610                     615                     620

Ser Leu Ala Thr Ser Lys Ala Thr Met Glu Thr Glu Ala Ile Gln Leu
625                     630                     635                     640

Ser Glu Asn Thr Ala Val Thr Gln Met Gly Thr Ile Ser Ala Arg Gln
                645                     650                     655

Glu Phe Tyr Ser Ser Tyr Pro Gly Leu Pro Glu Pro Ser Lys Val Thr
                660                     665                     670

Ser Pro Val Val Thr Ser Ser Thr Ile Lys Asp Ile Val Ser Thr Thr
                675                     680                     685

Ile Pro Ala Ser Ser Glu Ile Thr Arg Ile Glu Met Glu Ser Thr Ser
                690                     695                     700

Thr Leu Thr Pro Thr Pro Arg Glu Thr Ser Thr Ser Gln Glu Ile His
705                     710                     715                     720
```

```
Ser Ala Thr Lys Pro Ser Thr Val Pro Tyr Lys Ala Leu Thr Ser Ala
            725                 730                 735

Thr Ile Glu Asp Ser Met Thr Gln Val Met Ser Ser Arg Gly Pro
            740                 745                 750

Ser Pro Asp Gln Ser Thr Met Ser Gln Asp Ile Ser Thr Glu Val Ile
            755                 760                 765

Thr Arg Leu Ser Thr Ser Pro Ile Lys Thr Glu Ser Glu Met Thr
            770                 775                 780

Ile Thr Thr Gln Thr Gly Ser Pro Gly Ala Thr Ser Arg Gly Thr Leu
785                 790                 795                 800

Thr Leu Asp Thr Ser Thr Thr Phe Met Ser Gly Thr His Ser Thr Ala
                    805                 810                 815

Ser Gln Gly Phe Ser His Ser Gln Met Thr Ala Leu Met Ser Arg Thr
                    820                 825                 830

Pro Gly Glu Val Pro Trp Leu Ser His Pro Ser Val Glu Glu Ala Ser
                    835                 840                 845

Ser Ala Ser Phe Ser Leu Ser Ser Pro Val Met Thr Ser Ser Ser Pro
850                 855                 860

Val Ser Ser Thr Leu Pro Asp Ser Ile His Ser Ser Ser Leu Pro Val
865                 870                 875                 880

Thr Ser Leu Leu Thr Ser Gly Leu Val Lys Thr Thr Glu Leu Leu Gly
                    885                 890                 895

Thr Ser Ser Glu Pro Glu Thr Ser Ser Pro Pro Asn Leu Ser Ser Thr
                    900                 905                 910

Ser Ala Glu Ile Leu Ala Thr Thr Glu Val Thr Thr Asp Thr Glu Lys
                    915                 920                 925

Leu Glu Met Thr Asn Val Val Thr Ser Gly Tyr Thr His Glu Ser Pro
                    930                 935                 940

Ser Ser Val Leu Ala Asp Ser Val Thr Thr Lys Ala Thr Ser Ser Met
945                 950                 955                 960

Gly Ile Thr Tyr Pro Thr Gly Asp Thr Asn Val Leu Thr Ser Thr Pro
                    965                 970                 975

Ala Phe Ser Asp Thr Ser Arg Ile Gln Thr Lys Ser Lys Leu Ser Leu
                    980                 985                 990

Thr Pro Gly Leu Met Glu Thr Ser Ile Ser Glu Thr Ser Ser Ala
            995                 1000                1005

Thr Glu Lys Ser Thr Val Leu Ser Ser Val Pro Thr Gly Ala Thr Thr
            1010                1015                1020

Glu Val Ser Arg Thr Glu Ala Ile Ser Ser Arg Thr Ser Ile Pro
1025                1030                1035                1040

Gly Pro Ala Gln Ser Thr Met Ser Ser Asp Thr Ser Met Glu Thr Ile
                    1045                1050                1055

Thr Arg Ile Ser Thr Pro Leu Thr Arg Lys Glu Ser Thr Asp Met Ala
                    1060                1065                1070

Ile Thr Pro Lys Thr Gly Pro Ser Gly Ala Thr Ser Gln Gly Thr Phe
            1075                1080                1085

Thr Leu Asp Ser Ser Ser Thr Ala Ser Trp Pro Gly Thr His Ser Ala
            1090                1095                1100

Thr Thr Gln Arg Phe Pro Arg Ser Val Val Thr Thr Pro Met Ser Arg
1105                1110                1115                1120

Gly Pro Glu Asp Val Ser Trp Pro Ser Pro Leu Ser Val Glu Lys Asn
                    1125                1130                1135
```

```
Ser Pro Pro Ser Ser Leu Val Ser Ser Ser Val Thr Ser Pro Ser
            1140                1145                1150

Pro Leu Tyr Ser Thr Pro Ser Gly Ser Ser His Ser Ser Pro Val Pro
            1155                1160                1165

Val Thr Ser Leu Phe Thr Ser Ile Met Met Lys Ala Thr Asp Met Leu
    1170                1175                1180

Asp Ala Ser Leu Glu Pro Glu Thr Thr Ser Ala Pro Asn Met Asn Ile
1185            1190                1195                1200

Thr Ser Asp Glu Ser Leu Ala Ala Ser Lys Ala Thr Thr Glu Thr Glu
                1205                1210                1215

Ala Ile His Val Phe Glu Asn Thr Ala Ala Ser His Val Glu Thr Thr
                1220                1225                1230

Ser Ala Thr Glu Glu Leu Tyr Ser Ser Ser Pro Gly Phe Ser Glu Pro
            1235                1240                1245

Thr Lys Val Ile Ser Pro Val Val Thr Ser Ser Ser Ile Arg Asp Asn
    1250                1255                1260

Met Val Ser Thr Thr Met Pro Gly Ser Ser Gly Ile Thr Arg Ile Glu
1265                1270                1275                1280

Ile Glu Ser Met Ser Ser Leu Thr Pro Gly Leu Arg Glu Thr Arg Thr
                1285                1290                1295

Ser Gln Asp Ile Thr Ser Ser Thr Glu Thr Ser Thr Val Leu Tyr Lys
            1300                1305                1310

Met Pro Ser Gly Ala Thr Pro Glu Val Ser Arg Thr Glu Val Met Pro
            1315                1320                1325

Ser Ser Arg Thr Ser Ile Pro Gly Pro Ala Gln Ser Thr Met Ser Leu
            1330                1335                1340

Asp Ile Ser Asp Glu Val Val Thr Arg Leu Ser Thr Ser Pro Ile Met
1345            1350                1355                1360

Thr Glu Ser Ala Glu Ile Thr Ile Thr Thr Gln Thr Gly Tyr Ser Leu
                1365                1370                1375

Ala Thr Ser Gln Val Thr Leu Pro Leu Gly Thr Ser Met Thr Phe Leu
            1380                1385                1390

Ser Gly Thr His Ser Thr Met Ser Gln Gly Leu Ser His Ser Glu Met
            1395                1400                1405

Thr Asn Leu Met Ser Arg Gly Pro Glu Ser Leu Ser Trp Thr Ser Pro
    1410                1415                1420

Arg Phe Val Glu Thr Thr Arg Ser Ser Ser Ser Leu Thr Ser Leu Pro
1425                1430                1435                1440

Leu Thr Thr Ser Leu Ser Pro Val Ser Ser Thr Leu Leu Asp Ser Ser
            1445                1450                1455

Pro Ser Ser Pro Leu Pro Val Thr Ser Leu Ile Leu Pro Gly Leu Val
            1460                1465                1470

Lys Thr Thr Glu Val Leu Asp Thr Ser Ser Glu Pro Lys Thr Ser Ser
            1475                1480                1485

Ser Pro Asn Leu Ser Ser Thr Ser Val Glu Ile Pro Ala Thr Ser Glu
            1490                1495                1500

Ile Met Thr Asp Thr Glu Lys Ile His Pro Ser Ser Asn Thr Ala Val
1505                1510                1515                1520

Ala Lys Val Arg Thr Ser Ser Val His Glu Ser His Ser Ser Val
                1525                1530                1535

Leu Ala Asp Ser Glu Thr Thr Ile Thr Ile Pro Ser Met Gly Ile Thr
                1540                1545                1550

Ser Ala Val Glu Asp Thr Thr Val Phe Thr Ser Asn Pro Ala Phe Ser
```

-continued

```
                1555                1560                1565

Glu Thr Arg Arg Ile Pro Thr Glu Pro Thr Phe Ser Leu Thr Pro Gly
    1570                1575                1580

Phe Arg Glu Thr Ser Thr Ser Glu Gly Thr Thr Ser Ile Thr Glu Thr
1585                1590                1595                1600

Ser Ala Val Leu Phe Gly Val Pro Thr Ser Ala Thr Thr Glu Val Ser
                1605                1610                1615

Met Thr Glu Ile Met Ser Ser Asn Arg Thr His Ile Pro Asp Ser Asp
            1620                1625                1630

Gln Ser Thr Met Ser Pro Asp Ile Ile Thr Glu Val Ile Thr Arg Leu
            1635                1640                1645

Ser Ser Ser Ser Met Met Ser Glu Ser Thr Gln Met Thr Ile Thr Thr
        1650                1655                1660

Gln Lys Ser Ser Pro Gly Ala Thr Ala Gln Ser Thr Leu Thr Leu Ala
1665                1670                1675                1680

Thr Thr Thr Ala Pro Leu Ala Arg Thr His Ser Thr Val Pro Pro Arg
                1685                1690                1695

Phe Leu His Ser Glu Met Thr Thr Leu Met Ser Arg Ser Pro Glu Asn
                1700                1705                1710

Pro Ser Trp Lys Ser Ser Pro Phe Val Glu Lys Thr Ser Ser Ser Ser
            1715                1720                1725

Ser Leu Leu Ser Leu Pro Val Thr Thr Ser Pro Ser Val Ser Ser Thr
            1730                1735                1740

Leu Pro Gln Ser Ile Pro Ser Ser Phe Ser Val Thr Ser Leu Leu
1745                1750                1755                1760

Thr Pro Gly Met Val Lys Thr Thr Asp Thr Ser Thr Glu Pro Gly Thr
                1765                1770                1775

Ser Leu Ser Pro Asn Leu Ser Gly Thr Ser Val Glu Ile Leu Ala Ala
            1780                1785                1790

Ser Glu Val Thr Thr Asp Thr Glu Lys Ile His Pro Ser Ser Ser Met
            1795                1800                1805

Ala Val Thr Asn Val Gly Thr Thr Ser Ser Gly His Glu Leu Tyr Ser
        1810                1815                1820

Ser Val Ser Ile His Ser Glu Pro Ser Lys Ala Thr Tyr Pro Val Gly
1825                1830                1835                1840

Thr Pro Ser Ser Met Ala Glu Thr Ser Ile Ser Thr Ser Met Pro Ala
                1845                1850                1855

Asn Phe Glu Thr Thr Gly Phe Glu Ala Glu Pro Phe Ser His Leu Thr
            1860                1865                1870

Ser Gly Leu Arg Lys Thr Asn Met Ser Leu Asp Thr Ser Ser Val Thr
        1875                1880                1885

Pro Thr Asn Thr Pro Ser Ser Pro Gly Ser His Leu Leu Gln Ser
        1890                1895                1900

Ser Lys Thr Asp Phe Thr Ser Ser Ala Lys Thr Ser Ser Pro Asp Trp
1905                1910                1915                1920

Pro Pro Ala Ser Gln Tyr Thr Glu Ile Pro Val Asp Ile Ile Thr Pro
                1925                1930                1935

Phe Asn Ala Ser Pro Ser Ile Thr Glu Ser Thr Gly Ile Thr Ser Phe
            1940                1945                1950

Pro Glu Ser Arg Phe Thr Met Ser Val Thr Glu Ser Thr His His Leu
        1955                1960                1965

Ser Thr Asp Leu Leu Pro Ser Ala Glu Thr Ile Ser Thr Gly Thr Val
    1970                1975                1980
```

```
Met Pro Ser Leu Ser Glu Ala Met Thr Ser Phe Ala Thr Thr Gly Val
1985                1990                1995                2000

Pro Arg Ala Ile Ser Gly Ser Gly Ser Pro Phe Ser Arg Thr Glu Ser
            2005                2010                2015

Gly Pro Gly Asp Ala Thr Leu Ser Thr Ile Ala Glu Ser Leu Pro Ser
            2020                2025                2030

Ser Thr Pro Val Pro Phe Ser Ser Thr Phe Thr Thr Thr Asp Ser
            2035                2040                2045

Ser Thr Ile Pro Ala Leu His Glu Ile Thr Ser Ser Ala Thr Pro
            2050                2055                2060

Tyr Arg Val Asp Thr Ser Leu Gly Thr Glu Ser Ser Thr Glu Gly
2065                2070                2075                2080

Arg Leu Val Met Val Ser Thr Leu Asp Thr Ser Ser Gln Pro Gly Arg
                2085                2090                2095

Thr Ser Ser Ser Pro Ile Leu Asp Thr Arg Met Thr Glu Ser Val Glu
                2100                2105                2110

Leu Gly Thr Val Thr Ser Ala Tyr Gln Val Pro Ser Leu Ser Thr Arg
                2115                2120                2125

Leu Thr Arg Thr Asp Gly Ile Met Glu His Ile Thr Lys Ile Pro Asn
            2130                2135                2140

Glu Ala Ala His Arg Gly Thr Ile Arg Pro Val Lys Gly Pro Gln Thr
2145                2150                2155                2160

Ser Thr Ser Pro Ala Ser Pro Lys Gly Leu His Thr Gly Gly Thr Lys
                2165                2170                2175

Arg Met Glu Thr Thr Thr Thr Ala Leu Lys Thr Thr Thr Ala Leu
            2180                2185                2190

Lys Thr Thr Ser Arg Ala Thr Leu Thr Thr Ser Val Tyr Thr Pro Thr
                2195                2200                2205

Leu Gly Thr Leu Thr Pro Leu Asn Ala Ser Met Gln Met Ala Ser Thr
                2210                2215                2220

Ile Pro Thr Glu Met Met Ile Thr Thr Pro Tyr Val Phe Pro Asp Val
2225                2230                2235                2240

Pro Glu Thr Thr Ser Ser Leu Ala Thr Ser Leu Gly Ala Glu Thr Ser
                2245                2250                2255

Thr Ala Leu Pro Arg Thr Thr Pro Ser Val Phe Asn Arg Glu Ser Glu
                2260                2265                2270

Thr Thr Ala Ser Leu Val Ser Arg Ser Gly Ala Glu Arg Ser Pro Val
                2275                2280                2285

Ile Gln Thr Leu Asp Val Ser Ser Ser Glu Pro Asp Thr Thr Ala Ser
                2290                2295                2300

Trp Val Ile His Pro Ala Glu Thr Ile Pro Thr Val Ser Lys Thr Thr
2305                2310                2315                2320

Pro Asn Phe Phe His Ser Glu Leu Asp Thr Val Ser Ser Thr Ala Thr
                2325                2330                2335

Ser His Gly Ala Asp Val Ser Ser Ala Ile Pro Thr Asn Ile Ser Pro
                2340                2345                2350

Ser Glu Leu Asp Ala Leu Thr Pro Leu Val Thr Ile Ser Gly Thr Asp
                2355                2360                2365

Thr Ser Thr Thr Phe Pro Thr Leu Thr Lys Ser Pro His Glu Thr Glu
                2370                2375                2380

Thr Arg Thr Thr Trp Leu Thr His Pro Ala Glu Thr Ser Ser Thr Ile
2385                2390                2395                2400
```

```
Pro Arg Thr Ile Pro Asn Phe Ser His His Glu Ser Asp Ala Thr Pro
                2405                2410                2415
Ser Ile Ala Thr Ser Pro Gly Ala Glu Thr Ser Ser Ala Ile Pro Ile
                2420                2425                2430
Met Thr Val Ser Pro Gly Ala Glu Asp Leu Val Thr Ser Gln Val Thr
                2435                2440                2445
Ser Ser Gly Thr Asp Arg Asn Met Thr Ile Pro Thr Leu Thr Leu Ser
                2450                2455                2460
Pro Gly Glu Pro Lys Thr Ile Ala Ser Leu Val Thr His Pro Glu Ala
2465                2470                2475                2480
Gln Thr Ser Ser Ala Ile Pro Thr Ser Thr Ile Ser Pro Ala Val Ser
                2485                2490                2495
Arg Leu Val Thr Ser Met Val Thr Ser Leu Ala Ala Lys Thr Ser Thr
                2500                2505                2510
Thr Asn Arg Ala Leu Thr Asn Ser Pro Gly Glu Pro Ala Thr Thr Val
                2515                2520                2525
Ser Leu Val Thr His Ser Ala Gln Thr Ser Pro Thr Val Pro Trp Thr
                2530                2535                2540
Thr Ser Ile Phe Phe His Ser Lys Ser Asp Thr Thr Pro Ser Met Thr
2545                2550                2555                2560
Thr Ser His Gly Ala Glu Ser Ser Ser Ala Val Pro Thr Pro Thr Val
                2565                2570                2575
Ser Thr Glu Val Pro Gly Val Val Thr Pro Leu Val Thr Ser Ser Arg
                2580                2585                2590
Ala Val Ile Ser Thr Thr Ile Pro Ile Leu Thr Leu Ser Pro Gly Glu
                2595                2600                2605
Pro Glu Thr Thr Pro Ser Met Ala Thr Ser His Gly Glu Glu Ala Ser
                2610                2615                2620
Ser Ala Ile Pro Thr Pro Thr Val Ser Pro Gly Val Pro Gly Val Val
2625                2630                2635                2640
Thr Ser Leu Val Thr Ser Ser Arg Ala Val Thr Ser Thr Thr Ile Pro
                2645                2650                2655
Ile Leu Thr Phe Ser Leu Gly Glu Pro Glu Thr Thr Pro Ser Met Ala
                2660                2665                2670
Thr Ser His Gly Thr Glu Ala Gly Ser Ala Val Pro Thr Val Leu Pro
                2675                2680                2685
Glu Val Pro Gly Met Val Thr Ser Leu Val Ala Ser Ser Arg Ala Val
                2690                2695                2700
Thr Ser Thr Thr Leu Pro Thr Leu Thr Leu Ser Pro Gly Glu Pro Glu
2705                2710                2715                2720
Thr Thr Pro Ser Met Ala Thr Ser His Gly Ala Glu Ala Ser Ser Thr
                2725                2730                2735
Val Pro Thr Val Ser Pro Glu Val Pro Gly Val Val Thr Ser Leu Val
                2740                2745                2750
Thr Ser Ser Ser Gly Val Asn Ser Thr Ser Ile Pro Thr Leu Ile Leu
                2755                2760                2765
Ser Pro Gly Glu Leu Glu Thr Thr Pro Ser Met Ala Thr Ser His Gly
                2770                2775                2780
Ala Glu Ala Ser Ser Ala Val Pro Thr Pro Thr Val Ser Pro Gly Val
2785                2790                2795                2800
Ser Gly Val Val Thr Pro Leu Val Thr Ser Ser Arg Ala Val Thr Ser
                2805                2810                2815
Thr Thr Ile Pro Ile Leu Thr Leu Ser Ser Ser Glu Pro Glu Thr Thr
```

-continued

```
                2820                2825                2830
Pro Ser Met Ala Thr Ser His Gly Val Glu Ala Ser Ser Ala Val Leu
    2835                2840                2845

Thr Val Ser Pro Glu Val Pro Gly Met Val Thr Phe Leu Val Thr Ser
2850                2855                2860

Ser Arg Ala Val Thr Ser Thr Ile Pro Thr Leu Thr Ile Ser Ser
2865                2870                2875                2880

Asp Glu Pro Glu Thr Thr Thr Ser Leu Val Thr His Ser Glu Ala Lys
                2885                2890                2895

Met Ile Ser Ala Ile Pro Thr Leu Gly Val Ser Pro Thr Val Gln Gly
            2900                2905                2910

Leu Val Thr Ser Leu Val Thr Ser Ser Gly Ser Glu Thr Ser Ala Phe
            2915                2920                2925

Ser Asn Leu Thr Val Ala Ser Ser Gln Pro Glu Thr Ile Asp Ser Trp
        2930                2935                2940

Val Ala His Pro Gly Thr Glu Ala Ser Ser Val Pro Thr Leu Thr
2945                2950                2955                2960

Val Ser Thr Gly Glu Pro Phe Thr Asn Ile Ser Leu Val Thr His Pro
            2965                2970                2975

Ala Glu Ser Ser Ser Thr Leu Pro Arg Thr Thr Ser Arg Phe Ser His
            2980                2985                2990

Ser Glu Leu Asp Thr Met Pro Ser Thr Val Thr Ser Pro Glu Ala Glu
        2995                3000                3005

Ser Ser Ser Ala Ile Ser Thr Thr Ile Ser Pro Gly Ile Pro Gly Val
        3010                3015                3020

Leu Thr Ser Leu Val Thr Ser Ser Gly Arg Asp Ile Ser Ala Thr Phe
3025                3030                3035                3040

Pro Thr Val Pro Glu Ser Pro His Glu Ser Glu Ala Thr Ala Ser Trp
            3045                3050                3055

Val Thr His Pro Ala Val Thr Ser Thr Thr Val Pro Arg Thr Thr Pro
            3060                3065                3070

Asn Tyr Ser His Ser Glu Pro Asp Thr Thr Pro Ser Ile Ala Thr Ser
        3075                3080                3085

Pro Gly Ala Glu Ala Thr Ser Asp Phe Pro Thr Ile Thr Val Ser Pro
    3090                3095                3100

Asp Val Pro Asp Met Val Thr Ser Gln Val Thr Ser Ser Gly Thr Asp
3105                3110                3115                3120

Thr Ser Ile Thr Ile Pro Thr Leu Thr Leu Ser Ser Gly Glu Pro Glu
            3125                3130                3135

Thr Thr Thr Ser Phe Ile Thr Tyr Ser Glu Thr His Thr Ser Ser Ala
            3140                3145                3150

Ile Pro Thr Leu Pro Val Ser Pro Asp Ala Ser Lys Met Leu Thr Ser
        3155                3160                3165

Leu Val Ile Ser Ser Gly Thr Asp Ser Thr Thr Phe Pro Thr Leu
    3170                3175                3180

Thr Glu Thr Pro Tyr Glu Pro Glu Thr Thr Ala Ile Gln Leu Ile His
3185                3190                3195                3200

Pro Ala Glu Thr Asn Thr Met Val Pro Arg Thr Thr Pro Lys Phe Ser
            3205                3210                3215

His Ser Lys Ser Asp Thr Thr Leu Pro Val Ala Ile Thr Ser Pro Gly
            3220                3225                3230

Pro Glu Ala Ser Ser Ala Val Ser Thr Thr Thr Ile Ser Pro Asp Met
        3235                3240                3245
```

```
Ser Asp Leu Val Thr Ser Leu Val Pro Ser Ser Gly Thr Asp Thr Ser
    3250                3255                3260
Thr Thr Phe Pro Thr Leu Ser Glu Thr Pro Tyr Glu Pro Glu Thr Thr
3265                3270                3275                3280
Ala Thr Trp Leu Thr His Pro Ala Glu Thr Ser Thr Val Ser Gly
            3285                3290                3295
Thr Ile Pro Asn Phe Ser His Arg Gly Ser Asp Thr Ala Pro Ser Met
        3300                3305                3310
Val Thr Ser Pro Gly Val Asp Thr Arg Ser Gly Val Pro Thr Thr Thr
        3315                3320                3325
Ile Pro Pro Ser Ile Pro Gly Val Val Thr Ser Gln Val Thr Ser Ser
    3330                3335                3340
Ala Thr Asp Thr Ser Thr Ala Ile Pro Thr Leu Thr Pro Ser Pro Gly
3345                3350                3355                3360
Glu Pro Glu Thr Thr Ala Ser Ser Ala Thr His Pro Gly Thr Gln Thr
            3365                3370                3375
Gly Phe Thr Val Pro Ile Arg Thr Val Pro Ser Ser Glu Pro Asp Thr
        3380                3385                3390
Met Ala Ser Trp Val Thr His Pro Pro Gln Thr Ser Thr Pro Val Ser
        3395                3400                3405
Arg Thr Thr Ser Ser Phe Ser His Ser Ser Pro Asp Ala Thr Pro Val
    3410                3415                3420
Met Ala Thr Ser Pro Arg Thr Glu Ala Ser Ser Ala Val Leu Thr Thr
3425                3430                3435                3440
Ile Ser Pro Gly Ala Pro Glu Met Val Thr Ser Gln Ile Thr Ser Ser
            3445                3450                3455
Gly Ala Ala Thr Ser Thr Thr Val Pro Thr Leu Thr His Ser Pro Gly
        3460                3465                3470
Met Pro Glu Thr Thr Ala Leu Leu Ser Thr His Pro Arg Thr Glu Thr
        3475                3480                3485
Ser Lys Thr Phe Pro Ala Ser Thr Val Phe Pro Gln Val Ser Glu Thr
    3490                3495                3500
Thr Ala Ser Leu Thr Ile Arg Pro Gly Ala Glu Thr Ser Thr Ala Leu
3505                3510                3515                3520
Pro Thr Gln Thr Thr Ser Ser Leu Phe Thr Leu Leu Val Thr Gly Thr
            3525                3530                3535
Ser Arg Val Asp Leu Ser Pro Thr Ala Ser Pro Gly Val Ser Ala Lys
        3540                3545                3550
Thr Ala Pro Leu Ser Thr His Pro Gly Thr Glu Thr Ser Thr Met Ile
        3555                3560                3565
Pro Thr Ser Thr Leu Ser Leu Gly Leu Leu Glu Thr Thr Gly Leu Leu
    3570                3575                3580
Ala Thr Ser Ser Ser Ala Glu Thr Ser Thr Ser Thr Leu Thr Leu Thr
3585                3590                3595                3600
Val Ser Pro Ala Val Ser Gly Leu Ser Ser Ala Ser Ile Thr Thr Asp
            3605                3610                3615
Lys Pro Gln Thr Val Thr Ser Trp Asn Thr Glu Thr Ser Pro Ser Val
        3620                3625                3630
Thr Ser Val Gly Pro Pro Glu Phe Ser Arg Thr Val Thr Gly Thr Thr
        3635                3640                3645
Met Thr Leu Ile Pro Ser Glu Met Pro Thr Pro Pro Lys Thr Ser His
    3650                3655                3660
```

-continued

```
Gly Glu Gly Val Ser Pro Thr Ile Leu Arg Thr Thr Met Val Glu
3665                3670                3675                3680

Ala Thr Asn Leu Ala Thr Thr Gly Ser Ser Pro Thr Val Ala Lys Thr
                3685                3690                3695

Thr Thr Thr Phe Asn Thr Leu Ala Gly Ser Leu Phe Thr Pro Leu Thr
                3700                3705                3710

Thr Pro Gly Met Ser Thr Leu Ala Ser Glu Ser Val Thr Ser Arg Thr
                3715                3720                3725

Ser Tyr Asn His Arg Ser Trp Ile Ser Thr Ser Ser Tyr Asn Arg
                3730                3735                3740

Arg Tyr Trp Thr Pro Ala Thr Ser Thr Pro Val Thr Ser Thr Phe Ser
3745                3750                3755                3760

Pro Gly Ile Ser Thr Ser Ser Ile Pro Ser Ser Thr Ala Ala Thr Val
                3765                3770                3775

Pro Phe Met Val Pro Phe Thr Leu Asn Phe Thr Ile Thr Asn Leu Gln
                3780                3785                3790

Tyr Glu Glu Asp Met Arg His Pro Gly Ser Arg Lys Phe Asn Ala Thr
                3795                3800                3805

Glu Arg Glu Leu Gln Gly Leu Leu Lys Pro Leu Phe Arg Asn Ser Ser
                3810                3815                3820

Leu Glu Tyr Leu Tyr Ser Gly Cys Arg Leu Ala Ser Leu Arg Pro Glu
3825                3830                3835                3840

Lys Asp Ser Ser Ala Thr Ala Val Asp Ala Ile Cys Thr His Arg Pro
                3845                3850                3855

Asp Pro Glu Asp Leu Gly Leu Asp Arg Glu Arg Leu Tyr Trp Glu Leu
                3860                3865                3870

Ser Asn Leu Thr Asn Gly Ile Gln Glu Leu Gly Pro Tyr Thr Leu Asp
                3875                3880                3885

Arg Asn Ser Leu Tyr Val Asn Gly Phe Thr His Arg Ser Ser Met Pro
                3890                3895                3900

Thr Thr Ser Thr Pro Gly Thr Ser Thr Val Asp Val Gly Thr Ser Gly
3905                3910                3915                3920

Thr Pro Ser Ser Ser Pro Ser Pro Thr Thr Ala Gly Pro Leu Leu Met
                3925                3930                3935

Pro Phe Thr Leu Asn Phe Thr Ile Thr Asn Leu Gln Tyr Glu Glu Asp
                3940                3945                3950

Met Arg Arg Thr Gly Ser Arg Lys Phe Asn Thr Met Glu Ser Val Leu
                3955                3960                3965

Gln Gly Leu Leu Lys Pro Leu Phe Lys Asn Thr Ser Val Gly Pro Leu
                3970                3975                3980

Tyr Ser Gly Cys Arg Leu Thr Leu Leu Arg Pro Glu Lys Asp Gly Ala
3985                3990                3995                4000

Ala Thr Gly Val Asp Ala Ile Cys Thr His Arg Leu Asp Pro Lys Ser
                4005                4010                4015

Pro Gly Leu Asn Arg Glu Gln Leu Tyr Trp Glu Leu Ser Lys Leu Thr
                4020                4025                4030

Asn Asp Ile Glu Glu Leu Gly Pro Tyr Thr Leu Asp Arg Asn Ser Leu
                4035                4040                4045

Tyr Val Asn Gly Phe Thr His Gln Ser Ser Val Ser Thr Thr Ser Thr
                4050                4055                4060

Pro Gly Thr Ser Thr Val Asp Leu Arg Thr Ser Gly Thr Pro Ser Ser
4065                4070                4075                4080

Leu Ser Ser Pro Thr Ile Met Ala Ala Gly Pro Leu Leu Val Pro Phe
```

-continued

```
                4085                4090                4095
Thr Leu Asn Phe Thr Ile Thr Asn Leu Gln Tyr Gly Glu Asp Met Gly
                    4100                4105                4110
His Pro Gly Ser Arg Lys Phe Asn Thr Thr Glu Arg Val Leu Gln Gly
                    4115                4120                4125
Leu Leu Gly Pro Ile Phe Lys Asn Thr Ser Val Gly Pro Leu Tyr Ser
                    4130                4135                4140
Gly Cys Arg Leu Thr Ser Leu Arg Ser Glu Lys Asp Gly Ala Ala Thr
4145                4150                4155                4160
Gly Val Asp Ala Ile Cys Ile His His Leu Asp Pro Lys Ser Pro Gly
                    4165                4170                4175
Leu Asn Arg Glu Arg Leu Tyr Trp Glu Leu Ser Gln Leu Thr Asn Gly
                    4180                4185                4190
Ile Lys Glu Leu Gly Pro Tyr Thr Leu Asp Arg Asn Ser Leu Tyr Val
                    4195                4200                4205
Asn Gly Phe Thr His Arg Thr Ser Val Pro Thr Thr Ser Thr Pro Gly
                    4210                4215                4220
Thr Ser Thr Val Asp Leu Gly Thr Ser Gly Thr Pro Phe Ser Leu Pro
4225                4230                4235                4240
Ser Pro Ala Thr Ala Gly Pro Leu Leu Val Leu Phe Thr Leu Asn Phe
                    4245                4250                4255
Thr Ile Thr Asn Leu Lys Tyr Glu Glu Asp Met His Arg Pro Gly Ser
                    4260                4265                4270
Arg Lys Phe Asn Thr Thr Glu Arg Val Leu Gln Thr Leu Val Gly Pro
                    4275                4280                4285
Met Phe Lys Asn Thr Ser Val Gly Leu Leu Tyr Ser Gly Cys Arg Leu
                    4290                4295                4300
Thr Leu Leu Arg Ser Glu Lys Asp Gly Ala Ala Thr Gly Val Asp Ala
4305                4310                4315                4320
Ile Cys Thr His Arg Leu Asp Pro Lys Ser Pro Gly Val Asp Arg Glu
                    4325                4330                4335
Gln Leu Tyr Trp Glu Leu Ser Gln Leu Thr Asn Gly Ile Lys Glu Leu
                    4340                4345                4350
Gly Pro Tyr Thr Leu Asp Arg Asn Ser Leu Tyr Val Asn Gly Phe Thr
                    4355                4360                4365
His Trp Ile Pro Val Pro Thr Ser Ser Thr Pro Gly Thr Ser Thr Val
                    4370                4375                4380
Asp Leu Gly Ser Gly Thr Pro Ser Ser Leu Pro Ser Pro Thr Ser Ala
4385                4390                4395                4400
Thr Ala Gly Pro Leu Leu Val Pro Phe Thr Leu Asn Phe Thr Ile Thr
                    4405                4410                4415
Asn Leu Lys Tyr Glu Glu Asp Met His Cys Pro Gly Ser Arg Lys Phe
                    4420                4425                4430
Asn Thr Thr Glu Arg Val Leu Gln Ser Leu Leu Gly Pro Met Phe Lys
                    4435                4440                4445
Asn Thr Ser Val Gly Pro Leu Tyr Ser Gly Cys Arg Leu Thr Leu Leu
                    4450                4455                4460
Arg Ser Glu Lys Asp Gly Ala Ala Thr Gly Val Asp Ala Ile Cys Thr
4465                4470                4475                4480
His Arg Leu Asp Pro Lys Ser Pro Gly Val Asp Arg Glu Gln Leu Tyr
                    4485                4490                4495
Trp Glu Leu Ser Gln Leu Thr Asn Gly Ile Lys Glu Leu Gly Pro Tyr
                    4500                4505                4510
```

```
Thr Leu Asp Arg Asn Ser Leu Tyr Val Asn Gly Phe Thr His Gln Thr
            4515                4520                4525

Ser Ala Pro Asn Thr Ser Thr Pro Gly Thr Ser Thr Val Asp Leu Gly
        4530                4535                4540

Thr Ser Gly Thr Pro Ser Ser Leu Pro Ser Pro Thr Ser Ala Gly Pro
4545                4550                4555                4560

Leu Leu Val Pro Phe Thr Leu Asn Phe Thr Ile Thr Asn Leu Gln Tyr
            4565                4570                4575

Glu Glu Asp Met His His Pro Gly Ser Arg Lys Phe Asn Thr Thr Glu
                4580                4585                4590

Arg Val Leu Gln Gly Leu Leu Gly Pro Met Phe Lys Asn Thr Ser Val
            4595                4600                4605

Gly Leu Leu Tyr Ser Gly Cys Arg Leu Thr Leu Leu Arg Pro Glu Lys
            4610                4615                4620

Asn Gly Ala Ala Thr Gly Met Asp Ala Ile Cys Ser His Arg Leu Asp
4625                4630                4635                4640

Pro Lys Ser Pro Gly Leu Asn Arg Glu Gln Leu Tyr Trp Glu Leu Ser
            4645                4650                4655

Gln Leu Thr His Gly Ile Lys Glu Leu Gly Pro Tyr Thr Leu Asp Arg
            4660                4665                4670

Asn Ser Leu Tyr Val Asn Gly Phe Thr His Arg Ser Ser Val Ala Pro
            4675                4680                4685

Thr Ser Thr Pro Gly Thr Ser Thr Val Asp Leu Gly Thr Ser Gly Thr
            4690                4695                4700

Pro Ser Ser Leu Pro Ser Pro Thr Thr Ala Val Pro Leu Leu Val Pro
4705                4710                4715                4720

Phe Thr Leu Asn Phe Thr Ile Thr Asn Leu Gln Tyr Gly Glu Asp Met
            4725                4730                4735

Arg His Pro Gly Ser Arg Lys Phe Asn Thr Thr Glu Arg Val Leu Gln
            4740                4745                4750

Gly Leu Leu Gly Pro Leu Phe Lys Asn Ser Ser Val Gly Pro Leu Tyr
            4755                4760                4765

Ser Gly Cys Arg Leu Ile Ser Leu Arg Ser Glu Lys Asp Gly Ala Ala
    4770                4775                4780

Thr Gly Val Asp Ala Ile Cys Thr His His Leu Asn Pro Gln Ser Pro
4785                4790                4795                4800

Gly Leu Asp Arg Glu Gln Leu Tyr Trp Gln Leu Ser Gln Met Thr Asn
            4805                4810                4815

Gly Ile Lys Glu Leu Gly Pro Tyr Thr Leu Asp Arg Asn Ser Leu Tyr
            4820                4825                4830

Val Asn Gly Phe Thr His Arg Ser Ser Gly Leu Thr Thr Ser Thr Pro
            4835                4840                4845

Trp Thr Ser Thr Val Asp Leu Gly Thr Ser Gly Thr Pro Ser Pro Val
    4850                4855                4860

Pro Ser Pro Thr Thr Ala Gly Pro Leu Leu Val Pro Phe Thr Leu Asn
4865                4870                4875                4880

Phe Thr Ile Thr Asn Leu Gln Tyr Glu Glu Asp Met His Arg Pro Gly
            4885                4890                4895

Ser Arg Lys Phe Asn Ala Thr Glu Arg Val Leu Gln Gly Leu Leu Ser
            4900                4905                4910

Pro Ile Phe Lys Asn Ser Ser Val Gly Pro Leu Tyr Ser Gly Cys Arg
            4915                4920                4925
```

```
Leu Thr Ser Leu Arg Pro Glu Lys Asp Gly Ala Ala Thr Gly Met Asp
    4930                4935                4940

Ala Val Cys Leu Tyr His Pro Asn Pro Lys Arg Pro Gly Leu Asp Arg
4945                4950                4955                4960

Glu Gln Leu Tyr Trp Glu Leu Ser Gln Leu Thr His Asn Ile Thr Glu
            4965                4970                4975

Leu Gly Pro Tyr Ser Leu Asp Arg Asp Ser Leu Tyr Val Asn Gly Phe
            4980                4985                4990

Thr His Gln Asn Ser Val Pro Thr Thr Ser Thr Pro Gly Thr Ser Thr
            4995                5000                5005

Val Tyr Trp Ala Thr Thr Gly Thr Pro Ser Ser Phe Pro Gly His Thr
            5010                5015                5020

Glu Pro Gly Pro Leu Leu Ile Pro Phe Thr Phe Asn Phe Thr Ile Thr
5025                5030                5035                5040

Asn Leu His Tyr Glu Glu Asn Met Gln His Pro Gly Ser Arg Lys Phe
            5045                5050                5055

Asn Thr Thr Glu Arg Val Leu Gln Gly Leu Leu Lys Pro Leu Phe Lys
            5060                5065                5070

Asn Thr Ser Val Gly Pro Leu Tyr Ser Gly Cys Arg Leu Thr Leu Leu
            5075                5080                5085

Arg Pro Glu Lys Gln Glu Ala Ala Thr Gly Val Asp Thr Ile Cys Thr
            5090                5095                5100

His Arg Val Asp Pro Ile Gly Pro Gly Leu Asp Arg Glu Arg Leu Tyr
5105                5110                5115                5120

Trp Glu Leu Ser Gln Leu Thr Asn Ser Ile Thr Glu Leu Gly Pro Tyr
            5125                5130                5135

Thr Leu Asp Arg Asp Ser Leu Tyr Val Asn Gly Phe Asn Pro Trp Ser
            5140                5145                5150

Ser Val Pro Thr Thr Ser Thr Pro Gly Thr Ser Thr Val His Leu Ala
            5155                5160                5165

Thr Ser Gly Thr Pro Ser Ser Leu Pro Gly His Thr Ala Pro Val Pro
            5170                5175                5180

Leu Leu Ile Pro Phe Thr Leu Asn Phe Thr Ile Thr Asn Leu His Tyr
5185                5190                5195                5200

Glu Glu Asn Met Gln His Pro Gly Ser Arg Lys Phe Asn Thr Thr Glu
            5205                5210                5215

Arg Val Leu Gln Gly Leu Leu Lys Pro Leu Phe Lys Ser Thr Ser Val
            5220                5225                5230

Gly Pro Leu Tyr Ser Gly Cys Arg Leu Thr Leu Leu Arg Pro Glu Lys
            5235                5240                5245

His Gly Ala Ala Thr Gly Val Asp Ala Ile Cys Thr Leu Arg Leu Asp
            5250                5255                5260

Pro Thr Gly Pro Gly Leu Asp Arg Glu Arg Leu Tyr Trp Glu Leu Ser
5265                5270                5275                5280

Gln Leu Thr Asn Ser Val Thr Glu Leu Gly Pro Tyr Thr Leu Asp Arg
            5285                5290                5295

Asp Ser Leu Tyr Val Asn Gly Phe Thr His Arg Ser Ser Val Pro Thr
            5300                5305                5310

Thr Ser Ile Pro Gly Thr Ser Ala Val His Leu Glu Thr Ser Gly Thr
            5315                5320                5325

Pro Ala Ser Leu Pro Gly His Thr Ala Pro Gly Pro Leu Leu Val Pro
            5330                5335                5340

Phe Thr Leu Asn Phe Thr Ile Thr Asn Leu Gln Tyr Glu Glu Asp Met
```

```
            5345                5350                5355                5360
Arg His Pro Gly Ser Arg Lys Phe Asn Thr Thr Glu Arg Val Leu Gln
                5365                5370                5375
Gly Leu Leu Lys Pro Leu Phe Lys Ser Thr Ser Val Gly Pro Leu Tyr
            5380                5385                5390
Ser Gly Cys Arg Leu Thr Leu Leu Arg Pro Glu Lys Arg Gly Ala Ala
            5395                5400                5405
Thr Gly Val Asp Thr Ile Cys Thr His Arg Leu Asp Pro Leu Asn Pro
            5410                5415                5420
Gly Leu Asp Arg Glu Gln Leu Tyr Trp Glu Leu Ser Lys Leu Thr Arg
5425                5430                5435                5440
Gly Ile Ile Glu Leu Gly Pro Tyr Leu Leu Asp Arg Gly Ser Leu Tyr
                5445                5450                5455
Val Asn Gly Phe Thr His Arg Asn Phe Val Pro Ile Thr Ser Thr Pro
                5460                5465                5470
Gly Thr Ser Thr Val His Leu Gly Thr Ser Glu Thr Pro Ser Ser Leu
            5475                5480                5485
Pro Arg Pro Ile Val Pro Gly Pro Leu Leu Val Pro Phe Thr Leu Asn
            5490                5495                5500
Phe Thr Ile Thr Asn Leu Gln Tyr Glu Glu Ala Met Arg His Pro Gly
5505                5510                5515                5520
Ser Arg Lys Phe Asn Thr Thr Glu Arg Val Leu Gln Gly Leu Leu Arg
                5525                5530                5535
Pro Leu Phe Lys Asn Thr Ser Ile Gly Pro Leu Tyr Ser Ser Cys Arg
            5540                5545                5550
Leu Thr Leu Leu Arg Pro Glu Lys Asp Lys Ala Ala Thr Arg Val Asp
            5555                5560                5565
Ala Ile Cys Thr His His Pro Asp Pro Gln Ser Pro Gly Leu Asn Arg
            5570                5575                5580
Glu Gln Leu Tyr Trp Glu Leu Ser Gln Leu Thr His Gly Ile Thr Glu
5585                5590                5595                5600
Leu Gly Pro Tyr Thr Leu Asp Arg Asp Ser Leu Tyr Val Asp Gly Phe
                5605                5610                5615
Thr His Trp Ser Pro Ile Pro Thr Thr Ser Thr Pro Gly Thr Ser Ile
                5620                5625                5630
Val Asn Leu Gly Thr Ser Gly Ile Pro Pro Ser Leu Pro Glu Thr Thr
            5635                5640                5645
Ala Thr Gly Pro Leu Leu Val Pro Phe Thr Leu Asn Phe Thr Ile Thr
            5650                5655                5660
Asn Leu Gln Tyr Glu Glu Asn Met Gly His Pro Gly Ser Arg Lys Phe
5665                5670                5675                5680
Asn Ile Thr Glu Ser Val Leu Gln Gly Leu Leu Lys Pro Leu Phe Lys
                5685                5690                5695
Ser Thr Ser Val Gly Pro Leu Tyr Ser Gly Cys Arg Leu Thr Leu Leu
            5700                5705                5710
Arg Pro Glu Lys Asp Gly Val Ala Thr Arg Val Asp Ala Ile Cys Thr
            5715                5720                5725
His Arg Pro Asp Pro Lys Ile Pro Gly Leu Asp Arg Gln Gln Leu Tyr
            5730                5735                5740
Trp Glu Leu Ser Gln Leu Thr His Ser Ile Thr Glu Leu Gly Pro Tyr
5745                5750                5755                5760
Thr Leu Asp Arg Asp Ser Leu Tyr Val Asn Gly Phe Thr Gln Arg Ser
                5765                5770                5775
```

```
Ser Val Pro Thr Thr Ser Thr Pro Gly Thr Phe Thr Val Gln Pro Glu
            5780                5785                5790

Thr Ser Glu Thr Pro Ser Ser Leu Pro Gly Pro Thr Ala Thr Gly Pro
        5795                5800                5805

Val Leu Leu Pro Phe Thr Leu Asn Phe Thr Ile Ile Asn Leu Gln Tyr
        5810                5815                5820

Glu Glu Asp Met His Arg Pro Gly Ser Arg Lys Phe Asn Thr Thr Glu
5825                5830                5835                5840

Arg Val Leu Gln Gly Leu Leu Met Pro Leu Phe Lys Asn Thr Ser Val
                5845                5850                5855

Ser Ser Leu Tyr Ser Gly Cys Arg Leu Thr Leu Leu Arg Pro Glu Lys
            5860                5865                5870

Asp Gly Ala Ala Thr Arg Val Asp Ala Val Cys Thr His Arg Pro Asp
        5875                5880                5885

Pro Lys Ser Pro Gly Leu Asp Arg Glu Arg Leu Tyr Trp Lys Leu Ser
        5890                5895                5900

Gln Leu Thr His Gly Ile Thr Glu Leu Gly Pro Tyr Thr Leu Asp Arg
5905                5910                5915                5920

His Ser Leu Tyr Val Asn Gly Phe Thr His Gln Ser Ser Met Thr Thr
                5925                5930                5935

Thr Arg Thr Pro Asp Thr Ser Thr Met His Leu Ala Thr Ser Arg Thr
            5940                5945                5950

Pro Ala Ser Leu Ser Gly Pro Thr Thr Ala Ser Pro Leu Leu Val Leu
        5955                5960                5965

Phe Thr Ile Asn Phe Thr Ile Thr Asn Leu Arg Tyr Glu Glu Asn Met
        5970                5975                5980

His His Pro Gly Ser Arg Lys Phe Asn Thr Thr Glu Arg Val Leu Gln
5985                5990                5995                6000

Gly Leu Leu Arg Pro Val Phe Lys Asn Thr Ser Val Gly Pro Leu Tyr
            6005                6010                6015

Ser Gly Cys Arg Leu Thr Leu Leu Arg Pro Lys Lys Asp Gly Ala Ala
        6020                6025                6030

Thr Lys Val Asp Ala Ile Cys Thr Tyr Arg Pro Asp Pro Lys Ser Pro
        6035                6040                6045

Gly Leu Asp Arg Glu Gln Leu Tyr Trp Glu Leu Ser Gln Leu Thr His
        6050                6055                6060

Ser Ile Thr Glu Leu Gly Pro Tyr Thr Leu Asp Arg Asp Ser Leu Tyr
6065                6070                6075                6080

Val Asn Gly Phe Thr Gln Arg Ser Ser Val Pro Thr Thr Ser Ile Pro
            6085                6090                6095

Gly Thr Pro Thr Val Asp Leu Gly Thr Ser Gly Thr Pro Val Ser Lys
        6100                6105                6110

Pro Gly Pro Ser Ala Ala Ser Pro Leu Leu Val Leu Phe Thr Leu Asn
        6115                6120                6125

Phe Thr Ile Thr Asn Leu Arg Tyr Glu Glu Asn Met Gln His Pro Gly
        6130                6135                6140

Ser Arg Lys Phe Asn Thr Thr Glu Arg Val Leu Gln Gly Leu Leu Arg
6145                6150                6155                6160

Ser Leu Phe Lys Ser Thr Ser Val Gly Pro Leu Tyr Ser Gly Cys Arg
            6165                6170                6175

Leu Thr Leu Leu Arg Pro Glu Lys Asp Gly Thr Ala Thr Gly Val Asp
            6180                6185                6190
```

```
Ala Ile Cys Thr His His Pro Asp Pro Lys Ser Pro Arg Leu Asp Arg
        6195                6200                6205

Glu Gln Leu Tyr Trp Glu Leu Ser Gln Leu Thr His Asn Ile Thr Glu
    6210                6215                6220

Leu Gly Pro Tyr Ala Leu Asp Asn Asp Ser Leu Phe Val Asn Gly Phe
6225                6230                6235                6240

Thr His Arg Ser Ser Val Ser Thr Thr Ser Thr Pro Gly Thr Pro Thr
                6245                6250                6255

Val Tyr Leu Gly Ala Ser Lys Thr Pro Ala Ser Ile Phe Gly Pro Ser
            6260                6265                6270

Ala Ala Ser His Leu Leu Ile Leu Phe Thr Leu Asn Phe Thr Ile Thr
        6275                6280                6285

Asn Leu Arg Tyr Glu Glu Asn Met Trp Pro Gly Ser Arg Lys Phe Asn
    6290                6295                6300

Thr Thr Glu Arg Val Leu Gln Gly Leu Leu Arg Pro Leu Phe Lys Asn
6305                6310                6315                6320

Thr Ser Val Gly Pro Leu Tyr Ser Gly Cys Arg Leu Thr Leu Leu Arg
                6325                6330                6335

Pro Glu Lys Asp Gly Glu Ala Thr Gly Val Asp Ala Ile Cys Thr His
            6340                6345                6350

Arg Pro Asp Pro Thr Gly Pro Gly Leu Asp Arg Glu Gln Leu Tyr Leu
        6355                6360                6365

Glu Leu Ser Gln Leu Thr His Ser Ile Thr Glu Leu Gly Pro Tyr Thr
    6370                6375                6380

Leu Asp Arg Asp Ser Leu Tyr Val Asn Gly Phe Thr His Arg Ser Ser
6385                6390                6395                6400

Val Pro Thr Thr Ser Thr Gly Val Val Ser Glu Glu Pro Phe Thr Leu
                6405                6410                6415

Asn Phe Thr Ile Asn Asn Leu Arg Tyr Met Ala Asp Met Gly Gln Pro
            6420                6425                6430

Gly Ser Leu Lys Phe Asn Ile Thr Asp Asn Val Met Gln His Leu Leu
        6435                6440                6445

Ser Pro Leu Phe Gln Arg Ser Ser Leu Gly Ala Arg Tyr Thr Gly Cys
    6450                6455                6460

Arg Val Ile Ala Leu Arg Ser Val Lys Asn Gly Ala Glu Thr Arg Val
6465                6470                6475                6480

Asp Leu Leu Cys Thr Tyr Leu Gln Pro Leu Ser Gly Pro Gly Leu Pro
                6485                6490                6495

Ile Lys Gln Val Phe His Glu Leu Ser Gln Gln Thr His Gly Ile Thr
            6500                6505                6510

Arg Leu Gly Pro Tyr Ser Leu Asp Lys Asp Ser Leu Tyr Leu Asn Gly
        6515                6520                6525

Tyr Asn Glu Pro Gly Pro Asp Glu Pro Pro Thr Thr Pro Lys Pro Ala
    6530                6535                6540

Thr Thr Phe Leu Pro Pro Leu Ser Glu Ala Thr Thr Ala Met Gly Tyr
6545                6550                6555                6560

His Leu Lys Thr Leu Thr Leu Asn Phe Thr Ile Ser Asn Leu Gln Tyr
                6565                6570                6575

Ser Pro Asp Met Gly Lys Gly Ser Ala Thr Phe Asn Ser Thr Glu Gly
            6580                6585                6590

Val Leu Gln His Leu Leu Arg Pro Leu Phe Gln Lys Ser Ser Met Gly
        6595                6600                6605

Pro Phe Tyr Leu Gly Cys Gln Leu Ile Ser Leu Arg Pro Glu Lys Asp
```

```
                   6610                6615                6620
Gly Ala Ala Thr Gly Val Asp Thr Thr Cys Thr Tyr His Pro Asp Pro
6625                6630                6635                6640

Val Gly Pro Gly Leu Asp Ile Gln Gln Leu Tyr Trp Glu Leu Ser Gln
                6645                6650                6655

Leu Thr His Gly Val Thr Gln Leu Gly Phe Tyr Val Leu Asp Arg Asp
                6660                6665                6670

Ser Leu Phe Ile Asn Gly Tyr Ala Pro Gln Asn Leu Ser Ile Arg Gly
                6675                6680                6685

Glu Tyr Gln Ile Asn Phe His Ile Val Asn Trp Asn Leu Ser Asn Pro
                6690                6695                6700

Asp Pro Thr Ser Ser Glu Tyr Ile Thr Leu Leu Arg Asp Ile Gln Asp
6705                6710                6715                6720

Lys Val Thr Thr Leu Tyr Lys Gly Ser Gln Leu His Asp Thr Phe Arg
                6725                6730                6735

Phe Cys Leu Val Thr Asn Leu Thr Met Asp Ser Val Leu Val Thr Val
                6740                6745                6750

Lys Ala Leu Phe Ser Ser Asn Leu Asp Pro Ser Leu Val Glu Gln Val
                6755                6760                6765

Phe Leu Asp Lys Thr Leu Asn Ala Ser Phe His Trp Leu Gly Ser Thr
                6770                6775                6780

Tyr Gln Leu Val Asp Ile His Val Thr Glu Met Glu Ser Ser Val Tyr
6785                6790                6795                6800

Gln Pro Thr Ser Ser Ser Gln His Phe Tyr Leu Asn Phe Thr
                6805                6810                6815

Ile Thr Asn Leu Pro Tyr Ser Gln Asp Lys Ala Gln Pro Gly Thr Thr
                6820                6825                6830

Asn Tyr Gln Arg Asn Lys Arg Asn Ile Glu Asp Ala Leu Asn Gln Leu
                6835                6840                6845

Phe Arg Asn Ser Ser Ile Lys Ser Tyr Phe Ser Asp Cys Gln Val Ser
                6850                6855                6860

Thr Phe Arg Ser Val Pro Asn Arg His His Thr Gly Val Asp Ser Leu
6865                6870                6875                6880

Cys Asn Phe Ser Pro Leu Ala Arg Arg Val Asp Arg Val Ala Ile Tyr
                6885                6890                6895

Glu Glu Phe Leu Arg Met Thr Arg Asn Gly Thr Gln Leu Gln Asn Phe
                6900                6905                6910

Thr Leu Asp Arg Ser Ser Val Leu Val Asp Gly Tyr Ser Pro Asn Arg
                6915                6920                6925

Asn Glu Pro Leu Thr Gly Asn Ser Asp Leu Pro Phe Trp Ala Val Ile
                6930                6935                6940

Leu Ile Gly Leu Ala Gly Leu Leu Gly Leu Ile Thr Cys Leu Ile Cys
6945                6950                6955                6960

Gly Val Leu Val Thr Thr Arg Arg Arg Lys Lys Glu Gly Glu Tyr Asn
                6965                6970                6975

Val Gln Gln Gln Cys Pro Gly Tyr Tyr Gln Ser His Leu Asp Leu Glu
                6980                6985                6990

Asp Leu Gln
        6995

<210> SEQ ID NO 5
<211> LENGTH: 622
<212> TYPE: PRT
<213> ORGANISM: Homo sapiens
```

```
<220> FEATURE:
<223> OTHER INFORMATION: MSLN

<400> SEQUENCE: 5

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400
```

-continued

```
Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
    610                 615                 620

<210> SEQ ID NO 6
<211> LENGTH: 690
<212> TYPE: PRT
<213> ORGANISM: Homo sapiens
<220> FEATURE:
<223> OTHER INFORMATION: SLC34A2

<400> SEQUENCE: 6

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Gly Phe Leu Tyr Phe Phe Val
            100                 105                 110

Cys Ser Leu Asp Ile Leu Ser Ser Ala Phe Gln Leu Val Gly Gly Lys
        115                 120                 125

Met Ala Gly Gln Phe Phe Ser Asn Ser Ser Ile Met Ser Asn Pro Leu
    130                 135                 140
```

```
Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
            180                 185                 190

Ser Ile Thr Asn Thr Ile Val Ala Leu Met Gln Val Gly Asp Arg Ser
        195                 200                 205

Glu Phe Arg Arg Ala Phe Ala Gly Ala Thr Val His Asp Phe Phe Asn
    210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
        275                 280                 285

Asn Asp Glu Lys Ala Lys Asn Lys Ser Leu Val Lys Ile Trp Cys Lys
    290                 295                 300

Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
        355                 360                 365

Leu Ile Leu Ser Leu Leu Val Leu Cys Gly Cys Leu Ile Met Ile Val
    370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
        435                 440                 445

Ile Thr Ile Glu Arg Ala Tyr Pro Leu Thr Leu Gly Ser Asn Ile Gly
    450                 455                 460

Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Asn Ile
                485                 490                 495

Ser Gly Ile Leu Leu Trp Tyr Pro Ile Pro Phe Thr Arg Leu Pro Ile
            500                 505                 510

Arg Met Ala Lys Gly Leu Gly Asn Ile Ser Ala Lys Tyr Arg Trp Phe
        515                 520                 525

Ala Val Phe Tyr Leu Ile Ile Phe Phe Leu Ile Pro Leu Thr Val
    530                 535                 540

Phe Gly Leu Ser Leu Ala Gly Trp Arg Val Leu Val Gly Val Gly Val
545                 550                 555                 560
```

```
Pro Val Val Phe Ile Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
            580                 585                 590

Leu Pro Leu Trp Met Arg Ser Leu Lys Pro Trp Asp Ala Val Val Ser
            595                 600                 605

Lys Phe Thr Gly Cys Phe Gln Met Arg Cys Cys Tyr Cys Cys Arg Val
            610                 615                 620

Cys Cys Arg Ala Cys Cys Leu Cys Gly Cys Pro Lys Cys Cys Arg
625             630                 635                 640

Cys Ser Lys Cys Cys Glu Asp Leu Glu Glu Ala Gln Glu Gly Gln Asp
            645                 650                 655

Val Pro Val Lys Ala Pro Glu Thr Phe Asp Asn Ile Thr Ile Ser Arg
            660                 665                 670

Glu Ala Gln Gly Glu Val Pro Ala Ser Asp Ser Lys Thr Glu Cys Thr
            675                 680                 685

Ala Leu
    690

<210> SEQ ID NO 7
<211> LENGTH: 1093
<212> TYPE: PRT
<213> ORGANISM: Homo sapiens
<220> FEATURE:
<223> OTHER INFORMATION: KIAA1445

<400> SEQUENCE: 7

Met Val Leu Ala Gly Pro Leu Ala Val Ser Leu Leu Pro Ser Leu
1               5                   10                  15

Thr Leu Leu Val Ser His Leu Ser Ser Ser Gln Asp Val Ser Ser Glu
            20                  25                  30

Pro Ser Ser Glu Gln Gln Leu Cys Ala Leu Ser Lys His Pro Thr Val
            35                  40                  45

Ala Phe Glu Asp Leu Gln Pro Trp Val Ser Asn Phe Thr Tyr Pro Gly
    50                  55                  60

Ala Arg Asp Phe Ser Gln Leu Ala Leu Asp Pro Ser Gly Asn Gln Leu
65              70                  75                  80

Ile Val Gly Ala Arg Asn Tyr Leu Phe Arg Leu Ser Leu Ala Asn Val
                85                  90                  95

Ser Leu Leu Gln Ala Thr Glu Trp Ala Ser Ser Glu Asp Thr Arg Arg
            100                 105                 110

Ser Cys Gln Ser Lys Gly Lys Thr Glu Glu Glu Cys Gln Asn Tyr Val
            115                 120                 125

Arg Val Leu Ile Val Ala Gly Arg Lys Val Phe Met Cys Gly Thr Asn
    130                 135                 140

Ala Phe Ser Pro Met Cys Thr Ser Arg Gln Val Gly Asn Leu Ser Arg
145             150                 155                 160

Thr Thr Glu Lys Ile Asn Gly Val Ala Arg Cys Pro Tyr Asp Pro Arg
                165                 170                 175

His Asn Ser Thr Ala Val Ile Ser Ser Gln Gly Glu Leu Tyr Ala Ala
            180                 185                 190

Thr Val Ile Asp Phe Ser Gly Arg Asp Pro Ala Ile Tyr Arg Ser Leu
            195                 200                 205

Gly Ser Gly Pro Pro Leu Arg Thr Ala Gln Tyr Asn Ser Lys Trp Leu
    210                 215                 220
```

-continued

```
Asn Glu Pro Asn Phe Val Ala Ala Tyr Asp Ile Gly Leu Phe Ala Tyr
225                 230                 235                 240

Phe Phe Leu Arg Glu Asn Ala Val Glu His Asp Cys Gly Arg Thr Val
                245                 250                 255

Tyr Ser Arg Val Ala Arg Val Cys Lys Asn Asp Val Gly Gly Arg Phe
            260                 265                 270

Leu Leu Glu Asp Thr Trp Thr Thr Phe Met Lys Ala Arg Leu Asn Cys
        275                 280                 285

Ser Arg Pro Gly Glu Val Pro Phe Tyr Tyr Asn Glu Leu Gln Ser Ala
    290                 295                 300

Phe His Leu Pro Glu Gln Asp Leu Ile Tyr Gly Val Phe Thr Thr Asn
305                 310                 315                 320

Val Asn Ser Ile Ala Ala Ser Ala Val Cys Ala Phe Asn Leu Ser Ala
                325                 330                 335

Ile Ser Gln Ala Phe Asn Gly Pro Phe Arg Tyr Gln Glu Asn Pro Arg
            340                 345                 350

Ala Ala Trp Leu Pro Ile Ala Asn Pro Ile Pro Asn Phe Gln Cys Gly
        355                 360                 365

Thr Leu Pro Glu Thr Gly Pro Asn Glu Asn Leu Thr Glu Arg Ser Leu
    370                 375                 380

Gln Asp Ala Gln Arg Leu Phe Leu Met Ser Glu Ala Val Gln Pro Val
385                 390                 395                 400

Thr Pro Glu Pro Cys Val Thr Gln Asp Ser Val Arg Phe Ser His Leu
                405                 410                 415

Val Val Asp Leu Val Gln Ala Lys Asp Thr Leu Tyr His Val Leu Tyr
            420                 425                 430

Ile Gly Thr Glu Ser Gly Thr Ile Leu Lys Ala Leu Ser Thr Ala Ser
        435                 440                 445

Arg Ser Leu His Gly Cys Tyr Leu Glu Glu Leu His Val Leu Pro Pro
    450                 455                 460

Gly Arg Arg Glu Pro Leu Arg Ser Leu Arg Ile Leu His Ser Ala Arg
465                 470                 475                 480

Ala Leu Phe Val Gly Leu Arg Asp Gly Val Leu Arg Val Pro Leu Glu
                485                 490                 495

Arg Cys Ala Ala Tyr Arg Ser Gln Gly Ala Cys Leu Gly Ala Arg Asp
            500                 505                 510

Pro Tyr Cys Gly Trp Asp Gly Lys Gln Gln Arg Cys Ser Thr Leu Glu
        515                 520                 525

Asp Ser Ser Asn Met Ser Leu Trp Thr Gln Asn Ile Thr Ala Cys Pro
    530                 535                 540

Val Arg Asn Val Thr Arg Asp Gly Gly Phe Gly Pro Trp Ser Pro Trp
545                 550                 555                 560

Gln Pro Cys Glu His Leu Asp Gly Asp Asn Ser Gly Ser Cys Leu Cys
                565                 570                 575

Arg Ala Arg Ser Cys Asp Ser Pro Arg Pro Arg Cys Gly Gly Leu Asp
            580                 585                 590

Cys Leu Gly Pro Ala Ile His Ile Ala Asn Cys Ser Arg Asn Gly Ala
        595                 600                 605

Trp Thr Pro Trp Ser Ser Trp Ala Leu Cys Ser Thr Ser Cys Gly Ile
    610                 615                 620

Gly Phe Gln Val Arg Gln Arg Ser Cys Ser Asn Pro Ala Pro Arg His
625                 630                 635                 640

Gly Gly Arg Ile Cys Val Gly Lys Ser Arg Glu Glu Arg Phe Cys Asn
```

-continued

```
            645                 650                 655
Glu Asn Thr Pro Cys Pro Val Pro Ile Phe Trp Ala Ser Trp Gly Ser
            660                 665                 670

Trp Ser Lys Cys Ser Ser Asn Cys Gly Gly Gly Met Gln Ser Arg Arg
            675                 680                 685

Arg Ala Cys Glu Asn Gly Asn Ser Cys Leu Gly Cys Gly Val Glu Phe
            690                 695                 700

Lys Thr Cys Asn Pro Glu Gly Cys Pro Glu Val Arg Arg Asn Thr Pro
705                 710                 715                 720

Trp Thr Pro Trp Leu Pro Val Asn Val Thr Gln Gly Gly Ala Arg Gln
            725                 730                 735

Glu Gln Arg Phe Arg Phe Thr Cys Arg Ala Pro Leu Ala Asp Pro His
            740                 745                 750

Gly Leu Gln Phe Gly Arg Arg Thr Glu Thr Arg Thr Cys Pro Ala
            755                 760                 765

Asp Gly Ser Gly Ser Cys Asp Thr Asp Ala Leu Val Glu Asp Leu Leu
            770                 775                 780

Arg Ser Gly Ser Thr Ser Pro His Thr Val Ser Gly Gly Trp Ala Ala
785                 790                 795                 800

Trp Gly Pro Trp Ser Ser Cys Ser Arg Asp Cys Glu Leu Gly Phe Arg
            805                 810                 815

Val Arg Lys Arg Thr Cys Thr Asn Pro Glu Pro Arg Asn Gly Gly Leu
            820                 825                 830

Pro Cys Val Gly Asp Ala Ala Glu Tyr Gln Asp Cys Asn Pro Gln Ala
            835                 840                 845

Cys Pro Val Arg Gly Ala Trp Ser Cys Trp Thr Ser Trp Ser Pro Cys
850                 855                 860

Ser Ala Ser Cys Gly Gly Gly His Tyr Gln Arg Thr Arg Ser Cys Thr
865                 870                 875                 880

Ser Pro Ala Pro Ser Pro Gly Glu Asp Ile Cys Leu Gly Leu His Thr
            885                 890                 895

Glu Glu Ala Leu Cys Ala Thr Gln Ala Cys Pro Glu Gly Trp Ser Pro
            900                 905                 910

Trp Ser Glu Trp Ser Lys Cys Thr Asp Asp Gly Ala Gln Ser Arg Ser
            915                 920                 925

Arg His Cys Glu Glu Leu Leu Pro Gly Ser Ser Ala Cys Ala Gly Asn
            930                 935                 940

Ser Ser Gln Ser Arg Pro Cys Pro Tyr Ser Glu Ile Pro Val Ile Leu
945                 950                 955                 960

Pro Ala Ser Ser Met Glu Glu Ala Thr Gly Cys Ala Gly Phe Asn Leu
            965                 970                 975

Ile His Leu Val Ala Thr Gly Ile Ser Cys Phe Leu Gly Ser Gly Leu
            980                 985                 990

Leu Thr Leu Ala Val Tyr Leu Ser Cys Gln His Cys Gln Arg Gln Ser
            995                 1000                1005

Gln Glu Ser Thr Leu Val His Pro Ala Thr Pro Asn His Leu His Tyr
            1010                1015                1020

Lys Gly Gly Gly Thr Pro Lys Asn Glu Lys Tyr Thr Pro Met Glu Phe
1025                1030                1035                1040

Lys Thr Leu Asn Lys Asn Asn Leu Ile Pro Asp Asp Arg Ala Asn Phe
            1045                1050                1055

Tyr Pro Leu Gln Gln Thr Asn Val Tyr Thr Thr Thr Tyr Tyr Pro Ser
            1060                1065                1070
```

-continued

```
Pro Leu Asn Lys His Ser Phe Arg Pro Glu Ala Ser Pro Gly Gln Arg
        1075                1080                1085

Cys Phe Pro Asn Ser
    1090

<210> SEQ ID NO 8
<211> LENGTH: 141
<212> TYPE: PRT
<213> ORGANISM: Homo sapiens
<220> FEATURE:
<223> OTHER INFORMATION: PSCA hlg

<400> SEQUENCE: 8

Met Trp Val Leu Gly Ile Ala Ala Thr Phe Cys Gly Leu Phe Leu Leu
1               5                   10                  15

Pro Gly Phe Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95

Cys Ile Ser Cys Cys Asn Thr Pro Leu Cys Asn Gly Pro Arg Pro Lys
            100                 105                 110

Lys Arg Gly Ser Ser Ala Ser Ala Leu Arg Pro Gly Leu Arg Thr Thr
        115                 120                 125

Ile Leu Phe Leu Lys Leu Ala Leu Phe Ser Ala His Cys
    130                 135                 140

<210> SEQ ID NO 9
<211> LENGTH: 442
<212> TYPE: PRT
<213> ORGANISM: Homo sapiens
<220> FEATURE:
<223> OTHER INFORMATION: ETBR

<400> SEQUENCE: 9

Met Gln Pro Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
        115                 120                 125

Asn Lys Cys Met Arg Asn Gly Pro Asn Ile Leu Ile Ala Ser Leu Ala
```

-continued

```
                130                 135                 140
Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
                180                 185                 190

Cys Ala Leu Ser Ile Asp Arg Tyr Arg Ala Val Ala Ser Trp Ser Arg
                195                 200                 205

Ile Lys Gly Ile Gly Val Pro Lys Trp Thr Ala Val Glu Ile Val Leu
210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
                260                 265                 270

Lys Asp Trp Trp Leu Phe Ser Phe Tyr Phe Cys Leu Pro Leu Ala Ile
                275                 280                 285

Thr Ala Phe Phe Tyr Thr Leu Met Thr Cys Glu Met Leu Arg Lys Lys
                290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
                340                 345                 350

Asn Asp Pro Asn Arg Cys Glu Leu Leu Ser Phe Leu Leu Val Leu Asp
                355                 360                 365

Tyr Ile Gly Ile Asn Met Ala Ser Leu Asn Ser Cys Ile Asn Pro Ile
370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
                420                 425                 430

Phe Arg Ser Ser Asn Lys Tyr Ser Ser
                435                 440

<210> SEQ ID NO 10
<211> LENGTH: 783
<212> TYPE: PRT
<213> ORGANISM: Homo sapiens
<220> FEATURE:
<223> OTHER INFORMATION: RNF124

<400> SEQUENCE: 10

Met Ser Gly Gly His Gln Leu Gln Leu Ala Ala Leu Trp Pro Trp Leu
1               5                   10                  15

Leu Met Ala Thr Leu Gln Ala Gly Phe Gly Arg Thr Gly Leu Val Leu
                20                  25                  30

Ala Ala Ala Val Glu Ser Glu Arg Ser Ala Glu Gln Lys Ala Ile Ile
                35                  40                  45

Arg Val Ile Pro Leu Lys Met Asp Pro Thr Gly Lys Leu Asn Leu Thr
```

-continued

```
           50                  55                  60
Leu Glu Gly Val Phe Ala Gly Val Ala Glu Ile Thr Pro Ala Glu Gly
65                  70                  75                  80

Lys Leu Met Gln Ser His Pro Leu Tyr Leu Cys Asn Ala Ser Asp Asp
                    85                  90                  95

Asp Asn Leu Glu Pro Gly Phe Ile Ser Ile Val Lys Leu Glu Ser Pro
                100                 105                 110

Arg Arg Ala Pro Arg Pro Cys Leu Ser Leu Ala Ser Lys Ala Arg Met
                115                 120                 125

Ala Gly Glu Arg Gly Ala Ser Ala Val Leu Phe Asp Ile Thr Glu Asp
            130                 135                 140

Arg Ala Ala Glu Gln Leu Gln Gln Pro Leu Gly Leu Thr Trp Pro
145                 150                 155                 160

Val Val Leu Ile Trp Gly Asn Asp Ala Glu Lys Leu Met Glu Phe Val
                165                 170                 175

Tyr Lys Asn Gln Lys Ala His Val Arg Ile Glu Leu Lys Glu Pro Pro
                180                 185                 190

Ala Trp Pro Asp Tyr Asp Val Trp Ile Leu Met Thr Val Val Gly Thr
                195                 200                 205

Ile Phe Val Ile Ile Leu Ala Ser Val Leu Arg Ile Arg Cys Arg Pro
                210                 215                 220

Arg His Ser Arg Pro Asp Pro Leu Gln Gln Arg Thr Ala Trp Ala Ile
225                 230                 235                 240

Ser Gln Leu Ala Thr Arg Arg Tyr Gln Ala Ser Cys Arg Gln Ala Arg
                245                 250                 255

Gly Glu Trp Pro Asp Ser Gly Ser Ser Cys Ser Ser Ala Pro Val Cys
                260                 265                 270

Ala Ile Cys Leu Glu Glu Phe Ser Glu Gly Gln Glu Leu Arg Val Ile
                275                 280                 285

Ser Cys Leu His Glu Phe His Arg Asn Cys Val Asp Pro Trp Leu His
                290                 295                 300

Gln His Arg Thr Cys Pro Leu Cys Val Phe Asn Ile Thr Glu Gly Asp
305                 310                 315                 320

Ser Phe Ser Gln Ser Leu Gly Pro Ser Arg Ser Tyr Gln Glu Pro Gly
                325                 330                 335

Arg Arg Leu His Leu Ile Arg Gln His Pro Gly His Ala His Tyr His
                340                 345                 350

Leu Pro Ala Ala Tyr Leu Leu Gly Pro Ser Arg Ser Ala Val Ala Arg
                355                 360                 365

Pro Pro Arg Pro Gly Pro Phe Leu Pro Ser Gln Glu Pro Gly Met Gly
                370                 375                 380

Pro Arg His His Arg Phe Pro Arg Ala Ala His Pro Arg Ala Pro Gly
385                 390                 395                 400

Glu Gln Gln Arg Leu Ala Gly Ala Gln His Pro Tyr Ala Gln Gly Trp
                405                 410                 415

Gly Met Ser His Leu Gln Ser Thr Ser Gln His Pro Ala Ala Cys Pro
                420                 425                 430

Val Pro Leu Arg Arg Ala Arg Pro Asp Ser Ser Gly Ser Gly Glu
                435                 440                 445

Ser Tyr Cys Thr Glu Arg Ser Gly Tyr Leu Ala Asp Gly Pro Ala Ser
                450                 455                 460

Asp Ser Ser Ser Gly Pro Cys His Gly Ser Ser Ser Asp Ser Val Val
465                 470                 475                 480
```

```
Asn Cys Thr Asp Ile Ser Leu Gln Gly Val His Gly Ser Ser Ser Thr
                485                 490                 495

Phe Cys Ser Ser Leu Ser Ser Asp Phe Asp Pro Leu Val Tyr Cys Ser
            500                 505                 510

Pro Lys Gly Asp Pro Gln Arg Val Asp Met Gln Pro Ser Val Thr Ser
            515                 520                 525

Arg Pro Arg Ser Leu Asp Ser Val Val Pro Thr Gly Glu Thr Gln Val
        530                 535                 540

Ser Ser His Val His Tyr His Arg His Arg His His Tyr Lys Lys
545                 550                 555                 560

Arg Phe Gln Trp His Gly Arg Lys Pro Gly Pro Glu Thr Gly Val Pro
                565                 570                 575

Gln Ser Arg Pro Pro Ile Pro Arg Thr Gln Pro Gln Pro Glu Pro Pro
            580                 585                 590

Ser Pro Asp Gln Gln Val Thr Gly Ser Asn Ser Ala Ala Pro Ser Gly
            595                 600                 605

Arg Leu Ser Asn Pro Gln Cys Pro Arg Ala Leu Pro Glu Pro Ala Pro
        610                 615                 620

Gly Pro Val Asp Ala Ser Ser Ile Cys Pro Ser Thr Ser Ser Leu Phe
625                 630                 635                 640

Asn Leu Gln Lys Ser Ser Leu Ser Ala Arg His Pro Gln Arg Lys Arg
                645                 650                 655

Arg Gly Gly Pro Ser Glu Pro Thr Pro Gly Ser Arg Pro Gln Asp Ala
            660                 665                 670

Thr Val His Pro Ala Cys Gln Ile Phe Pro His Tyr Thr Pro Ser Val
        675                 680                 685

Ala Tyr Pro Trp Ser Pro Glu Ala His Pro Leu Ile Cys Gly Pro Pro
        690                 695                 700

Gly Leu Asp Lys Arg Leu Leu Pro Glu Thr Pro Gly Pro Cys Tyr Ser
705                 710                 715                 720

Asn Ser Gln Pro Val Trp Leu Cys Leu Thr Pro Arg Gln Pro Leu Glu
                725                 730                 735

Pro His Pro Pro Gly Glu Gly Pro Ser Glu Trp Ser Ser Asp Thr Ala
            740                 745                 750

Glu Gly Arg Pro Cys Pro Tyr Pro His Cys Gln Val Leu Ser Ala Gln
        755                 760                 765

Pro Gly Ser Glu Glu Glu Leu Glu Glu Leu Cys Glu Gln Ala Val
        770                 775                 780

<210> SEQ ID NO 11
<211> LENGTH: 490
<212> TYPE: PRT
<213> ORGANISM: Homo sapiens
<220> FEATURE:
<223> OTHER INFORMATION: STEAP2

<400> SEQUENCE: 11

Met Glu Ser Ile Ser Met Met Gly Ser Pro Lys Ser Leu Ser Glu Thr
1               5                   10                  15

Val Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60
```

-continued

```
Phe Ala Ser Glu Phe Phe Pro His Val Val Asp Val Thr His His Glu
 65                  70                  75                  80

Asp Ala Leu Thr Lys Thr Asn Ile Ile Phe Val Ala Ile His Arg Glu
                 85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Ala Ile Ser Leu Ala Thr
210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Ile Leu Gly Lys Ile Ile
        435                 440                 445

Leu Phe Leu Pro Cys Ile Ser Gln Lys Leu Lys Arg Ile Lys Lys Gly
450                 455                 460

Trp Glu Lys Ser Gln Phe Leu Glu Glu Gly Ile Gly Gly Thr Ile Pro
465                 470                 475                 480
```

-continued

```
His Val Ser Pro Glu Arg Val Thr Val Met
            485             490

<210> SEQ ID NO 12
<211> LENGTH: 1214
<212> TYPE: PRT
<213> ORGANISM: Homo sapiens
<220> FEATURE:
<223> OTHER INFORMATION: TrpM4

<400> SEQUENCE: 12

Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Ala Val Val Thr Val Trp Asp Ser Asp
    50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
        115                 120                 125

Val Leu Gln Thr Trp Leu Gln Asp Leu Leu Arg Arg Gly Leu Val Arg
    130                 135                 140

Ala Ala Gln Ser Thr Gly Ala Trp Ile Val Thr Gly Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
            180                 185                 190

Val Val Arg Asn Arg Asp Thr Leu Ile Asn Pro Lys Gly Ser Phe Pro
        195                 200                 205

Ala Arg Tyr Arg Trp Arg Gly Asp Pro Glu Asp Gly Val Gln Phe Pro
    210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255

Ile Ser Gln Gln Lys Thr Gly Val Gly Gly Thr Gly Ile Asp Ile Pro
            260                 265                 270

Val Leu Leu Leu Leu Ile Asp Gly Asp Glu Lys Met Leu Thr Arg Ile
        275                 280                 285

Glu Asn Ala Thr Gln Ala Gln Leu Pro Cys Leu Leu Val Ala Gly Ser
    290                 295                 300

Gly Gly Ala Ala Asp Cys Leu Ala Glu Thr Leu Glu Asp Thr Leu Ala
305                 310                 315                 320

Pro Gly Ser Gly Gly Ala Arg Gln Gly Glu Ala Arg Asp Arg Ile Arg
                325                 330                 335

Arg Phe Phe Pro Lys Gly Asp Leu Glu Val Leu Gln Ala Gln Val Glu
            340                 345                 350
```

```
Arg Ile Met Thr Arg Lys Glu Leu Leu Thr Val Tyr Ser Ser Glu Asp
        355                 360                 365

Gly Ser Glu Glu Phe Glu Thr Ile Val Leu Lys Ala Leu Val Lys Ala
        370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
                405                 410                 415

Asp Ile Gln Trp Arg Ser Phe His Leu Glu Ala Ser Leu Met Asp Ala
                420                 425                 430

Leu Leu Asn Asp Arg Pro Glu Phe Val Arg Leu Leu Ile Ser His Gly
            435                 440                 445

Leu Ser Leu Gly His Phe Leu Thr Pro Met Arg Leu Ala Gln Leu Tyr
        450                 455                 460

Ser Ala Ala Pro Ser Asn Ser Leu Ile Arg Asn Leu Leu Asp Gln Ala
465                 470                 475                 480

Ser His Ser Ala Gly Thr Lys Ala Pro Ala Leu Lys Gly Gly Ala Ala
                485                 490                 495

Glu Leu Arg Pro Pro Asp Val Gly His Val Leu Arg Met Leu Leu Gly
            500                 505                 510

Lys Met Cys Ala Pro Arg Tyr Pro Ser Gly Gly Ala Trp Asp Pro His
        515                 520                 525

Pro Gly Gln Gly Phe Gly Glu Ser Met Tyr Leu Leu Ser Asp Lys Ala
        530                 535                 540

Thr Ser Pro Leu Ser Leu Asp Ala Gly Leu Gly Gln Ala Pro Trp Ser
545                 550                 555                 560

Asp Leu Leu Leu Trp Ala Leu Leu Leu Asn Arg Ala Gln Met Ala Met
                565                 570                 575

Tyr Phe Trp Glu Met Gly Ser Asn Ala Val Ser Ser Ala Leu Gly Ala
            580                 585                 590

Cys Leu Leu Leu Arg Val Met Ala Arg Leu Glu Pro Asp Ala Glu Glu
        595                 600                 605

Ala Ala Arg Arg Lys Asp Leu Ala Phe Lys Phe Glu Gly Met Gly Val
        610                 615                 620

Asp Leu Phe Gly Glu Cys Tyr Arg Ser Ser Glu Val Arg Ala Ala Arg
625                 630                 635                 640

Leu Leu Leu Arg Arg Cys Pro Leu Trp Gly Asp Ala Thr Cys Leu Gln
                645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Asp Met Ala Ser Thr Thr
        675                 680                 685

Pro Ile Trp Ala Leu Val Leu Ala Phe Phe Cys Pro Pro Leu Ile Tyr
        690                 695                 700

Thr Arg Leu Ile Thr Phe Arg Lys Ser Glu Glu Pro Thr Arg Glu
705                 710                 715                 720

Glu Leu Glu Phe Asp Met Asp Ser Val Ile Asn Gly Glu Gly Pro Val
                725                 730                 735

Gly Thr Ala Asp Pro Ala Glu Lys Thr Pro Leu Gly Val Pro Arg Gln
            740                 745                 750

Ser Gly Arg Pro Gly Cys Cys Gly Gly Arg Cys Gly Gly Arg Arg Cys
        755                 760                 765

Leu Arg Arg Trp Phe His Phe Trp Gly Ala Pro Val Thr Ile Phe Met
```

-continued

```
            770                 775                 780
Gly Asn Val Val Ser Tyr Leu Leu Phe Leu Leu Phe Ser Arg Val
785                 790                 795                 800

Leu Leu Val Asp Phe Gln Pro Ala Pro Pro Gly Ser Leu Glu Leu Leu
                805                 810                 815

Leu Tyr Phe Trp Ala Phe Thr Leu Leu Cys Glu Glu Leu Arg Gln Gly
                820                 825                 830

Leu Ser Gly Gly Gly Ser Leu Ala Ser Gly Gly Pro Gly Pro Gly
                835                 840                 845

His Ala Ser Leu Ser Gln Arg Leu Arg Leu Tyr Leu Ala Asp Ser Trp
850                 855                 860

Asn Gln Cys Asp Leu Val Ala Leu Thr Cys Phe Leu Leu Gly Val Gly
865                 870                 875                 880

Cys Arg Leu Thr Pro Gly Leu Tyr His Leu Gly Arg Thr Val Leu Cys
                885                 890                 895

Ile Asp Phe Met Val Phe Thr Val Arg Leu Leu His Ile Phe Thr Val
                900                 905                 910

Asn Lys Gln Leu Gly Pro Lys Ile Val Ile Val Ser Lys Met Met Lys
                915                 920                 925

Asp Val Phe Phe Phe Leu Phe Phe Leu Gly Val Trp Leu Val Ala Tyr
                930                 935                 940

Gly Val Ala Thr Glu Gly Leu Leu Arg Pro Arg Asp Ser Asp Phe Pro
945                 950                 955                 960

Ser Ile Leu Arg Arg Val Phe Tyr Arg Pro Tyr Leu Gln Ile Phe Gly
                965                 970                 975

Gln Ile Pro Gln Glu Asp Met Asp Val Ala Leu Met Glu His Ser Asn
                980                 985                 990

Cys Ser Ser Glu Pro Gly Phe Trp Ala His Pro Pro Gly Ala Gln Ala
                995                 1000                1005

Gly Thr Cys Val Ser Gln Tyr Ala Asn Trp Leu Val Val Leu Leu Leu
                1010                1015                1020

Val Ile Phe Leu Leu Val Ala Asn Ile Leu Leu Val Asn Leu Leu Ile
1025                1030                1035                1040

Ala Met Phe Ser Tyr Thr Phe Gly Lys Val Gln Gly Asn Ser Asp Leu
                1045                1050                1055

Tyr Trp Lys Ala Gln Arg Tyr Arg Leu Ile Arg Glu Phe His Ser Arg
                1060                1065                1070

Pro Ala Leu Ala Pro Pro Phe Ile Val Ile Ser His Leu Arg Leu Leu
                1075                1080                1085

Leu Arg Gln Leu Cys Arg Arg Pro Arg Ser Pro Gln Pro Ser Ser Pro
                1090                1095                1100

Ala Leu Glu His Phe Arg Val Tyr Leu Ser Lys Glu Ala Glu Arg Lys
1105                1110                1115                1120

Leu Leu Thr Trp Glu Ser Val His Lys Glu Asn Phe Leu Leu Ala Arg
                1125                1130                1135

Ala Arg Asp Lys Arg Glu Ser Asp Ser Glu Arg Leu Lys Arg Thr Ser
                1140                1145                1150

Gln Lys Val Asp Leu Ala Leu Lys Gln Leu Gly His Ile Arg Glu Tyr
                1155                1160                1165

Glu Gln Arg Leu Lys Val Leu Glu Arg Glu Val Gln Gln Cys Ser Arg
                1170                1175                1180

Val Leu Gly Trp Val Ala Glu Ala Leu Ser Arg Ser Ala Leu Leu Pro
1185                1190                1195                1200
```

```
Pro Gly Gly Pro Pro Pro Pro Asp Leu Pro Gly Ser Lys Asp
            1205                1210
```

```
<210> SEQ ID NO 13
<211> LENGTH: 188
<212> TYPE: PRT
<213> ORGANISM: Homo sapiens
<220> FEATURE:
<223> OTHER INFORMATION: TDGF1

<400> SEQUENCE: 13
```

```
Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185
```

```
<210> SEQ ID NO 14
<211> LENGTH: 1033
<212> TYPE: PRT
<213> ORGANISM: Homo sapiens
<220> FEATURE:
<223> OTHER INFORMATION: CD21

<400> SEQUENCE: 14
```

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
```

-continued

```
            100                 105                 110
Ser Val Thr Phe Ala Cys Lys Thr Asn Phe Ser Met Asn Gly Asn Lys
        115                 120                 125
Ser Val Trp Cys Gln Ala Asn Asn Met Trp Gly Pro Thr Arg Leu Pro
130                 135                 140
Thr Cys Val Ser Val Phe Pro Leu Glu Cys Pro Ala Leu Pro Met Ile
145                 150                 155                 160
His Asn Gly His His Thr Ser Glu Asn Val Gly Ser Ile Ala Pro Gly
                165                 170                 175
Leu Ser Val Thr Tyr Ser Cys Ser Gly Tyr Leu Leu Val Gly Glu
            180                 185                 190
Lys Ile Ile Asn Cys Leu Ser Ser Gly Lys Trp Ser Ala Val Pro Pro
            195                 200                 205
Thr Cys Glu Glu Ala Arg Cys Lys Ser Leu Gly Arg Phe Pro Asn Gly
            210                 215                 220
Lys Val Lys Glu Pro Pro Ile Leu Arg Val Gly Val Thr Ala Asn Phe
225                 230                 235                 240
Phe Cys Asp Glu Gly Tyr Arg Leu Gln Gly Pro Pro Ser Ser Arg Cys
                245                 250                 255
Val Ile Ala Gly Gln Gly Val Ala Trp Thr Lys Met Pro Val Cys Glu
            260                 265                 270
Glu Ile Phe Cys Pro Ser Pro Pro Ile Leu Asn Gly Arg His Ile
            275                 280                 285
Gly Asn Ser Leu Ala Asn Val Ser Tyr Gly Ser Ile Val Thr Tyr Thr
            290                 295                 300
Cys Asp Pro Asp Pro Glu Glu Gly Val Asn Phe Ile Leu Ile Gly Glu
305                 310                 315                 320
Ser Thr Leu Arg Cys Thr Val Asp Ser Gln Lys Thr Gly Thr Trp Ser
                325                 330                 335
Gly Pro Ala Pro Arg Cys Glu Leu Ser Thr Ser Ala Val Gln Cys Pro
            340                 345                 350
His Pro Gln Ile Leu Arg Gly Arg Met Val Ser Gly Gln Lys Asp Arg
            355                 360                 365
Tyr Thr Tyr Asn Asp Thr Val Ile Phe Ala Cys Met Phe Gly Phe Thr
            370                 375                 380
Leu Lys Gly Ser Lys Gln Ile Arg Cys Asn Ala Gln Gly Thr Trp Glu
385                 390                 395                 400
Pro Ser Ala Pro Val Cys Glu Lys Glu Cys Gln Ala Pro Pro Asn Ile
                405                 410                 415
Leu Asn Gly Gln Lys Glu Asp Arg His Met Val Arg Phe Asp Pro Gly
            420                 425                 430
Thr Ser Ile Lys Tyr Ser Cys Asn Pro Gly Tyr Val Leu Val Gly Glu
            435                 440                 445
Glu Ser Ile Gln Cys Thr Ser Glu Gly Val Trp Thr Pro Pro Val Pro
            450                 455                 460
Gln Cys Lys Val Ala Ala Cys Glu Ala Thr Gly Arg Gln Leu Leu Thr
465                 470                 475                 480
Lys Pro Gln His Gln Phe Val Arg Pro Asp Val Asn Ser Ser Cys Gly
                485                 490                 495
Glu Gly Tyr Lys Leu Ser Gly Ser Val Tyr Gln Glu Cys Gln Gly Thr
            500                 505                 510
Ile Pro Trp Phe Met Glu Ile Arg Leu Cys Lys Glu Ile Thr Cys Pro
            515                 520                 525
```

```
Pro Pro Pro Val Ile Tyr Asn Gly Ala His Thr Gly Ser Ser Leu Glu
        530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                    565                 570                 575

Thr Ser Asn Asp Gln Glu Arg Gly Thr Trp Ser Gly Pro Ala Pro Leu
                580                 585                 590

Cys Lys Leu Ser Leu Leu Ala Val Gln Cys Ser His Val His Ile Ala
                595                 600                 605

Asn Gly Tyr Lys Ile Ser Gly Lys Glu Ala Pro Tyr Phe Tyr Asn Asp
            610                 615                 620

Thr Val Thr Phe Lys Cys Tyr Ser Gly Phe Thr Leu Lys Gly Ser Ser
625                 630                 635                 640

Gln Ile Arg Cys Lys Ala Asp Asn Thr Trp Asp Pro Glu Ile Pro Val
                645                 650                 655

Cys Glu Lys Glu Thr Cys Gln His Val Arg Gln Ser Leu Gln Glu Leu
                660                 665                 670

Pro Ala Gly Ser Arg Val Glu Leu Val Asn Thr Ser Cys Gln Asp Gly
            675                 680                 685

Tyr Gln Leu Thr Gly His Ala Tyr Gln Met Cys Gln Asp Ala Glu Asn
        690                 695                 700

Gly Ile Trp Phe Lys Lys Ile Pro Leu Cys Lys Val Ile His Cys His
705                 710                 715                 720

Pro Pro Pro Val Ile Val Asn Gly Lys His Thr Gly Met Met Ala Glu
                725                 730                 735

Asn Phe Leu Tyr Gly Asn Glu Val Ser Tyr Glu Cys Asp Gln Gly Phe
                740                 745                 750

Tyr Leu Leu Gly Glu Lys Lys Leu Gln Cys Arg Ser Asp Ser Lys Gly
                755                 760                 765

His Gly Ser Trp Ser Gly Pro Ser Pro Gln Cys Leu Arg Ser Pro Pro
        770                 775                 780

Val Thr Arg Cys Pro Asn Pro Glu Val Lys His Gly Tyr Lys Leu Asn
785                 790                 795                 800

Lys Thr His Ser Ala Tyr Ser His Asn Asp Ile Val Tyr Val Asp Cys
                805                 810                 815

Asn Pro Gly Phe Ile Met Asn Gly Ser Arg Val Ile Arg Cys His Thr
                820                 825                 830

Asp Asn Thr Trp Val Pro Gly Val Pro Thr Cys Ile Lys Lys Ala Phe
            835                 840                 845

Ile Gly Cys Pro Pro Pro Lys Thr Pro Asn Gly Asn His Thr Gly
850                 855                 860

Gly Asn Ile Ala Arg Phe Ser Pro Gly Met Ser Ile Leu Tyr Ser Cys
865                 870                 875                 880

Asp Gln Gly Tyr Leu Leu Val Gly Glu Ala Leu Leu Leu Cys Thr His
                885                 890                 895

Glu Gly Thr Trp Ser Gln Pro Ala Pro His Cys Lys Glu Val Asn Cys
                900                 905                 910

Ser Ser Pro Ala Asp Met Asp Gly Ile Gln Lys Gly Leu Glu Pro Arg
            915                 920                 925

Lys Met Tyr Gln Tyr Gly Ala Val Val Thr Leu Glu Cys Glu Asp Gly
    930                 935                 940
```

-continued

```
Tyr Met Leu Glu Gly Ser Pro Gln Ser Gln Cys Gln Ser Asp His Gln
945                 950                 955                 960

Trp Asn Pro Pro Leu Ala Val Cys Arg Ser Arg Ser Leu Ala Pro Val
            965                 970                 975

Leu Cys Gly Ile Ala Ala Gly Leu Ile Leu Thr Phe Leu Ile Val
        980                 985                 990

Ile Thr Leu Tyr Val Ile Ser Lys His Arg Glu Arg Asn Tyr Tyr Thr
        995                 1000                1005

Asp Thr Ser Gln Lys Glu Ala Phe His Leu Glu Ala Arg Glu Val Tyr
        1010                1015                1020

Ser Val Asp Pro Tyr Asn Pro Ala Ser
1025                1030
```

<210> SEQ ID NO 15
<211> LENGTH: 229
<212> TYPE: PRT
<213> ORGANISM: Homo sapiens
<220> FEATURE:
<223> OTHER INFORMATION: CD79B

<400> SEQUENCE: 15

```
Met Ala Arg Leu Ala Leu Ser Pro Val Pro Ser His Trp Met Val Ala
1               5                   10                  15

Leu Leu Leu Leu Leu Ser Ala Glu Pro Val Pro Ala Ala Arg Ser Glu
            20                  25                  30

Asp Arg Tyr Arg Asn Pro Lys Gly Ser Ala Cys Ser Arg Ile Trp Gln
        35                  40                  45

Ser Pro Arg Phe Ile Ala Arg Lys Arg Gly Phe Thr Val Lys Met His
50                  55                  60

Cys Tyr Met Asn Ser Ala Ser Gly Asn Val Ser Trp Leu Trp Lys Gln
65                  70                  75                  80

Glu Met Asp Glu Asn Pro Gln Gln Leu Lys Leu Glu Lys Gly Arg Met
                85                  90                  95

Glu Glu Ser Gln Asn Glu Ser Leu Ala Thr Leu Thr Ile Gln Gly Ile
            100                 105                 110

Arg Phe Glu Asp Asn Gly Ile Tyr Phe Cys Gln Gln Lys Cys Asn Asn
        115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
            180                 185                 190

Asp His Thr Tyr Glu Gly Leu Asp Ile Asp Gln Thr Ala Thr Tyr Glu
        195                 200                 205

Asp Ile Val Thr Leu Arg Thr Gly Glu Val Lys Trp Ser Val Gly Glu
    210                 215                 220

His Pro Gly Gln Glu
225
```

<210> SEQ ID NO 16
<211> LENGTH: 508
<212> TYPE: PRT
<213> ORGANISM: Homo sapiens
<220> FEATURE:

<223> OTHER INFORMATION: FcRH2

<400> SEQUENCE: 16

```
Met Leu Leu Trp Ser Leu Leu Val Ile Phe Asp Ala Val Thr Glu Gln
1               5                   10                  15

Ala Asp Ser Leu Thr Leu Val Ala Pro Ser Ser Val Phe Glu Gly Asp
            20                  25                  30

Ser Ile Val Leu Lys Cys Gln Gly Glu Gln Asn Trp Lys Ile Gln Lys
        35                  40                  45

Met Ala Tyr His Lys Asp Asn Lys Glu Leu Ser Val Phe Lys Lys Phe
    50                  55                  60

Ser Asp Phe Leu Ile Gln Ser Ala Val Leu Ser Asp Ser Gly Asn Tyr
65                  70                  75                  80

Phe Cys Ser Thr Lys Gly Gln Leu Phe Leu Trp Asp Lys Thr Ser Asn
                85                  90                  95

Ile Val Lys Ile Lys Val Gln Glu Leu Phe Gln Arg Pro Val Leu Thr
            100                 105                 110

Ala Ser Ser Phe Gln Pro Ile Glu Gly Gly Pro Val Ser Leu Lys Cys
        115                 120                 125

Glu Thr Arg Leu Ser Pro Gln Arg Leu Asp Val Gln Leu Gln Phe Cys
    130                 135                 140

Phe Phe Arg Glu Asn Gln Val Leu Gly Ser Gly Trp Ser Ser Ser Pro
145                 150                 155                 160

Glu Leu Gln Ile Ser Ala Val Trp Ser Glu Asp Thr Gly Ser Tyr Trp
                165                 170                 175

Cys Lys Ala Glu Thr Val Thr His Arg Ile Arg Lys Gln Ser Leu Gln
            180                 185                 190

Ser Gln Ile His Val Gln Arg Ile Pro Ile Ser Asn Val Ser Leu Glu
        195                 200                 205

Ile Arg Ala Pro Gly Gly Gln Val Thr Glu Gly Gln Lys Leu Ile Leu
    210                 215                 220

Leu Cys Ser Val Ala Gly Gly Thr Gly Asn Val Thr Phe Ser Trp Tyr
225                 230                 235                 240

Arg Glu Ala Thr Gly Thr Ser Met Gly Lys Lys Thr Gln Arg Ser Leu
                245                 250                 255

Ser Ala Glu Leu Glu Ile Pro Ala Val Lys Ser Asp Ala Gly Lys
            260                 265                 270

Tyr Tyr Cys Arg Ala Asp Asn Gly His Val Pro Ile Gln Ser Lys Val
        275                 280                 285

Val Asn Ile Pro Val Arg Ile Pro Val Ser Arg Pro Val Leu Thr Leu
    290                 295                 300

Arg Ser Pro Gly Ala Gln Ala Val Gly Asp Leu Leu Glu Leu His
305                 310                 315                 320

Cys Glu Ala Leu Arg Gly Ser Pro Pro Ile Leu Tyr Gln Phe Tyr His
                325                 330                 335

Glu Asp Val Thr Leu Gly Asn Ser Ser Ala Pro Ser Gly Gly Gly Ala
            340                 345                 350

Ser Phe Asn Leu Ser Leu Thr Ala Glu His Ser Gly Asn Tyr Ser Cys
        355                 360                 365

Glu Ala Asn Asn Gly Leu Gly Ala Gln Cys Ser Glu Ala Val Pro Val
    370                 375                 380

Ser Ile Ser Gly Pro Asp Gly Tyr Arg Arg Asp Leu Met Thr Ala Gly
385                 390                 395                 400
```

```
Val Leu Trp Gly Leu Phe Gly Val Leu Gly Phe Thr Gly Val Ala Leu
                405                 410                 415

Leu Leu Tyr Ala Leu Phe His Lys Ile Ser Gly Glu Ser Ser Ala Thr
            420                 425                 430

Asn Glu Pro Arg Gly Ala Ser Arg Pro Asn Pro Gln Glu Phe Thr Tyr
        435                 440                 445

Ser Ser Pro Thr Pro Asp Met Glu Glu Leu Gln Pro Val Tyr Val Asn
    450                 455                 460

Val Gly Ser Val Asp Val Asp Val Val Tyr Ser Gln Val Trp Ser Met
465                 470                 475                 480

Gln Gln Pro Glu Ser Ser Ala Asn Ile Arg Thr Leu Leu Glu Asn Lys
                485                 490                 495

Asp Ser Gln Val Ile Tyr Ser Ser Val Lys Lys Ser
            500                 505
```

<210> SEQ ID NO 17
<211> LENGTH: 1255
<212> TYPE: PRT
<213> ORGANISM: Homo sapiens
<220> FEATURE:
<223> OTHER INFORMATION: HER2

<400> SEQUENCE: 17

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

-continued

```
His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
```

-continued

```
                675                 680                 685
Arg Leu Leu Gln Glu Thr Glu Leu Val Glu Pro Leu Thr Pro Ser Gly
690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
                835                 840                 845
Arg Asn Val Leu Val Lys Ser Pro Asn His Val Lys Ile Thr Asp Phe
                850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
                915                 920                 925
Arg Glu Ile Pro Asp Leu Leu Glu Lys Gly Glu Arg Leu Pro Gln Pro
                930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
                980                 985                 990
Asp Leu Gly Pro Ala Ser Pro Leu Asp Ser Thr Phe Tyr Arg Ser Leu
                995                 1000                1005
Leu Glu Asp Asp Asp Met Gly Asp Leu Val Asp Ala Glu Glu Tyr Leu
                1010                1015                1020
Val Pro Gln Gln Gly Phe Phe Cys Pro Asp Pro Ala Pro Gly Ala Gly
1025                1030                1035                1040
Gly Met Val His His Arg His Arg Ser Ser Ser Thr Arg Ser Gly Gly
                1045                1050                1055
Gly Asp Leu Thr Leu Gly Leu Glu Pro Ser Glu Glu Glu Ala Pro Arg
                1060                1065                1070
Ser Pro Leu Ala Pro Ser Glu Gly Ala Gly Ser Asp Val Phe Asp Gly
                1075                1080                1085
Asp Leu Gly Met Gly Ala Ala Lys Gly Leu Gln Ser Leu Pro Thr His
                1090                1095                1100
```

-continued

```
Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
                1220                1225                1230

Pro Pro Ser Thr Phe Lys Gly Thr Pro Thr Ala Glu Asn Pro Glu Tyr
                1235                1240                1245

Leu Gly Leu Asp Val Pro Val
        1250                1255

<210> SEQ ID NO 18
<211> LENGTH: 344
<212> TYPE: PRT
<213> ORGANISM: Homo sapiens
<220> FEATURE:
<223> OTHER INFORMATION: CEACAM6

<400> SEQUENCE: 18

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205
```

```
Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Val Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 19
<211> LENGTH: 411
<212> TYPE: PRT
<213> ORGANISM: Homo sapiens
<220> FEATURE:
<223> OTHER INFORMATION: DPEP1

<400> SEQUENCE: 19

Met Trp Ser Gly Trp Trp Leu Trp Pro Leu Val Ala Val Cys Thr Ala
1               5                   10                  15

Asp Phe Phe Arg Asp Glu Ala Glu Arg Ile Met Arg Asp Ser Pro Val
                20                  25                  30

Ile Asp Gly His Asn Asp Leu Pro Trp Gln Leu Leu Asp Met Phe Asn
            35                  40                  45

Asn Arg Leu Gln Asp Glu Arg Ala Asn Leu Thr Thr Leu Ala Gly Thr
        50                  55                  60

His Thr Asn Ile Pro Lys Leu Arg Ala Gly Phe Val Gly Gly Gln Phe
65                  70                  75                  80

Trp Ser Val Tyr Thr Pro Cys Asp Thr Gln Asn Lys Asp Ala Val Arg
                85                  90                  95

Arg Thr Leu Glu Gln Met Asp Val Val His Arg Met Cys Arg Met Tyr
                100                 105                 110

Pro Glu Thr Phe Leu Tyr Val Thr Ser Ser Ala Gly Ile Arg Gln Ala
            115                 120                 125

Phe Arg Glu Gly Lys Val Ala Ser Leu Ile Gly Val Glu Gly Gly His
        130                 135                 140

Ser Ile Asp Ser Ser Leu Gly Val Leu Arg Ala Leu Tyr Gln Leu Gly
145                 150                 155                 160

Met Arg Tyr Leu Thr Leu Thr His Ser Cys Asn Thr Pro Trp Ala Asp
                165                 170                 175

Asn Trp Leu Val Asp Thr Gly Asp Ser Glu Pro Gln Ser Gln Gly Leu
            180                 185                 190

Ser Pro Phe Gly Gln Arg Val Val Lys Glu Leu Asn Arg Leu Gly Val
        195                 200                 205

Leu Ile Asp Leu Ala His Val Ser Val Ala Thr Met Lys Ala Thr Leu
    210                 215                 220
```

```
Gln Leu Ser Arg Ala Pro Val Ile Phe Ser His Ser Ser Ala Tyr Ser
225                 230                 235                 240

Val Cys Ala Ser Arg Arg Asn Val Pro Asp Val Leu Arg Leu Val
                245                 250                 255

Lys Gln Thr Asp Ser Leu Val Met Val Asn Phe Tyr Asn Asn Tyr Ile
                260                 265                 270

Ser Cys Thr Asn Lys Ala Asn Leu Ser Gln Val Ala Asp His Leu Asp
                275                 280                 285

His Ile Lys Glu Val Ala Gly Ala Arg Ala Val Gly Phe Gly Gly Asp
        290                 295                 300

Phe Asp Gly Val Pro Arg Val Pro Glu Gly Leu Glu Asp Val Ser Lys
305                 310                 315                 320

Tyr Pro Asp Leu Ile Ala Glu Leu Leu Arg Arg Asn Trp Thr Glu Ala
                325                 330                 335

Glu Val Lys Gly Ala Leu Ala Asp Asn Leu Leu Arg Val Phe Glu Ala
                340                 345                 350

Val Glu Gln Ala Ser Asn Leu Thr Gln Ala Pro Glu Glu Pro Ile
                355                 360                 365

Pro Leu Asp Gln Leu Gly Gly Ser Cys Arg Thr His Tyr Gly Tyr Ser
370                 375                 380

Ser Gly Ala Ser Ser Leu His Arg His Trp Gly Leu Leu Leu Ala Ser
385                 390                 395                 400

Leu Ala Pro Leu Val Leu Cys Leu Ser Leu Leu
                405                 410

<210> SEQ ID NO 20
<211> LENGTH: 553
<212> TYPE: PRT
<213> ORGANISM: Homo sapiens
<220> FEATURE:
<223> OTHER INFORMATION: IL20Ra

<400> SEQUENCE: 20

Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
                20                  25                  30

Val Ser Gly Gly Leu Pro Lys Pro Ala Asn Ile Thr Phe Leu Ser Ile
                35                  40                  45

Asn Met Lys Asn Val Leu Gln Trp Thr Pro Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
                115                 120                 125

Phe Tyr Pro Phe Leu Glu Thr Gln Ile Gly Pro Pro Glu Val Ala Leu
                130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175
```

-continued

```
Ser Asn Leu Lys Tyr Asn Val Ser Val Leu Asn Thr Lys Ser Asn Arg
            180                 185                 190
Thr Trp Ser Gln Cys Val Thr Asn His Thr Leu Val Leu Thr Trp Leu
        195                 200                 205
Glu Pro Asn Thr Leu Tyr Cys Val His Val Glu Ser Phe Val Pro Gly
    210                 215                 220
Pro Pro Arg Arg Ala Gln Pro Ser Glu Lys Gln Cys Ala Arg Thr Leu
225                 230                 235                 240
Lys Asp Gln Ser Ser Glu Phe Lys Ala Lys Ile Ile Phe Trp Tyr Val
                245                 250                 255
Leu Pro Ile Ser Ile Thr Val Phe Leu Phe Ser Val Met Gly Tyr Ser
            260                 265                 270
Ile Tyr Arg Tyr Ile His Val Gly Lys Glu Lys His Pro Ala Asn Leu
        275                 280                 285
Ile Leu Ile Tyr Gly Asn Glu Phe Asp Lys Arg Phe Phe Val Pro Ala
    290                 295                 300
Glu Lys Ile Val Ile Asn Phe Ile Thr Leu Asn Ile Ser Asp Asp Ser
305                 310                 315                 320
Lys Ile Ser His Gln Asp Met Ser Leu Leu Gly Lys Ser Ser Asp Val
                325                 330                 335
Ser Ser Leu Asn Asp Pro Gln Pro Ser Gly Asn Leu Arg Pro Pro Gln
            340                 345                 350
Glu Glu Glu Glu Val Lys His Leu Gly Tyr Ala Ser His Leu Met Glu
        355                 360                 365
Ile Phe Cys Asp Ser Glu Glu Asn Thr Glu Gly Thr Ser Phe Thr Gln
    370                 375                 380
Gln Glu Ser Leu Ser Arg Thr Ile Pro Pro Asp Lys Thr Val Ile Glu
385                 390                 395                 400
Tyr Glu Tyr Asp Val Arg Thr Thr Asp Ile Cys Ala Gly Pro Glu Glu
                405                 410                 415
Gln Glu Leu Ser Leu Gln Glu Glu Val Ser Thr Gln Gly Thr Leu Leu
            420                 425                 430
Glu Ser Gln Ala Ala Leu Ala Val Leu Gly Pro Gln Thr Leu Gln Tyr
        435                 440                 445
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                485                 490                 495
Phe Asp Gln Asp Ser Glu Gly Cys Glu Pro Ser Glu Gly Asp Gly Leu
            500                 505                 510
Gly Glu Glu Gly Leu Leu Ser Arg Leu Tyr Glu Pro Ala Pro Asp
        515                 520                 525
Arg Pro Pro Gly Glu Asn Glu Thr Tyr Leu Met Gln Phe Met Glu Glu
    530                 535                 540
Trp Gly Leu Tyr Val Gln Met Glu Asn
545                 550
```

<210> SEQ ID NO 21
<211> LENGTH: 911
<212> TYPE: PRT
<213> ORGANISM: Homo sapiens
<220> FEATURE:

-continued

<223> OTHER INFORMATION: BCAN

<400> SEQUENCE: 21

```
Met Ala Gln Leu Phe Leu Pro Leu Leu Ala Leu Leu Ala Gln
1               5                   10                  15

Ala Pro Ala Ala Leu Ala Asp Val Leu Glu Gly Asp Ser Ser Glu Asp
            20                  25                  30

Arg Ala Phe Arg Val Arg Ile Ala Gly Asp Ala Pro Leu Gln Gly Val
        35                  40                  45

Leu Gly Gly Ala Leu Thr Ile Pro Cys His Val His Tyr Leu Arg Pro
    50                  55                  60

Pro Pro Ser Arg Arg Ala Val Leu Gly Ser Pro Arg Val Lys Trp Thr
65                  70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
                100                 105                 110

Tyr Pro Ala Ser Leu Thr Asp Val Ser Leu Ala Leu Ser Glu Leu Arg
            115                 120                 125

Pro Asn Asp Ser Gly Ile Tyr Arg Cys Glu Val Gln His Gly Ile Asp
        130                 135                 140

Asp Ser Ser Asp Ala Val Glu Val Lys Val Lys Gly Val Val Phe Leu
145                 150                 155                 160

Tyr Arg Glu Gly Ser Ala Arg Tyr Ala Phe Ser Phe Ser Gly Ala Gln
                165                 170                 175

Glu Ala Cys Ala Arg Ile Gly Ala His Ile Ala Thr Pro Glu Gln Leu
                180                 185                 190

Tyr Ala Ala Tyr Leu Gly Gly Tyr Glu Gln Cys Asp Ala Gly Trp Leu
            195                 200                 205

Ser Asp Gln Thr Val Arg Tyr Pro Ile Gln Thr Pro Arg Glu Ala Cys
210                 215                 220

Tyr Gly Asp Met Asp Gly Phe Pro Gly Val Arg Asn Tyr Gly Val Val
225                 230                 235                 240

Asp Pro Asp Asp Leu Tyr Asp Val Tyr Cys Tyr Ala Glu Asp Leu Asn
                245                 250                 255

Gly Glu Leu Phe Leu Gly Asp Pro Pro Glu Lys Leu Thr Leu Glu Glu
            260                 265                 270

Ala Arg Ala Tyr Cys Gln Glu Arg Gly Ala Glu Ile Ala Thr Thr Gly
        275                 280                 285

Gln Leu Tyr Ala Ala Trp Asp Gly Gly Leu Asp His Cys Ser Pro Gly
    290                 295                 300

Trp Leu Ala Asp Gly Ser Val Arg Tyr Pro Ile Val Thr Pro Ser Gln
305                 310                 315                 320

Arg Cys Gly Gly Gly Leu Pro Gly Val Lys Thr Leu Phe Leu Phe Pro
                325                 330                 335

Asn Gln Thr Gly Phe Pro Asn Lys His Ser Arg Phe Asn Val Tyr Cys
                340                 345                 350

Phe Arg Asp Ser Ala Gln Pro Ser Ala Ile Pro Glu Ala Ser Asn Pro
            355                 360                 365

Ala Ser Asn Pro Ala Ser Asp Gly Leu Glu Ala Ile Val Thr Val Thr
        370                 375                 380

Glu Thr Leu Glu Glu Leu Gln Leu Pro Gln Glu Ala Thr Glu Ser Glu
385                 390                 395                 400
```

```
Ser Arg Gly Ala Ile Tyr Ser Ile Pro Ile Met Glu Asp Gly Gly
                405                 410                 415
Gly Ser Ser Thr Pro Glu Asp Pro Ala Glu Ala Pro Arg Thr Leu Leu
            420                 425                 430
Glu Phe Glu Thr Gln Ser Met Val Pro Pro Thr Gly Phe Ser Glu Glu
        435                 440                 445
Glu Gly Lys Ala Leu Glu Glu Glu Lys Tyr Glu Asp Glu Glu Glu
    450                 455                 460
Lys Glu Glu Glu Glu Glu Glu Val Glu Asp Glu Ala Leu Trp
465                 470                 475                 480
Ala Trp Pro Ser Glu Leu Ser Ser Pro Gly Pro Glu Ala Ser Leu Pro
                485                 490                 495
Thr Glu Pro Ala Ala Gln Glu Lys Ser Leu Ser Gln Ala Pro Ala Arg
            500                 505                 510
Ala Val Leu Gln Pro Gly Ala Ser Pro Leu Pro Asp Gly Glu Ser Glu
        515                 520                 525
Ala Ser Arg Pro Pro Arg Val His Gly Pro Pro Thr Glu Thr Leu Pro
    530                 535                 540
Thr Pro Arg Glu Arg Asn Leu Ala Ser Pro Ser Pro Ser Thr Leu Val
545                 550                 555                 560
Glu Ala Arg Glu Val Gly Glu Ala Thr Gly Gly Pro Glu Leu Ser Gly
                565                 570                 575
Val Pro Arg Gly Glu Ser Glu Glu Thr Gly Ser Ser Glu Gly Ala Pro
            580                 585                 590
Ser Leu Leu Pro Ala Thr Arg Ala Pro Glu Gly Thr Arg Glu Leu Glu
        595                 600                 605
Ala Pro Ser Glu Asp Asn Ser Gly Arg Thr Ala Pro Ala Gly Thr Ser
    610                 615                 620
Val Gln Ala Gln Pro Val Leu Pro Thr Asp Ser Ala Ser Arg Gly Gly
625                 630                 635                 640
Val Ala Val Val Pro Ala Ser Gly Asp Cys Val Pro Ser Pro Cys His
                645                 650                 655
Asn Gly Gly Thr Cys Leu Glu Glu Glu Gly Val Arg Cys Leu Cys
            660                 665                 670
Leu Pro Gly Tyr Gly Gly Asp Leu Cys Asp Val Gly Leu Arg Phe Cys
        675                 680                 685
Asn Pro Gly Trp Asp Ala Phe Gln Gly Ala Cys Tyr Lys His Phe Ser
    690                 695                 700
Thr Arg Arg Ser Trp Glu Glu Ala Glu Thr Gln Cys Arg Met Tyr Gly
705                 710                 715                 720
Ala His Leu Ala Ser Ile Ser Thr Pro Glu Glu Gln Asp Phe Ile Asn
                725                 730                 735
Asn Arg Tyr Arg Glu Tyr Gln Trp Ile Gly Leu Asn Asp Arg Thr Ile
            740                 745                 750
Glu Gly Asp Phe Leu Trp Ser Asp Gly Val Pro Leu Leu Tyr Glu Asn
        755                 760                 765
Trp Asn Pro Gly Gln Pro Asp Ser Tyr Phe Leu Ser Gly Glu Asn Cys
    770                 775                 780
Val Val Met Val Trp His Asp Gly Gln Trp Ser Asp Val Pro Cys
785                 790                 795                 800
Asn Tyr His Leu Ser Tyr Thr Cys Lys Met Gly Leu Val Ser Cys Gly
                805                 810                 815
Pro Pro Pro Glu Leu Pro Leu Ala Gln Val Phe Gly Arg Pro Arg Leu
```

-continued

Arg Tyr Glu Val Asp Thr Val Leu Arg Tyr Arg Cys Arg Glu Gly Leu
    820                 825                 830
835                         840                     845

Ala Gln Arg Asn Leu Pro Leu Ile Arg Cys Gln Glu Asn Gly Arg Trp
850                         855                     860

Glu Ala Pro Gln Ile Ser Cys Val Pro Arg Arg Pro Ala Arg Ala Leu
865                         870                     875             880

His Pro Glu Glu Asp Pro Glu Gly Arg Gln Gly Arg Leu Leu Gly Arg
                    885                     890                     895

Trp Lys Ala Leu Leu Ile Pro Pro Ser Ser Pro Met Pro Gly Pro
            900                     905                 910

<210> SEQ ID NO 22
<211> LENGTH: 987
<212> TYPE: PRT
<213> ORGANISM: Homo sapiens
<220> FEATURE:
<223> OTHER INFORMATION: EphB2R

<400> SEQUENCE: 22

Met Ala Leu Arg Arg Leu Gly Ala Ala Leu Leu Leu Leu Pro Leu Leu
1               5                   10                  15

Ala Ala Val Glu Glu Thr Leu Met Asp Ser Thr Thr Ala Thr Ala Glu
            20                  25                  30

Leu Gly Trp Met Val His Pro Pro Ser Gly Trp Glu Glu Val Ser Gly
        35                  40                  45

Tyr Asp Glu Asn Met Asn Thr Ile Arg Thr Tyr Gln Val Cys Asn Val
    50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
            100                 105                 110

Leu Tyr Tyr Tyr Glu Ala Asp Phe Asp Ser Ala Thr Lys Thr Phe Pro
        115                 120                 125

Asn Trp Met Glu Asn Pro Trp Val Lys Val Asp Thr Ile Ala Ala Asp
    130                 135                 140

Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
            180                 185                 190

Phe Tyr Arg Lys Cys Pro Arg Ile Ile Gln Asn Gly Ala Ile Phe Gln
        195                 200                 205

Glu Thr Leu Ser Gly Ala Glu Ser Thr Ser Leu Val Ala Ala Arg Gly
    210                 215                 220

Ser Cys Ile Ala Asn Ala Glu Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
            260                 265                 270

Pro Ser Gly Thr Phe Lys Ala Asn Gln Gly Asp Glu Ala Cys Thr His

-continued

```
                275                 280                 285
Cys Pro Ile Asn Ser Arg Thr Thr Ser Glu Gly Ala Thr Asn Cys Val
    290                 295                 300
Cys Arg Asn Gly Tyr Tyr Arg Ala Asp Leu Asp Pro Leu Asp Met Pro
305                 310                 315                 320
Cys Thr Thr Ile Pro Ser Ala Pro Gln Ala Val Ile Ser Ser Val Asn
                325                 330                 335
Glu Thr Ser Leu Met Leu Glu Trp Thr Pro Pro Arg Asp Ser Gly Gly
                340                 345                 350
Arg Glu Asp Leu Val Tyr Asn Ile Ile Cys Lys Ser Cys Gly Ser Gly
                355                 360                 365
Arg Gly Ala Cys Thr Arg Cys Gly Asp Asn Val Gln Tyr Ala Pro Arg
            370                 375                 380
Gln Leu Gly Leu Thr Glu Pro Arg Ile Tyr Ile Ser Asp Leu Leu Ala
385                 390                 395                 400
His Thr Gln Tyr Thr Phe Glu Ile Gln Ala Val Asn Gly Val Thr Asp
                405                 410                 415
Gln Ser Pro Phe Ser Pro Gln Phe Ala Ser Val Asn Ile Thr Thr Asn
                420                 425                 430
Gln Ala Ala Pro Ser Ala Val Ser Ile Met His Gln Val Ser Arg Thr
            435                 440                 445
Val Asp Ser Ile Thr Leu Ser Trp Ser Gln Pro Asp Gln Pro Asn Gly
    450                 455                 460
Val Ile Leu Asp Tyr Glu Leu Gln Tyr Tyr Glu Lys Glu Leu Ser Glu
465                 470                 475                 480
Tyr Asn Ala Thr Ala Ile Lys Ser Pro Thr Asn Thr Val Thr Val Gln
                485                 490                 495
Gly Leu Lys Ala Gly Ala Ile Tyr Val Phe Gln Val Arg Ala Arg Thr
            500                 505                 510
Val Ala Gly Tyr Gly Arg Tyr Ser Gly Lys Met Tyr Phe Gln Thr Met
            515                 520                 525
Thr Glu Ala Glu Tyr Gln Thr Ser Ile Gln Glu Lys Leu Pro Leu Ile
    530                 535                 540
Ile Gly Ser Ser Ala Ala Gly Leu Val Phe Leu Ile Ala Val Val Val
545                 550                 555                 560
Ile Ala Ile Val Cys Asn Arg Arg Gly Phe Glu Arg Ala Asp Ser
                565                 570                 575
Glu Tyr Thr Asp Lys Leu Gln His Tyr Thr Ser Gly His Met Thr Pro
                580                 585                 590
Gly Met Lys Ile Tyr Ile Asp Pro Phe Thr Tyr Glu Asp Pro Asn Glu
            595                 600                 605
Ala Val Arg Glu Phe Ala Lys Glu Ile Asp Ile Ser Cys Val Lys Ile
        610                 615                 620
Glu Gln Val Ile Gly Ala Gly Glu Phe Gly Glu Val Cys Ser Gly His
625                 630                 635                 640
Leu Lys Leu Pro Gly Lys Arg Glu Ile Phe Val Ala Ile Lys Thr Leu
                645                 650                 655
Lys Ser Gly Tyr Thr Glu Lys Gln Arg Arg Asp Phe Leu Ser Glu Ala
            660                 665                 670
Ser Ile Met Gly Gln Phe Asp His Pro Asn Val Ile His Leu Glu Gly
        675                 680                 685
Val Val Thr Lys Ser Thr Pro Val Met Ile Ile Thr Glu Phe Met Glu
    690                 695                 700
```

-continued

Asn Gly Ser Leu Asp Ser Phe Leu Arg Gln Asn Asp Gly Gln Phe Thr
705                 710                 715                 720

Val Ile Gln Leu Val Gly Met Leu Arg Gly Ile Ala Ala Gly Met Lys
            725                 730                 735

Tyr Leu Ala Asp Met Asn Tyr Val His Arg Asp Leu Ala Ala Arg Asn
                740                 745                 750

Ile Leu Val Asn Ser Asn Leu Val Cys Lys Val Ser Asp Phe Gly Leu
            755                 760                 765

Ser Arg Phe Leu Glu Asp Asp Thr Ser Asp Pro Thr Tyr Thr Ser Ala
770                 775                 780

Leu Gly Gly Lys Ile Pro Ile Arg Trp Thr Ala Pro Glu Ala Ile Gln
785                 790                 795                 800

Tyr Arg Lys Phe Thr Ser Ala Ser Asp Val Trp Ser Tyr Gly Ile Val
                805                 810                 815

Met Trp Glu Val Met Ser Tyr Gly Glu Arg Pro Tyr Trp Asp Met Thr
            820                 825                 830

Asn Gln Asp Val Ile Asn Ala Ile Glu Gln Asp Tyr Arg Leu Pro Pro
835                 840                 845

Pro Met Asp Cys Pro Ser Ala Leu His Gln Leu Met Leu Asp Cys Trp
850                 855                 860

Gln Lys Asp Arg Asn His Arg Pro Lys Phe Gly Gln Ile Val Asn Thr
865                 870                 875                 880

Leu Asp Lys Met Ile Arg Asn Pro Asn Ser Leu Lys Ala Met Ala Pro
                885                 890                 895

Leu Ser Ser Gly Ile Asn Leu Pro Leu Leu Asp Arg Thr Ile Pro Asp
            900                 905                 910

Tyr Thr Ser Phe Asn Thr Val Asp Glu Trp Leu Glu Ala Ile Lys Met
            915                 920                 925

Gly Gln Tyr Lys Glu Ser Phe Ala Asn Ala Gly Phe Thr Ser Phe Asp
930                 935                 940

Val Val Ser Gln Met Met Met Glu Asp Ile Leu Arg Val Gly Val Thr
945                 950                 955                 960

Leu Ala Gly His Gln Lys Lys Ile Leu Asn Ser Ile Gln Val Met Arg
                965                 970                 975

Ala Gln Met Asn Gln Ile Gln Ser Val Glu Val
            980                 985

<210> SEQ ID NO 23
<211> LENGTH: 282
<212> TYPE: PRT
<213> ORGANISM: Homo sapiens
<220> FEATURE:
<223> OTHER INFORMATION: ASLG659

<400> SEQUENCE: 23

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

```
His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
    195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
            245                 250                 255

Lys Ala Ser Leu Cys Val Ser Ser Phe Phe Ala Ile Ser Trp Ala Leu
        260                 265                 270

Leu Pro Leu Ser Pro Tyr Leu Met Leu Lys
        275                 280

<210> SEQ ID NO 24
<211> LENGTH: 123
<212> TYPE: PRT
<213> ORGANISM: Homo sapiens
<220> FEATURE:
<223> OTHER INFORMATION: PSCA

<400> SEQUENCE: 24

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
        115                 120

<210> SEQ ID NO 25
<211> LENGTH: 236
<212> TYPE: PRT
<213> ORGANISM: Homo sapiens
```

```
<220> FEATURE:
<223> OTHER INFORMATION: GEDA

<400> SEQUENCE: 25

Met Pro Gly Ala Ala Ala Ala Ala Ala Ala Ala Ala Met Leu
1               5                   10                  15

Pro Ala Gln Glu Ala Ala Lys Leu Tyr His Thr Asn Tyr Val Arg Asn
                20                  25                  30

Ser Arg Ala Ile Gly Val Leu Trp Ala Ile Phe Thr Ile Cys Phe Ala
            35                  40                  45

Ile Val Asn Val Val Cys Phe Ile Gln Pro Tyr Trp Ile Gly Asp Gly
50                  55                  60

Val Asp Thr Pro Gln Ala Gly Tyr Phe Gly Leu Phe His Tyr Cys Ile
65                  70                  75                  80

Gly Asn Gly Phe Ser Arg Glu Leu Thr Cys Arg Gly Ser Phe Thr Asp
                85                  90                  95

Phe Ser Thr Leu Pro Ser Gly Ala Phe Lys Ala Ala Ser Phe Phe Ile
                100                 105                 110

Gly Leu Ser Met Met Leu Ile Ile Ala Cys Ile Ile Cys Phe Thr Leu
            115                 120                 125

Phe Phe Phe Cys Asn Thr Ala Thr Val Tyr Lys Ile Cys Ala Trp Met
130                 135                 140

Gln Leu Thr Ser Ala Ala Cys Leu Val Leu Gly Cys Met Ile Phe Pro
145                 150                 155                 160

Asp Gly Trp Asp Ser Asp Glu Val Lys Arg Met Cys Gly Glu Lys Thr
                165                 170                 175

Asp Lys Tyr Thr Leu Gly Ala Cys Ser Val Arg Trp Ala Tyr Ile Leu
            180                 185                 190

Ala Ile Ile Gly Ile Leu Asp Ala Leu Ile Leu Ser Phe Leu Ala Phe
        195                 200                 205

Val Leu Gly Asn Arg Gln Asp Ser Leu Met Ala Glu Leu Lys Ala
        210                 215                 220

Glu Asn Lys Val Leu Leu Ser Gln Tyr Ser Leu Glu
225                 230                 235

<210> SEQ ID NO 26
<211> LENGTH: 184
<212> TYPE: PRT
<213> ORGANISM: Homo sapiens
<220> FEATURE:
<223> OTHER INFORMATION: BAFF-R

<400> SEQUENCE: 26

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
                20                  25                  30

Val Ala Cys Gly Leu Leu Arg Thr Pro Arg Pro Lys Pro Ala Gly Ala
            35                  40                  45

Ser Ser Pro Ala Pro Arg Thr Ala Leu Gln Pro Gln Glu Ser Val Gly
        50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
```

-continued

```
            100                 105                 110
Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
130                 135                 140

Trp Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 27
<211> LENGTH: 847
<212> TYPE: PRT
<213> ORGANISM: Homo sapiens
<220> FEATURE:
<223> OTHER INFORMATION: CD22

<400> SEQUENCE: 27

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
```

-continued

```
                275                 280                 285
Gln Asn Thr Phe Thr Leu Asn Leu Arg Glu Val Thr Lys Asp Gln Ser
            290                 295                 300
Gly Lys Tyr Cys Cys Gln Val Ser Asn Asp Val Gly Pro Gly Arg Ser
305                 310                 315                 320
Glu Glu Val Phe Leu Gln Val Gln Tyr Ala Pro Glu Pro Ser Thr Val
                325                 330                 335
Gln Ile Leu His Ser Pro Ala Val Glu Gly Ser Gln Val Glu Phe Leu
                340                 345                 350
Cys Met Ser Leu Ala Asn Pro Leu Pro Thr Asn Tyr Thr Trp Tyr His
                355                 360                 365
Asn Gly Lys Glu Met Gln Gly Arg Thr Glu Glu Lys Val His Ile Pro
            370                 375                 380
Lys Ile Leu Pro Trp His Ala Gly Thr Tyr Ser Cys Val Ala Glu Asn
385                 390                 395                 400
Ile Leu Gly Thr Gly Gln Arg Gly Pro Gly Ala Glu Leu Asp Val Gln
                405                 410                 415
Tyr Pro Pro Lys Lys Val Thr Thr Val Ile Gln Asn Pro Met Pro Ile
            420                 425                 430
Arg Glu Gly Asp Thr Val Thr Leu Ser Cys Asn Tyr Asn Ser Ser Asn
            435                 440                 445
Pro Ser Val Thr Arg Tyr Glu Trp Lys Pro His Gly Ala Trp Glu Glu
        450                 455                 460
Pro Ser Leu Gly Val Leu Lys Ile Gln Asn Val Gly Trp Asp Asn Thr
465                 470                 475                 480
Thr Ile Ala Cys Ala Arg Cys Asn Ser Trp Cys Ser Trp Ala Ser Pro
                485                 490                 495
Val Ala Leu Asn Val Gln Tyr Ala Pro Arg Asp Val Arg Val Arg Lys
            500                 505                 510
Ile Lys Pro Leu Ser Glu Ile His Ser Gly Asn Ser Val Ser Leu Gln
            515                 520                 525
Cys Asp Phe Ser Ser Ser His Pro Lys Glu Val Gln Phe Phe Trp Glu
530                 535                 540
Lys Asn Gly Arg Leu Leu Gly Lys Glu Ser Gln Leu Asn Phe Asp Ser
545                 550                 555                 560
Ile Ser Pro Glu Asp Ala Gly Ser Tyr Ser Cys Trp Val Asn Asn Ser
                565                 570                 575
Ile Gly Gln Thr Ala Ser Lys Ala Trp Thr Leu Glu Val Leu Tyr Ala
            580                 585                 590
Pro Arg Arg Leu Arg Val Ser Met Ser Pro Gly Asp Gln Val Met Glu
            595                 600                 605
Gly Lys Ser Ala Thr Leu Thr Cys Glu Ser Asp Ala Asn Pro Pro Val
610                 615                 620
Ser His Tyr Thr Trp Phe Asp Trp Asn Asn Gln Ser Leu Pro His His
625                 630                 635                 640
Ser Gln Lys Leu Arg Leu Glu Pro Val Lys Val Gln His Ser Gly Ala
                645                 650                 655
Tyr Trp Cys Gln Gly Thr Asn Ser Val Gly Lys Gly Arg Ser Pro Leu
                660                 665                 670
Ser Thr Leu Thr Val Tyr Tyr Ser Pro Glu Thr Ile Gly Arg Arg Val
            675                 680                 685
Ala Val Gly Leu Gly Ser Cys Leu Ala Ile Leu Ile Leu Ala Ile Cys
            690                 695                 700
```

```
Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
            725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
            755                 760                 765

Glu Met Asn Ile Pro Arg Thr Gly Asp Ala Glu Ser Ser Glu Met Gln
            770                 775                 780

Arg Pro Pro Arg Thr Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
            835                 840                 845
```

```
<210> SEQ ID NO 28
<211> LENGTH: 226
<212> TYPE: PRT
<213> ORGANISM: Homo sapiens
<220> FEATURE:
<223> OTHER INFORMATION: CD79A

<400> SEQUENCE: 28

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
                20                  25                  30

Leu Trp Met His Lys Val Pro Ala Ser Leu Met Val Ser Leu Gly Glu
            35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220
```

Lys Pro
225

<210> SEQ ID NO 29
<211> LENGTH: 372
<212> TYPE: PRT
<213> ORGANISM: Homo sapiens
<220> FEATURE:
<223> OTHER INFORMATION: CXCR5

<400> SEQUENCE: 29

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

```
                Pro Ser Trp Arg Arg Ser Ser Leu Ser Glu Ser Glu Asn Ala Thr Ser
                        355                 360                 365

Leu Thr Thr Phe
                        370

<210> SEQ ID NO 30
<211> LENGTH: 273
<212> TYPE: PRT
<213> ORGANISM: Homo sapiens
<220> FEATURE:
<223> OTHER INFORMATION: HLA-DOB

<400> SEQUENCE: 30

Met Gly Ser Gly Trp Val Pro Trp Val Ala Leu Leu Val Asn Leu
1               5                   10                  15

Thr Arg Leu Asp Ser Ser Met Thr Gln Gly Thr Asp Ser Pro Glu Asp
                20                  25                  30

Phe Val Ile Gln Ala Lys Ala Asp Cys Tyr Phe Thr Asn Gly Thr Glu
                35                  40                  45

Lys Val Gln Phe Val Val Arg Phe Ile Phe Asn Leu Glu Glu Tyr Val
50                  55                  60

Arg Phe Asp Ser Asp Val Gly Met Phe Val Ala Leu Thr Lys Leu Gly
65                  70                  75                  80

Gln Pro Asp Ala Glu Gln Trp Asn Ser Arg Leu Asp Leu Leu Glu Arg
                85                  90                  95

Ser Arg Gln Ala Val Asp Gly Val Cys Arg His Asn Tyr Arg Leu Gly
                100                 105                 110

Ala Pro Phe Thr Val Gly Arg Lys Val Gln Pro Glu Val Thr Val Tyr
                115                 120                 125

Pro Glu Arg Thr Pro Leu Leu His Gln His Asn Leu Leu His Cys Ser
            130                 135                 140

Val Thr Gly Phe Tyr Pro Gly Asp Ile Lys Ile Lys Trp Phe Leu Asn
145                 150                 155                 160

Gly Gln Glu Glu Arg Ala Gly Val Met Ser Thr Gly Pro Ile Arg Asn
                165                 170                 175

Gly Asp Trp Thr Phe Gln Thr Val Val Met Leu Glu Met Thr Pro Glu
                180                 185                 190

Leu Gly His Val Tyr Thr Cys Leu Val Asp His Ser Ser Leu Leu Ser
                195                 200                 205

Pro Val Ser Val Glu Trp Arg Ala Gln Ser Glu Tyr Ser Trp Arg Lys
            210                 215                 220

Met Leu Ser Gly Ile Ala Ala Phe Leu Leu Gly Leu Ile Phe Leu Leu
225                 230                 235                 240

Val Gly Ile Val Ile Gln Leu Arg Ala Gln Lys Gly Tyr Val Arg Thr
                245                 250                 255

Gln Met Ser Gly Asn Glu Val Ser Arg Ala Val Leu Leu Pro Gln Ser
                260                 265                 270

Cys

<210> SEQ ID NO 31
<211> LENGTH: 422
<212> TYPE: PRT
<213> ORGANISM: Homo sapiens
<220> FEATURE:
<223> OTHER INFORMATION: Purinergic receptor P2X ligand-gated ion
      channel 5
```

<400> SEQUENCE: 31

```
Met Gly Gln Ala Gly Cys Lys Gly Leu Cys Leu Ser Leu Phe Asp Tyr
1               5                   10                  15

Lys Thr Glu Lys Tyr Val Ile Ala Lys Asn Lys Lys Val Gly Leu Leu
            20                  25                  30

Tyr Arg Leu Leu Gln Ala Ser Ile Leu Ala Tyr Leu Val Val Trp Val
        35                  40                  45

Phe Leu Ile Lys Lys Gly Tyr Gln Asp Val Asp Thr Ser Leu Gln Ser
    50                  55                  60

Ala Val Ile Thr Lys Val Lys Gly Val Ala Phe Thr Asn Thr Ser Asp
65                  70                  75                  80

Leu Gly Gln Arg Ile Trp Asp Val Ala Asp Tyr Val Ile Pro Ala Gln
                85                  90                  95

Gly Glu Asn Val Phe Phe Val Val Thr Asn Leu Ile Val Thr Pro Asn
            100                 105                 110

Gln Arg Gln Asn Val Cys Ala Glu Asn Glu Gly Ile Pro Asp Gly Ala
        115                 120                 125

Cys Ser Lys Asp Ser Asp Cys His Ala Gly Glu Ala Val Thr Ala Gly
    130                 135                 140

Asn Gly Val Lys Thr Gly Arg Cys Leu Arg Arg Glu Asn Leu Ala Arg
145                 150                 155                 160

Gly Thr Cys Glu Ile Phe Ala Trp Cys Pro Leu Glu Thr Ser Ser Arg
                165                 170                 175

Pro Glu Glu Pro Phe Leu Lys Glu Ala Glu Asp Phe Thr Ile Phe Ile
            180                 185                 190

Lys Asn His Ile Arg Phe Pro Lys Phe Asn Phe Ser Lys Ser Asn Val
        195                 200                 205

Met Asp Val Lys Asp Arg Ser Phe Leu Lys Ser Cys His Phe Gly Pro
    210                 215                 220

Lys Asn His Tyr Cys Pro Ile Phe Arg Leu Gly Ser Val Ile Arg Trp
225                 230                 235                 240

Ala Gly Ser Asp Phe Gln Asp Ile Ala Leu Glu Gly Gly Val Ile Gly
                245                 250                 255

Ile Asn Ile Glu Trp Asn Cys Asp Leu Asp Lys Ala Ala Ser Glu Cys
            260                 265                 270

His Pro His Tyr Ser Phe Ser Arg Leu Asp Asn Lys Leu Ser Lys Ser
        275                 280                 285

Val Ser Ser Gly Tyr Asn Phe Arg Phe Ala Arg Tyr Tyr Arg Asp Ala
    290                 295                 300

Ala Gly Val Glu Phe Arg Thr Leu Met Lys Ala Tyr Gly Ile Arg Phe
305                 310                 315                 320

Asp Val Met Val Asn Gly Lys Gly Ala Phe Phe Cys Asp Leu Val Leu
                325                 330                 335

Ile Tyr Leu Ile Lys Lys Arg Glu Phe Tyr Arg Asp Lys Lys Tyr Glu
            340                 345                 350

Glu Val Arg Gly Leu Glu Asp Ser Ser Gln Glu Ala Glu Asp Glu Ala
        355                 360                 365

Ser Gly Leu Gly Leu Ser Glu Gln Leu Thr Ser Gly Pro Gly Leu Leu
    370                 375                 380

Gly Met Pro Glu Gln Gln Glu Leu Gln Glu Pro Pro Glu Ala Lys Arg
385                 390                 395                 400

Gly Ser Ser Ser Gln Lys Gly Asn Gly Ser Val Cys Pro Gln Leu Leu
                405                 410                 415
```

```
Glu Pro His Arg Ser Thr
            420

<210> SEQ ID NO 32
<211> LENGTH: 359
<212> TYPE: PRT
<213> ORGANISM: Homo sapiens
<220> FEATURE:
<223> OTHER INFORMATION: CD72

<400> SEQUENCE: 32

Met Ala Glu Ala Ile Thr Tyr Ala Asp Leu Arg Phe Val Lys Ala Pro
1               5                   10                  15

Leu Lys Lys Ser Ile Ser Ser Arg Leu Gly Gln Asp Pro Gly Ala Asp
                20                  25                  30

Asp Asp Gly Glu Ile Thr Tyr Glu Asn Val Gln Val Pro Ala Val Leu
            35                  40                  45

Gly Val Pro Ser Ser Leu Ala Ser Ser Val Leu Gly Asp Lys Ala Ala
        50                  55                  60

Val Lys Ser Glu Gln Pro Thr Ala Ser Trp Arg Ala Val Thr Ser Pro
65                  70                  75                  80

Ala Val Gly Arg Ile Leu Pro Cys Arg Thr Thr Cys Leu Arg Tyr Leu
                85                  90                  95

Leu Leu Gly Leu Leu Leu Thr Cys Leu Leu Gly Val Thr Ala Ile
                100                 105                 110

Cys Leu Gly Val Arg Tyr Leu Gln Val Ser Gln Gln Leu Gln Gln Thr
                115                 120                 125

Asn Arg Val Leu Glu Val Thr Asn Ser Ser Leu Arg Gln Gln Leu Arg
            130                 135                 140

Leu Lys Ile Thr Gln Leu Gly Gln Ser Ala Glu Asp Leu Gln Gly Ser
145                 150                 155                 160

Arg Arg Glu Leu Ala Gln Ser Gln Glu Ala Leu Gln Val Glu Gln Arg
                165                 170                 175

Ala His Gln Ala Ala Glu Gly Gln Leu Gln Ala Cys Gln Ala Asp Arg
            180                 185                 190

Gln Lys Thr Lys Glu Thr Leu Gln Ser Glu Gln Gln Arg Arg Ala
        195                 200                 205

Leu Glu Gln Lys Leu Ser Asn Met Glu Asn Arg Leu Lys Pro Phe Phe
    210                 215                 220

Thr Cys Gly Ser Ala Asp Thr Cys Cys Pro Ser Gly Trp Ile Met His
225                 230                 235                 240

Gln Lys Ser Cys Phe Tyr Ile Ser Leu Thr Ser Lys Asn Trp Gln Glu
                245                 250                 255

Ser Gln Lys Gln Cys Glu Thr Leu Ser Ser Lys Leu Ala Thr Phe Ser
            260                 265                 270

Glu Ile Tyr Pro Gln Ser His Ser Tyr Tyr Phe Leu Asn Ser Leu Leu
        275                 280                 285

Pro Asn Gly Gly Ser Gly Asn Ser Tyr Trp Thr Gly Leu Ser Ser Asn
    290                 295                 300

Lys Asp Trp Lys Leu Thr Asp Asp Thr Gln Arg Thr Arg Thr Tyr Ala
305                 310                 315                 320

Gln Ser Ser Lys Cys Asn Lys Val His Lys Thr Trp Ser Trp Trp Thr
                325                 330                 335

Leu Glu Ser Glu Ser Cys Arg Ser Ser Leu Pro Tyr Ile Cys Glu Met
            340                 345                 350
```

-continued

```
Thr Ala Phe Arg Phe Pro Asp
        355

<210> SEQ ID NO 33
<211> LENGTH: 661
<212> TYPE: PRT
<213> ORGANISM: Homo sapiens
<220> FEATURE:
<223> OTHER INFORMATION: LY64

<400> SEQUENCE: 33

Met Ala Phe Asp Val Ser Cys Phe Phe Trp Val Val Leu Phe Ser Ala
1               5                   10                  15

Gly Cys Lys Val Ile Thr Ser Trp Asp Gln Met Cys Ile Glu Lys Glu
                20                  25                  30

Ala Asn Lys Thr Tyr Asn Cys Glu Asn Leu Gly Leu Ser Glu Ile Pro
            35                  40                  45

Asp Thr Leu Pro Asn Thr Thr Glu Phe Leu Glu Phe Ser Phe Asn Phe
    50                  55                  60

Leu Pro Thr Ile His Asn Arg Thr Phe Ser Arg Leu Met Asn Leu Thr
65                  70                  75                  80

Phe Leu Asp Leu Thr Arg Cys Gln Ile Asn Trp Ile His Glu Asp Thr
                85                  90                  95

Phe Gln Ser His His Gln Leu Ser Thr Leu Val Leu Thr Gly Asn Pro
            100                 105                 110

Leu Ile Phe Met Ala Glu Thr Ser Leu Asn Gly Pro Lys Ser Leu Lys
        115                 120                 125

His Leu Phe Leu Ile Gln Thr Gly Ile Ser Asn Leu Glu Phe Ile Pro
    130                 135                 140

Val His Asn Leu Glu Asn Leu Glu Ser Leu Tyr Leu Gly Ser Asn His
145                 150                 155                 160

Ile Ser Ser Ile Lys Phe Pro Lys Asp Phe Pro Ala Arg Asn Leu Lys
                165                 170                 175

Val Leu Asp Phe Gln Asn Asn Ala Ile His Tyr Ile Ser Arg Glu Asp
            180                 185                 190

Met Arg Ser Leu Glu Gln Ala Ile Asn Leu Ser Leu Asn Phe Asn Gly
        195                 200                 205

Asn Asn Val Lys Gly Ile Glu Leu Gly Ala Phe Asp Ser Thr Val Phe
    210                 215                 220

Gln Ser Leu Asn Phe Gly Gly Thr Pro Asn Leu Ser Val Ile Phe Asn
225                 230                 235                 240

Gly Leu Gln Asn Ser Thr Thr Gln Ser Leu Trp Leu Gly Thr Phe Glu
                245                 250                 255

Asp Ile Asp Asp Glu Asp Ile Ser Ser Ala Met Leu Lys Gly Leu Cys
            260                 265                 270

Glu Met Ser Val Glu Ser Leu Asn Leu Gln Glu His Arg Phe Ser Asp
        275                 280                 285

Ile Ser Ser Thr Thr Phe Gln Cys Phe Thr Gln Leu Gln Glu Leu Asp
    290                 295                 300

Leu Thr Ala Thr His Leu Lys Gly Leu Pro Ser Gly Met Lys Gly Leu
305                 310                 315                 320

Asn Leu Leu Lys Lys Leu Val Leu Ser Val Asn His Phe Asp Gln Leu
                325                 330                 335

Cys Gln Ile Ser Ala Ala Asn Phe Pro Ser Leu Thr His Leu Tyr Ile
            340                 345                 350
```

-continued

Arg Gly Asn Val Lys Lys Leu His Leu Gly Val Gly Cys Leu Glu Lys
            355                 360                 365

Leu Gly Asn Leu Gln Thr Leu Asp Leu Ser His Asn Asp Ile Glu Ala
    370                 375                 380

Ser Asp Cys Cys Ser Leu Gln Leu Lys Asn Leu Ser His Leu Gln Thr
385                 390                 395                 400

Leu Asn Leu Ser His Asn Glu Pro Leu Gly Leu Gln Ser Gln Ala Phe
                405                 410                 415

Lys Glu Cys Pro Gln Leu Glu Leu Leu Asp Leu Ala Phe Thr Arg Leu
            420                 425                 430

His Ile Asn Ala Pro Gln Ser Pro Phe Gln Asn Leu His Phe Leu Gln
        435                 440                 445

Val Leu Asn Leu Thr Tyr Cys Phe Leu Asp Thr Ser Asn Gln His Leu
    450                 455                 460

Leu Ala Gly Leu Pro Val Leu Arg His Leu Asn Leu Lys Gly Asn His
465                 470                 475                 480

Phe Gln Asp Gly Thr Ile Thr Lys Thr Asn Leu Leu Gln Thr Val Gly
                485                 490                 495

Ser Leu Glu Val Leu Ile Leu Ser Ser Cys Gly Leu Leu Ser Ile Asp
            500                 505                 510

Gln Gln Ala Phe His Ser Leu Gly Lys Met Ser His Val Asp Leu Ser
        515                 520                 525

His Asn Ser Leu Thr Cys Asp Ser Ile Asp Ser Leu Ser His Leu Lys
    530                 535                 540

Gly Ile Tyr Leu Asn Leu Ala Ala Asn Ser Ile Asn Ile Ile Ser Pro
545                 550                 555                 560

Arg Leu Leu Pro Ile Leu Ser Gln Gln Ser Thr Ile Asn Leu Ser His
                565                 570                 575

Asn Pro Leu Asp Cys Thr Cys Ser Asn Ile His Phe Leu Thr Trp Tyr
            580                 585                 590

Lys Glu Asn Leu His Lys Leu Glu Gly Ser Glu Glu Thr Thr Cys Ala
        595                 600                 605

Asn Pro Pro Ser Leu Arg Gly Val Lys Leu Ser Asp Val Lys Leu Ser
    610                 615                 620

Cys Gly Ile Thr Ala Ile Gly Ile Phe Phe Leu Ile Val Phe Leu Leu
625                 630                 635                 640

Leu Leu Ala Ile Leu Leu Phe Phe Ala Val Lys Tyr Leu Leu Arg Trp
                645                 650                 655

Lys Tyr Gln His Ile
            660

<210> SEQ ID NO 34
<211> LENGTH: 429
<212> TYPE: PRT
<213> ORGANISM: Homo sapiens
<220> FEATURE:
<223> OTHER INFORMATION: FCRH1

<400> SEQUENCE: 34

Met Leu Pro Arg Leu Leu Leu Ile Cys Ala Pro Leu Cys Glu Pro
1               5                   10                  15

Ala Glu Leu Phe Leu Ile Ala Ser Pro Ser His Pro Thr Glu Gly Ser
            20                  25                  30

Pro Val Thr Leu Thr Cys Lys Met Pro Phe Leu Gln Ser Ser Asp Ala
        35                  40                  45

```
Gln Phe Gln Phe Cys Phe Phe Arg Asp Thr Arg Ala Leu Gly Pro Gly
     50                  55                  60

Trp Ser Ser Ser Pro Lys Leu Gln Ile Ala Ala Met Trp Lys Glu Asp
 65                  70                  75                  80

Thr Gly Ser Tyr Trp Cys Glu Ala Gln Thr Met Ala Ser Lys Val Leu
                 85                  90                  95

Arg Ser Arg Arg Ser Gln Ile Asn Val His Arg Val Pro Val Ala Asp
            100                 105                 110

Val Ser Leu Glu Thr Gln Pro Pro Gly Gly Gln Val Met Glu Gly Asp
            115                 120                 125

Arg Leu Val Leu Ile Cys Ser Val Ala Met Gly Thr Gly Asp Ile Thr
            130                 135                 140

Phe Leu Trp Tyr Lys Gly Ala Val Gly Leu Asn Leu Gln Ser Lys Thr
145                 150                 155                 160

Gln Arg Ser Leu Thr Ala Glu Tyr Glu Ile Pro Ser Val Arg Glu Ser
                165                 170                 175

Asp Ala Glu Gln Tyr Tyr Cys Val Ala Glu Asn Gly Tyr Gly Pro Ser
            180                 185                 190

Pro Ser Gly Leu Val Ser Ile Thr Val Arg Ile Pro Val Ser Arg Pro
            195                 200                 205

Ile Leu Met Leu Arg Ala Pro Arg Ala Gln Ala Ala Val Glu Asp Val
210                 215                 220

Leu Glu Leu His Cys Glu Ala Leu Arg Gly Ser Pro Pro Ile Leu Tyr
225                 230                 235                 240

Trp Phe Tyr His Glu Asp Ile Thr Leu Gly Ser Arg Ser Ala Pro Ser
                245                 250                 255

Gly Gly Gly Ala Ser Phe Asn Leu Ser Leu Thr Glu Glu His Ser Gly
            260                 265                 270

Asn Tyr Ser Cys Glu Ala Asn Asn Gly Leu Gly Ala Gln Arg Ser Glu
            275                 280                 285

Ala Val Thr Leu Asn Phe Thr Val Pro Thr Gly Ala Arg Ser Asn His
            290                 295                 300

Leu Thr Ser Gly Val Ile Glu Gly Leu Leu Ser Thr Leu Gly Pro Ala
305                 310                 315                 320

Thr Val Ala Leu Leu Phe Cys Tyr Gly Leu Lys Arg Lys Ile Gly Arg
                325                 330                 335

Arg Ser Ala Arg Asp Pro Leu Arg Ser Leu Pro Ser Pro Leu Pro Gln
            340                 345                 350

Glu Phe Thr Tyr Leu Asn Ser Pro Thr Pro Gly Gln Leu Gln Pro Ile
            355                 360                 365

Tyr Glu Asn Val Asn Val Val Ser Gly Asp Glu Val Tyr Ser Leu Ala
            370                 375                 380

Tyr Tyr Asn Gln Pro Glu Gln Glu Ser Val Ala Ala Glu Thr Leu Gly
385                 390                 395                 400

Thr His Met Glu Asp Lys Val Ser Leu Asp Ile Tyr Ser Arg Leu Arg
                405                 410                 415

Lys Ala Asn Ile Thr Asp Val Asp Tyr Glu Asp Ala Met
            420                 425

<210> SEQ ID NO 35
<211> LENGTH: 977
<212> TYPE: PRT
<213> ORGANISM: Homo sapiens
<220> FEATURE:
```

<223> OTHER INFORMATION: IRTA2

<400> SEQUENCE: 35

```
Met Leu Leu Trp Val Ile Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
                35                  40                  45

Phe Tyr Ser Pro Gln Lys Thr Lys Trp Tyr His Arg Tyr Leu Gly Lys
        50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
                100                 105                 110

Val Phe Glu Gly Asp Ser Val Val Leu Arg Cys Arg Ala Lys Ala Glu
            115                 120                 125

Val Thr Leu Asn Asn Thr Ile Tyr Lys Asn Asp Asn Val Leu Ala Phe
130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
            195                 200                 205

Leu Thr Cys Glu Thr Gln Leu Ser Leu Glu Arg Ser Asp Val Pro Leu
210                 215                 220

Arg Phe Arg Phe Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro His Ser Val Ile Ser Asp
            260                 265                 270

Ser Pro Arg Ser Trp Ile Gln Val Gln Ile Pro Ala Ser His Pro Val
            275                 280                 285

Leu Thr Leu Ser Pro Glu Lys Ala Leu Asn Phe Glu Gly Thr Lys Val
290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
            325                 330                 335

Arg Gly Ala Ser Ile Ser Phe Ser Leu Thr Thr Glu Asn Ser Gly Asn
            340                 345                 350

Tyr Tyr Cys Thr Ala Asp Asn Gly Leu Gly Ala Lys Pro Ser Lys Ala
        355                 360                 365

Val Ser Leu Ser Val Thr Val Pro Val Ser His Pro Val Leu Asn Leu
370                 375                 380

Ser Ser Pro Glu Asp Leu Ile Phe Glu Gly Ala Lys Val Thr Leu His
385                 390                 395                 400
```

-continued

```
Cys Glu Ala Gln Arg Gly Ser Leu Pro Ile Leu Tyr Gln Phe His His
            405                 410                 415
Glu Asp Ala Ala Leu Glu Arg Arg Ser Ala Asn Ser Ala Gly Gly Val
        420                 425                 430
Ala Ile Ser Phe Ser Leu Thr Ala Glu His Ser Gly Asn Tyr Tyr Cys
            435                 440                 445
Thr Ala Asp Asn Gly Phe Gly Pro Gln Arg Ser Lys Ala Val Ser Leu
450                 455                 460
Ser Ile Thr Val Pro Val Ser His Pro Val Leu Thr Leu Ser Ser Ala
465                 470                 475                 480
Glu Ala Leu Thr Phe Glu Gly Ala Thr Val Thr Leu His Cys Glu Val
                485                 490                 495
Gln Arg Gly Ser Pro Gln Ile Leu Tyr Gln Phe Tyr His Glu Asp Met
            500                 505                 510
Pro Leu Trp Ser Ser Ser Thr Pro Ser Val Gly Arg Val Ser Phe Ser
        515                 520                 525
Phe Ser Leu Thr Glu Gly His Ser Gly Asn Tyr Tyr Cys Thr Ala Asp
        530                 535                 540
Asn Gly Phe Gly Pro Gln Arg Ser Glu Val Val Ser Leu Phe Val Thr
545                 550                 555                 560
Val Pro Val Ser Arg Pro Ile Leu Thr Leu Arg Val Pro Arg Ala Gln
                565                 570                 575
Ala Val Val Gly Asp Leu Leu Glu Leu His Cys Glu Ala Pro Arg Gly
            580                 585                 590
Ser Pro Pro Ile Leu Tyr Trp Phe Tyr His Glu Asp Val Thr Leu Gly
        595                 600                 605
Ser Ser Ser Ala Pro Ser Gly Gly Glu Ala Ser Phe Asn Leu Ser Leu
        610                 615                 620
Thr Ala Glu His Ser Gly Asn Tyr Ser Cys Glu Ala Asn Asn Gly Leu
625                 630                 635                 640
Val Ala Gln His Ser Asp Thr Ile Ser Leu Ser Val Ile Val Pro Val
                645                 650                 655
Ser Arg Pro Ile Leu Thr Phe Arg Ala Pro Arg Ala Gln Ala Val Val
            660                 665                 670
Gly Asp Leu Leu Glu Leu His Cys Glu Ala Leu Arg Gly Ser Ser Pro
        675                 680                 685
Ile Leu Tyr Trp Phe Tyr His Glu Asp Val Thr Leu Gly Lys Ile Ser
        690                 695                 700
Ala Pro Ser Gly Gly Gly Ala Ser Phe Asn Leu Ser Leu Thr Thr Glu
705                 710                 715                 720
His Ser Gly Ile Tyr Ser Cys Glu Ala Asp Asn Gly Pro Glu Ala Gln
                725                 730                 735
Arg Ser Glu Met Val Thr Leu Lys Val Ala Val Pro Val Ser Arg Pro
            740                 745                 750
Val Leu Thr Leu Arg Ala Pro Gly Thr His Ala Ala Val Gly Asp Leu
        755                 760                 765
Leu Glu Leu His Cys Glu Ala Leu Arg Gly Ser Pro Leu Ile Leu Tyr
        770                 775                 780
Arg Phe Phe His Glu Asp Val Thr Leu Gly Asn Arg Ser Ser Pro Ser
785                 790                 795                 800
Gly Gly Ala Ser Leu Asn Leu Ser Leu Thr Ala Glu His Ser Gly Asn
                805                 810                 815
Tyr Ser Cys Glu Ala Asp Asn Gly Leu Gly Ala Gln Arg Ser Glu Thr
```

```
                        820                 825                 830
Val Thr Leu Tyr Ile Thr Gly Leu Thr Ala Asn Arg Ser Gly Pro Phe
            835                 840                 845

Ala Thr Gly Val Ala Gly Gly Leu Leu Ser Ile Ala Gly Leu Ala Ala
    850                 855                 860

Gly Ala Leu Leu Leu Tyr Cys Trp Leu Ser Arg Lys Ala Gly Arg Lys
865                 870                 875                 880

Pro Ala Ser Asp Pro Ala Arg Ser Pro Pro Asp Ser Asp Ser Gln Glu
                885                 890                 895

Pro Thr Tyr His Asn Val Pro Ala Trp Glu Glu Leu Gln Pro Val Tyr
                900                 905                 910

Thr Asn Ala Asn Pro Arg Gly Glu Asn Val Val Tyr Ser Glu Val Arg
            915                 920                 925

Ile Ile Gln Glu Lys Lys Lys His Ala Val Ala Ser Asp Pro Arg His
            930                 935                 940

Leu Arg Asn Lys Gly Ser Pro Ile Ile Tyr Ser Glu Val Lys Val Ala
945                 950                 955                 960

Ser Thr Pro Val Ser Gly Ser Leu Phe Leu Ala Ser Ser Ala Pro His
                965                 970                 975

Arg
```

US 7,745,394 B2

MONOMETHYLVALINE COMPOUNDS CAPABLE OF CONJUGATION TO LIGANDS

CONTINUITY

This application is a division of U.S. application Ser. No. 10/983,340 filed Nov. 5, 2004, now U.S. Pat. No. 7,498,298 which claims the benefit of U.S. Provisional Patent Application Ser. No. 60/622,455, filed Oct. 27, 2004; U.S. Provisional Patent Application Ser. No. 60/598,899, filed Aug. 4, 2004; U.S. Provisional Patent Application Ser. No. 60/557,116, filed Mar. 26, 2004; and U.S. Provisional Patent Application Ser. No. 60/518,534, filed Nov. 6, 2003; the disclosures of which are incorporated by reference herein.

JOINT RESEARCH AGREEMENT

Some of the subject matter in this application was made by or on behalf of Seattle Genetics, Inc. and Genentech, Inc. as a result of activities undertaken within the scope of a joint research agreement effective on or before the date the claimed invention was made.

1. FIELD OF THE INVENTION

The present invention is directed to a Drug Compound and more particularly to Drug-Linker-Ligand Conjugates, Drug-Linker Compounds, and Drug-Ligand Conjugates, to compositions including the same, and to methods for using the same to treat cancer, an autoimmune disease or an infectious disease. The present invention is also directed to antibody-drug conjugates, to compositions including the same, and to methods for using the same to treat cancer, an autoimmune disease or an infectious disease. The invention also relates to methods of using antibody-drug conjugate compounds for in vitro, in situ, and in vivo diagnosis or treatment of mammalian cells, or associated pathological conditions.

2. BACKGROUND OF THE INVENTION

Improving the delivery of drugs and other agents to target cells, tissues and tumors to achieve maximal efficacy and minimal toxicity has been the focus of considerable research for many years. Though many attempts have been made to develop effective methods for importing biologically active molecules into cells, both in vivo and in vitro, none has proved to be entirely satisfactory. Optimizing the association of the drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., chemotherapeutic (anti-cancer), cytotoxic, enzyme inhibitor agents and antiviral or antimicrobial drugs) that can be administered. By comparison, although oral administration of drugs is considered to be a convenient and economical mode of administration, it shares the same concerns of non-specific toxicity to unaffected cells once the drug has been absorbed into the systemic circulation. Further complications involve problems with oral bioavailability and residence of drug in the gut leading to additional exposure of gut to the drug and hence risk of gut toxicities. Accordingly, a major goal has been to develop methods for specifically targeting agents to cells and tissues. The benefits of such treatment include avoiding the general physiological effects of inappropriate delivery of such agents to other cells and tissues, such as uninfected cells. Intracellular targeting may be achieved by methods, compounds and formulations which allow accumulation or retention of biologically active agents, i.e. active metabolites, inside cells.

Monoclonal antibody therapy has been established for the targeted treatment of patients with cancer, immunological and angiogenic disorders.

The use of antibody-drug conjugates for the local delivery of cytotoxic or cytostatic agents, e.g., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) theoretically allows targeted delivery of the drug moiety to tumors, and intracellular accumulation therein, while systemic administration of these unconjugated drug agents may result in unacceptable levels of toxicity to normal cells as well as the tumor cells sought to be eliminated (Baldwin et al., 1986, Lancet pp. (Mar. 15, 1986):603-05; Thorpe, 1985, "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., 1986, Cancer Immunol. Immunother. 21:183-87). Drugs used in these methods include daunomycin, doxorubicin, methotrexate, and vindesine (Rowland et al., 1986, supra). Toxins used in antibody-toxin conjugates include bacterial toxins such as diphtheria toxin, plant toxins such as ricin, small molecule toxins such as geldanamycin (Kerr et al., 1997, Bioconjugate Chem. 8(6):781-784; Mandler et al. (2000) Jour. of the Nat. Cancer Inst. 92(19): 1573-1581; Mandler et al. (2000) Bioorganic & Med. Chem. Letters 10:1025-1028; Mandler et al. (2002) Bioconjugate Chem. 13:786-791), maytansinoids (EP 1391213; Liu et al., (1996) Proc. Natl. Acad. Sci. USA 93:8618-8623), and calicheamicin (Lode et al. (1998) Cancer Res. 58:2928; Hinman et al. (1993) Cancer Res. 53:3336-3342). The toxins may affect their cytotoxic and cytostatic effects by mechanisms including tubulin binding, DNA binding, or topoisomerase inhibition (Meyer, D. L. and Senter, P. D. "Recent Advances in Antibody Drug Conjugates for Cancer Therapy" in Annual Reports in Medicinal Chemistry, Vol 38 (2003) Chapter 23, 229-237). Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al. (2000) Eur. Jour. Nucl. Med. 27(7):766-77; Wiseman et al. (2002) Blood 99(12):4336-42; Witzig et al. (2002) J. Clin. Oncol. 20(10):2453-63; Witzig et al. (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The same maytansinoid drug moiety, DM1, was linked through a non-disulfide linker, SMCC, to a mouse murine monoclonal antibody, TA.1 (Chari et al. (1992) Cancer Research 52:127-131). This conjugate was reported to be 200-fold less potent than the corresponding disulfide linker conjugate. The SMCC linker was considered therein to be "noncleavable."

Several short peptidic compounds have been isolated from the marine mollusc *Dolabella auricularia* and found to have biological activity (Pettit et al. (1993) Tetrahedron 49:9151; Nakamura et al. (1995) Tetrahedron Letters 36:5059-5062; Sone et al. (1995) Jour. Org. Chem. 60:4474). Analogs of these compounds have also been prepared, and some were found to have biological activity (for a review, see Pettit et al. (1998) Anti-Cancer Drug Design 13:243-277). For example, auristatin E (U.S. Pat. No. 5,635,483) is a synthetic analogue of the marine natural product Dolastatin 10, an agent that inhibits tubulin polymerization by binding to the same domain on tubulin as the anticancer drug vincristine (G. R. Pettit, (1997) Prog. Chem. Org. Nat. Prod. 70:1-79). Dolastatin 10, auristatin PE, and auristatin E are linear peptides having four amino acids, three of which are unique to the dolastatin class of compounds, and a C-terminal amide.

The auristatin peptides, auristain E (AE) and monomethyl-lauristatin (MMAE), synthetic analogs of dolastatin, were conjugated to: (i) chimeric monoclonal antibodies cBR96 (specific to Lewis Y on carcinomas); (ii) cAC10 which is specific to CD30 on hematological malignancies (Klussman, et al. (2004), Bioconjugate Chemistry 15(4):765-773; Doronina et al. (2003) Nature Biotechnology 21(7):778-784; "Monomethylvaline Compounds Capable of Conjugation to Ligands"; Francisco et al. (2003) Blood 102(4):1458-1465; U.S. Publication 2004/0018194; (iii) anti-CD20 antibodies such as RITUXAN®[[®]] (WO 04/032828) for the treatment of CD20-expressing cancers and immune disorders; (iv) anti-EphB2 antibodies 2H9 and anti-IL-8 for treatment of colorectal cancer (Mao, et al. (2004) Cancer Research 64(3):781-788); (v) E-selectin antibody (Bhaskar et al. (2003) Cancer Res. 63:6387-6394); and (vi) other anti-CD30 antibodies (WO 03/043583).

Auristatin E conjugated to monoclonal antibodies are disclosed in Senter et al, Proceedings of the American Association for Cancer Research, Volume 45, Abstract Number 623, presented Mar. 28, 2004.

Despite in vitro data for compounds of the dolastatin class and its analogs, significant general toxicities at doses required for achieving a therapeutic effect compromise their efficacy in clinical studies. Accordingly, there is a clear need in the art for dolastatin/auristatin derivatives having significantly lower toxicity, yet useful therapeutic efficiency. These and other limitations and problems of the past are addressed by the present invention.

The ErbB family of receptor tyrosine kinases are important mediators of cell growth, differentiation and survival. The receptor family includes four distinct members including epidermal growth factor receptor (EGFR, ErbB1, HER1), HER2 (ErbB2 or p185$^{neu}$), HER3 (ErbB3) and HER4 (ErbB4 or tyro2). A panel of anti-ErbB2 antibodies has been characterized using the human breast tumor cell line SKBR3 (Hudziak et al., (1989) *Mol. Cell. Biol.* 9(3):1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α (U.S. Pat. No. 5,677,171). The anti-ErbB2 antibodies discussed in Hudziak et al. are further characterized in Fendly et al. (1990) Cancer Research 50:1550-1558; Kotts et al. (1990) *In vitro* 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2):979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20): 14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

Other anti-ErbB2 antibodies with various properties have been described in Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovski et al. *Proc. Natl. Acad. Sci. USA* 88:8691-8695 (1991); Bacus et al. Cancer Research 52:2580-2589 (1992); Xu et al. Int. J. Cancer 53:401-408 (1993); WO94/00136; Kasprzyk et al. Cancer Research 52:2771-2776 (1992); Hancock et al. (1991) Cancer Res. 51:4575-4580; Shawver et al. (1994) Cancer Res. 54:1367-1373; Arteaga et al. (1994) Cancer Res. 54:3758-3765; Harwerth et al. (1992) J. Biol. Chem. 267:15160-15167; U.S. Pat. No. 5,783,186; and Klapper et al. (1997) Oncogene 14:2099-2109.

Homology screening has resulted in the identification of two other ErbB receptor family members; ErbB3 (U.S. Pat. No. 5,183,884; U.S. Pat. No. 5,480,968; KraU.S. et al. (1989) *Proc. Natl. Acad. Sci. USA* 86:9193-9197) and ErbB4 (EP 599274; Plowman et al. (1993) *Proc. Natl. Acad. Sci. USA* 90:1746-1750; and Plowman et al. (1993) Nature 366:473-475). Both of these receptors display increased expression on at least some breast cancer cell lines.

HERCEPTIN® (Trastuzumab) is a recombinant DNA-derived humanized monoclonal antibody that selectively binds with high affinity in a cell-based assay (Kd=5 nM) to the extracellular domain of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens L, et al. (1985) Science 230:1132-9; Slamon D J, et al (1989) Science 244:707-12). Trastuzumab is an IgG1 kappa antibody that contains human framework regions with the complementarity-determining regions of a murine antibody (4D5) that binds to HER2. Trastuzumab binds to the HER2 antigen and thus. inhibits the growth of cancerous cells. Because Trastuzumab is a humanized antibody, it minimizes any HAMA response in patients. The humanized antibody against HER2 is produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. HER2 protein overexpression is observed in 25%-30% of primary breast cancers and can be determined using an immunohistochemistry based assessment of fixed tumor blocks (Press M F, et al. (1993) Cancer Res 53:4960-70. Trastuzumab has been shown, in both in vitro assays and in animals, to inhibit the proliferation of human tumor cells that overexpress HER2 (Hudziak R M, et al. (1989) Mol Cell Biol 9:1165-72; Lewis G D, et al. (1993) Cancer Immunol Immunother; 37:255-63; Baselga J, et al. (1998) Cancer Res. 58:2825-2831). Trastuzumab is a mediator of antibody-dependent cellular cytotoxicity, ADCC (Hotaling T E, et al. (1996) [abstract]. Proc. Annual Meeting Am Assoc Cancer Res; 37:471; Pegram M D, et al. (1997) [abstract]. Proc Am Assoc Cancer Res; 38:602). In vitro, Trastuzumab mediated ADCC has been shown to be preferentially exerted on HER2 overexpressing cancer cells compared with cancer cells that do not overexpress HER2. HERCEPTIN® as a single agent is indicated for the treatment of patients with metastatic breast cancer whose tumors overexpress the HER2 protein and who have received one or more chemotherapy regimens for their metastatic disease. HERCEPTIN® in combination with paclitaxel is indicated for treatment of patients with metastatic breast cancer whose tumors overexpress the HER2 protein and who have not received chemotherapy for their metastatic disease. HERCEPTIN® is clinically active in patients with ErbB2-overexpressing metastatic breast cancers that have received extensive prior anti-cancer therapy (Baselga et al, (1996) J. Clin. Oncol. 14:737-744).

The murine monoclonal anti-HER2 antibody inhibits the growth of breast cancer cell lines that overexpress HER2 at the 2+ and 3+ (1–2×10⁶ HER2 receptors per cell) level, but has no activity on cells that express lower levels of HER2 (Lewis et al., (1993) Cancer Immunol. Immunother. 37:255-263). Based on this observation, antibody 4D5 was humanized (huMAb4D5-8, rhuMAb HER2, U.S. Pat. No. 5,821,337; Carter et al., (1992) Proc. Natl. Acad. Sci. USA 89: 4285-4289) and tested in breast cancer patients whose tumors overexpress HER2 but who had progressed after conventional chemotherapy (Cobleigh et al., (1999) J. Clin. Oncol. 17: 2639-2648).

Although HERCEPTIN is a breakthrough in treating patients with ErbB2-overexpressing breast cancers that have received extensive prior anti-cancer therapy, some patients in this population fail to respond or respond only poorly to HERCEPTIN treatment.

Therefore, there is a significant clinical need for developing further HER2-directed cancer therapies for those patients with HER2-overexpressing tumors or other diseases associated with HER2 expression that do not respond, or respond poorly, to HERCEPTIN treatment.

The recitation of any reference in this application is not an admission that the reference is prior art to this application.

3. SUMMARY OF THE INVENTION

In one aspect, the present invention provides Drug-Linker-Ligand compounds having the Formula Ia:

or a pharmaceutically acceptable salt or solvate thereof wherein,

L- is a Ligand unit;

-$A_a$-$W_w$—$Y_y$— is a Linker unit (LU), wherein the Linker unit includes:

-A- is a Stretcher unit, a is 0 or 1, each —W— is independently an Amino Acid unit, w is an integer ranging from 0 to 12, —Y— is a Spacer unit, and y is 0, 1 or 2;

p ranges from 1 to about 20; and

-D is a Drug unit having the Formulas $D_E$ and $D_F$:

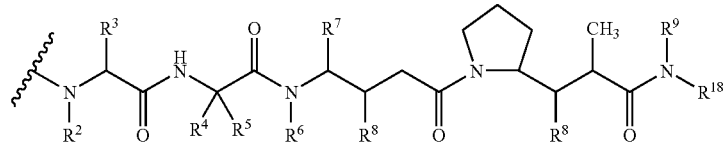

$D_E$

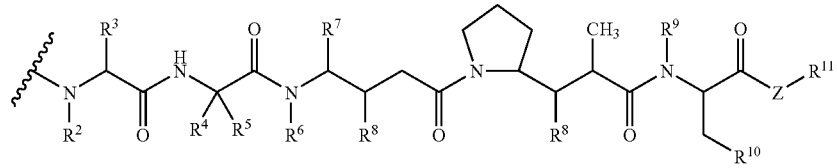

$D_F$ wherein, independently at each location:

R² is selected from H and C₁-C₈ alkyl;

R³ is selected from H, C₁-C₈ alkyl, C₃-C₈ carbocycle, aryl, C₁-C₈ alkyl-aryl, C₁-C₈ alkyl-(C₃-C₈ carbocycle), C₃-C₈ heterocycle and C₁-C₈ alkyl-(C₃-C₈ heterocycle);

R⁴ is selected from H, C₁-C₈ alkyl, C₃-C₈ carbocycle, aryl, C₁-C₈ alkyl-aryl, C₁-C₈ alkyl-(C₃-C₈ carbocycle), C₃-C₈ heterocycle and C₁-C₈ alkyl-(C₃-C₈ heterocycle);

R⁵ is selected from H and methyl;

or R⁴ and R⁵ jointly form a carbocyclic ring and have the formula —(CRᵃRᵇ)ₙ— wherein Rᵃ and Rᵇ are independently selected from H, C₁-C₈ alkyl and C₃-C₈ carbocycle and n is selected from 2, 3, 4, 5 and 6;

R⁶ is selected from H and C₁-C₈ alkyl;

R⁷ is selected from H, C₁-C₈ alkyl, C₃-C₈ carbocycle, aryl, C₁-C₈ alkyl-aryl, C₁-C₈ alkyl-(C₃-C₈ carbocycle), C₃-C₈ heterocycle and C₁-C₈ alkyl-(C₃-C₈ heterocycle);

each R⁸ is independently selected from H, OH, C₁-C₈ alkyl, C₃-C₈ carbocycle and O—(C₁-C₈ alkyl);

R⁹ is selected from H and C₁-C₈ alkyl;

R¹⁰ is selected from aryl or C₃-C₈ heterocycle;

Z is O, S, NH, or NR¹², wherein R¹² is C₁-C₈ alkyl;

R¹¹ is selected from H, C₁-C₂₀ alkyl, aryl, C₃-C₈ heterocycle, —(R¹³O)ₘ—R¹⁴, or —(R¹³O)ₘ—CH(R¹⁵)₂;

m is an integer ranging from 1-1000;

R¹³ is C₂-C₈ alkyl;

R¹⁴ is H or C₁-C₈ alkyl;

each occurrence of R¹⁵ is independently H, COOH, —(CH₂)ₙ—N(R¹⁶)₂, —(CH₂)ₙ—SO₃H, or —(CH₂)ₙ—SO₃—C₁-C₈ alkyl;

each occurrence of R¹⁶ is independently H, C₁-C₈ alkyl, or —(CH₂)ₙ—COOH; where; n is an integer ranging from 0 to 6; and R¹⁸ is selected from —C(R⁸)₂—C(R⁸)₂-aryl, —C(R⁸)₂—C(R⁸)₂—(C₃-C₈ heterocycle), and —C(R⁸)₂—C(R⁸)₂—(C₃-C₈ carbocycle).

In another aspect, Drug Compounds having the Formula Ib are provided:

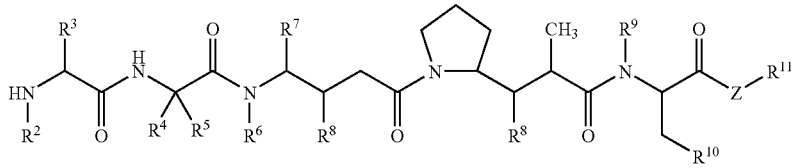

Ib or pharmaceutically acceptable salts or solvates thereof, wherein:

R² is selected from hydrogen and —C₁-C₈ alkyl;

R³ is selected from hydrogen, —C₁-C₈ alkyl, —C₃-C₈ carbocycle, aryl, —C₁-C₈ alkyl-aryl, —C₁-C₈ alkyl-(C₃-C₈ carbocycle), —C₃-C₈ heterocycle and —C₁-C₈ alkyl-(C₃-C₈ heterocycle);

R⁴ is selected from hydrogen, —C₁-C₈ alkyl, —C₃-C₈ carbocycle, -aryl, —C₁-C₈ alkyl-aryl, —C₁-C₈ alkyl-(C₃-C₈ carbocycle), —C₃-C₈ heterocycle and —C₁-C₈ alkyl-(C₃-C₈ heterocycle) wherein R⁵ is selected from —H and -methyl; or R⁴ and R⁵ jointly, have the formula —(CRᵃRᵇ)ₙ— wherein Rᵃ and Rᵇ are independently selected from —H, —C₁-C₈ alkyl and —C₃-C₈ carbocycle and n is selected from 2, 3, 4, 5 and 6, and form a ring with the carbon atom to which they are attached;

R⁶ is selected from H and —C₁-C₈ alkyl;

R⁷ is selected from H, —C₁-C₈ alkyl, —C₃-C₈ carbocycle, aryl, —C₁-C₈ alkyl-aryl, —C₁-C₈ alkyl-(C₃-C₈ carbocycle), —C₃-C₈ heterocycle and —C₁-C₈ alkyl-(C₃-C₈ heterocycle);

each R⁸ is independently selected from H, —OH, —C₁-C₈ alkyl, —C₃-C₈ carbocycle and —O—(C₁-C₈ alkyl);

R⁹ is selected from H and —C₁-C₈ alkyl;

R¹⁰ is selected from aryl group or —C₃-C₈ heterocycle;

Z is —O—, —S—, —NH—, or —NR¹²—, wherein R¹² is C₁-C₈ alkyl;

R¹¹ is selected from H, C₁-C₂₀ alkyl, aryl, —C₃-C₈ heterocycle, —(R¹³O)ₘ—R¹⁴, or —(R¹³O)ₘ—CH(R¹⁵)₂;

m is an integer ranging from 1-1000;

R¹³ is —C₂-C₈ alkyl;

R¹⁴ is H or —C₁-C₈ alkyl;

each occurrence of R¹⁵ is independently H, —COOH, —(CH₂)ₙ—N(R¹⁶)₂, —(CH₂)ₙ—SO₃H, or —(CH₂)ₙ—SO₃—C₁-C₈ alkyl;

each occurrence of R¹⁶ is independently H, —C₁-C₈ alkyl, or —(CH₂)ₙ—COOH; and n is an integer ranging from 0 to 6.

The compounds of Formula (Ib) are useful for treating cancer, an autoimmune disease or an infectious disease in a patient or useful as an intermediate for the synthesis of a Drug-Linker, Drug-Linker-Ligand Conjugate, and Drug-Ligand Conjugate having a cleavable Drug unit.

In another aspect, compositions are provided including an effective amount of a Drug-Linker-Ligand Conjugate and a pharmaceutically acceptable carrier or vehicle.

In still another aspect, the invention provides pharmaceutical compositions comprising an effective amount of a Drug-Linker Compound and a pharmaceutically acceptable carrier or vehicle.

In still another aspect, the invention provides compositions comprising an effective amount of a Drug-Ligand Conjugate having a cleavable Drug unit from the Drug-Ligand Conjugate and a pharmaceutically acceptable carrier or vehicle.

In yet another aspect, the invention provides methods for killing or inhibiting the multiplication of a tumor cell or cancer cell including administering to a patient in need thereof an effective amount of a Drug-Linker Compound.

In another aspect, the invention provides methods for killing or inhibiting the multiplication of a tumor cell or cancer cell including administering to a patient in need thereof an effective amount of a Drug-Linker-Ligand Conjugate.

In another aspect, the invention provides methods for killing or inhibiting the multiplication of a tumor cell or cancer cell including administering to a patient in need thereof an effective amount of a Drug-Ligand Conjugate having a cleavable Drug unit from the Drug-Ligand Conjugate.

In still another aspect, the invention provides methods for treating cancer including administering to a patient in need thereof an effective amount of a Drug-Linker Compound.

In yet another aspect, the invention provides methods for treating cancer including administering to a patient in need thereof an effective amount of a Drug-Linker-Ligand Conjugate.

In yet another aspect, the invention provides methods for treating cancer including administering to a patient in need thereof an effective amount of a Drug-Ligand Conjugate having a cleavable Drug unit from the Drug-Ligand Conjugate.

In still another aspect, the invention provides methods for killing or inhibiting the replication of a cell that expresses an autoimmune antibody including administering to a patient in need thereof an effective amount of a Drug-Linker Compound.

In another aspect, the invention provides methods for killing or inhibiting the replication of a cell that expresses an autoimmune antibody including administering to a patient in need thereof an effective amount of a Drug-Linker-Ligand Conjugate.

In another aspect, the invention provides methods for killing or inhibiting the replication of a cell that expresses an autoimmune antibody including administering to a patient in need thereof an effective amount of a Drug-Ligand Conjugate having a cleavable Drug unit from the Drug-Ligand Conjugate.

In yet another aspect, the invention provides methods for treating an autoimmune disease including administering to a patient in need thereof an effective amount of a Drug-Linker Compound.

In yet another aspect, the invention provides methods for treating an autoimmune disease including administering to a patient in need thereof an effective amount of a Drug-Linker-Ligand Conjugate.

In yet another aspect, the invention provides methods for treating an autoimmune disease including administering to a patient in need thereof an effective amount of a Drug-Ligand Conjugate having a cleavable Drug unit from the Drug-Ligand Conjugate.

In still another aspect, the invention provides methods for treating an infectious disease including administering to a patient in need thereof an effective amount of a Drug-Linker Compound.

In still another aspect, the invention provides methods for treating an infectious disease including administering to a patient in need thereof an effective amount of a Drug-Linker-Ligand Conjugate.

In still another aspect, the invention provides methods for treating an infectious disease including administering to a patient in need thereof an effective amount of a Drug-Ligand Conjugate having a cleavable Drug unit from the Drug-Ligand Conjugate.

In yet another aspect, the invention provides methods for preventing the multiplication of a tumor cell or cancer cell including administering to a patient in need thereof an effective amount of a Drug-Linker Compound.

In another aspect, the invention provides methods for preventing the multiplication of a tumor cell or cancer cell including administering to a patient in need thereof an effective amount of a Drug-Linker-Ligand Conjugate.

In another aspect, the invention provides methods for preventing the multiplication of a tumor cell or cancer cell including administering to a patient in need thereof an effective amount of a Drug-Ligand Conjugate having a cleavable Drug unit from the Drug-Ligand Conjugate.

In still another aspect, the invention provides methods for preventing cancer including administering to a patient in need thereof an effective amount of a Drug-Linker Compound.

In yet another aspect, the invention provides methods for preventing cancer including administering to a patient in need thereof an effective amount of a Drug-Linker-Ligand Conjugate.

In yet another aspect, the invention provides methods for preventing cancer including administering to a patient in need thereof an effective amount of a Drug-Ligand Conjugate having a cleavable Drug unit from the Drug-Ligand Conjugate.

In still another aspect, the invention provides methods for preventing the multiplication of a cell that expresses an autoimmune antibody including administering to a patient in need thereof an effective amount of a Drug-Linker Compound.

In another aspect, the invention provides methods for preventing the multiplication of a cell that expresses an autoimmune antibody including administering to a patient in need thereof an effective amount of a Drug-Linker-Ligand Conjugate.

In another aspect, the invention provides methods for preventing the multiplication of a cell that expresses an autoimmune antibody including administering to a patient in need thereof an effective amount of a Drug-Ligand Conjugate having a cleavable Drug unit from the Drug-Ligand Conjugate.

In yet another aspect, the invention provides methods for preventing an autoimmune disease including administering to a patient in need thereof an effective amount of a Drug-Linker Compound.

In yet another aspect, the invention provides methods for preventing an autoimmune disease including administering to a patient in need thereof an effective amount of a Drug-Linker-Ligand Conjugate.

In yet another aspect, the invention provides methods for preventing an autoimmune disease including administering to a patient in need thereof an effective amount of a Drug-Ligand Conjugate having a cleavable Drug unit from the Drug-Ligand Conjugate.

In still another aspect, the invention provides methods for preventing an infectious disease including administering to a patient in need thereof an effective amount of a Drug-Linker Compound.

In still another aspect, the invention provides methods for preventing an infectious disease including administering to a patient in need thereof an effective amount of a Drug-Linker-Ligand Conjugate.

In still another aspect, the invention provides methods for preventing an infectious disease including administering to a patient in need thereof an effective amount of a Drug-Ligand Conjugate having a cleavable Drug unit from the Drug-Ligand Conjugate.

In another aspect, a Drug Compound is provided which can be used as an intermediate for the synthesis of a Drug-Linker Compound having a cleavable Drug unit from the Drug-Ligand Conjugate.

In another aspect, a Drug-Linker Compound is provided which can be used as an intermediate for the synthesis of a Drug-Linker-Ligand Conjugate.

In another aspect, compounds having Formula Ia' are provided:

$$\text{Ab-}(A_a\text{-}W_w\text{—}Y_y\text{-}D)_p \qquad \text{Ia'}$$

or a pharmaceutically acceptable salt or solvate thereof, wherein:
Ab includes an antibody including one which binds to CD30, CD40, CD70, and Lewis Y antigen, A is a Stretcher unit,
a is 0 or 1,
each W is independently an Amino Acid unit,
w is an integer ranging from 0 to 12,
Y is a Spacer unit, and
y is 0, 1 or 2,
p ranges from 1 to about 20, and
D is a Drug unit selected from Formulas $D_E$ and $D_F$:

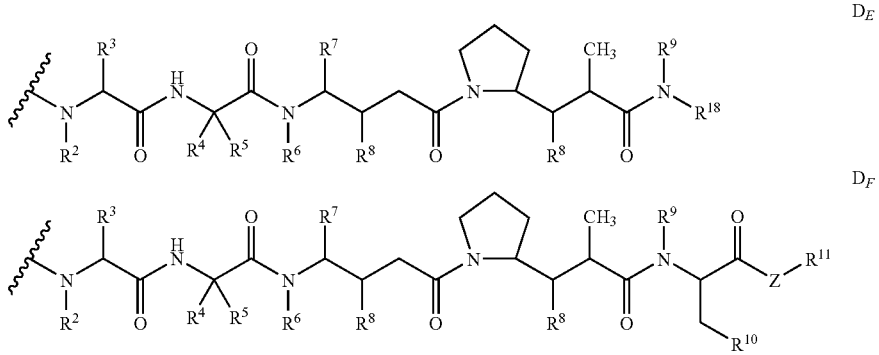

wherein, independently at each location:
$R^2$ is selected from H and $C_1$-$C_8$ alkyl;
$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
$R^5$ is selected from H and methyl;
or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;
$R^6$ is selected from H and $C_1$-$C_8$ alkyl;
$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
each $R^8$ is independently selected from H, OH, $C_1$-$C_8$ alkyl, $C_3$-$C_8$ carbocycle and O—($C_1$-$C_8$ alkyl);
$R^9$ is selected from H and $C_1$-$C_8$ alkyl;
$R^{10}$ is selected from aryl or $C_3$-$C_8$ heterocycle;
Z is O, S, NH, or $NR^{12}$, wherein $R^{12}$ is $C_1$-$C_8$ alkyl;
$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;
m is an integer ranging from 1-1000;
$R^{13}$ is $C_2$-$C_8$ alkyl;
$R^{14}$ is H or $C_1$-$C_8$ alkyl;
each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;
each occurrence of $R^{16}$ is independently H, $C_1$-$C_8$ alkyl, or —$(CH_2)_n$—COOH;
$R^{18}$ is selected from —$C(R^8)_2$—$C(R^8)$-2-aryl, —$C(R^8)_2$—$C(R^8)_2$—($C_3$-$C_8$ heterocycle), and —$C(R^8)_2$—$C(R^8)_2$—($C_3$-$C_8$ carbocycle); and
n is an integer ranging from 0 to 6.

In one embodiment, Ab is not an antibody which binds to an ErbB receptor or which binds to one or more of receptors (1)-(35):

(1) BMPR1B (bone morphogenetic protein receptor-type IB, Genbank accession no. NM_001203);
(2) E16 (LAT1, SLC7A5, Genbank accession no. NM_003486);
(3) STEAP1 (six transmembrane epithelial antigen of prostate, Genbank accession no. NM_012449);
(4) 0772P (CA125, MUC16, Genbank accession no. AF361486);
(5) MPF (MPF, MSLN, SMR, megakaryocyte potentiating factor, mesothelin, Genbank accession no. NM_005823);
(6) Napi3b (NAPI-3B, NPTIIb, SLC34A2, solute carrier family 34 (sodium phosphate), member 2, type II sodium-dependent phosphate transporter 3b, Genbank accession no. NM_006424);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);
(8) PSCA hlg (2700050C12Rik, C530008O16Rik, RIKEN cDNA 2700050C12, RIKEN cDNA 2700050C12 gene, Genbank accession no. AY358628);
(9) ETBR (Endothelin type B receptor, Genbank accession no. AY275463);
(10) MSG783 (RNF124, hypothetical protein FLJ20315, Genbank accession no. NM_017763);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);
(12) TrpM4 (BR22450, FLJ20041, TRPM4, TRPM4B, transient receptor potential cation channel, subfamily M, member 4, Genbank accession no. NM_017636);
(13) CRIPTO (CR, CR1, CRGF, CRIPTO, TDGF1, teratocarcinoma-derived growth factor, Genbank accession no. NP_003203 or NM_003212);
(14) CD21 ($CR^2$ (Complement receptor 2) or C3DR (C3d/Epstein Barr virus receptor) or Hs.73792, Genbank accession no. M26004);
(15) CD79b (IGb (immunoglobulin-associated beta), B29, Genbank accession no. NM_000626);
(16) FcRH2 (IFGP4, IRTA4, SPAP1A (SH2 domain containing phosphatase anchor protein 1a), SPAP1B, SPAP1C, Genbank accession no. NM_030764);
(17) HER2 (Genbank accession no. M11730);
(18) NCA (Genbank accession no. M18728);
(19) MDP (Genbank accession no. BC017023);

(20) IL20Rα (Genbank accession no. AF184971);
(21) Brevican (Genbank accession no. AF229053);
(22) Ephb2R (Genbank accession no. NM_004442);
(23) ASLG659 (Genbank accession no. AX092328);
(24) PSCA (Genbank accession no. AJ297436);
(25) GEDA (Genbank accession no. AY260763);
(26) BAFF-R (Genbank accession no. NP_443177.1);
(27) CD22 (Genbank accession no. NP_001762.1);
(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank accession No. NP_001774.1);
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);
(30) HLA-DOB (Beta subunit of MHC class II molecule (Ia antigen) that binds peptides and presents them to CD4+ T lymphocytes, Genbank accession No. NP_002111.1);
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);
(32) CD72 (B-cell differentiation antigen CD72, Lyb-2, Genbank accession No. NP_001773.1);
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);
(34) FCRH1 (Fc receptor-like protein 1, a putative receptor for the immunoglobulin Fc domain that contains C2 type Ig-like and ITAM domains, may have a role in B-lymphocyte differentiation, Genbank accession No. NP_443170.1); or
(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP_112571.1).

In still another aspect, the invention provides pharmaceutical compositions comprising an effective amount of a Drug-Linker-Antibody Conjugate and a pharmaceutically acceptable carrier or vehicle.

In still another aspect, the invention provides compositions comprising an effective amount of a Drug-Antibody Conjugate having a cleavable Drug unit (moiety) from the Drug-Antibody Conjugate and a pharmaceutically acceptable carrier or vehicle.

In another aspect, the invention provides methods for killing or inhibiting the multiplication of a tumor cell or cancer cell including administering to a patient in need thereof an effective amount of a Drug-Linker-Antibody Conjugate.

In another aspect, the invention provides methods for killing or inhibiting the multiplication of a tumor cell or cancer cell including administering to a patient in need thereof an effective amount of a Drug-Antibody Conjugate having a cleavable Drug unit from the Drug-Antibody Conjugate.

In yet another aspect, the invention provides methods for treating cancer including administering to a patient in need thereof an effective amount of a Drug-Linker-Antibody Conjugate.

In yet another aspect, the invention provides methods for treating cancer including administering to a patient in need thereof an effective amount of a Drug-Antibody Conjugate having a cleavable Drug unit from the Drug-Antibody Conjugate.

In another aspect, the invention provides methods for killing or inhibiting the replication of a cell that expresses an autoimmune antibody including administering to a patient in need thereof an effective amount of a Drug-Linker-Antibody Conjugate.

In another aspect, the invention provides methods for killing or inhibiting the replication of a cell that expresses an autoimmune antibody including administering to a patient in need thereof an effective amount of a Drug-Antibody Conjugate having a cleavable Drug unit from the Drug-Antibody Conjugate.

In yet another aspect, the invention provides methods for treating an autoimmune disease including administering to a patient in need thereof an effective amount of a Drug-Linker-Antibody Conjugate.

In yet another aspect, the invention provides methods for treating an autoimmune disease including administering to a patient in need thereof an effective amount of a Drug-Antibody Conjugate having a cleavable Drug unit from the Drug-Antibody Conjugate.

In still another aspect, the invention provides methods for treating an infectious disease including administering to a patient in need thereof an effective amount of a Drug-Linker-Antibody Conjugate.

In still another aspect, the invention provides methods for treating an infectious disease including administering to a patient in need thereof an effective amount of a Drug-Antibody Conjugate having a cleavable Drug unit from the Drug-Antibody Conjugate.

In another aspect, the invention provides methods for preventing the multiplication of a tumor cell or cancer cell including administering to a patient in need thereof an effective amount of a Drug-Linker-Antibody Conjugate.

In another aspect, the invention provides methods for preventing the multiplication of a tumor cell or cancer cell including administering to a patient in need thereof an effective amount of a Drug-Antibody Conjugate having a cleavable Drug unit from the Drug-Antibody Conjugate.

In yet another aspect, the invention provides methods for preventing cancer including administering to a patient in need thereof an effective amount of a Drug-Linker-Antibody Conjugate.

In yet another aspect, the invention provides methods for preventing cancer including administering to a patient in need thereof an effective amount of a Drug-Antibody Conjugate having a cleavable Drug unit from the Drug-Antibody Conjugate.

In another aspect, the invention provides methods for preventing the multiplication of a cell that expresses an autoimmune antibody including administering to a patient in need thereof an effective amount of a Drug-Linker-Antibody Conjugate.

In another aspect, the invention provides methods for preventing the multiplication of a cell that expresses an autoimmune antibody including administering to a patient in need thereof an effective amount of a Drug-Antibody Conjugate having a cleavable Drug unit from the Drug-Antibody Conjugate.

In yet another aspect, the invention provides methods for preventing an autoimmune disease including administering to a patient in need thereof an effective amount of a Drug-Linker-Antibody Conjugate.

In yet another aspect, the invention provides methods for preventing an autoimmune disease including administering to a patient in need thereof an effective amount of a Drug-Antibody Conjugate having a cleavable Drug unit from the Drug-Antibody Conjugate.

In still another aspect, the invention provides methods for preventing an infectious disease including administering to a patient in need thereof an effective amount of a Drug-Linker-Antibody Conjugate.

In still another aspect, the invention provides methods for preventing an infectious disease including administering to a patient in need thereof an effective amount of a Drug-Antibody Conjugate having a cleavable Drug unit from the Drug-Antibody Conjugate.

In another aspect, a Drug Compound is provided which can be used as an intermediate for the synthesis of a Drug-Linker Compound having a cleavable Drug unit from the Drug-Antibody Conjugate.

In another aspect, a Drug-Linker Compound is provided which can be used as an intermediate for the synthesis of a Drug-Linker-Antibody Conjugate.

In one aspect, the present invention provides Drug-Linker-Antibody Conjugates (also referred to as antibody-drug conjugates) having Formula Ic:

Ab—(A$_a$-W$_w$—Y$_y$-D)$_p$     Ic or a pharmaceutically acceptable salt or solvate thereof, wherein:

Ab is an antibody which binds to one or more of the antigens (1)-(35):

(1) BMPR1B (bone morphogenetic protein receptor-type IB, Genbank accession no. NM_001203);

(2) E16 (LAT1, SLC7A5, Genbank accession no. NM_003486);

(3) STEAP1 (six transmembrane epithelial antigen of prostate, Genbank accession no. NM_012449);

(4) 0772P (CA125, MUC16, Genbank accession no. AF361486);

(5) MPF (MPF, MSLN, SMR, megakaryocyte potentiating factor, mesothelin, Genbank accession no. NM_005823);

(6) Napi3b (NAPI-3B, NPTIIb, SLC34A2, solute carrier family 34 (sodium phosphate), member 2, type II sodium-dependent phosphate transporter 3b, Genbank accession no. NM_006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

(8) PSCA hlg (2700050C12Rik, C530008O16Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM_017636);

(13) CRIPTO (CR, CR1, CRGF, CRIPTO, TDGF1, teratocarcinoma-derived growth factor, Genbank accession no. NP_003203 or NM_003212);

(14) CD21 (CR2 (Complement receptor 2) or C3DR (C3d/Epstein Barr virus receptor) or Hs.73792, Genbank accession no. M26004);

(15) CD79b (IGb (immunoglobulin-associated beta), B29, Genbank accession no. NM_000626);

(16) FcRH2 (IFGP4, IRTA4, SPAP1A (SH2 domain containing phosphatase anchor protein 1a), SPAP1B, SPAP1C, Genbank accession no. NM_030764);

(17) HER2 (Genbank accession no. M11730);

(18) NCA (Genbank accession no. M18728);

(19) MDP (Genbank accession no. BC017023);

(20) IL20Rα (Genbank accession no. AF184971);

(21) Brevican (Genbank accession no. AF229053);

(22) Ephb2R (Genbank accession no. NM_004442);

(23) ASLG659 (Genbank accession no. AX092328);

(24) PSCA (Genbank accession no. AJ297436);

(25) GEDA (Genbank accession no. AY260763);

(26) BAFF-R (Genbank accession no. NP_443177.1);

(27) CD22 (Genbank accession no. NP_001762.1);

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank accession No. NP_001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+ T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);

(34) FCRH1 (Fc receptor-like protein 1, a putative receptor for the immunoglobulin Fc domain that contains C2 type Ig-like and ITAM domains, may have a role in B-lymphocyte differentiation, Genbank accession No. NP 443170.1); or

(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP_112571.1);

A is a Stretcher unit, a is 0 or 1, each W is independently an Amino Acid unit, w is an integer ranging from 0 to 12, Y is a Spacer unit, and y is 0, 1 or 2, p ranges from 1 to about 20, and D is a Drug moiety selected from Formulas D$_E$ and D$_F$:

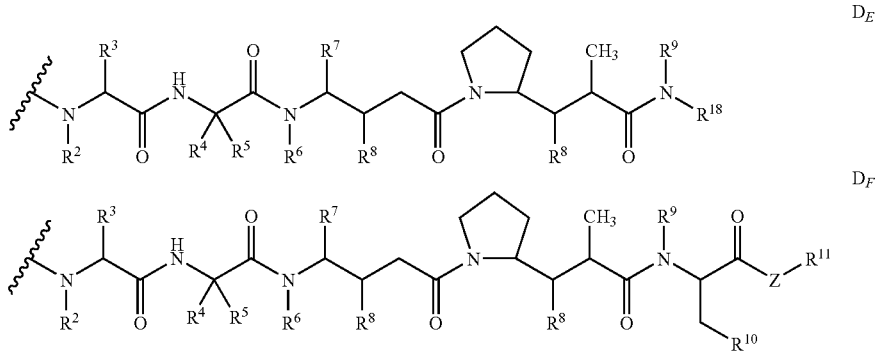

wherein the wavy line of $D_E$ and $D_F$ indicates the covalent attachment site to A, W, or Y, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)m$-$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C^1$-$C^8$ alkyl;

each occurrence of $R^{15}$ is independently H, COOH, —$(CH_2)n$-$N(R^{16})_2$, —$(CH_2)_n$—$SO_3H$, or —$(CH_2)n$-$SO_3$-$C_1$-$C_8$ alkyl;

each occurrence of $R^{16}$ is independently H, $C_1$-$C_8$ alkyl, or —$(CH_2)_n$—COOH;

$R^{18}$ is selected from —$C(R)_2$—$C(R^8)_2$-aryl, —$C(R^8)_2$—$C(R)_2$—($C_1$-$C_8$ heterocycle), and —$C(R^8)_2$—$C(R^8)_2$—($C_3$-$C_8$ carbocycle); and n is an integer ranging from 0 to 6.

In another aspect, the antibody of the antibody-drug conjugate (ADC) of the invention specifically binds to a receptor encoded by an ErbB2 gene.

In another aspect, the antibody of the antibody-drug conjugate is a humanized antibody selected from huMAb4D5-1, huMAb4D5-2, huMAb4D5-3, huMAb4D5-4, huMAb4D5-5, huMAb4D5-6, huMAb4D5-7 and huMAb4D5-8 (Trastuzumab).

In another aspect, the invention includes an article of manufacture comprising an antibody-drug conjugate compound of the invention; a container; and a package insert or label indicating that the compound can be used to treat cancer characterized by the overexpression of an ErbB2 receptor.

In another aspect, the invention includes a method for the treatment of cancer in a mammal, wherein the cancer is characterized by the overexpression of an ErbB2 receptor and does not respond, or responds poorly, to treatment with an anti-ErbB2 antibody, comprising administering to the mammal a therapeutically effective amount of an antibody-drug conjugate compound of the invention.

In another aspect, a substantial amount of the drug moiety is not cleaved from the antibody until the antibody-drug conjugate compound enters a cell with a cell-surface receptor specific for the antibody of the antibody-drug conjugate, and the drug moiety is cleaved from the antibody when the antibody-drug conjugate does enter the cell.

In another aspect, the bioavailability of the antibody-drug conjugate compound or an intracellular metabolite of the compound in a mammal is improved when compared to a drug compound comprising the drug moiety of the antibody-drug conjugate compound, or when compared to an analog of the compound not having the drug moiety.

In another aspect, the drug moiety is intracellularly cleaved in a mammal from the antibody of the compound, or an intracellular metabolite of the compound.

In another aspect, the invention includes a pharmaceutical composition comprising an effective amount of the antibody-drug conjugate compound of the invention, or a pharmaceutically acceptable salt thereof, and a pharmaceutically acceptable diluent, carrier or excipient. The composition may further comprise a therapeutically effective amount of chemotherapeutic agent such as a tubulin-forming inhibitor, a topoisomerase inhibitor, and a DNA binder.

In another aspect, the invention includes a method for killing or inhibiting the proliferation of tumor cells or cancer cells comprising treating tumor cells or cancer cells with an amount of the antibody-drug conjugate compound of the invention, or a pharmaceutically acceptable salt or solvate thereof, being effective to kill or inhibit the proliferation of the tumor cells or cancer cells.

In another aspect, the invention includes a method of inhibiting cellular proliferation comprising exposing mammalian cells in a cell culture medium to an antibody drug conjugate compound of the invention, wherein the antibody drug conjugate compound enters the cells and the drug is cleaved from the remainder of the antibody drug conjugate compound; whereby proliferation of the cells is inhibited.

In another aspect, the invention includes a method of treating cancer comprising administering to a patient a formulation of an antibody-drug conjugate compound of the invention and a pharmaceutically acceptable diluent, carrier or excipient.

In another aspect, the invention includes an assay for detecting cancer cells comprising:
(a) exposing cells to an antibody-drug conjugate compound of the invention; and
(b) determining the extent of binding of the antibody-drug conjugate compound to the cells.

The invention will best be understood by reference to the following detailed description of the exemplary embodiments, taken in conjunction with the accompanying drawings, figures, and schemes. The discussion below is descriptive, illustrative and exemplary and is not to be taken as limiting the scope defined by any appended claims.

BRIEF DESCRIPTION OF THE DRAWINGS

FIGS. 3a and 3b show in vivo efficacy of cBR96-mcMMAF in subcutaneous L2987. The filed triangles in FIG. 3a and arrows in FIG. 3b indicate the days of therapy.

4. DETAILED DESCRIPTION OF THE EXEMPLARY EMBODIMENTS

4.1 Definitions and Abbreviations

Figure 1:
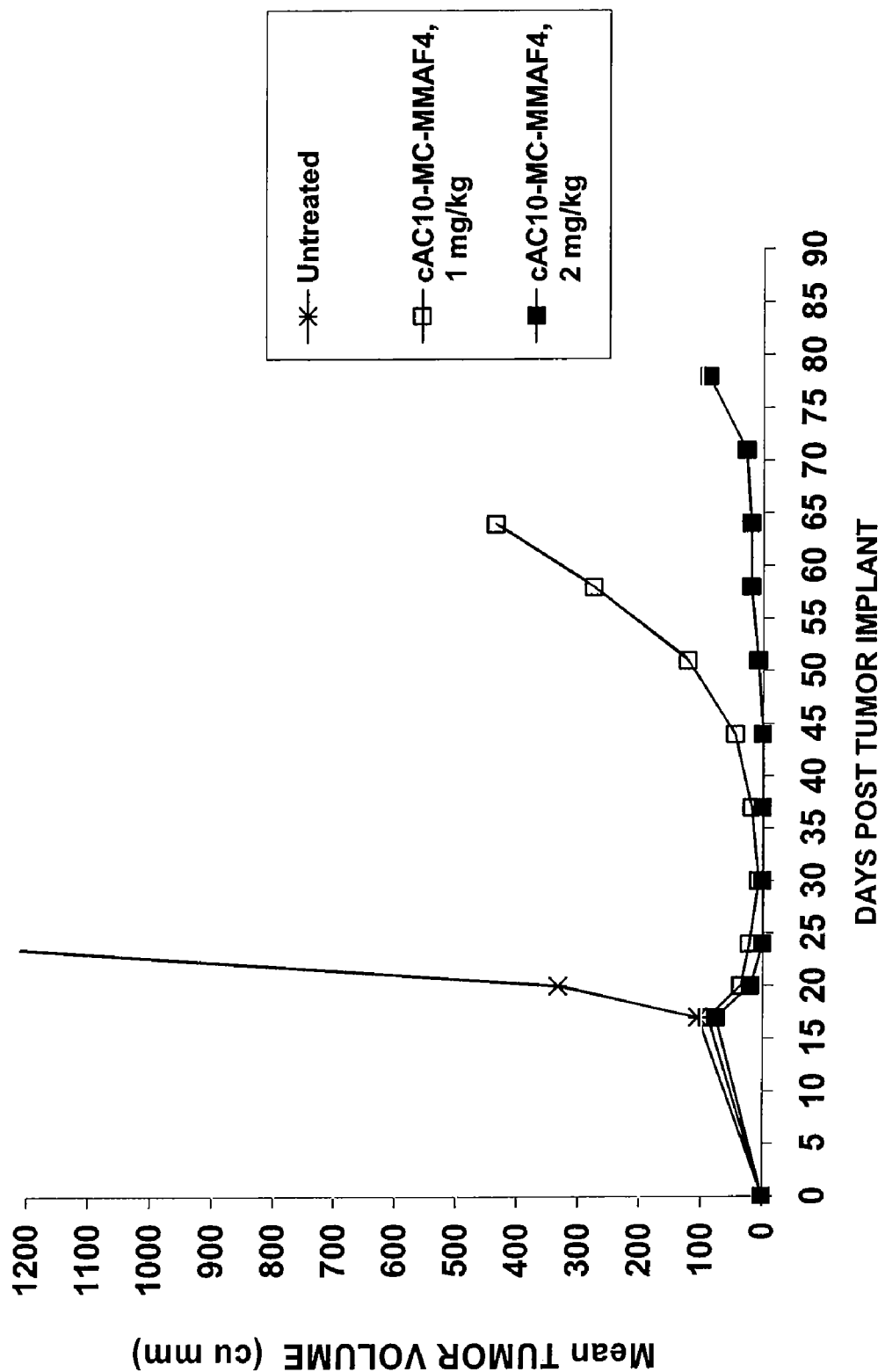
FIG. 1 shows an in vivo, single dose, efficacy assay of cAC10-mcMMAF in subcutaneous Karpas-299 ALCL xenografts.

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. An antibody is a protein generated by the immune system that is capable of recognizing and binding to a specific antigen. Described in terms of its structure, an antibody typically has a Y-shaped protein consisting of four amino acid chains, two heavy and two light. Each antibody has primarily two regions: a variable region and a constant region. The variable region, located on the ends of the arms of the Y, binds to and interacts with the target antigen. This variable region includes a complementary determining region (CDR) that recognizes and binds to a specific binding site on a particular antigen. The constant region, located on the tail of the Y, is recognized by and interacts with the immune system (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The term "antibody" as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin. In another aspect, the antibodies are polyclonal, monoclonal, bispecific, human, humanized or chimeric antibodies, single chain antibodies, Fv, Fab fragments, F(ab') fragments, F(ab')$_2$ fragments, fragments produced by a Fab expression library, anti-idiotypic (anti-Id) antibodies, CDR's, and epitope-binding fragments of any of the above which immunospecifically bind to cancer cell antigens, viral antigens or microbial antigens.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, U.S. Pat. No. 4,816,567). The "monoclonal antibodies" may also be isolated from phage antibody libraries using the techniques described in Clackson et al. (1991) *Nature*, 352:624-628 and Marks et al. (1991) *J. Mol. Biol.*, 222:581-597, for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA*, 81:6851-6855).

Various methods have been employed to produce monoclonal antibodies (MAbs). Hybridoma technology, which refers to a cloned cell line that produces a single type of antibody, uses the cells of various species, including mice (murine), hamsters, rats, and humans. Another method to prepare MAbs uses genetic engineering including recombinant DNA techniques. Monoclonal antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

As noted, murine antibodies can be used. While useful for diagnostics and short-term therapies, murine antibodies cannot be administered to people long-term without increasing the risk of a deleterious immunogenic response. This response, called Human Anti-Mouse Antibody (HAMA), occurs when a human immune system recognizes the murine antibody as foreign and attacks it. A HAMA response can cause toxic shock or even death.

Chimeric and humanized antibodies reduce the likelihood of a HAMA response by minimizing the nonhuman portions of administered antibodies. Furthermore, chimeric and humanized antibodies have the additional benefit of activating secondary human immune responses, such as antibody dependent cellular cytotoxicity.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The expressions "ErbB2" and "HER2" are used interchangeably herein and refer to human HER2 protein described, for example, in Semba et al., *Proc. Natl. Acad. Sci. USA*, 82:6497-6501 (1985) and Yamamoto et al., (1986) *Nature*, 319:230-234 (Genebank accession number X03363). The term "erbB2" refers to the gene encoding human ErbB2 and "neu" refers to the gene encoding rat p185neu. Preferred ErbB2 is native sequence human ErbB2.

Antibodies to ErbB receptors are available commercially from a number of sources, including, for example, Santa Cruz Biotechnology, Inc., California, USA.

By "ErbB ligand" is meant a polypeptide which binds to and/or activates an ErbB receptor. The ErbB ligand may be a native sequence human ErbB ligand such as epidermal growth factor (EGF) (Savage et al. (1972) *J. Biol. Chem.*, 247:7612-7621); transforming growth factor alpha (TGF-α) (Marquardt et al. (1984) *Science* 223:1079-1082); amphiregulin also known as schwanoma or keratinocyte autocrine growth factor (Shoyab et al. (1989) *Science* 243:1074-1076; Kimura et al, *Nature*, 348:257-260 (1990); and Cook et al., *Mol. Cell. Biol.*, 11:2547-2557 (1991)); betacellulin (Shing et al., *Science*, 259:1604-1607 (1993); and Sasada et al., *Biochem. Biophys. Res. Commun.*, 190:1173 (1993)); heparin-binding epidermal growth factor (HB-EGF) (Higashiyama et al., *Science*, 251:936-939 (1991)); epiregulin (Toyoda et al., *J. Biol. Chem.*, 270:7495-7500 (1995); and Komurasaki et al., *Oncogene*, 15:2841-2848 (1997)); a heregulin (see below); neuregulin-2 (NRG-2) (Carraway et al., *Nature*, 387:512-516 (1997)); neuregulin-3 (NRG-3) (Zhang et al., *Proc. Natl. Acad. Sci.*, 94:9562-9567 (1997)); neuregulin-4 (NRG-4) (Harari et al., *Oncogene*, 18:2681-89 (1999)) or cripto (CR-1) (Kannan et al., *J. Biol. Chem.*, 272(6):3330-3335 (1997)). ErbB ligands which bind EGFR include EGF, TGF-α, amphiregulin, betacellulin, HB-EGF and epiregulin. ErbB ligands which bind ErbB3 include heregulins. ErbB ligands capable of binding ErbB4 include betacellulin, epiregulin, HB-EGF, NRG-2, NRG-3, NRG-4 and heregulins. The ErbB ligand may also be a synthetic ErbB ligand. The synthetic ligand may be specific for a particular ErbB receptor, or may recognize particular ErbB receptor complexes. An example of a synthetic ligand is the synthetic heregulin/EGF chimera biregulin (see, for example, Jones et al., (1999) *FEBS Letters*, 447:227-231, which is incorporated by reference).

"Heregulin" (HRG) refers to a polypeptide encoded by the heregulin gene product as disclosed in U.S. Pat. No. 5,641,869 or Marchionni et al., *Nature*, 362:312-318 (1993). Examples of heregulins include heregulin-α, heregulin-β1, heregulin-β2 and heregulin-β3 (Holmes et al., *Science*, 256:1205-1210 (1992); and U.S. Pat. No. 5,641,869); neu differentiation factor (NDF) (Peles et al., *Cell* 69: 205-216 (1992)); acetylcholine receptor-inducing activity (ARIA) (Falls et al. (1993) *Cell* 72:801-815); glial growth factors (GGFs) (Marchionni et al., *Nature*, 362:312-318 (1993)); sensory and motor neuron derived factor (SMDF) (Ho et al., *J. Biol. Chem.*, 270:14523-14532 (1995)); γ-heregulin (Schaefer et al., *Oncogene*, 15:1385-1394 (1997)). The term includes biologically active fragments and/or amino acid sequence variants of a native sequence HRG polypeptide, such as an EGF-like domain fragment thereof (e.g., HRGβ1177-244).

"ErbB hetero-oligomer" is a noncovalently associated oligomer comprising at least two different ErbB receptors. An "ErbB dimer" is a noncovalently associated oligomer that comprises two different ErbB receptors. Such complexes may form when a cell expressing two or more ErbB receptors is exposed to an ErbB ligand. ErbB oligomers, such as ErbB dimers, can be isolated by immunoprecipitation and analyzed by SDS-PAGE as described in Sliwkowski et al., *J. Biol. Chem.*, 269(20):14661-14665 (1994), for example. Examples of such ErbB hetero-oligomers include EGFR-ErbB2 (also referred to as HER1/HER2), ErbB2-ErbB3 (HER2/HER3) and ErbB3-ErbB4 (HER3/HER4) complexes. Moreover, the ErbB hetero-oligomer may comprise two or more ErbB2 receptors combined with a different ErbB receptor, such as ErbB3, ErbB4 or EGFR (ErbB1). Other proteins, such as a cytokine receptor subunit (e.g., gp130) may be included in the hetero-oligomer.

A "native sequence" polypeptide is one which has the same amino acid sequence as a polypeptide, e.g., tumor-associated antigen receptor, derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

The term "amino acid sequence variant" refers to polypeptides having amino acid sequences that differ to some extent from a native sequence polypeptide. Ordinarily, amino acid sequence variants will possess at least about 70% homology with at least one receptor binding domain of a native ligand, or with at least one ligand binding domain of a native receptor, such as a tumor-associated antigen, and preferably, they will be at least about 80%, more preferably, at least about 90% homologous with such receptor or ligand binding domains. The amino acid sequence variants possess substitutions, deletions, and/or insertions at certain positions within the amino acid sequence of the native amino acid sequence.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, (1991) *Annu. Rev. Immunol*, 9:457-92. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *Proc. Natl. Acad. Sci. USA*, 95:652-656 (1998).

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in *Daëron, Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus. (Guyer et al., *J. Immunol.*, 117:587 (1976) and Kim et al., *J. Immunol.*, 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., *J. Immunol. Methods*, 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al. (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al. supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. (1986) Nature, 321:522-525; Riechmann et al. (1988) Nature 332:323-329; and Presta, (1992) Curr. Op. Struct. Biol., 2:593-596.

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®[[®]]) as described in Table 3 of U.S. Pat. No. 5,821,337 expressly incorporated herein by reference; humanized 520C9 (WO 93/21319) and humanized 2C4 antibodies as described herein below.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

A "disorder" is any condition that would benefit from treatment of the present invention. This includes chronic and acute disorders or diseases including those pathological conditions which predispose the mammal to the disorder in question. Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. >50% of a population, of a collection or a sample.

The term "intracellular metabolite" refers to a compound resulting from a metabolic process or reaction inside a cell on an antibody drug conjugate (ADC). The metabolic process or reaction may be an enzymatic process such as proteolytic cleavage of a peptide linker of the ADC, or hydrolysis of a functional group such as a hydrazone, ester, or amide. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an Drug-Ligand Conjugate, a Drug-Linker-Ligand Conjugate, an antibody drug conjugate (ADC) or the like whereby the covalent attachment, e.g., the linker, between the drug moiety (D) and the antibody (Ab) is broken, resulting in the free drug dissociated from the antibody inside the cell. The cleaved moieties of the Drug-Ligand Conjugate, a Drug-Linker-Ligand Conjugate or ADC are thus intracellular metabolites.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or anti-proliferation effect of an antibody drug conjugate compound or an intracellular metabolite of an antibody drug conjugate compound. Cytotoxic activity may be expressed as the $IC_{50}$ value which is the concentration (molar or mass) per unit volume at which half the cells survive.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB2-expressing cancer" is one which produces sufficient levels of ErbB2 at the surface of cells thereof, such that an anti-ErbB2 antibody can bind thereto and have a therapeutic effect with respect to the cancer.

A cancer "characterized by excessive activation" of an ErbB2 receptor is one in which the extent of ErbB2 receptor activation in cancer cells significantly exceeds the level of activation of that receptor in non-cancerous cells of the same tissue type. Such excessive activation may result from overexpression of the ErbB2 receptor and/or greater than normal levels of an ErbB2 ligand available for activating the ErbB2 receptor in the cancer cells. Such excessive activation may cause and/or be caused by the malignant state of a cancer cell. In some embodiments, the cancer will be subjected to a diagnostic or prognostic assay to determine whether amplification and/or overexpression of an ErbB2 receptor is occurring which results in such excessive activation of the ErbB2 receptor. Alternatively, or additionally, the cancer may be subjected to a diagnostic or prognostic assay to determine whether amplification and/or overexpression an ErbB2 ligand is occurring in the cancer which attributes to excessive activation of the receptor. In a subset of such cancers, excessive activation of the receptor may result from an autocrine stimulatory pathway.

A cancer which "overexpresses" an ErbB2 receptor is one which has significantly higher levels of an ErbB2 receptor at the cell surface thereof, compared to a noncancerous cell of the same tissue type. Such overexpression may be caused by gene amplification or by increased transcription or translation. ErbB2 receptor overexpression may be determined in a diagnostic or prognostic assay by evaluating increased levels of the ErbB2 protein present on the surface of a cell (e.g., via an immunohistochemistry assay; IHC). Alternatively, or additionally, one may measure levels of ErbB2-encoding nucleic acid in the cell, e.g., via fluorescent in situ hybridization (FISH; see WO 98/45479), southern blotting, or polymerase chain reaction (PCR) techniques, such as real time quantitative PCR (RT-PCR). Overexpression of the ErbB2 ligand, may be determined diagnostically by evaluating levels of the ligand (or nucleic acid encoding it) in the patient, e.g., in a tumor biopsy or by various diagnostic assays such as the IHC, FISH, southern blotting, PCR or in vivo assays described above. One may also study ErbB2 receptor overexpression by measuring shed antigen (e.g., ErbB2 extracellular domain) in a biological fluid such as serum (see, e.g., U.S. Pat. No. 4,933,294; WO 91/05264; U.S. Pat. No. 5,401, 638; and Sias et al., (1990) *J. Immunol. Methods*, 132: 73-80). Aside from the above assays, various other in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

The tumors overexpressing HER2 are rated by immunohistochemical scores corresponding to the number of copies of HER2 molecules expressed per cell, and can been determined biochemically: 0=0-10,000 copies/cell, 1+=at least about 200,000 copies/cell, 2+=at least about 500,000 copies/cell, 3+=about $1-2 \times 10^6$ copies/cell. Overexpression of HER2 at the 3+ level, which leads to ligand-independent activation of the tyrosine kinase (Hudziak et al., (1987) *Proc. Natl. Acad. Sci. USA*, 84:7159-7163), occurs in approximately 30% of breast cancers, and in these patients, relapse-free survival and overall survival are diminished (Slamon et al., (1989) *Science*, 244:707-712; Slamon et al., (1987) *Science*, 235:177-182).

Conversely, a cancer which is "not characterized by overexpression of the ErbB2 receptor" is one which, in a diagnostic assay, does not express higher than normal levels of ErbB2 receptor compared to a noncancerous cell of the same tissue type.

The term "cytotoxic agent" as used herein refers to a substance that inhibits or prevents the function of cells and/or causes destruction of cells. The term is intended to include radioactive isotopes (e.g., $^{211}At$, $^{131}I$, $^{125}I$, $^{90}Y$, $^{18}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof. In one aspect, the term is not intended to include radioactive isotopes.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX$^{RM}$, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitracrine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO 98/50433, Abgenix). The anti-EGFR antibody may be conjugated with a cyotoxic agent, thus generating an immunoconjugate (see, e.g., EP 659,439A2, Merck Patent GmbH). Examples of small molecules that bind to EGFR include ZD1839 or Gefitinib (IRESSA™; Astra Zeneca), Erlotinib HCl (CP-358774, TARCEVA™; Genentech/OSI) and AG1478, AG1571 (SU 5271; Sugen).

A "tyrosine kinase inhibitor" is a molecule which inhibits to some extent tyrosine kinase activity of a tyrosine kinase such as an ErbB receptor. Examples of such inhibitors include the EGFR-targeted drugs noted in the preceding paragraph as well as quinazolines such as PD 153035, 4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis(4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in any of the following patent publications: U.S. Pat. No. 5,804,396; WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. In one embodiment, the anti-angiogenic factor is an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as including the anti-CD30, CD40, CD70 or Lewis Y antibodies and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, the synthetic oligonucleotide adaptors or linkers can be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic throbocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, $CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2$ $CH_2CH_2CH_2$CH=$CH_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —$O^-$, —OR, —SR, —$S^-$, —$NR_2$, —$NR_3$, =NR, —$CX_3$, —CN, —OCN, —SCN, —N=C=O, —NCS, —NO, —$NO_2$, =$N_2$, —$N_3$, NC(=O) R, —C(=O)R, —C(=O)$NR_2$, —$SO_3^-$, —$SO_3H$, —S(=O)$_2$R, —OS(=O)$_2$OR, —S(=O)$_2$NR, —S(=O)R, —OP(=O)(OR)$_2$, —P(=O)(OR)$_2$, —$PO^-_3$, —$PO_3H_2$, —C(=O)R, —C(=O)X, —C(=S)R, —$CO_2$R, —$CO_2^-$, —C(=S)OR, —C(=O)SR, —C(=S)SR, —C(=O)$NR_2$, —C(=S)$NR_2$, —C(=NR)$NR_2$, where each X is independently a halogen: F, Cl, Br, or I; and each R is independently —H, $C_2$-$C_{18}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl" and "Heterocycle" refer to a ring system in which one or more ring atoms is a heteroatom, e.g., nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system.

Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

"Linker", "Linker Unit", or "link" means a chemical moiety comprising a covalent bond or a chain of atoms that covalently attaches an antibody to a drug moiety. In various embodiments, a linker is specified as LU. Linkers include a divalent radical such as an alkyldiyl, an aryldiyl, a heteroaryldiyl, moieties such as: —$(CR_2)_nO(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Examples of a "patient" include, but are not limited to, a human, rat, mouse, guinea pig, monkey, pig, goat, cow, horse, dog, cat, bird and fowl. In an exemplary embodiment, the patient is a human.

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$— NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$— NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

An "arylene" is an aryl group which has two covalent bonds and can be in the ortho, meta, or para configurations as shown in the following structures:

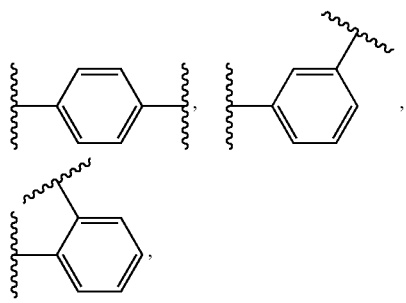

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$— NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O) NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

An "Exemplary Compound" is a Drug Compound or a Drug-Linker Compound.

An "Exemplary Conjugate" is a Drug-Ligand Conjugate having a cleavable Drug unit from the Drug-Ligand Conjugate or a Drug-Linker-Ligand Conjugate.

In some embodiments, the Exemplary Compounds and Exemplary Conjugates are in isolated or purified form. As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of Exemplary Compound or Exemplary Conjugate by weight of the isolate.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of an Exemplary Compound or Exemplary Conjugate. The Exemplary Compounds and Exemplary Conjugates contain at least one amino group, and accordingly acid addition salts can be formed with this amino group. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound of the invention, e.g., an Exemplary Compound or Exemplary Conjugate. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: AE is auristatin E, Boc is N-(t-butoxycarbonyl), cit is citrulline, dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN(CH$_3$CN) is acetonitrile, MeOH is methanol, Mtr is 4-anisyldiphenylmethyl (or 4-methoxytrityl), nor is (1S,2R)-(+)-norephedrine, PAB is p-aminobenzyl, PBS is phosphate-buffered saline (pH 7.4), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TBTU is O-benzotriazol-1-yl-N,N,N,N-tetramethyluronium tetrafluoroborate, TFA is trifluoroacetic acid, TLC is thin layer chromatography, UV is ultraviolet, and val is valine.

The following linker abbreviations are used herein and have the indicated definitions: Val Cit is a valine-citrulline, dipeptide site in protease cleavable linker; PAB is p-aminobenzylcarbamoyl; (Me)vc is N-methyl-valine citrulline, where the linker peptide bond has been modified to prevent its cleavage by cathepsin B; MC(PEG)6-OH is maleimidocaproyl- polyethylene glycol; SPP is N-Succinimidyl 4-(2-pyridylthio) pentanoate; and SMCC is N-Succinimidyl 4-(N-maleimidomethyl)cyclohexane-1 carboxylate.

The terms "treat" or "treatment," unless otherwise indicated by context, refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In the context of cancer, the term "treating" includes any or all of: preventing growth of tumor cells, cancer cells, or of a tumor; preventing replication of tumor cells or cancer cells, lessening of overall tumor burden or decreasing the number of cancerous cells, and ameliorating one or more symptoms associated with the disease.

In the context of an autoimmune disease, the term "treating" includes any or all of: preventing replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

The following cytotoxic drug abbreviations are used herein and have the indicated definitions: MMAE is mono-methyl auristatin E (MW 718); MMAF is N-methylvaline-valine-dolaisoleuine-dolaproine-phenylalanine (MW 731.5); MMAF-DMAEA is MMAF with DMAEA (dimethylaminoethylamine) in an amide linkage to the C-terminal phenylalanine (MW 801.5); MMAF-TEG is MMAF with tetraethylene glycol esterified to the phenylalanine; MMAF-NtBu is N-t-butyl, attached as an amide to C-terminus of MMAF; AEVB is auristatin E valeryl benzylhydrazone, acid labile linker through the C-terminus of AE (MW 732); and AFP is Monoamide of p-phenylene diamine with C-terminal Phenylalanine of Auristatin F (MW 732).

4.2 The Compounds of the Invention

4.2.1 The Compounds of Formula (Ia)

In one aspect, the invention provides Drug-Linker-Ligand Conjugates having Formula Ia:

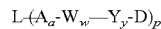

or a pharmaceutically acceptable salt or solvate thereof wherein,

L- is a Ligand unit;

-A$_a$-W$_w$—Y$_y$— is a Linker unit (LU), wherein the Linker unit includes:

-A- is a Stretcher unit, a is 0 or 1, each —W— is independently an Amino Acid unit, w is an integer ranging from 0 to 12, —Y— is a Spacer unit, and y is 0, 1 or 2;

p ranges from 1 to about 20; and

-D is a Drug unit having the Formulas D$_E$ and D$_F$:

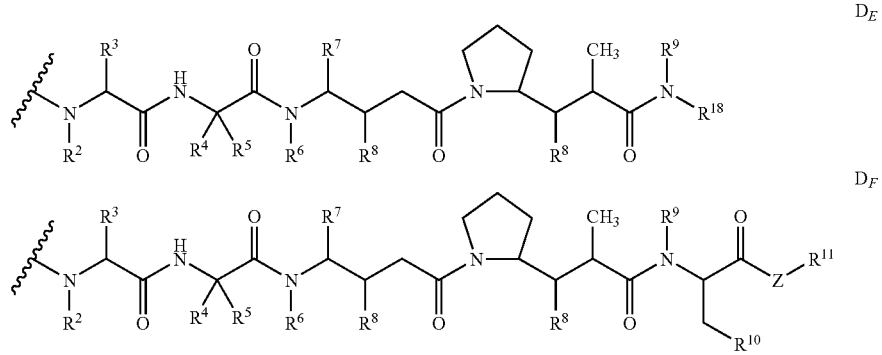

wherein, independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In another embodiment, the present invention provides Drug Compounds having the Formula Ib:

$R^4$ is selected from hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ jointly, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from H and —$C_1$-$C_8$ alkyl;

$R^7$ is selected from H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from H, —OH, —$C_1$-$C_8$ alkyl, —$C_3$-$C_8$ carbocycle and —O—($C_1$-$C_8$ alkyl);

$R^9$ is selected from H and —$C_1$-$C_8$ alkyl;

$R^{10}$ is selected from aryl group or —$C_3$-$C_8$ heterocycle;

Z is —O—, —S—, —NH—, or —$NR^{12}$—, wherein $R^{12}$ is $C_1$-$C_8$ alkyl;

$R^{11}$ is selected from H, $C_1$-$C_{20}$ alkyl, aryl, —$C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is —$C_2$-$C_8$ alkyl;

$R^{14}$ is H or —$C_1$-$C_8$ alkyl;

each occurrence of $R^{15}$ is independently H, —COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, —$C_1$-$C_8$ alkyl, or —$(CH_2)_n$—COOH; and n is an integer ranging from 0 to 6.

In yet another embodiment, the invention provides Drug-Linker-Ligand Conjugates having the Formula Ia':

$$Ab\text{-}(A_a\text{-}W_w\text{-}Y_y\text{-}D)_p \qquad \text{Formula Ia'}$$

or pharmaceutically acceptable salts or solvates thereof.

wherein:

Ab is an antibody,

A is a Stretcher unit,

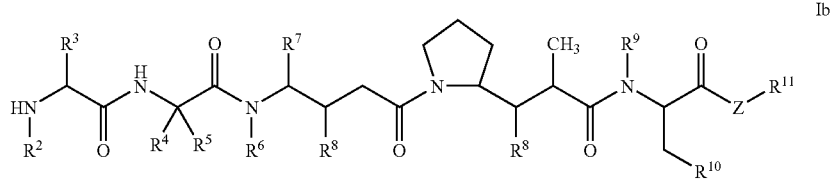

Ib or pharmaceutically acceptable salts or solvates thereof, wherein:

$R^2$ is selected from hydrogen and —$C_1$-$C_8$ alkyl;

$R^3$ is selected from hydrogen, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

a is 0 or 1, each W is independently an Amino Acid unit, w is an integer ranging from 0 to 12, Y is a Spacer unit, and y is 0, 1 or 2, p ranges from 1 to about 20, and D is a Drug moiety selected from Formulas $D_E$ and $D_F$:

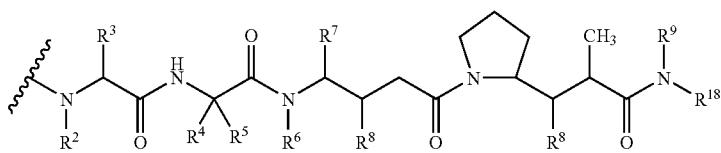

D_E

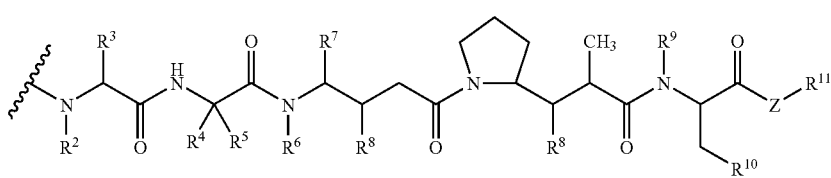

D_F wherein, independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

Ab is any antibody covalently attached to one or more drug units. Ab includes an antibody which binds to CD30, CD40, CD70, Lewis Y antigen. In another embodiment, Ab does not include an antibody which binds to an ErbB receptor or to one or more of receptors (1)-(35):

(1) BMPR1B (bone morphogenetic protein receptor-type IB, Genbank accession no. NM_001203);

(2) E16 (LAT1, SLC7A5, Genbank accession no. NM_003486);

(3) STEAP1 (six transmembrane epithelial antigen of prostate, Genbank accession no. NM_012449);

(4) 0772P (CA125, MUC16, Genbank accession no. AF361486);

(5) MPF (MPF, MSLN, SMR, megakaryocyte potentiating factor, mesothelin, Genbank accession no. NM_005823);

(6) Napi3b (NAPI-3B, NPTIIb, SLC34A2, solute carrier family 34 (sodium phosphate), member 2, type II sodium-dependent phosphate transporter 3b, Genbank accession no. NM_006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

(8) PSCA hlg (2700050C12Rik, C530008O16Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM_017636);

(13) CRIPTO (CR, CR1, CRGF, CRIPTO, TDGF1, teratocarcinoma-derived growth factor, Genbank accession no. NP_003203 or NM_003212);

(14) CD21 (CR2 (Complement receptor 2) or C3DR (C3d/Epstein Barr virus receptor) or Hs.73792, Genbank accession no. M26004);

(15) CD79b (IGb (immunoglobulin-associated beta), B29, Genbank accession no. NM_000626);

(16) FcRH2 (IFGP4, IRTA4, SPAP1A (SH2 domain containing phosphatase anchor protein 1a), SPAP1B, SPAP1C, Genbank accession no. NM_030764);

(17) HER2 (Genbank accession no. M11730);

(18) NCA (Genbank accession no. M18728);

(19) MDP (Genbank accession no. BC017023);

(20) IL20Rα (Genbank accession no. AF184971);

(21) Brevican (Genbank accession no. AF229053);

(22) Ephb2R (Genbank accession no. NM_004442);

(23) ASLG659 (Genbank accession no. AX092328);

(24) PSCA (Genbank accession no. AJ297436);

(25) GEDA (Genbank accession no. AY260763);

(26) BAFF-R (Genbank accession no. NP_443177.1);

(27) CD22 (Genbank accession no. NP_001762.1);

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank accession No. NP_001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+ T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);

(34) FCRH1 (Fc receptor-like protein 1, a putative receptor for the immunoglobulin Fc domain that contains C2 type Ig-like and ITAM domains, may have a role in B-lymphocyte differentiation, Genbank accession No. NP_443170.1); and/or

(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP_112571.1).

In one embodiment —Ww- is -Val-Cit-.

In another embodiment, $R^3$, $R^4$ and $R^7$ are independently isopropyl or sec-butyl and $R^5$ is —H. In an exemplary embodiment, $R^3$ and $R^4$ are each isopropyl, $R^5$ is —H, and $R^7$ is sec-butyl. In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one embodiment, Z is —O— or —NH—.

In one embodiment, $R^{10}$ is aryl

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —CH($R^{15}$)$_2$, wherein $R^{15}$ is —(CH$_2$)$_n$—N($R^{16}$)$_2$, and $R^{16}$ is —C$_1$-C$_8$ alkyl or —(CH$_2$)$_n$—COOH.

In another embodiment, when Z is —NH, $R^{11}$ is —CH($R^{15}$)$_2$, wherein $R^{15}$ is —(CH$_2$)$_n$—SO$_3$H.

In one aspect, Ab is cAC10, cBR96, cS2C6, c1F6, c2F2, hAC10, hBR96, hS2C6, h1F6, and h2F2.

Exemplary embodiments of Formula Ia have the following structures:

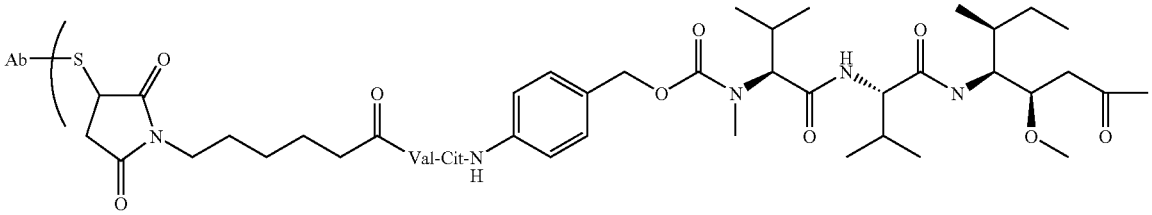

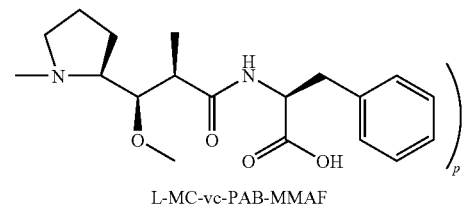

L-MC-vc-PAB-MMAF

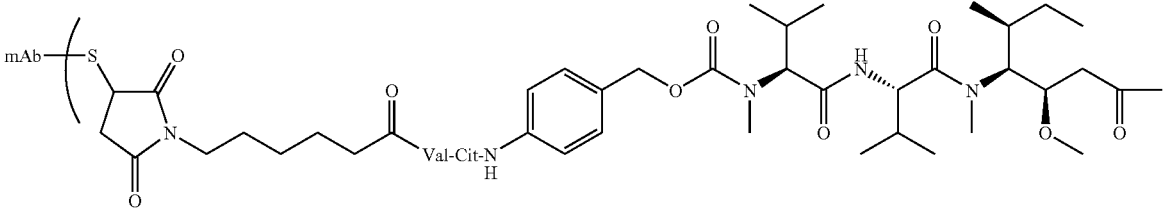

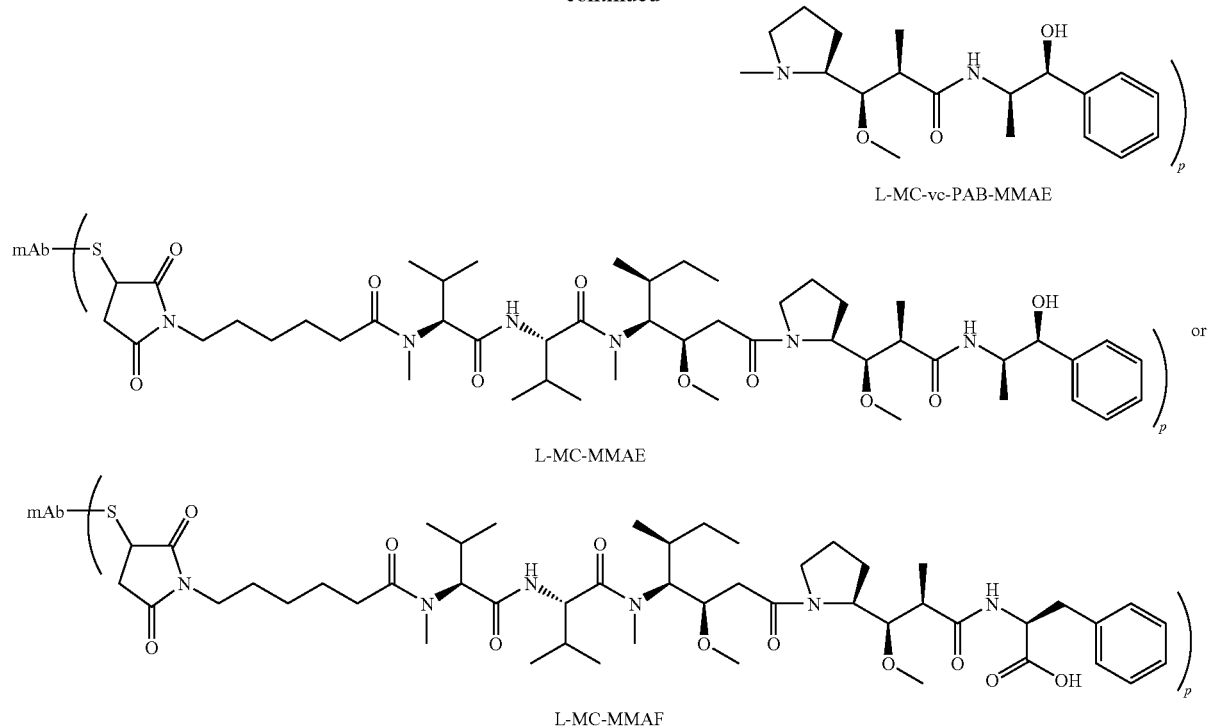

L-MC-vc-PAB-MMAE

L-MC-MMAE

L-MC-MMAF wherein L is an antibody, Val is valine, and Cit is citrulline.

The drug loading is represented by p, the average number of drug molecules per antibody in a molecule (e.g., of Formula Ia, Ia' and Ic). Drug loading may range from 1 to 20 drugs (D) per Ligand (e.g., Ab or mAb). Compositions of Formula Ia and Formula Ia' include collections of antibodies conjugated with a range of drugs, from 1 to 20. The average number of drugs per antibody in preparation of conjugation reactions may be characterized by conventional means such as mass spectroscopy, ELISA assay, and HPLC. The quantitative distribution of Ligand-Drug-Conjugates in terms of p may also be determined. In some instances, separation, purification, and characterization of homogeneous Ligand-Drug-conjugates where p is a certain value from Ligand-Drug-Conjugates with other drug loadings may be achieved by means such as reverse phase HPLC or electrophoresis.

4.2.2 The Drug Compounds of Formula (Ib)

In another aspect, the present invention provides Drug Compounds having the Formula (Ib):

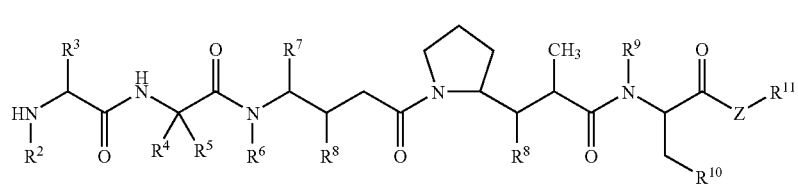

Ib or a pharmaceutically acceptable salt or solvate thereof, wherein:

$R^2$ is selected from -hydrogen and —$C_1$-$C_8$ alkyl;

$R^3$ is selected from -hydrogen, —$C_1$-$C_8$ alkyl, —$C_3$-$C_8$ carbocycle, aryl, —$C_1$-C8 alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ jointly, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from aryl group or —$C_3$-$C_8$ heterocycle;

Z is —O—, —S—, —NH—, or —$NR^{12}$—, wherein $R^{12}$ is $C_1$-$C_8$ alkyl;

$R^{11}$ is selected from —H, $C_1$-$C_{20}$ alkyl, aryl, —$C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is —$C_2$-$C_8$ alkyl;

$R^{14}$ is —H or —$C_1$-$C_8$ alkyl;

each occurrence of $R^{15}$ is independently —H, —COOH, —$(CH_2)_n$—$N(R^6)_2$, —$(CH_2)_n$—$SO_3H$, or —$(CH_2)_n$—$SO_3$—$C_1$-$C_8$ alkyl;

each occurrence of $R^{16}$ is independently —H, —$C_1$-$C_8$ alkyl, or —$(CH_2)_n$—COOH; and n is an integer ranging from 0 to 6.

In one embodiment, $R^3$, $R^4$ and $R^7$ are independently isopropyl or sec-butyl and $R^5$ is —H. In an exemplary embodiment, $R^3$ and $R^4$ are each isopropyl, $R^5$ is —H, and $R^7$ is sec-butyl.

In another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

Illustrative Compounds of Formula (Ib), each of which may be used as drug moieties (D) in ADC, include compounds having the following structures:

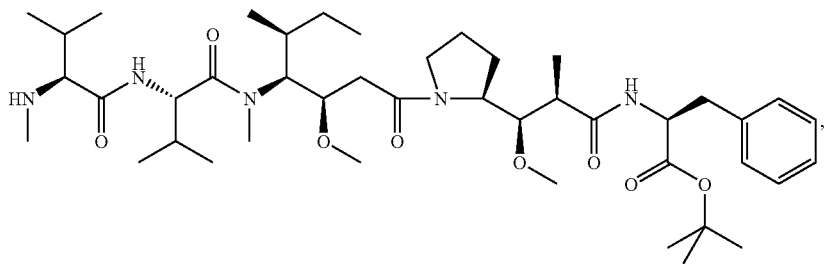

1

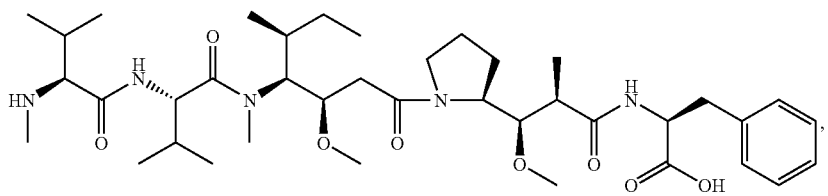

2

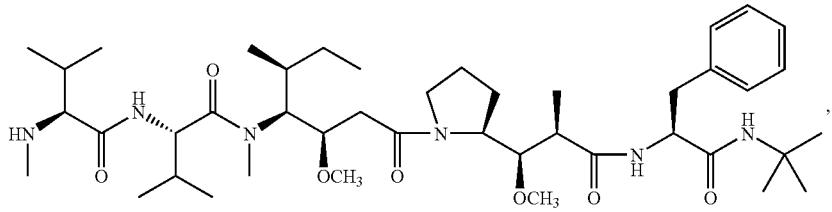

3

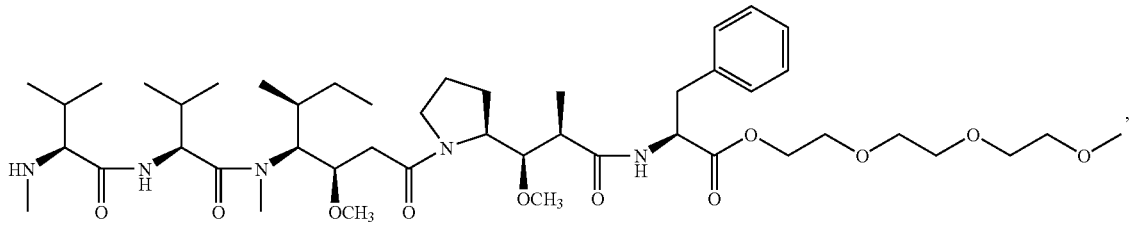

4

-continued
5
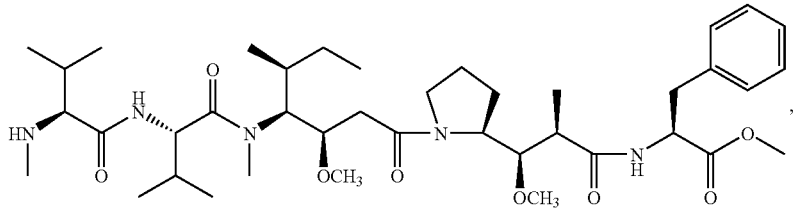
6
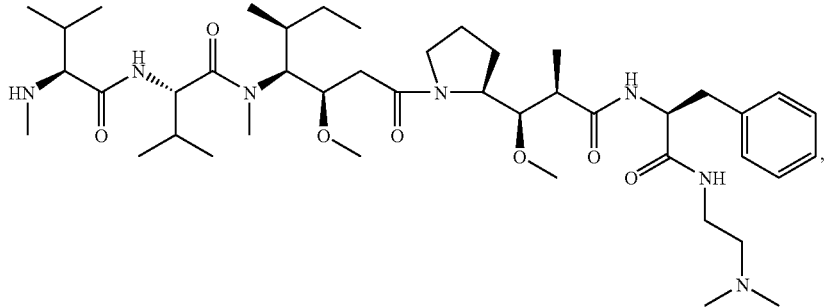
7
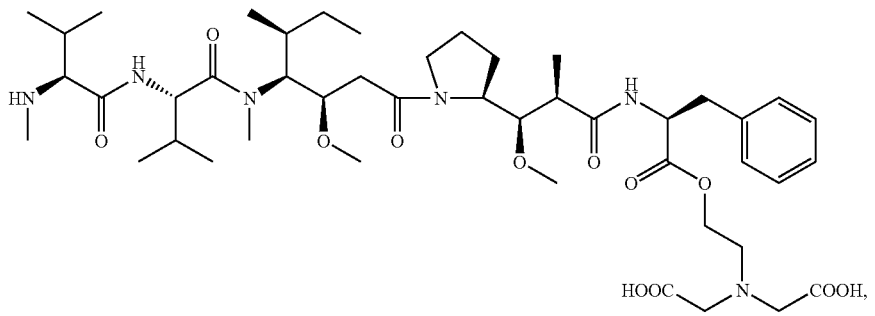
8
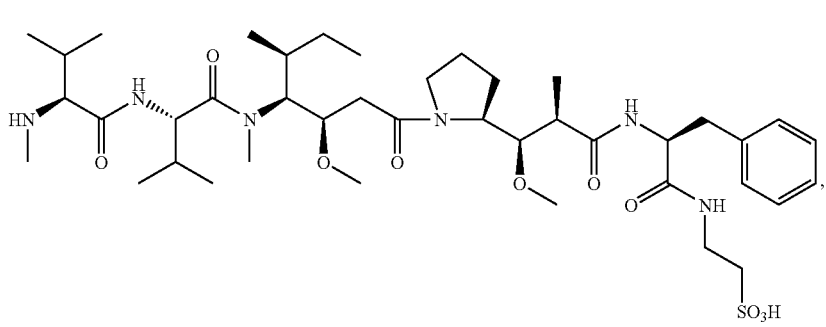
9
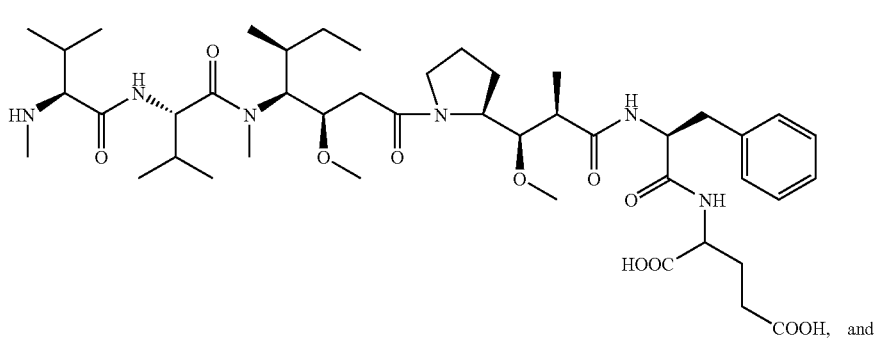
and

-continued

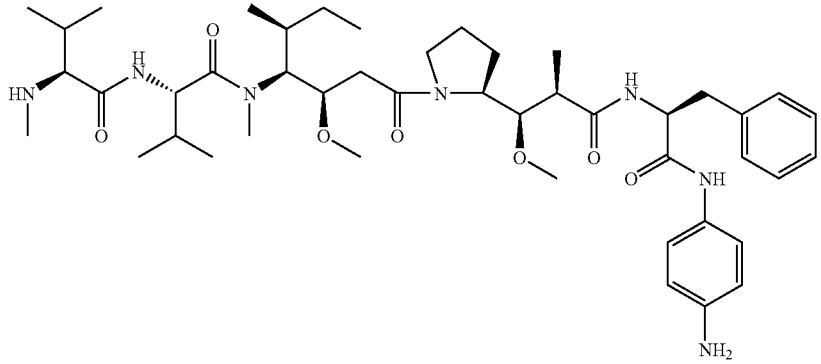

and pharmaceutically acceptable salts or solvates thereof.

The Compounds of Formula (Ic)

In another aspect, the invention provides antibody-drug conjugate compounds (ADC) having Formula Ic:

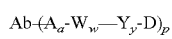

Ic comprising an antibody covalently attached to one or more drug units (moieties). The antibody-drug conjugate compounds include pharmaceutically acceptable salts or solvates thereof.

Formula Ic compounds are defined wherein:

Ab is an antibody which binds to one or more tumor-associated antigen receptors (1)-(35):

(1) BMPR1B (bone morphogenetic protein receptor-type IB, Genbank accession no. NM_001203);

(2) E16 (LAT1, SLC7A5, Genbank accession no. NM_003486);

(3) STEAP1 (six transmembrane epithelial antigen of prostate, Genbank accession no. NM_012449);

(4) 0772P (CA125, MUC16, Genbank accession no. AF361486);

(5) MPF (MPF, MSLN, SMR, megakaryocyte potentiating factor, mesothelin, Genbank accession no. NM_005823);

(6) Napi3b (NAPI-3B, NPTIIb, SLC34A2, solute carrier family 34 (sodium phosphate), member 2, type II sodium-dependent phosphate transporter 3b, Genbank accession no. NM_006424);

(7) Sema 5b (FLJ10372, KIAA1445, Mm.42015, SEMA5B, SEMAG, Semaphorin 5b Hlog, sema domain, seven thrombospondin repeats (type I and type 1-like), transmembrane domain (TM) and short cytoplasmic domain, (semaphorin) 5B, Genbank accession no. AB040878);

(8) PSCA hlg (2700050C12Rik, C530008O16Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM_017636);

(13) CRIPTO (CR, CR1, CRGF, CRIPTO, TDGF1, teratocarcinoma-derived growth factor, Genbank accession no. NP_003203 or NM_003212);

(14) CD21 (CR2 (Complement receptor 2) or C3DR (C3d/Epstein Barr virus receptor) or Hs.73792 Genbank accession no. M26004);

(15) CD79b (CD79B, CD79β, IGb (immunoglobulin-associated beta), B29, Genbank accession no. NM_000626);

(16) FcRH2 (IFGP4, IRTA4, SPAP1A (SH2 domain containing phosphatase anchor protein 1a), SPAP1B, SPAP1C, Genbank accession no. NM_030764);

(17) HER2 (Genbank accession no. M11730);

(18) NCA (Genbank accession no. M18728);

(19) MDP (Genbank accession no. BC017023);

(20) IL20Rα (Genbank accession no. AF184971);

(21) Brevican (Genbank accession no. AF229053);

(22) Ephb2R (Genbank accession no. NM_004442);

(23) ASLG659 (Genbank accession no. AX092328);

(24) PSCA (Genbank accession no. AJ297436);

(25) GEDA (Genbank accession no. AY260763;

(26) BAFF-R (B cell-activating factor receptor, BLyS receptor 3, BR3, NP_443177.1);

(27) CD22 (B-cell receptor CD22-B isoform, NP-001762.1);

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank accession No. NP_001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+ T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);

(34) FCRH1 (Fc receptor-like protein 1, a putative receptor for the immunoglobulin Fc domain that contains C2 type Ig-like and ITAM domains, may have a role in B-lymphocyte differentiation, Genbank accession No. NP_443170.1); and

(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP_112571.1).

A is a Stretcher unit, a is 0 or 1, each W is independently an Amino Acid unit, w is an integer ranging from 0 to 12, Y is a Spacer unit, and y is 0, 1 or 2, p ranges from 1 to about 8, and D is a Drug moiety selected from Formulas $D_E$ and $D_F$:

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, $-(R^{13}O)_m-R^{14}$, or $-(R^{13}O)_m-CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, $-(CH_2)_n-N(R^{16})_2$, $-(CH_2)_n-SO_3H$, or $-(CH_2)_n-SO_3-C_1-C_8$ alkyl;

each occurrence of $R^{16}$ is independently H, $C_1$-$C_8$ alkyl, or $-(CH_2)_n-COOH$;

$R^{18}$ is selected from $-C(R^8)_2-C(R^8)_2$-aryl, $-C(R^8)_2-C(R^8)_2-(C_3-C_8$ heterocycle), and $-C(R^8)_2-C(R^8)_2-(C_3-C_8$ carbocycle); and n is an integer ranging from 0 to 6.

In one embodiment —Ww- is -Val-Cit-.

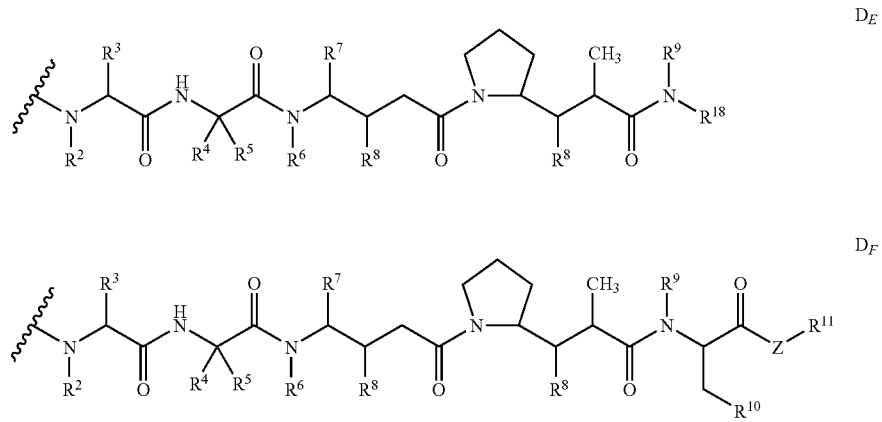

wherein the wavy line of $D_E$ and $D_F$ indicates the covalent attachment site to A, W, or Y, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula $-(CR^aR^b)_n-$ wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

In another embodiment, $R^3$, $R^4$ and $R^7$ are independently isopropyl or sec-butyl and $R^5$ is —H. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is $-OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is $-OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is $-CH(R^{15})_2$, wherein $R^{15}$ is $-(CH_2)_n-N(R^{16})_2$, and $R^{16}$ is $-C_1$-$C_8$ alkyl or $-(CH_2)_n-COOH$.

In another embodiment, when Z is —NH, $R^{11}$ is —CH$(R^{15})_2$, wherein $R^{15}$ is $-(CH_2)_n-SO_3H$.

Exemplary embodiments of Formula Ic ADC have the following structures:

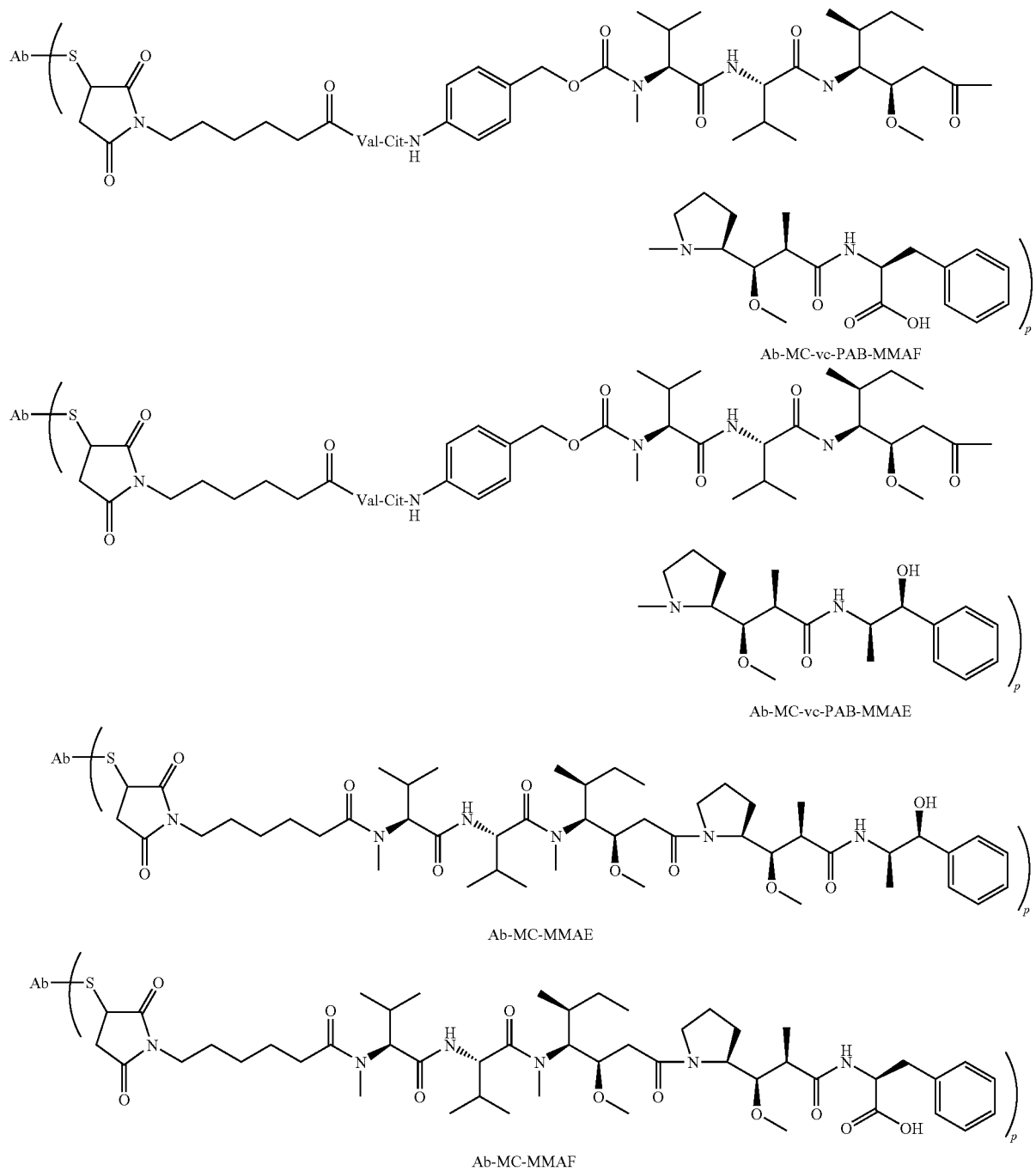

wherein Ab is an antibody which binds to one or more tumor-associated antigen receptors (1)-(35); Val is valine; and Cit is citrulline.

The drug loading is represented by p, the average number of drugs per antibody in a molecule of Formula I. Drug loading may range from 1 to 20 drugs (D) per antibody (Ab or mAb). Compositions of ADC of Formula I include collections of antibodies conjugated with a range of drugs, from 1 to 20. The average number of drugs per antibody in preparations of ADC from conjugation reactions may be characterized by conventional means such as UV/visible spectroscopy, mass spectrometry, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached.

Typically, fewer than the theoretical maximum of drug moieties are conjugated to an antibody during a conjugation reaction. An antibody may contain, for example, many lysine residues that do not react with the drug-linker intermediate or linker reagent. Only the most reactive lysine groups may react with an amine-reactive linker reagent. Generally, antibodies do not contain many, if any, free and reactive cysteine thiol groups which may be linked to a drug moiety. Most cysteine thiol residues in the antibodies of the compounds of the invention exist as disulfide bridges and must be reduced with a reducing agent such as dithiothreitol (DTT). Additionally, the antibody must be subjected to denaturing conditions to reveal reactive nucleophilic groups such as lysine or cysteine. The loading (drug/antibody ratio) of an ADC may be controlled in several different manners, including: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate, or linker reagent followed by drug moiety reagent, then the resulting product is a mixture of ADC compounds with a distribution of one or more drug moieties attached to an antibody. The average number of drugs per antibody may be calculated from the mixture by dual ELISA antibody assay, specific for antibody and specific for the drug. Individual ADC molecules may be identified in the mixture by mass spectroscopy, and separated by HPLC, e.g., hydrophobic interaction chromatography ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). Thus, a homogeneous ADC with a single loading value may be isolated from the conjugation mixture by electrophoresis or chromatography.

4.3 The Linker Unit

A "Linker unit" (LU) is a bifunctional compound which can be used to link a Drug unit and an Ligand unit to form Drug-Linker-Ligand Conjugates, or which are useful in the formation of immunoconjugates directed against tumor associated antigens. Such immunoconjugates allow the selective delivery of toxic drugs to tumor cells.

In one embodiment, the Linker unit of the Drug-Linker Compound and Drug-Linker-Ligand Conjugate has the formula:

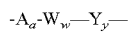

wherein:
-A- is a Stretcher unit;
a is 0 or 1;
each —W— is independently an Amino Acid unit;
w is independently an integer ranging from 0 to 12;
—Y— is a Spacer unit; and
y is 0, 1 or 2.

In the Drug-Linker-Ligand Conjugate, the Linker is capable of linking the Drug moiety and the Ligand unit.

4.3.1 The Stretcher Unit

The Stretcher unit (-A-), when present, is capable of linking a Ligand unit to an amino acid unit (—W—). In this regard a Ligand (L) has a functional group that can form a bond with a functional group of a Stretcher. Useful functional groups that can be present on a ligand, either naturally or via chemical manipulation include, but are not limited to, sulfhydryl (—SH), amino, hydroxyl, carboxy, the anomeric hydroxyl group of a carbohydrate, and carboxyl. In one aspect, the Ligand functional groups are sulfhydryl and amino. Sulfhydryl groups can be generated by reduction of an intramolecular disulfide bond of a Ligand. Alternatively, sulfhydryl groups can be generated by reaction of an amino group of a lysine moiety of a Ligand using 2-iminothiolane (Traut's reagent) or another sulfhydryl generating reagent.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas IIIa and IIIb, wherein L-, —W—, —Y—, -D, w and y are as defined above, and $R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; and r is an integer ranging from 1-10. It is to be understood from all the exemplary embodiments of Formula Ia, such as III-VI, that even where not denoted expressly, from 1 to 20 drug moieties are linked to a Ligand (p=1-20).

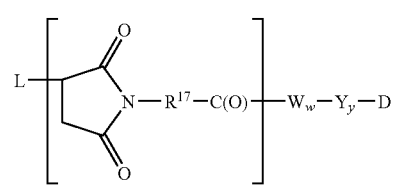

IIIa

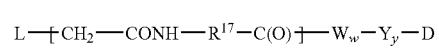

IIIb

An illustrative Stretcher unit is that of Formula IIIa wherein $R^{17}$ is —$(CH_2)_5$—:

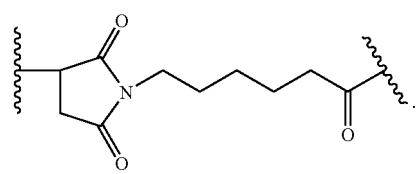

Another illustrative Stretcher unit is that of Formula IIIa wherein $R^{17}$ is —$(CH_2CH_2O)_r$—$CH_2$—; and r is 2:

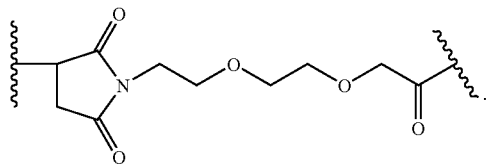

Still another illustrative Stretcher unit is that of Formula IIIb wherein $R^{17}$ is —$(CH_2)_5$—:

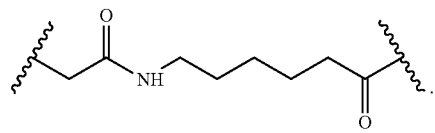

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R^{17}$, L-, —W—, —Y—, -D, w and y are as defined above.

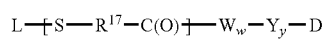
IV

In yet another embodiment, the reactive group of the Stretcher contains a reactive site that can form a bond with a primary or secondary amino group of a Ligand. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, —W—, —Y—, -D, w and y are as defined above;

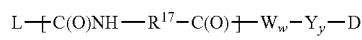
Va

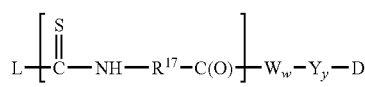
Vb

In yet another aspect, the reactive group of the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al. (1991) Bioconjugate Chem 2:133-41. Representative Stretcher units of this embodiment are depicted within the square brackets of Formulas VIa, VIb, and VIc, wherein —$R^{17}$—, L-, —W—, —Y—, -D, w and y are as defined above.

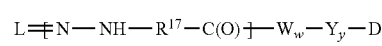
VIa

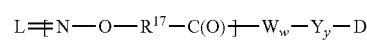
VIb

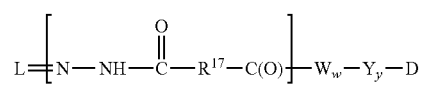
VIc 4.3.2 The Amino Acid Unit

The Amino Acid unit (—W—), when present, links the Stretcher unit to the Spacer unit if the Spacer unit is present, links the Stretcher unit to the Drug moiety if the Spacer unit is absent, and links the Ligand unit to the Drug unit if the Stretcher unit and Spacer unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

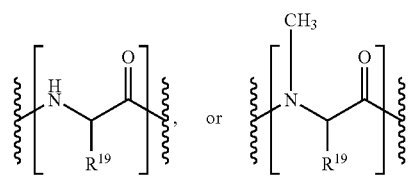

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

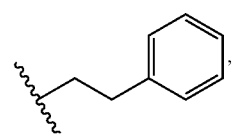

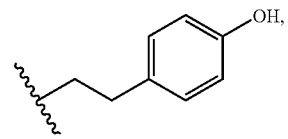

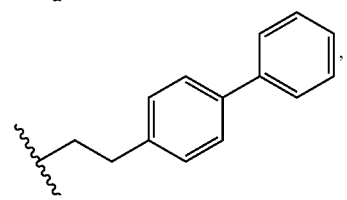

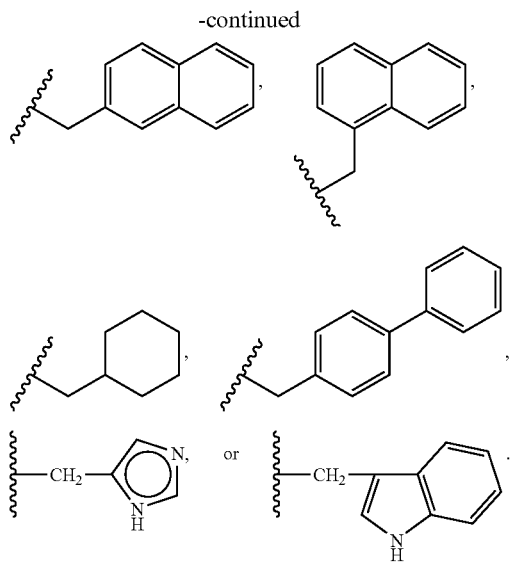

The Amino Acid unit can be enzymatically cleaved by one or more enzymes, including a tumor-associated protease, to liberate the Drug unit (-D), which in one embodiment is protonated in vivo upon release to provide a Drug (D). Illustrative $W_w$ units are represented by formulas (VII)-(IX):

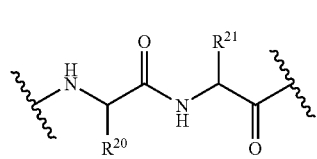

(VII)

wherein $R^{20}$ and $R^{21}$ are as follows:

| $R^{20}$ | $R^{21}$ |
|---|---|
| benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| ⸺CH$_2$-indole | $(CH_2)_3NHCONH_2$; |
| benzyl | methyl; and |
| benzyl | $(CH_2)_3NHC(=NH)NH_2$; |

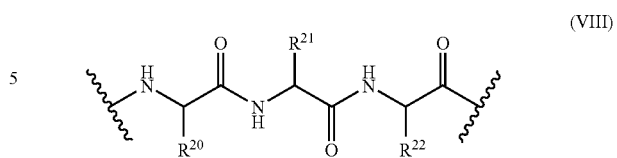

(VIII)

wherein $R^{20}$, $R^{21}$ and $R^{22}$ are as follows:

| $R^{20}$ | $R^{21}$ | $R^{22}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; |

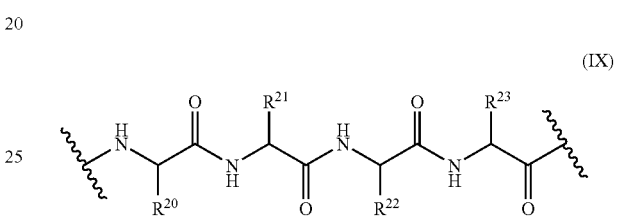

(IX)

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Exemplary Amino Acid units include, but are not limited to, units of formula (VII) where: $R^{20}$ is benzyl and $R^{21}$ is —$(CH_2)_4NH_2$; $R^{20}$ isopropyl and $R^{21}$ is —$(CH_2)_4NH_2$; $R^{20}$ isopropyl and $R^{21}$ is —$(CH_2)_3NHCONH_2$. Another exemplary Amino Acid unit is a unit of formula (VIII) wherein $R^{20}$ is benzyl, $R^{21}$ is benzyl, and $R^{22}$ is —$(CH_2)_4NH_2$.

Useful —$W_w$— units can be designed and optimized in their selectivity for enzymatic cleavage by a particular enzymes, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide.

When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

In one aspect of the Amino Acid unit, the Amino Acid unit is valine-citrulline. In another aspect, the Amino Acid unit is phenylalanine-lysine (i.e. fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

In certain embodiments, the Amino Acid unit can comprise natural amino acids. In other embodiments, the Amino Acid unit can comprise non-natural amino acids.

4.3.3 The Spacer Unit

The Spacer unit (—Y—), when present, links an Amino Acid unit to the Drug moiety when an Amino Acid unit is present. Alternately, the Spacer unit links the Stretcher unit to the Drug moiety when the Amino Acid unit is absent. The Spacer unit also links the Drug moiety to the Ligand unit when both the Amino Acid unit and Stretcher unit are absent.

Figure 20:
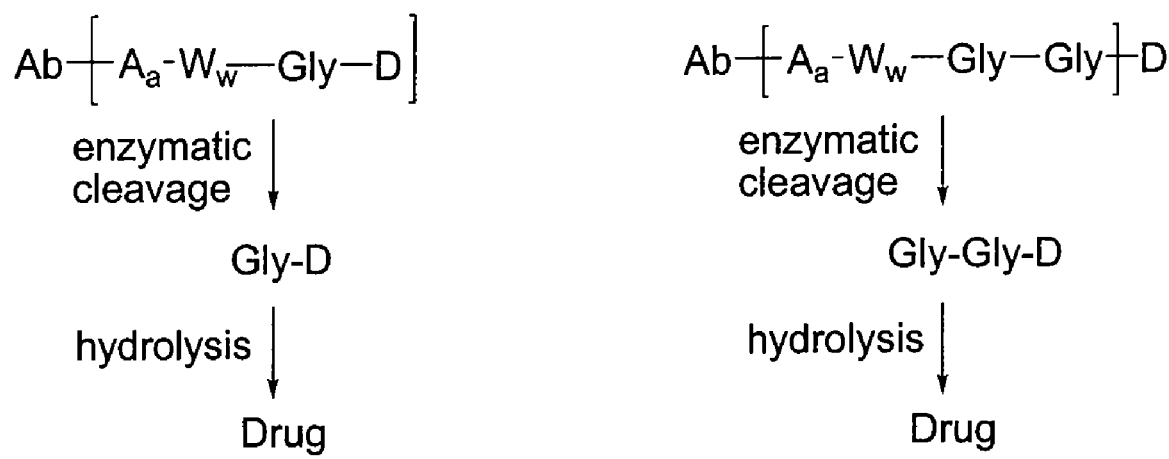
FIG. 20 shows examples of compounds with a non self-immolative Spacer unit.

Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the Drug-Linker-Ligand Conjugate or the Drug-Linker Compound. Examples of a non self-immolative Spacer unit include, but are not limited to a (glycine-glycine) Spacer unit and a glycine Spacer unit (both depicted in FIG. 20) (infra). When an Exemplary Compound containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from L-$A_a$-Ww-. In one embodiment, an independent hydrolysis reaction takes place within the target cell, cleaving the glycine—Drug moiety bond and liberating the Drug.

In another embodiment, —$Y_y$— is a p-aminobenzyl alcohol (PAB) unit (see FIGS. 21 and 22) whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

In one embodiment, a non self-immolative Spacer unit (—Y—) is -Gly-Gly-. In another embodiment, a non self-immolative the Spacer unit (—Y—) is -Gly-.

In one embodiment, a Drug-Linker Compound or a Drug-Linker Ligand Conjugate is provided in which the Spacer unit is absent (y=0), or a pharmaceutically acceptable salt or solvate thereof.

Figure 21:
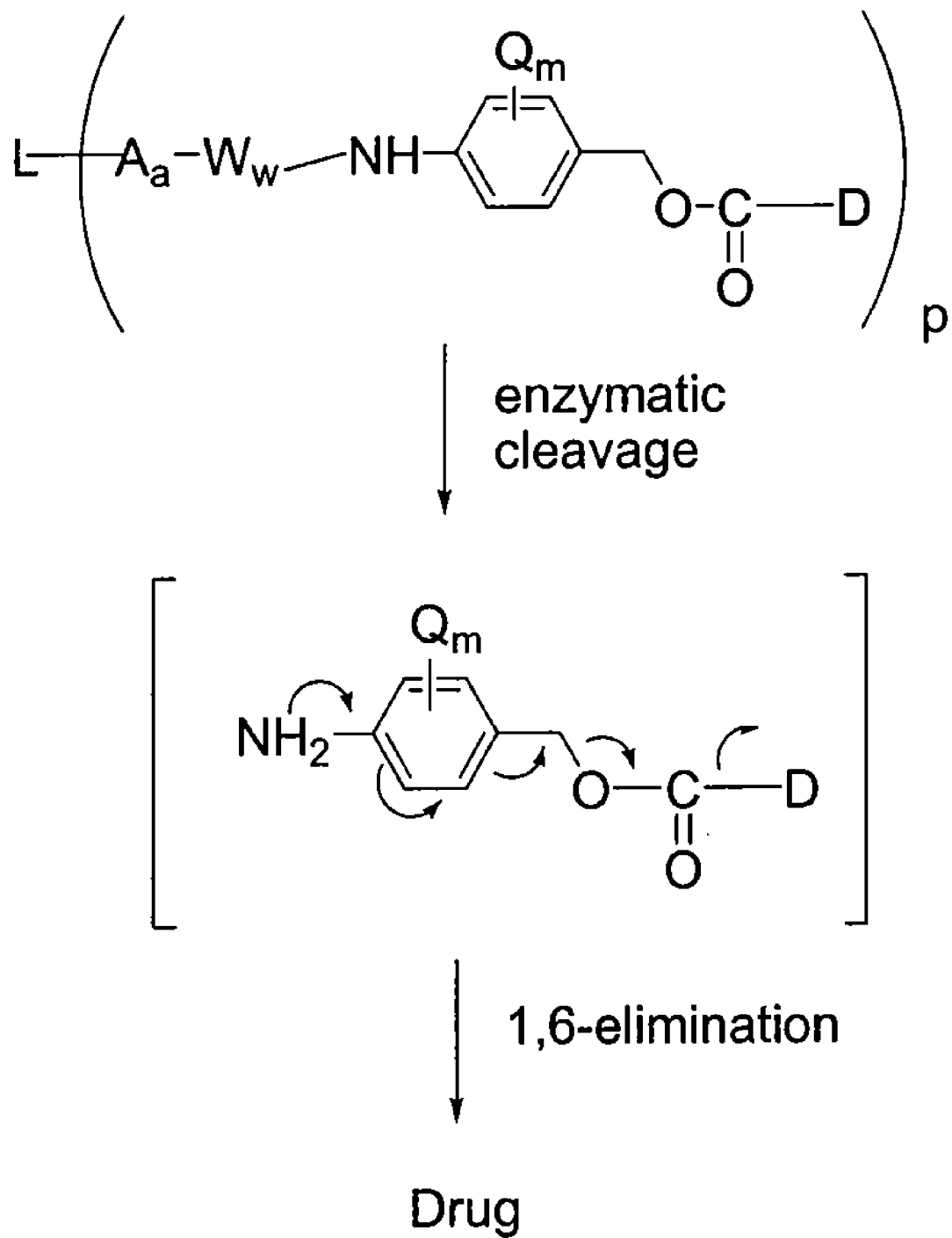
FIG. 21 shows a scheme of a possible mechanism of Drug release from a PAB group which is attached directly to -D via a carbamate or carbonate group.

Alternatively, an Exemplary Compound containing a self-immolative Spacer unit can release -D without the need for a separate hydrolysis step. In this embodiment, —Y— is a PAB group that is linked to —$W_w$— via the amino nitrogen atom of the PAB group, and connected directly to -D via a carbonate, carbamate or ether group. Without being bound by any particular theory or mechanism, FIG. 21 depicts a possible mechanism of Drug release of a PAB group which is attached directly to -D via a carbamate or carbonate group espoused by Toki et al. (2002) J. Org. Chem. 67:1866-1872.

In FIG. 21 Q is —$C_1$-$C_8$ alkyl, —O—($C_1$-$C_8$ alkyl), -halogen, -nitro or -cyano; m is an integer ranging from 0-4; and p ranges from 1 to about 20.

Figure 22:
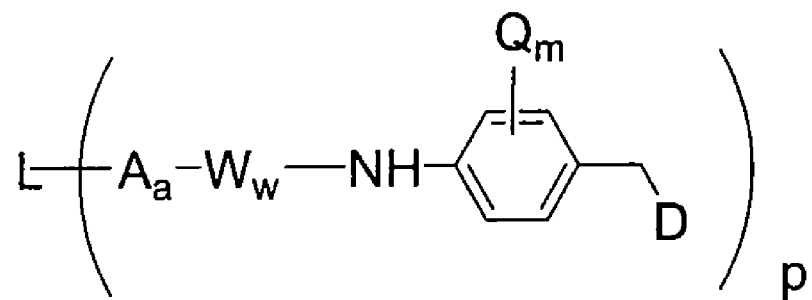
FIG. 22 shows a scheme of a possible mechanism of Drug release from a PAB group which is attached directly to -D via an ether or amine linkage.
Figure 22:
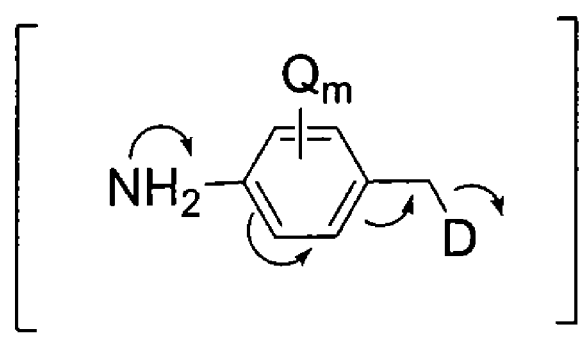
Figure 22:
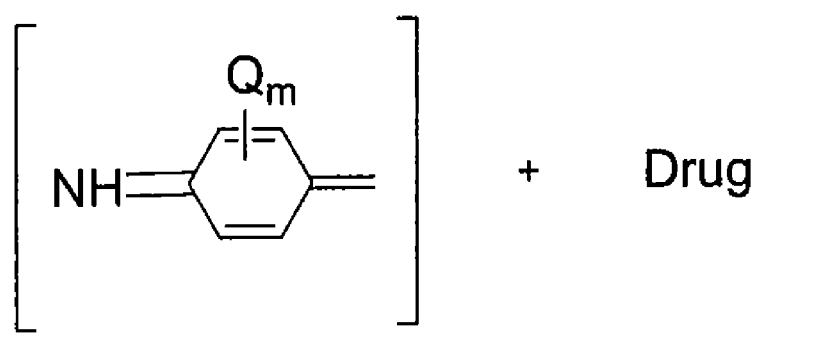

Without being bound by any particular theory or mechanism, FIG. 22 depicts a possible mechanism of Drug release of a PAB group which is attached directly to -D via an ether or amine linkage.

In FIG. 22 Q is —$C_1$-$C_8$ alkyl, —O—($C_1$-$C_8$ alkyl), -halogen, -nitro or -cyano; m is an integer ranging from 0-4; and p ranges from 1 to about 20.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al., J. Org. Chem., 1990, 55, 5867). Elimination of amine-containing drugs that are substituted at the a-position of glycine (Kingsbury, et al., J. Med. Chem., 1984, 27, 1447) are also examples of self-immolative spacer useful in Exemplary Compounds.

Figure 23:
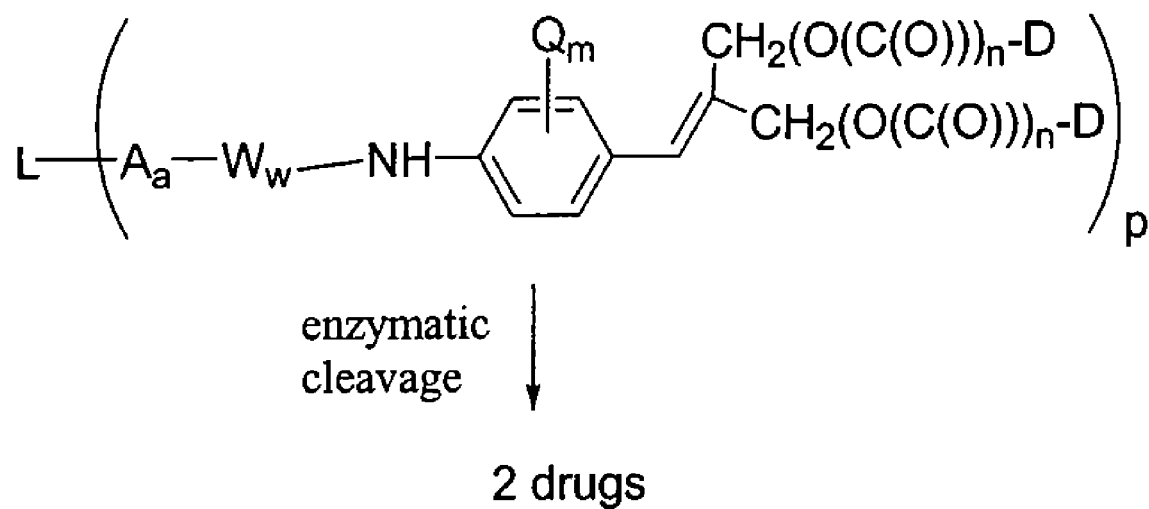
FIG. 23 shows an example of a branched spacer unit, bis(hydroxymethyl)styrene (BHMS) unit, which can be used to incorporate and release multiple drug.

In one embodiment, the Spacer unit is a branched bis(hydroxymethyl)styrene (BHMS) unit as depicted in FIG. 23, which can be used to incorporate and release multiple drugs.

In FIG. 23 Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to about 20.

In one embodiment, the -D moieties are the same. In yet another embodiment, the -D moieties are different.

In one aspect, Spacer units (—$Y_y$—) are represented by Formulas (X)-(XII):

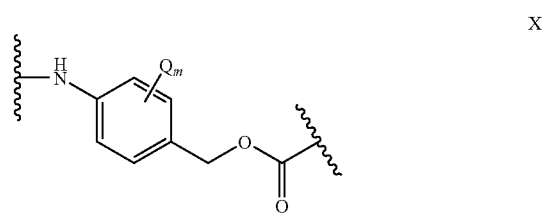

X wherein Q is —$C_1$-$C_8$ alkyl, —O—($C_1$-$C_8$ alkyl), -halogen, -nitro or -cyano; and m is an integer ranging from 0-4;

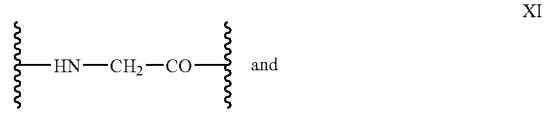

XI

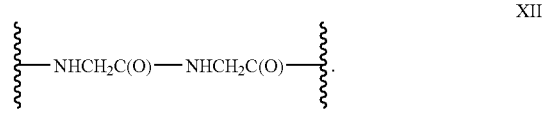

XII

Embodiments of the Formula Ia' and Ic antibody-drug conjugate compounds include:

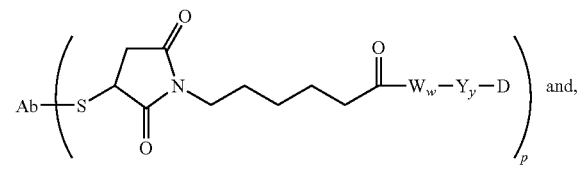

and,

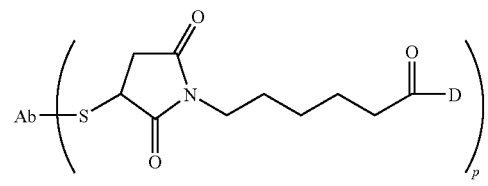

wherein w and y are each 0,

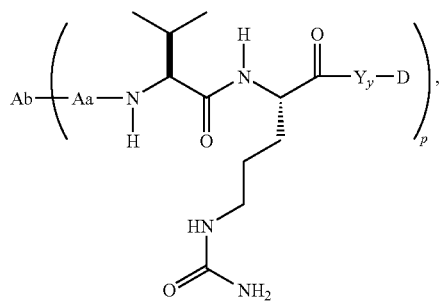

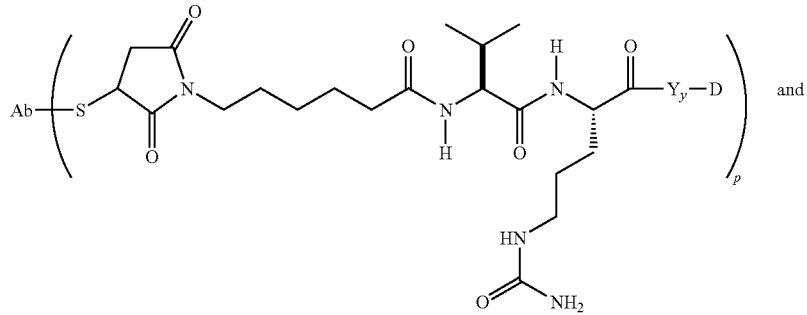

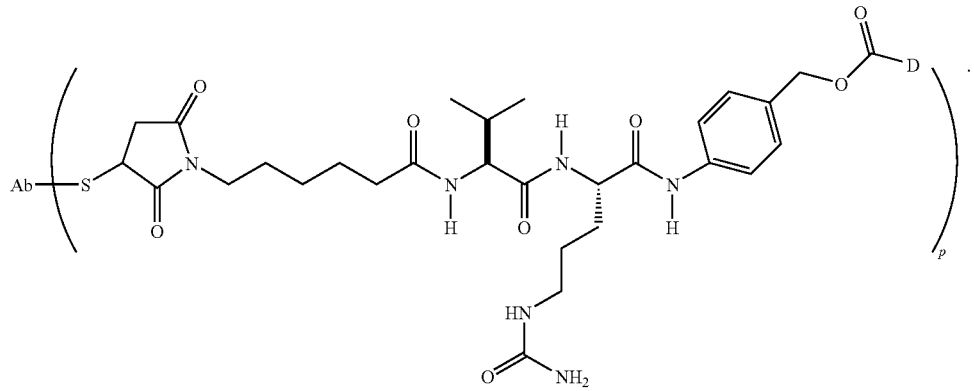

4.4 The Drug Unit (Moiety)

The drug moiety (D) of the antibody drug conjugates (ADC) are of the dolastatin/auristatin type (U.S. Pat. Nos. 5,635,483; 5,780,588) which have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and antifungal activity (Pettit et al. (1998) Antimicrob. Agents Chemother. 42:2961-2965)

D is a Drug unit (moiety) having a nitrogen atom that can form a bond with the Spacer unit when y=1 or 2, with the C-terminal carboxyl group of an Amino Acid unit when y=0, with the carboxyl group of a Stretcher unit when w and y=0, and with the carboxyl group of a Drug unit when a, w, and y=0. It is to be understood that the terms "drug unit" and "drug moiety" are synonymous and used interchangeably herein.

In one embodiment, -D is either formula $D_E$ or $D_F$:

$D_E$

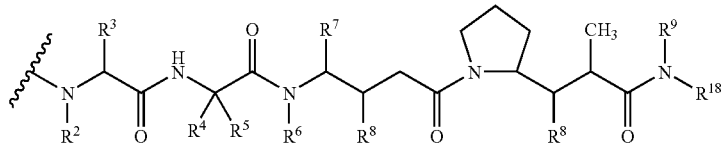

-continued $D_F$

[Chemical structure diagram showing a peptide chain with R2-R11 substituents]

wherein, independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl.

In another embodiment, $R^2$ and $R^6$ are each methyl, and $R^9$ is H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H.

In one embodiment, Z is —O— or —NH—.

In one embodiment, $R^{10}$ is aryl

In an exemplary embodiment, $R^{10}$ is -phenyl.

In an exemplary embodiment, when Z is —O—, $R^{11}$ is H, methyl or t-butyl.

In one embodiment, when Z is —NH, $R^{11}$ is —$CH(R^{15})_2$, wherein $R^{15}$ is —$(CH_2)_n$—$N(R^6)_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

Illustrative Drug units (-D) include the drug units having the following structures:

MMAE

MMAF

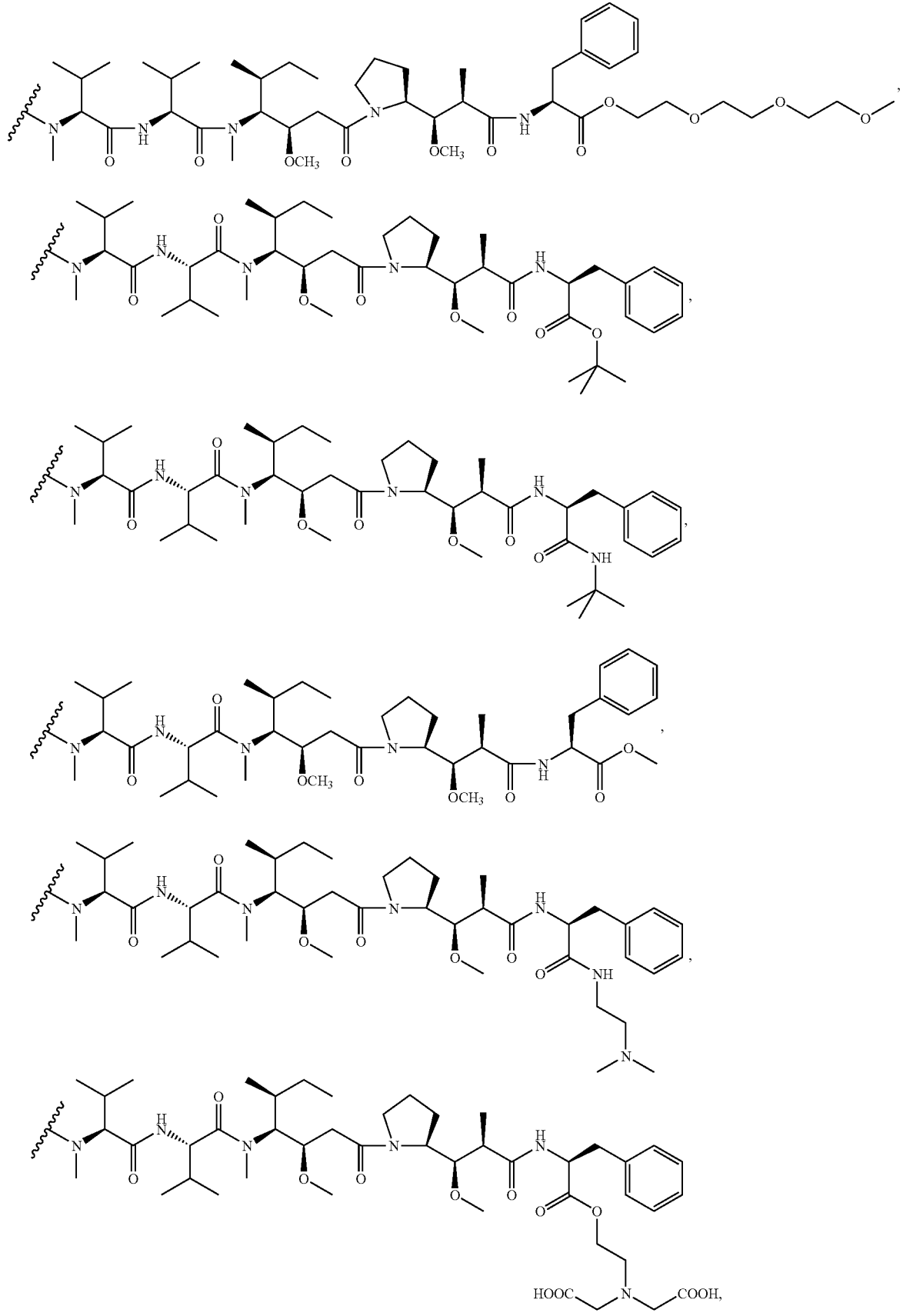

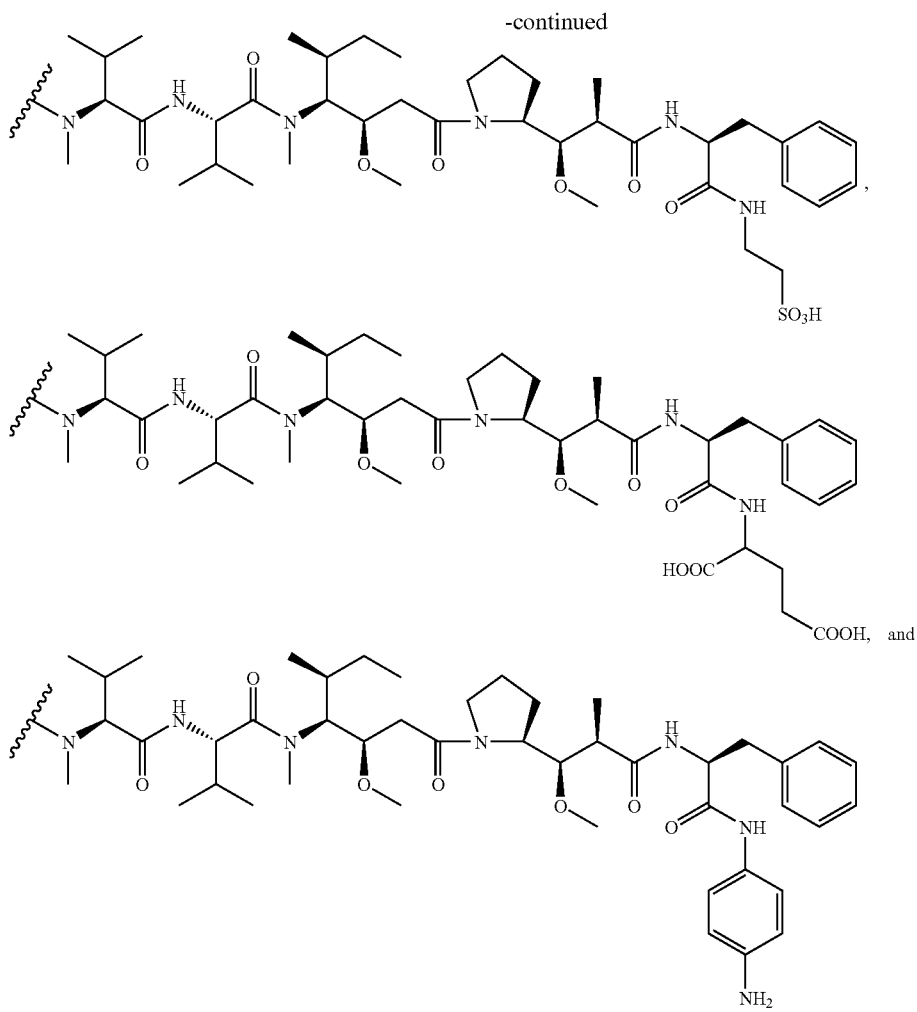

and pharmaceutically acceptable salts or solvates thereof.

In one aspect, hydrophilic groups, such as but not limited to triethylene glycol esters (TEG), as shown above, can be attached to the Drug Unit at $R^{11}$. Without being bound by theory, the hydrophilic groups assist in the internalization and non-agglomeration of the Drug Unit.

4.5 The Ligand Unit

The Ligand unit (L-) includes within its scope any unit of a Ligand (L) that binds or reactively associates or complexes with a receptor, antigen or other receptive moiety associated with a given target-cell population. A Ligand is a molecule that binds to, complexes with, or reacts with a moiety of a cell population sought to be therapeutically or otherwise biologically modified. In one aspect, the Ligand unit acts to deliver the Drug unit to the particular target cell population with which the Ligand unit reacts. Such Ligands include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferring, or any other cell binding molecule or substance.

A Ligand unit can form a bond to a Stretcher unit, an Amino Acid unit, a Spacer Unit, or a Drug Unit. A Ligand unit can form a bond to a Linker unit via a heteroatom of the Ligand. Heteroatoms that may be present on a Ligand unit include sulfur (in one embodiment, from a sulfhydryl group of a Ligand), oxygen (in one embodiment, from a carbonyl, carboxyl or hydroxyl group of a Ligand) and nitrogen (in one embodiment, from a primary or secondary amino group of a Ligand). These heteroatoms can be present on the Ligand in the Ligand's natural state, for example a naturally-occurring antibody, or can be introduced into the Ligand via chemical modification.

In one embodiment, a Ligand has a sulfhydryl group and the Ligand bonds to the Linker unit via the sulfhydryl group's sulfur atom.

In yet another aspect, the Ligand has one or more lysine residues that can be chemically modified to introduce one or more sulfhydryl groups. The Ligand unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the Ligand can have one or more carbohydrate groups that can be chemically modified to have one or more sulfhydryl groups. The Ligand unit bonds to the Linker Unit, such as the Stretcher Unit, via the sulfhydryl group's sulfur atom.

In yet another embodiment, the Ligand can have one or more carbohydrate groups that can be oxidized to provide an aldehyde (—CHO) group (see, for e.g., Laguzza, et al., *J. Med. Chem.* 1989, 32(3), 548-55). The corresponding aldehyde can form a bond with a Reactive Site on a Stretcher. Reactive sites on a Stretcher that can react with a carbonyl group on a Ligand include, but are not limited to, hydrazine and hydroxylamine. Other protocols for the modification of proteins for the attachment or association of Drug Units are described in Coligan et al., *Current Protocols in Protein Science*, vol. 2, John Wiley & Sons (2002), incorporated herein by reference.

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

Useful polyclonal antibodies are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture. These include, but are not limited to, the hybridoma technique originally described by Köhler and Milstein (1975, *Nature* 256, 495-497), the human B cell hybridoma technique (Kozbor et al., 1983, *Immunology Today* 4: 72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al., 1983, *Proc. Natl. Acad. Sci. USA.* 80, 7308-7312; Kozbor et al., 1983, *Immunology Today* 4, 72-79; and Olsson et al., 1982, *Meth. Enzymol.* 92, 3-16).

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al., *Methods in Enzymology*, 1986, 121:210; Rodrigues et al., 1993, *J. of Immunology* 151:6954-6961; Carter et al., 1992, *Bio/Technology* 10: 163-167; Carter et al., 1995, *J. of Hematotherapy* 4:463-470; Merchant et al., 1998, *Nature Biotechnology* 16:677-681. Using such techniques, bispecific antibodies can be prepared for use in the treatment or prevention of disease as defined herein.

Bifunctional antibodies are also described, in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, for e.g., Kabat et al., 1991, *Sequences of Proteins of Immunological Interest*, Fifth Edition, National Institute of Health, Bethesda, Md.; Kabat E et al., 1980, *J. of Immunology* 125 (3):961-969).

Other useful antibodies include fragments of antibodies such as, but not limited to, F(ab')$_2$ fragments, which contain the variable region, the light chain constant region and the CH1 domain of the heavy chain can be produced by pepsin digestion of the antibody molecule, and Fab fragments, which can be generated by reducing the disulfide bridges of the F(ab')$_2$ fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 184,187; European Patent Publication No. 171496; European Patent Publication No. 173494; International Publication No. WO 86/01533; U.S. Pat. No. 4,816,567; European Patent Publication No. 12,023; Berter et al., 1988, Science 240: 1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229: 1202-1207; Oi et al., 1986, BioTechniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies. See, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Biotechnology* 12:899-903). Human antibodies can also be produced using various techniques known in the art, including phage display libraries (Hoogenboom and Winter, J. Mol. Biol., 227:381 (1991); Marks et al., J. Mol. Biol., 222:581 (1991); Quan, M. P. and Carter, P. 2002. *The rise of monoclonal antibodies as therapeutics*. In Anti-IgE and Allergic Disease, Jardieu, P. M. and Fick Jr., R. B, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not the antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies include antibodies having modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a cancer cell antigen can be obtained commercially, for example, from Genentech (San Francisco, Calif.) or produced by any method known to one of skill in the art such as, e.g., chemical synthesis or recombinant expression techniques.

The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment or prevention of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti-HER2 monoclonal antibody, HERCEPTIN® (trastuzumab; Genentech) for the treatment of patients with metastatic breast cancer; RITUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., Willner, D., Lasch, S. J., Henderson, A. J., Hofstead, S. J., Casazza, A. M., Firestone, R. A., Hellström, I., Hellström, K. E., "Cure of Xenografted Human Carcinomas by BR96-Doxorubicin Immunoconjugates" *Science* 1993, 261, 212-215), BR64 (Trail, P A, Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" *Cancer Research* 1997, 57, 100-105, mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" *Cancer Res.* 2000, 60, 3225-3231), mAbs against the CD70 antigen, such as 1F6 mAb and 2F2 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" *J. Immunol.*, 151, 5896-5906, 1993: Wahl et al., 2002 *Cancer Res.* 62(13):3736-42). Many other internalizing antibodies that bind to tumor associated antigens can be used and have been reviewed (Franke, A. E., Sievers, E. L., and Scheinberg, D. A., "Cell surface receptor-targeted therapy of acute myeloid leukemia: a review" *Cancer Biother Radiopharm.* 2000, 15, 459-76; Murray, J. L., "Monoclonal antibody treatment of solid tumors: a coming of age" *Semin Oncol.* 2000, 27, 64-70; Breitling, F., and Dubel, S., *Recombinant Antibodies*, John Wiley, and Sons, New York, 1998).

In certain embodiments, the antibody is not Trastuzumab (full length, humanized anti-HER2 (MW 145167)), HerceptinF(ab')$_2$ (derived from anti-HER2 enzymatically (MW 100000)), 4D5 (full-length, murine antiHER2, from hybridoma), rhu4D5 (transiently expressed, full-length humanized antibody), rhuFab4D5 (recombinant humanized Fab (MW 47738)), 4D5Fc8 (full-length, murine antiHER2, with mutated FcRn binding domain), or Hg ("Hingeless" full-length humanized 4D5, with heavy chain hinge cysteines mutated to serines. Expressed in *E. coli* (therefore non-glycosylated)).

In another specific embodiment, known antibodies for the treatment or prevention of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques. In another embodiment, useful antibodies are immunospecific for the treatment of autoimmune diseases include, but are not limited to, Anti-Nuclear Antibody; Anti-ds DNA; Anti-ss DNA, Anti-Cardiolipin Antibody IgM, IgG; Anti-Phospholipid Antibody IgM, IgG; Anti-SM Antibody; Anti-Mitochondrial Antibody; Thyroid Antibody; Microsomal Antibody; Thyroglobulin Antibody; Anti-SCL-70; Anti-Jo; Anti-U$_1$RNP; Anti-La/SSB; Anti SSA; Anti-SSB; Anti-Perital Cells Antibody; Anti-Histones; Anti-RNP; C-ANCA; P-ANCA; Anti centromere; Anti-Fibrillarin, and Anti-GBM Antibody.

In certain embodiments, useful antibodies can bind to both a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the Ligand binds to an activated lymphocyte that is associated with an autoimmune disease.

In another specific embodiment, useful Ligands immunospecific for a viral or a microbial antigen are monoclonal antibodies. The antibodies may be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful Ligands are those that are useful for the treatment or prevention of viral or microbial infection in accordance with the methods disclosed herein. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG$_1$ antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma spp., Rickettsia prowazeki, Rickettsia tsutsugumushi, Chlamydia spp.*); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or *Helminiths (Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies which comprise Ab in Formula Ic antibody drug conjugates (ADC) and which may be useful in the treatment of cancer include, but are not limited to, antibodies against tumor-associated antigens (TAA). Such tumor-associated antigens are known in the art, and can prepared for use in generating antibodies using methods and information which are well known in the art. Examples of TAA include (1)-(35), but are not limited to TAA (1)-(35) listed below. For convenience, information relating to these antigens, all of which are known in the art, is listed below and includes names, alternative names, Genbank accession numbers and primary reference(s). Tumor-associated antigens targeted by antibodies include all amino acid sequence variants and isoforms possessing at least about 70%, 80%, 85%, 90%, or 95% sequence identity relative to the sequences identified in the corresponding sequences listed (SEQ ID NOS: 1-35) or the sequences identified in the cited references. In some embodiments, TAA having amino acid sequence variants exhibit substantially the same biological properties or characteristics as a TAA having the sequence found in the corresponding sequences listed (SEQ ID NOS: 1-35). For example, a TAA having a variant sequence generally is able to bind specifically to an antibody that binds specifically to the TAA with the corresponding sequence listed. The sequences and disclosure specifically recited herein are expressly incorporated by reference.

Tumor-Associated Antigens (1)-(35):

(1) BMPR1B (bone morphogenetic protein receptor-type IB, Genbank accession no. NM_001203, ten Dijke, P., et al. Science 264 (5155):101-104 (1994), Oncogene 14 (11): 1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4)

NP_001194 bone morphogenetic protein receptor, type IB/pid=NP_001194.1—Cross-references: MIM:603248; NP_001194.1; NM_001203_1

502 aa (SEQ ID NO: 1)
MLLRSAGKLNVGTKKEDGESTAPTPRPKVLRCKCHHHCPEDSVNNICSTD

GYCFTMIEEDDSGLPVVTSGCLGLEGSDFQCRDTPIPHQRRSIECCTERN

ECNKDLHPTLPPLKNRDFVDGPIHHRALLISVTVCSLLLVLIILFCYFRY

KRQETRPRYSIGLEQDETYIPPGESLRDLIEQSQSSGSGSGLPLLVQRTI

AKQIQMVKQIGKGRYGEVWMGKWRGEKVAVKVFFTTEEASWFRETEIYQT

VLMRHENILGFIAADIKGTGSWTQLYLITDYHENGSLYDYLKSTTLDAKS

MLKLAYSSVSGLCHLHTEIFSTQGKPAIAHRDLKSKNILVKKNGTCCIAD

LGLAVKFISDTNEVDIPPNTRVGTKRYMPPEVLDESLNRNHFQSYIMADM

YSFGLILWEVARRCVSGGIVEEYQLPYHDLVPSDPSYEDMREIVCIKKLR

PSFPNRWSSDECLRQMGKLMTECWAHNPASRLTALRVKKTLAKMSESQDI

KL (2) E16 (LAT1, SLC7A5, Genbank accession no. NM_003486); Biochem. Biophys. Res. Commun. 255 (2), 283-288 (1999), Nature 395 (6699):288-291 (1998), Gaugitsch, H. W., et al. (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150);

NP_003477 solute carrier family 7 (cationic amino acid transporter, y+system), member 5/pid=NP_003477.3—*Homo sapiens*

Cross-references: MIM:600182; NP_003477.3; NM_015923; NM_003486_1

507 aa (SEQ ID NO: 2)
MAGAGPKRRALAAPAAEEKEEAREKMLAAKSADGSAPAGEGEGVTLQRNI

TLLNGVAIIVGTIIGSGIFVTPTGVLKEAGSPGLALVVWAACGVFSIVGA

LCYAELGTTISKSGGDYAYMLEVYGSLPAFLKLWIELLIIRPSSQYIVAL

VFATYLLKPLFPTCPVPEEAAKLVACLCVLLLTAVNCYSVKAATRVQDAF

AAAKLLALALIILLGFVQIGKGVVSNLDPNFSFEGTKLDVGNIVLALYSG

LFAYGGWNYLNFVTEEMINPYRNLPLAIIISLPIVTLVYVLTNLAYFTTL

STEQMLSSEAVAVDFGNYHLGVMSWIIPVFVGLSCFGSVNGSLFTSSRLF

FVGSREGHLPSILSMIHPQLLTPVPSLVFTCVMTLLYAFSKDIFSVINFF

SFFNWLCVALAIIGMIWLRHRKPELERPIKVNLALPVFFILACLFLIAVS

FWKTPVECGIGFTIILSGLPVYEFGVWWKNKPKWLLQGIFSTTVLCQKLM

QVVPQET (3) STEAP1 (six transmembrane epithelial antigen of prostate, Genbank accession no. NM_012449

Figure 2:
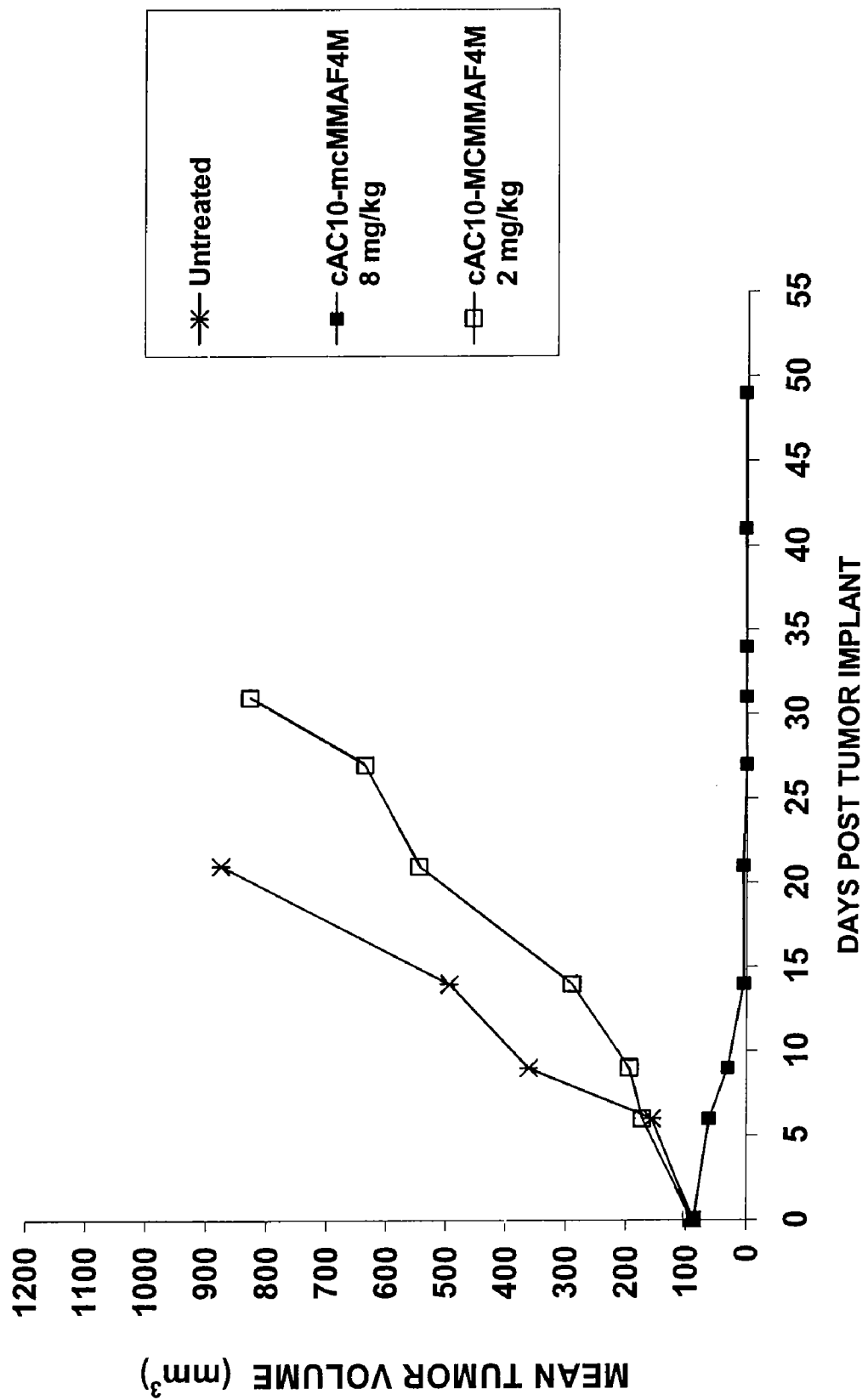
FIG. 2 shows an in vivo, single dose, efficacy assay of cAC10-mcMMAF in subcutaneous L540cy. For this study there were 4 mice in the untreated group and 10 in each of the treatment groups.

Cancer Res. 61 (15), 5857-5860 (2001), Hubert, R. S., et al. (1999) Proc. Natl. Acad. Sci. USA. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);

NP_036581 six transmembrane epithelial antigen of the prostate

Cross-references: MIM:604415; NP_036581.1; NM_012449_1

339 aa (SEQ ID NO 3)
MESRKDITNQEELWKMKPRRNLEEDDYLHKDTGETSMLKRPVLLHLHQTA

HADEFDCPSELQHTQELFPQWHLPIKIAAIIASLTFLYTLLREVIHPLAT

SHQQYFYKIPILVINKVLPMVSITLLALVYLPGVIAAIVQLHNGTKYKKF

PHWLDKWMLTRKQFGLLSFFFAVLHAIYSLSYPMRRSYRYKLLNWAYQQV

QQNKEDAWIEHDVWRMEIYVSLGIVGLAILALLAVTSIPSVSDSLTWREF

HYIQSKLGIVSLLLGTIHALIFAWNKWIDIKQFVWYTPPTFMIAVFLPIV

Figure 12:
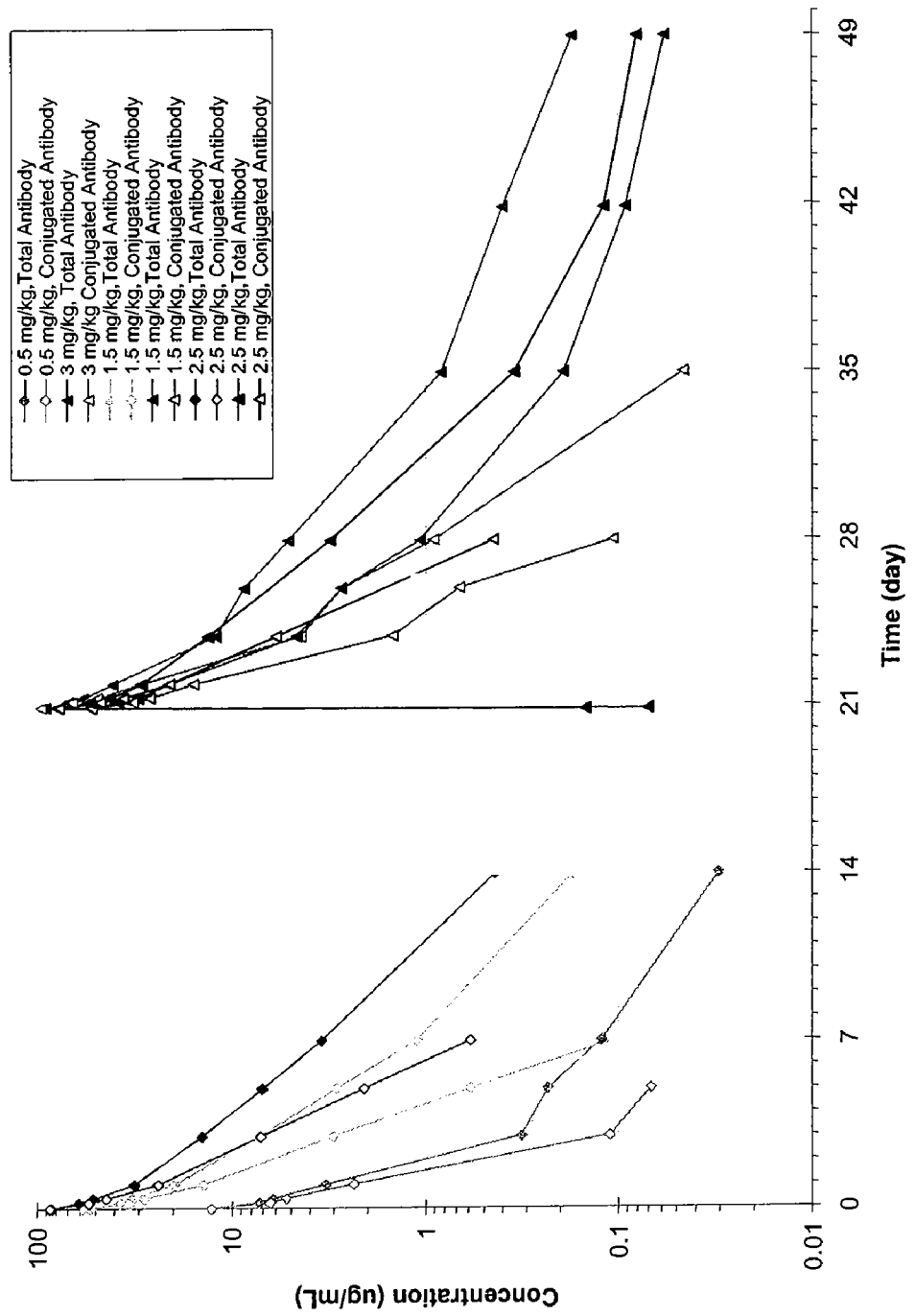
FIG. 12 shows a plasma concentration clearance study after administration of H-MC-vc-MMAE to Cynomolgus monkeys at different doses: 0.5, 1.5, 2.5, and 3.0 mg/kg administered at day 1 and day 21. Concentrations of total antibody and ADC were measured over time. (H=Trastuzumab).

VLIFKSILFLPCLRKKILKIRHGWEDVTKINKTEICSQL (4) 0772P (CA125, MUC16, Genbank accession no. AF361486 J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); US2003091580 (claim 6); WO200206317 (claim 6; Page 400-408);

Cross-references: GI:34501467; AAK74120.3; AF361486_1

6995 aa (SEQ ID NO: 4)
PVTSLLTPGLVITTDRMGISREPGTSSTSNLSSTSHERLTTLEDTVDTEA
MQPSTHTAVTNVRTSISGHESQSSVLSDSETPKATSPMGTTYTMGETSVS
ISTSDFFETSRIQIEPTSSLTSGLRETSSSERISSATEGSTVLSEVPSGA
TTEVSRTEVISSRGTSMSGPDQFTISPDISTEAITRLSTSPIMTESAESA
ITIETGSPGATSEGTLTLDTSTTTFWSGTHSTASPGFSHSEMTTLMSRTP
GDVPWPSLPSVEEASSVSSSLSSPAMTSTSFTSTLPESISSSPHPVTALL
TLGPVKTTDMLRTSSEPETSSPPNLSSTSAEILATSEVTKDREKIHPSSN
TPVVNVGTVIYKHLSPSSVLADLVTTKPTSPMATTSTLGNTSVSTSTPAF
PETMMTQPTSSLTSGLREISTSQETSSATERSASLSGMPTGATTKVSRTE
ALSLGRTSTPGPAQSTISPEISTETITRISTPLTTTGSAEMTITPKTGHS
GASSQGTFTLDTSSRASWPGTHSAATHRSPHSGMTTPMSRGPEDVSWPSR
PSVEKTSPPSSLVSLSAVTSPSPLYSTPSESSHSSPLRVTSLFTPVMMKT
TDMLDTSLEPVTTSPPSMNITSDESLATSKATMETEAIQLSENTAVTQMG
TISARQEFYSSYPGLPEPSKVTSPVVTSSTIKDIVSTTIPASSEITRIEM
ESTSTLTPTPRETSTSQEIHSATKPSTVPYKALTSATIEDSMTQVMSSSR
GPSPDQSTMSQDISTEVITRLSTSPIKTESTEMTITTQTGSPGATSRGTL
TLDTSTTTFMSGTHSTASQGFSHSQMTALMSRTPGEVPWLSHPSVEEASSA
SFSLSSPVMTSSSPVSSTLPDSIHSSSLPVTSLLTSGLVKTTELLGTSSE
PETSSPPNLSSTSAEILATTEVTTDTEKLSMTNVVTSGYTHESPSSVLAD
SVTTKATSSMGITYPTGDTNVLTSTPAFSDTSRIQTKSKLSLTPGLMETS
ISEETSSSATEKSTVLSSVPTGATTEVSRTEAISSSRTSIPGPAQSTMSSD
TSMETITRISTPLTRKESTDMAITPKTGPSGATSQGTFTLDSSSTASWPG
THSATTQRFPRSVVTTPMSRGPEDVSWPSPLSVEKNSPPSSLVSSSSVTS
PSPLYSTPSGSSHSSPVPVTSLFTSIMMKATDMLDASLEPETTSAPNMNI
TSDESLAASKATTETEAIHVFENTAASHVETTSATEELYSSSPGFSEPTK
VISPVVTSSSIRDNMVSTTMPGSSGITRIEIESMSSLTPGLRETRTSQDI
TSSTETSTVLYKMPSGATPEVSRTEVMPSSRTSIPGPAQSTMSLDISDEV
VTRLSTSPIMTESAEITITTQTGYSLATSQVTLPLGTSMTFLSGTHSTMS
QGLSHSEMTNLMSRGPESLSWTSPRFVETTRSSSSLTSLPLTTSLSPVSS
TLLDSSPSSPLPVTSLILPGLVKTTEVLDTSSEPKTSSSPNLSSTSVEIP
ATSEIMTDTEKIHPSSNTAVAKVRTSSSVHESHSSVLADSETTITIPSMG
ITSAVEDTTVFTSNPAFSETRRIPTEPTFSLTPGFRETSTSEETTSITET
SAVLFGVPTSATTEVSMTEIMSSNRTHIPDSDQSTMSPDIITEVITRLSS
SSMMSESTQMTITTQKSSPGATAQSTLTLATTTAPLARTHSTVPPRFLHS
EMTTLMSRSPENPSWKSSPFVEKTSSSSSLLSLPVTTSPSVSSTLPQSIP
SSSFSVTSLLTPGMVKTTDTSTEPGTSLSPNLSGTSVEILAASEVTTDTE
KIHPSSSMAVTNVGTTSSGHELYSSVSIHSEPSKATYPVGTPSSMAETSI
STSMPANFETTGFEAEPFSHLTSGLRKTNMSLDTSSVTPTNTPSSPGSTH
LLQSSKTDFTSSAKTSSPDWPPASQYTEIPVDIITPFNASPSITESTGIT

-continued

SFPESRFTMSVTESTHHLSTDLLPSAETISTGTVMPSLSEAMTSFATTGV
PRAISGSGSPFSRTESGPGDATLSTIAESLPSSTPVPFSSSTFTTTDSST
IPALHEITSSSATPYRVDTSLGTESSTTEGRLVMVSTLDTSSQPGRTSSS
PILDTRMTESVELGTVTSAYQVPSLSTRLTRTDGIMEHITKIPNEAAHRG
TIRPVKGPQTSTSPASPKGLHTGGTKRMETTTTALKTTTTALKTTSRATL
TTSVYTPTLGTLTPLNASMQMASTIPTEMMITTPYVFPDVPETTSSLATS
LGAETSTALPRTTPSVFNRESETTASLVSRSGAERSPVIQTLDVSSSEPD
TTASWVIHPAETIPTVSKTTPNFFHSELDTVSSTATSHGADVSSAIPTNI
SPSELDALTPLVTISGTDTSTTFPTLTKSPHETETRTTWLTHPAETSSTI
PRTIPNFSHHESDATPSIATSPGAETSSAIPIMTVSPGAEDLVTSQVTSS
GTDRNMTIPTLTLSPGEPKTIASLVTHPEAQTSSAIPTSTISPAVSRLVT
SMVTSLAAKTSTTNRALTNSPGEPATTVSLVTHSAQTSPTVPWTTSIFFH
SKSDTTPSMTTSHGAESSSAVPTPTVSTEVPGVVTPLVTSSRAVISTTIP
ILTLSPGEPETTPSMATSHGEEASSAIPTPTVSPGVPGVVTSLVTSSRAV
TSTTIPILTFSLGEPETTPSMATSHGTEAGSAVPTVLPEVPGMVTSLVAS
SRAVTSTTLPTLTLSPGEPETTPSMATSHGAEASSTVPTVSPEVPGVVTS
LVTSSSGVNSTSIPTLILSPGELETTPSMATSHGAEASSAVPTPTVSPGV
SGVVTPLVTSSRAVTSTTIPILTLSSSEPETTPSMATSHGVEASSAVLTV
SPEVPGMVTFLVTSSRAVTSTTIPTLTISSDEPETTTSLVTHSEAKMISA
IPTLGVSPTVQGLVTSLVTSSGSETSAFSNLTVASSQPETIDSWVAHPGT
EASSVVPTLTVSTGEPFTNISLVTHPAESSSTLPRTTSRFSHSELDTMPS
TVTSPEAESSSAISTTISPGIPGVLTSLVTSSGRDISATFPTVPESPHES
EATASWVTHPAVTSTTVPRTTPNYSHSEPDTTPSIATSPGAEATSDFPTI
TVSPDVPDMVTSQVTSSGTDTSITIPTLTLSSGEPETTTSFITYSETHTS
SAIPTLPVSPDASKMLTSLVISSGTDSTTTFPTLTETPYEPETTAIQLIH
PAETNTMVPRTTPKFSHSKSDTTLPVAITSPGPEASSAVSTTTISPDMSD
LVTSLVPSSGTDTSTTFPTLSETPYEPETTATWLTHPAETSTTVSGTIPN
FSHRGSDTAPSMVTSPGVDTRSGVPTTTIPPSIPGVVTSQVTSSATDTST
AIPTLTPSPGEPETTASSATHPGTQTGFTVPIRTVPSSEPDTMASWVTHP
PQTSTPVSRTTSSFSHSSPDATPVMATSPRTEASSAVLTTISPGAPEMVT
SQITSSGAATSTTVPTLTHSPGMPETTALLSTHPRTETSKTFPASTVFPQ
VSETTASLTIRPGAETSTALPTQTTSSLFTLLVTGTSRVDLSPTASPGVS
AKTAPLSTHPGTETSTMIPTSTLSLGLLETTGLLATSSSAETSTSTLTLT
VSPAVSGLSSASITTDKPQTVTSWNTETSPSVTSVGPPEFSRTVTGTTMT
LIPSEMPTPPKTSHGEGVSPTTILRTTMVEATNLATTGSSPTVAKTTTTF
NTLAGSLFTPLTTPGMSTLASESVTSRTSYNHRSWISTTSSYNRRYWTPA
TSTPVTSTFSPGISTSSIPSSTAATVPFMVPFTLNFTITNLQYEEDMRHP
GSRKFNATERELQGLLKPLFRNSSLFYLYSGCRLASLRPEKDSSATAVDA
ICTHRPDPEDLGLDRERLYWELSNLTNGIQELGPYTLDRNSLYVNGFTHR
SSMPTTSTPGTSTVDVGTSGTPSSSPSPTTAGPLLMPFTLNFTITNLQYE

-continued

```
EDMRRTGSRKFNTMESVLQGLLKPLFKNTSVGPLYSGCRLTLLRPEKDGA
ATGVDAICTHRLDPKSPGLNREQLYWELSKLTNDIEELGPYTLDRNSLYV
NGFTHQSSVSTTSTPGTSTVDLRTSGTPSSLSSPTIMAAGPLLVPFTLNF
TITNLQYGEDMGHPGSRKFNTTERVLQGLLGPIFKNTSVGPLYSGCRLTS
LRSEKDGAATGVDAICIHHLDPKSPGLNRERLYWELSQLTNGIKELGPYT
LDRNSLYVNGFTHRTSVPTTSTPGTSTVDLGTSGTPFSLPSPATAGPLLV
LFTLNFTITNLKYEEDMHRPGSRKFNTTERVLQTLVGPMFKNTSVGLLYS
GCRLTLLRSEKDGAATGVDAICTHRLDPKSPGVDREQLYWELSQLTNGIK
ELGPYTLDRNSLYVNGFTHWIPVPTSSTPGTSTVDLGSGTPSSLPSPTSA
TAGPLLVPFTLNFTITNLKYEEDMHCPGSRKFNTTERVLQSLLGPMFKNT
SVGPLYSGCRLTLLRSEKDGAATGVDAICTHRLDPKSPGVDREQLYWELS
QLTNGIKELGPYTLDRNSLYVNGFTHQTSAPNTSTPGTSTVDLGTSGTPS
SLPSPTSAGPLLVPFTLNFTITNLQYEEDMHHPGSRKFNTTERVLQGLLG
PMFKNTSVGLLYSGCRLTLLRPEKNGAATGMDAICSHRLDPKSPGLNREQ
LYWELSQLTHGIKELGPYTLDRNSLYVNGFTHRSSVAPTSTPGTSTVDLG
TSGTPSSLPSPTTAVPLLVPFTLNFTITNLQYGEDMRHPGSRKFNTTERV
LQGLLGPLFKNSSVGPLYSGCRLISLRSEKDGAATGVDAICTHHLNPQSP
GLDREQLYWQLSQMTNGIKELGPYTLDRNSLYVNGFTHRSSGLTTSTPWT
STVDLGTSGTPSPVPSPTTAGPLLVPFTLNFTITNLQYEEDMHRPGSRKF
NATERVLQGLLSPIFKNSSVGPLYSGCRLTSLRPEKDGAATGMDAVCLYH
PNPKRPGLDREQLYWELSQLTHNITELGPYSLDRDSLYVNGFTHQNSVPT
TSTPGTSTVYWATTGTPSSFPGHTEPGPLLIPFTFNFTITNLHYEENMQH
PGSRKFNTTERVLQGLLKPLFKNTSVGPLYSGCRLTLLRPEKQEAATGVD
TICTHRVDPIGPGLDRERLYWELSQLTNSITELGPYTLDRDSLYVNGFNP
WSSVPTTSTPGTSTVHLATSGTPSSLPGHTAPVPLLIPFTLNFTITNLHY
EENMQHPGSRKFNTTERVLQGLLKPLFKSTSVGPLYSGCRLTLLRPEKHG
AATGVDAICTLRLDPTGPGLDRERLYWELSQLTNSVTELGPYTLDRDSLY
VNGFTHRSSVPTTSIPGTSAVHLETSGTPASLPGHTAPGPLLVPFTLNFT
ITNLQYEEDMRHPGSRKFNTTERVLQGLLKPLFKSTSVGPLYSGCRLTLL
RPEKRGAATGVDTICTHRLDPLNPGLDREQLYWELSKLTRGIIELGPYLL
DRGSLYVNGFTHRNFVPITSTPGTSTVHLGTSETPSSLPRPIVPGPLLVP
FTLNFTITNLQYEEAMRHPGSRKFNTTERVLQGLLRPLFKNTSIGPLYSS
CRLTLLRPEKDKAATRVDAICTHHPDPQSPGLNREQLYWELSQLTHGITE
LGPYTLDRDSLYVDGFTHWSPIPTTSTPGTSIVNLGTSGIPPSLPETTAT
GPLLVPFTLNFTITNLQYEENMGHPGSRKFNITESVLQGLLKPLFKSTSV
GPLYSGCRLTLLRPEKDGVATRVDAICTHRPDPKIPGLDRQQLYWELSQL
THSITELGPYTLDRDSLYVNGFTQRSSVPTTSTPGTFTVQPETSETPSSL
PGPTATGPVLLPFTLNFTIINLQYEEDMHRPGSRKFNTTERVLQGLLMPL
FKNTSVSSLYSGCRLTLLRPEKDGAATRVDAVCTHRPDPKSPGLDRERLY
WKLSQLTHGITELGPYTLDRHSLYVNGFTHQSSMTTTRTPDTSTMHLATS
RTPASLSGPTTASPLLVLFTINFTITNLRYEENMHHPGSRKFNTTERVLQ
GLLRPVFKNTSVGPLYSGCRLTLLRPKKDGAATKVDAICTYRPDPKSPGL
DREQLYWELSQLTHSITELGPYTLDRDSLYVNGFTQRSSVPTTSIPGTPT
VDLGTSGTPVSKPGPSAASPLLVLFTLNFTITNLRYEENMQHPGSRKFNT
TERVLQGLLRSLFKSTSVGPLYSGCRLTLLRPEKDGTATGVDAICTHHPD
PKSPRLDREQLYWELSQLTHNITELGPYALDNDSLFVNGFTHRSSVSTTS
TPGTPTVYLGASKTPASIFGPSAASHLLILFTLNFTITNLRYEENMWPGS
RKFNTTERVLQGLLRPLFKNTSVGPLYSGCRLTLLRPEKDGEATGVDAIC
THRPDPTGPGLDREQLYLELSQLTHSITELGPYTLDRDSLYVNGFTHRSS
VPTTSTGVVSEEPFTLNFTINNLRYMADMGQPGSLKFNITDNVMQHLLSP
LFQRSSLGARYTGCRVIALRSVKNGAETRVDLLCTYLQPLSGPGLPIKQV
FHELSQQTHGITRLGPYSLDKDSLYLNGYNEPGPDEPPTTPKPATTFLPP
LSEATTAMGYHLKTLTLNFTISNLQYSPDMGKGSATFNSTEGVLQHLLRP
LFQKSSMGPFYLGCQLISLRPEKDGAATGVDTTCTYHPDPVGPGLDIQQL
YWELSQLTHGVTQLGFYVLDRDSLFINGYAPQNLSIRGEYQINFHIVNWN
LSNPDPTSSEYITLLRDIQDKVTTLYKGSQLHDTFRFCLVTNLTMDSVLV
TVKALFSSNLDPSLVEQVFLDKTLNASFHWLGSTYQLVDIHVTEMESSVY
QPTSSSSTQHFYLNFTITNLPYSQDKAQPGTTNYQRNKRNIEDALNQLFR
NSSIKSYFSDCQVSTFRSVPNRHHTGVDSLCNFSPLARRVDRVAIYEEFL
RMTRNGTQLQNFTLDRSSVLVDGYSPNRNEPLTGNSDLPFWAVILIGLAG
LLGLITCLICGVLVTTRRRKKEGEYNVQQQCPGYYQSHLDLEDLQ
```

(5) MPF (MPF, MSLN, SMR, megakaryocyte potentiating factor, mesothelin, Genbank accession no. NM_005823

Yamaguchi, N., et al. Biol. Chem. 269 (2), 805-808 (1994), Proc. Natl. Acad. Sci. USA. 96 (20):11531-11536 (1999), Proc. Natl. Acad. Sci. USA. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57);

Cross-references: MIM:601051; NP_005814.2; NM_005823_1

622 aa (SEQ ID NO: 5)
```
MALPTARPLLGSCGTPALGSLLFLLFSLGWVQPSRTLAGETGQEAAPLDG
VLANPPNISSLSPRQLLGFPCAEVSGLSTERVRELAVALAQKNVKLSTEQ
LRCLAHRLSEPPEDLDALPLDLLLFLNPDAFSGPQACTRFFSRITKANVD
LLPRGAPERQRLLPAALACWGVRGSLLSEADVRALGGLACDLPGRFVAES
AEVLLPRLVSCPGPLDQDQQEAARAALQGGGPPYGPPSTWSVSTMDALRG
LLPVLGQPIIRSIPQGIVAAWRQRSSRDPSWRQPERTILRPRFRREVEKT
ACPSGKKAREIDESLIFYKKWELEACVDAALLATQMDRVNAIPFTYEQLD
VLKHKLDELYPQGYPESVIQHLGYLFLKMSPEDIRKWNVTSLETLKALLE
```

-continued

```
VNKGHEMSPQVATLIDRFVKGRGQLDKDTLDTLTAFYPGYLCSLSPEELS

SVPPSSIWAVRPQDLDTCDPRQLDVLYPKARLAFQNMNGSEYFVKIQSFL

GGAPTEDLKALSQQNVSMDLATFMKLRTDAVLPLTVAEVQKLLGPHVEGL

KAEERHRPVRDWILRQRQDDLDTLGLGLQGGIPNGYLVLDLSMQEALSGT

PCLLGPGPVLTVLALLLASTLA
```

(6) Napi3b (NAPI-3B, NPTIIb, SLC34A2, solute carrier family 34 (sodium phosphate), member 2, type II sodium-dependent phosphate transporter 3b, Genbank accession no. NM_006424, J. Biol. Chem. 277 (22):19665-19672 (2002), Genomics 62 (2):281-284 (1999), Feild, J. A., et al. (1999) Biochem. Biophys. Res. Commun. 258 (3):578-582); WO2004022778 (claim 2); EP1394274 (Example 11); WO2002102235 (claim 13; Page 326); EP875569 (claim 1;Page 17-19); WO200157188 (claim 20; Page 329); WO2004032842 (Example IV); WO200175177 (claim 24; Page 139-140);

Cross-references: MIM:604217; NP_006415.1; NM_006424_1

690 aa

```
                                            (SEQ ID NO: 6)
MAPWPELGDAQPNPDKYLEGAAGQQPTAPDKSKETNKTDNTEAPVTKIEL

LPSYSTATLIDEPTEVDDPWNLPTLQDSGIKWSERDTKGKILCFFQGIGR

LILLLGFLYFFVCSLDILSSAFQLVGGKMAGQFFSNSSIMSNPLLGLVIG

VLVTVLVQSSSTSTSIVVSMVSSSLLTVRAAIPIIMGANIGTSITNTIVA

LMQVGDRSEFRRAFAGATVHDFFNWLSVLVLLPVEVATHYLEIITQLIVE

SEHFKNGEDAPDLLKVITKPETKLIVQLDKKVISQIAMNDEKAKNKSLVK

IWCKTFTNKTQINVTVPSTANCTSPSLCWTDGIQNWTMKNVTYKENIAKC

QHIFVNFHLPDLAVGTILLILSLLVLCGCLIMIVKILGSVLKGQVATVIK

KTINTDFPFPFAWLTGYLAILVGAGMTFIVQSSSVFTSALTPLIGIGVIT

IERAYPLTLGSNIGTTTTAILAALASPGNALRSSLQIALCHFFFNISGIL

LWYPIPFTRLPIRMAKGLGNISAKYRWFAVFYLIIFFFLIPLTVFGLSLA

GWRVLVGVGVPVVFIIILVLCLRLLQSRCPRVLPKKLQNWNFLPLWMRSL

KPWDAVVSKFTGCFQMRCCYCCRVCCRACCLLCGCPKCCRCSKCCEDLEE

AQEGQDVPVKAPETFDNITISREAQGEVPASDSKTECTAL
```

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878, Nagase T., et al. (2000) DNA Res. 7 (2):143-150); WO2004000997 (claim 1); WO2003003984 (claim 1); WO200206339 (claim 1; Page 50); WO200188133 (claim 1;Page 41-43, 48-58); WO2003054152 (claim 20); WO2003101400 (claim 11); Accession: Q9P283; EMBL; AB040878; BAA95969.1. Genew; HGNC:10737;

1093 aa

```
                                            (SEQ ID NO: 7)
MVLAGPLAVSLLLPSLTLLVSHLSSSQDVSSEPSSEQQLCALSKHPTVAF

EDLQPWVSNFTYPGARDFSQLALDPSGNQLIVGARNYLFRLSLANVSLLQ

ATEWASSEDTRRSCQSKGKTEEECQNYVRVLIVAGRKVFMCGTNAFSPMC

TSRQVGNLSRTTEKINGVARCPYDPRHNSTAVISSQGELYAATVIDFSGR

DPAIYRSLGSGPPLRTAQYNSKWLNEPNFVAAYDIGLFAYFFLRENAVEH

DCGRTVYSRVARVCKNDVGGRFLLEDTWTTFMKARLNCSRPGEVPFYYNE

LQSAFHLPEQDLIYGVFTTNVNSIAASAVCAFNLSAISQAFNGPFRYQEN

PRAAWLPIANPIPNFQCGTLPETGPNENLTERSLQDAQRLFLMSEAVQPV

TPEPCVTQDSVRFSHLVVDLVQAKDTLYHVLYIGTESGTILKALSTASRS

LHGCYLEELHVLPPGRREPLRSLRILHSARALFVGLRDGVLRVPLERCAA

YRSQGACLGARDPYCGWDGKQQRCSTLEDSSNMSLWTQNITACPVRNVTR

DGGFGPWSPWQPCEHLDGDNSGSCLCRARSCDSPRPRCGGLDCLGPAIHI

ANCSRNGAWTPWSSWALCSTSCGIGFQVRQRSCSNPAPRHGGRICVGKSR

EERFCNENTPCPVPIFWASWGSWSKCSSNCGGGMQSRRRACENGNSCLGC

GVEFKTCNPEGCPEVRRNTPWTPWLPVNVTQGGARQEQRFRFTCRAPLAD

PHGLQFGRRRTETRTCPADGSGSCDTDALVEDLLRSGSTSPHTVSGGWAA

WGPWSSCSRDCELGFRVRKRTCTNPEPRNGGLPCVGDAAEYQDCNPQACP

VRGAWSCWTSWSPCSASCGGGHYQRTRSCTSPAPSPGEDICLGLHTEEAL

CATQACPEGWSPWSEWSKCTDDGAQSRSRHCEELLPGSSACAGNSSQSRP

CPYSEIPVILPASSMEEATGCAGFNLIHLVATGISCFLGSGLLTLAVYLS

CQHCQRQSQESTLVHPATPNHLHYKGGGTPKNEKYTPMEFKTLNKNNLIP

DDRANFYPLQQTNVYTTTYYPSPLNKHSFRPEASPGQRCFPNS
```

(8) PSCA hlg (2700050C12Rik, C530008O16Rik, RIKEN cDNA 2700050C12, RIKEN cDNA 2700050C12 gene, Genbank accession no. AY358628);

US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1

141 aa

```
                                            (SEQ ID NO: 8)
MWVLGIAATFCGLFLLPGFALQIQCYQCEEFQLNNDCSSPEFIVNCTVNV

QDMCQKEVMEQSAGIMYRKSCASSAACLIASAGYQSFCSPGKLNSVCISC

CNTPLCNGPRPKKRGSSASALRPGLRTTILFLKLALFSAHC
```

(9) ETBR (Endothelin type B receptor, Genbank accession no. AY275463);

Nakamuta M., et al. Biochem. Biophys. Res. Commun. 177, 34-39, 1991; Ogawa Y., et al. Biochem. Biophys. Res. Commun. 178, 248-255, 1991; Arai H., et al. Jpn. Circ. J. 56, 1303-1307, 1992; Arai H., et al. J. Biol. Chem. 268, 3463-3470, 1993; Sakamoto A., Yanagisawa M., et al. Biochem. Biophys. Res. Commun. 178, 656-663, 1991; Elshourbagy N.

A., et al. J. Biol. Chem. 268, 3873-3879, 1993; Haendler B., et al. J. Cardiovasc. Pharmacol. 20, s1-S4, 1992; Tsutsumi M., et al. Gene 228, 43-49, 1999; Strausberg R. L., et al. Proc. Natl. Acad. Sci. USA. 99, 16899-16903, 2002; Bourgeois C., et al. J. Clin. Endocrinol. Metab. 82, 3116-3123, 1997; Okamoto Y., et al. Biol. Chem. 272, 21589-21596, 1997; Verheij J. B., et al. Am. J. Med. Genet. 108, 223-225, 2002; Hofstra R. M. W., et al. Eur. J. Hum. Genet. 5, 180-185, 1997; Puffenberger E. G., et al. Cell 79, 1257-1266, 1994; Attie T., et al, Hum. Mol. Genet. 4, 2407-2409, 1995; Auricchio A., et al. Hum. Mol. Genet. 5:351-354, 1996; Amiel J., et al. Hum. Mol. Genet. 5, 355-357, 1996; Hofstra R. M. W., et al. Nat. Genet. 12, 445-447, 1996; Svensson P. J., et al. Hum. Genet. 103, 145-148, 1998; Fuchs S., et al. Mol. Med. 7, 115-124, 2001; Pingault V., et al. (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1;Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004;

442 aa (SEQ ID NO: 9)
MQPPPSLCGRALVALVLACGLSRIWGEERGFPPDRATPLLQTAEIMTPPT

KTLWPKGSNASLARSLAPAEVPKGDRTAGSPPRTISPPPCQGPIEIKETF

KYINTVVSCLVFVLGIIGNSTLLRIIYKNKCMRNGPNILIASLALGDLLH

IVIDIPINVYKLLAEDWPFGAEMCKLVPFIQKASVGITVLSLCALSIDRY

RAVASWSRIKGIGVPKWTAVEIVLIWVVSVVLAVPEAIGFDIITMDYKGS

YLRICLLHPVQKTAFMQFYKTAKDWWLFSFYFCLPLAITAFFYTLMTCEM

LRKKSGMQIALNDHLKQRREVAKTVFCLVLVFALCWLPLHLSRILKLTLY

NQNDPNRCELLSFLLVLDYIGINMASLNSCINPIALYLVSKRFKNCFKSC

LCCWCQSFEEKQSLEEKQSCLKFKANDHGYDNFRSSNKYSSS

(10) MSG783 (RNF124, hypothetical protein FLJ20315, Genbank accession no. NM_017763);

WO2003104275 (claim 1); WO2004046342 (Example 2); WO2003042661 (claim 12); WO2003083074 (claim 14; Page 61); WO2003018621 (claim 1); WO2003024392 (claim 2;FIG. 93); WO200166689 (Example 6);

Cross-references: LocusID:54894; NP_060233.2; NM_017763_1

783 aa (SEQ ID NO: 10)
MSGGHQLQLAALWPWLLMATLQAGFGRTGLVLAAAVESERSAEQKAIIRV

IPLKMDPTGKLNLTLEGVFAGVAEITPAEGKLMQSHPLYLCNASDDDNLE

PGFISIVKLESPRRAPRPCLSLASKARMAGERGASAVLFDITEDRAAAEQ

LQQPLGLTWPVVLIWGNDAEKLMEFVYKNQKAHVRIELKEPPAWPDYDVW

ILMTVVGTIFVIILASVLRIRCRPRHSRPDPLQQRTAWAISQLATRRYQA

SCRQARGEWPDSGSSCSSAPVCAICLEEFSEGQELRVISCLHEFHRNCVD

PWLHQHRTCPLCVFNITEGDSFSQSLGPSRSYQEPGRRLHLIRQHPGHAH

YHLPAAYLLGPSRSAVARPPRPGPFLPSQEPGMGPRHHRFPRAAHPRAPG

EQQRLAGAQHPYAQGWGMSHLQSTSQHPAACPVPLRRARPPDSSGSGESY

CTERSGYLADGPASDSSSGPCHGSSSDSVVNCTDISLQGVHGSSSTFCSS

LSSDFDPLVYCSPKGDPQRVDMQPSVTSRPRSLDSVVPTGETQVSSHVHY

HRHRHHHYKKRFQWHGRKPGPETGVPQSRPPIPRTQPQPEPPSPDQQVTG

SNSAAPSGRLSNPQCPRALPEPAPGPVDASSICPSTSSLFNLQKSSLSAR

HPQRKRRGGPSEPTPGSRPQDATVHPACQIFPHYTPSVAYPWSPEAHPLI

CGPPGLDKRLLPETPGPCYSNSQPVWLCLTPRQPLEPHPPGEGPSEWSSD

TAEGRPCPYPHCQVLSAQPGSEEELEELCEQAV

Figure 4A:
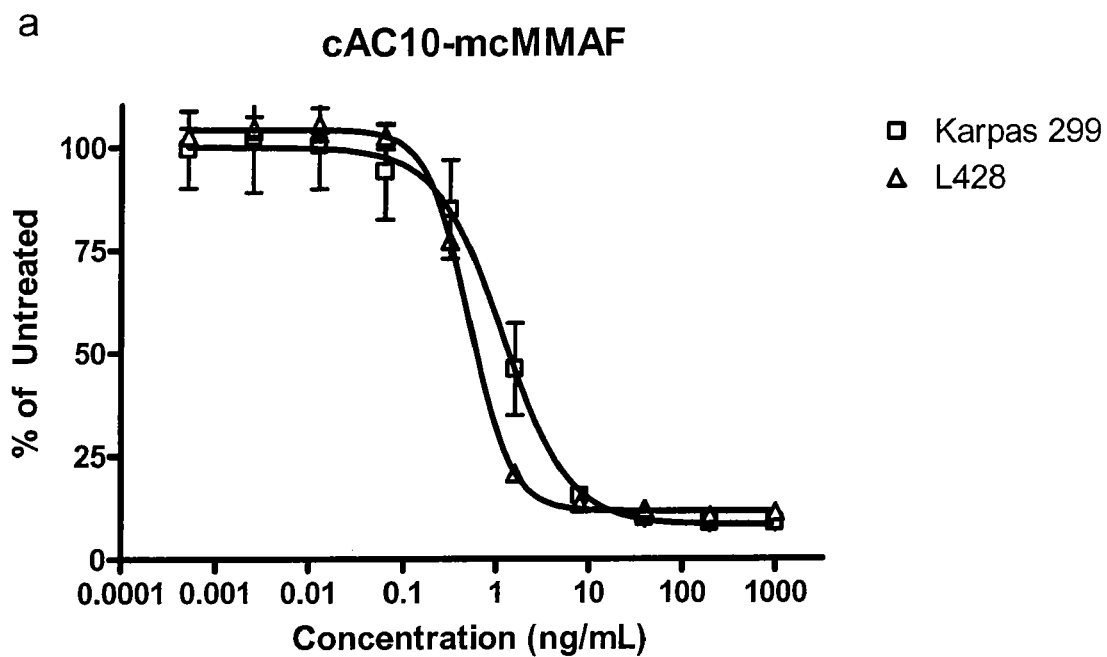
FIGS. 4a and 4b show in vitro activity of cAC10-antibody-drug conjugates against $CD30^+$ cell lines.
Figure 4B:
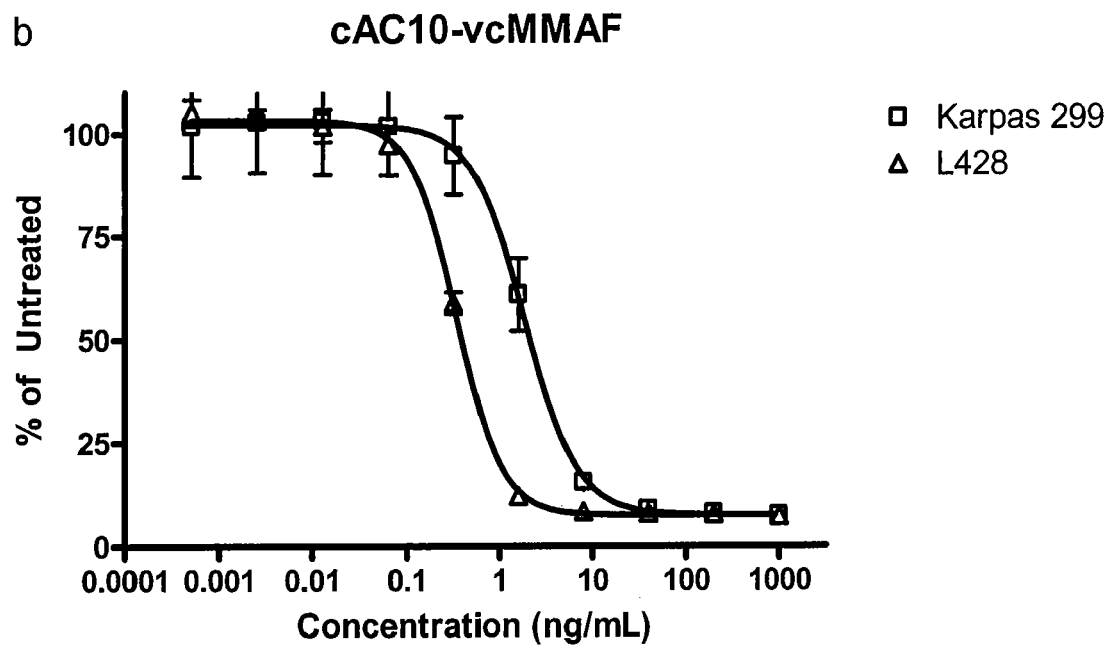
Figure 10:
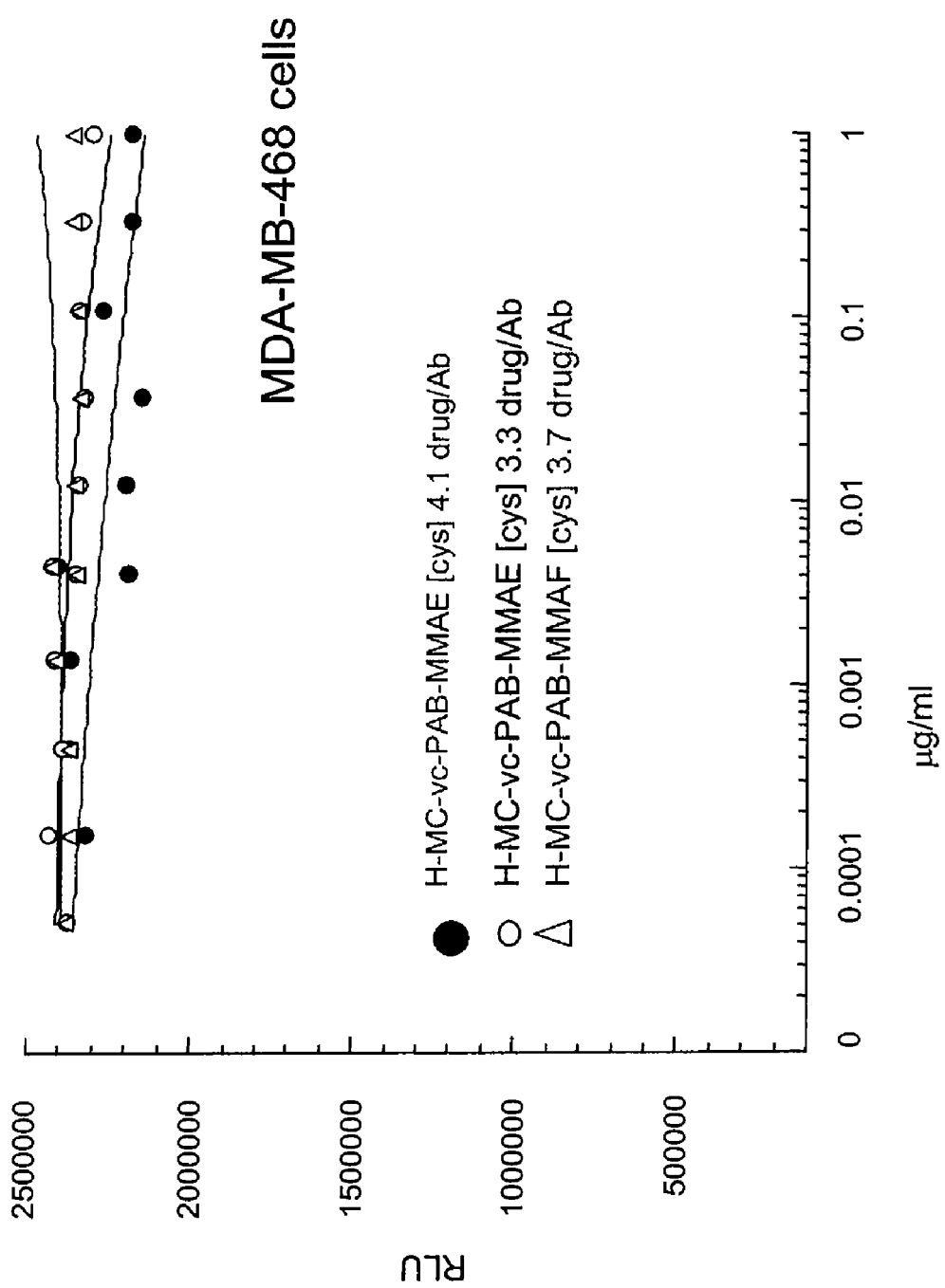
FIG. 10 shows an in vitro, cell proliferation assay with MDA-MB-468 cells treated with ADC: -●-Trastuzumab-MC-vc-PAB-MMAE, 4.1 MMAE/Ab, -○- Trastuzumab-MC-vc-PAB-MMAE, 3.3 MMAE/Ab, and -Δ- Trastuzumab-MC-vc-PAB-MMAF, 3.7 MMAF/Ab.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138, Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10);

Cross-references: GI:22655488; AAN04080.1; AF455138_1

490 aa (SEQ ID NO: 11)
MESISMMGSPKSLSETVLPNGINGIKDARKVTVGVIGSGDFAKSLTIRLI

RCGYHVVIGSRNPKFASEFFPHVVDVTHHEDALTKTNIIFVAIHREHYTS

LWDLRHLLVGKILIDVSNNMRINQYPESNAEYLASLFPDSLIVKGFNVVS

AWALQLGPKDASRQVYICSNNIQARQQVIELARQLNFIPIDLGSLSSARE

IENLPLRLFTLWRGPVVVAISLATFFFLYSFVRDVIHPYARNQQSDFYKI

PIEIVNKTLPIVAITLLSLVYLAGLLAAAYQLYYGTKYRRFPPWLETWLQ

CRKQLGLLSFFFAMVHVAYSLCLPMRRSERYLFLNMAYQQVHANIENSWN

EEEVWRIEMYISFGIMSLGLLSLLAVTSIPSVSNALNWREFSFIQSTLGY

VALLISTFHVLIYGWKRAFEEEYYRFYTPPNFVLALVLPSIVILGKIILF

LPCISQKLKRIKKGWEKSQFLEEGIGGTIPHVSPERVTVM

(12) TrpM4 (BR22450, FLJ20041, TRPM4, TRPM4B, transient receptor potential cation channel, subfamily M, member 4, Genbank accession no. NM_017636

Xu, X. Z., et al. Proc. Natl. Acad. Sci. USA. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D);

Cross-references: MIM:606936; NP_060106.2; NM_017636_1

1214 aa (SEQ ID NO: 12)
MVVPEKEQSWISKIFKKKTCTTFIVDSTDPGGTLCQCGRPRTAHPAVAME

DAFGAAVVTVWDSDAHTTEKPTDAYGELDFTGAGRKHSNFLRLSDRTDPA

AVYSLVTRTWGFRAPNLVVSVLGGSGGPVLQTWLQDLLRRGLVRAAQSTG

AWIVTGGLHTGIGRHVGVAVRDHQMASTGGTKVVAMGVAPWGVVRNRDTL

INPKGSFPARYRWRGDPEDGVQFPLDYNYSAFFLVDDGTHGCLGGENRFR

LRLESYISQQKTGVGGTGIDIPVLLLLIDGDEKMLTRIENATQAQLPCLL

VAGSGGAADCLAETLEDTLAPGSGGARQGEARDRIRRFFPKGDLEVLQAQ

VERIMTRKELLTVYSSEDGSEEFETIVLKALVKACGSSEASAYLDELRLA

VAWNRVDIAQSELFRGDIQWRSFHLEASLMDALLNDRPEFVRLLISHGLS

LGHFLTPMRLAQLYSAAPSNSLIRNLLDQASHSAGTKAPALKGGAAELRP

PDVGHVLRMLLGKMCAPRYPSGGAWDPHPGQGFGESMYLLSDKATSPLSL

DAGLGQAPWSDLLLWALLLNRAQMAMYFWEMGSNAVSSALGACLLLRVMA

RLEPDAEEAARRKDLAFKFEGMGVDLEGECYRSSEVRAARLLLRRCPLWG

DATCLQLAMQADARAFFAQDGVQSLLTQKWWGDMASTTPIWALVLAFFCP

PLIYTRLITFRKSEEEPTREELEFDMDSVINGEGPVGTADPAEKTPLGVP

RQSGRPGCCGGRCGGRRCLRRWFHFWGAPVTIFMGNVVSYLLFLLLFSRV

LLVDFQPAPPGSLELLLYFWAFTLLCEELRQGLSGGGGSLASGGPGPGHA

SLSQRLRLYLADSWNQCDLVALTCFLLGVGCRLTPGLYHLGRTVLCIDFM

VFTVRLLHIFTVNKQLGPKIVIVSKMMKDVFFFLFFLGVWLVAYGVATEG

LLRPRDSDFPSILRRVFYRPYLQIFGQIPQEDMDVALMEHSNCSSEPGFW

AHPPGAQAGTCVSQYANWLVVLLLVIFLLVANILLVNLLIAMFSYTFGKV

QGNSDLYWKAQRYRLIREFHSRPALAPPFIVISHLRLLLRQLCRRPRSPQ

PSSPALEHFRVYLSKEAERKLLTWESVHKENFLLARARDKRESDSERLKR

TSQKVDLALKQLGHIREYEQRLKVLEREVQQCSRVLGWVAEALSRSALLP

PGGPPPPDLPGSKD

(13) CRIPTO (CR, CR1, CRGF, CRIPTO, TDGF1, teratocarcinoma-derived growth factor, Genbank accession no. NP_003203 or NM_003212, Ciccodicola, A., et al. EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

188 aa (SEQ ID NO: 13)
MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGICLSIQSYY

Figure 9:
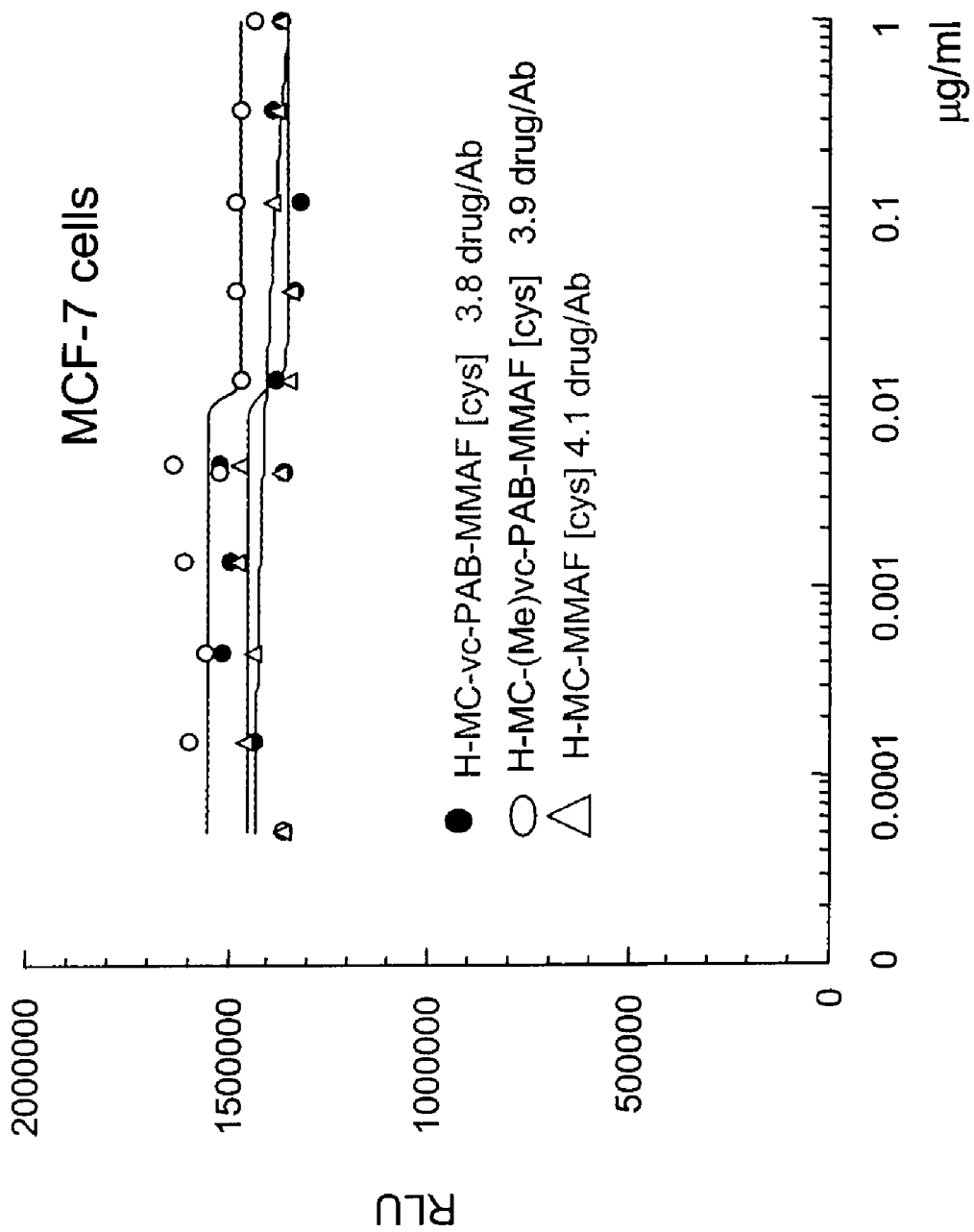
FIG. 9 shows an in vitro, cell proliferation assay with MCF-7 cells treated with ADC: -●- Trastuzumab-MC-vc-PAB-MMAF, 3.8 MMAF/Ab, -○- Trastuzumab-MC-(N-Me)vc-PAB-MMAF, 3.9 MMAF/Ab, and -Δ- Trastuzumab-MC-MMAF, 4.1 MMAF/Ab.

(14) CD21 (CR2 (Complement receptor 2) or C3DR (C3d/Epstein Barr virus receptor) or Hs.73792 Genbank accession no. M26004, Fujisaku et al. (1989) J. Biol. Chem. 264 (4):2118-2125); Weis J. J., et al. J. Exp. Med. 167, 1047-1066, 1988; Moore M., et al. Proc. Natl. Acad. Sci. USA. 84, 9194-9198, 1987; Barel M., et al. Mol. Immunol. 35, 1025-1031, 1998; Weis J. J., et al. Proc. Natl. Acad. Sci. USA. 83, 5639-5643, 1986; Sinha S. K., et al. (1993) J. Immunol. 150, 5311-5320; WO2004045520 (Example 4); US2004005538 (Example 1); WO2003062401 (claim 9); WO2004045520 (Example 4); WO9102536 (FIG. 9.1-9.9); WO2004020595 (claim 1);

Accession: P20023; Q13866; Q14212; EMBL; M26004; AAA35786.1.

1033 aa (SEQ ID NO: 14)
MGAAGLLGVFLALVAPGVLGISCGSPPPILNGRISYYSTPIAVGTVIRYS

CSGTFRLIGEKSLLCITKDKVDGTWDKPAPKCEYFNKYSSCPEPIVPGGY

KIRGSTPYRHGDSVTFACKTNFSMNGNKSVWCQANNMWGPTRLPTCVSVF

PLECPALPMIHNGHHTSENVGSIAPGLSVTYSCESGYLLVGEKIINCLSS

GKWSAVPPTCEEARCKSLGRFPNGKVKEPPILRVGVTANFFCDEGYRLQG

PPSSRCVIAGQGVAWTKMPVCEEIFCPSPPPILNGRHIGNSLANVSYGSI

VTYTCDPDPEEGVNFILIGESTLRCTVDSQKTGTWSGPAPRCELSTSAVQ

CPHPQILRGRMVSGQKDRYTYNDTVIFACMFGFTLKGSKQIRCNAQGTWE

PSAPVCEKECQAPPNILNGQKEDRHMVRFDPGTSIKYSCNPGYVLVGEES

IQCTSEGVWTPPVPQCKVAACEATGRQLLTKPQHQFVRPDVNSSCGEGYK

LSGSVYQECQGTIPWFMEIRLCKEITCPPPPVIYNGAHTGSSLEDFPYGT

TVTYTCNPGPERGVEFSLIGESTIRCTSNDQERGTWSGPAPLCKLSLLAV

QCSHVHIANGYKISGKEAPYFYNDTVTFKCYSGFTLKGSSQIRCKADNTW

DPEIPVCEKETCQHVRQSLQELPAGSRVELVNTSCQDGYQLTGHAYQMCQ

DAENGIWFKKIPLCKVIHCHPPPVIVNGKHTGMMAENFLYGNEVSYECDQ

GFYLLGEKKLQCRSDSKGHGSWSGPSPQCLRSPPVTRCPNPEVKHGYKLN

KTHSAYSHNDIVYVDCNPGFIMNGSRVIRCHTDNTWVPGVPTCIKKAFIG

CPPPPKTPNGNHTGGNIARFSPGMSILYSCDQGYLLVGEALLLCTHEGTW

SQPAPHCKEVNCSSPADMDGIQKGLEPRKMYQYGAVVTLECEDGYMLEGS

PQSQCQSDHQWNPPLAVCRSRSLAPVLCGIAAGLILLTFLIVITLYVISK

HRERNYYTDTSQKEAFHLEAREVYSVDPYNPAS

(15) CD79b (CD79B, CD79β, IGb (immunoglobulin-associated beta), B29, Genbank accession no. NM_000626 or 11038674, Proc. Natl. Acad. Sci. USA. (2003) 100 (7):4126-4131, Blood (2002) 100 (9):3068-3076, Muller et al. (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No.

5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP_000617.1; NM_000626_1

229 aa (SEQ ID NO: 15)
MARLALSPVPSHWMVALLLLLSAEPVPAARSEDRYRNPKGSACSRIWQSP

RFIARKRGFTVKMHCYMNSASGNVSWLWKQEMDENPQQLKLEKGRMEESQ

NESLATLTIQGIRFEDNGIYFCQQKCNNTSEVYQGCGTELRVMGFSTLAQ

LKQRNTLKDGIIMIQTLLIILFIIVPIFLLLDKDDSKAGMEEDHTYEGLD

IDQTATYEDIVTLRTGEVKWSVGEHPGQE

(16) FcRH2 (IFGP4, IRTA4, SPAP1A (SH2 domain containing phosphatase anchor protein 1a), SPAP1B, SPAP1C, Genbank accession no. NM_030764, Genome Res. 13 (10):2265-2270 (2003), Immunogenetics 54 (2):87-95 (2002), Blood 99 (8):2662-2669 (2002), Proc. Natl. Acad. Sci. USA. 98 (17):9772-9777 (2001), Xu, M. J., et al. (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12); WO2003089624 (claim 25);

Cross-references: MIM:606509; NP_110391.2; NM_030764_1

508 aa (SEQ ID NO: 16)
MLLWSLLVIFDAVTEQADSLTLVAPSSVFEGDSIVLKCQGEQNWKIQKMA

YHKDNKELSVFKKFSDFLIQSAVLSDSGNYFCSTKGQLFLWDKTSNIVKI

KVQELFQRPVLTASSFQPIEGGPVSLKCETRLSPQRLDVQLQFCFFRENQ

VLGSGWSSSPELQISAVWSEDTGSYWCKAETVTHRIRKQSLQSQIHVQRI

PISNVSLEIRAPGGQVTEGQKLILLCSVAGGTGNVTFSWYREATGTSMGK

KTQRSLSAELEIPAVKESDAGKYYCRADNGHVPIQSKVVNIPVRIPVSRP

VLTLRSPGAQAAVGDLLELHCEALRGSPPILYQFYHEDVTLGNSSAPSGG

GASFNLSLTAEHSGNYSCEANNGLGAQCSEAVPVSISGPDGYRRDLMTAG

VLWGLFGVLGFTGVALLLYALFHKISGESSATNEPRGASRPNPQEFTYSS

PTPDMEELQPVYVNVGSVDVDVVYSQVWSMQQPESSANIRTLLENKDSQV

IYSSVKKS

Figure 7:
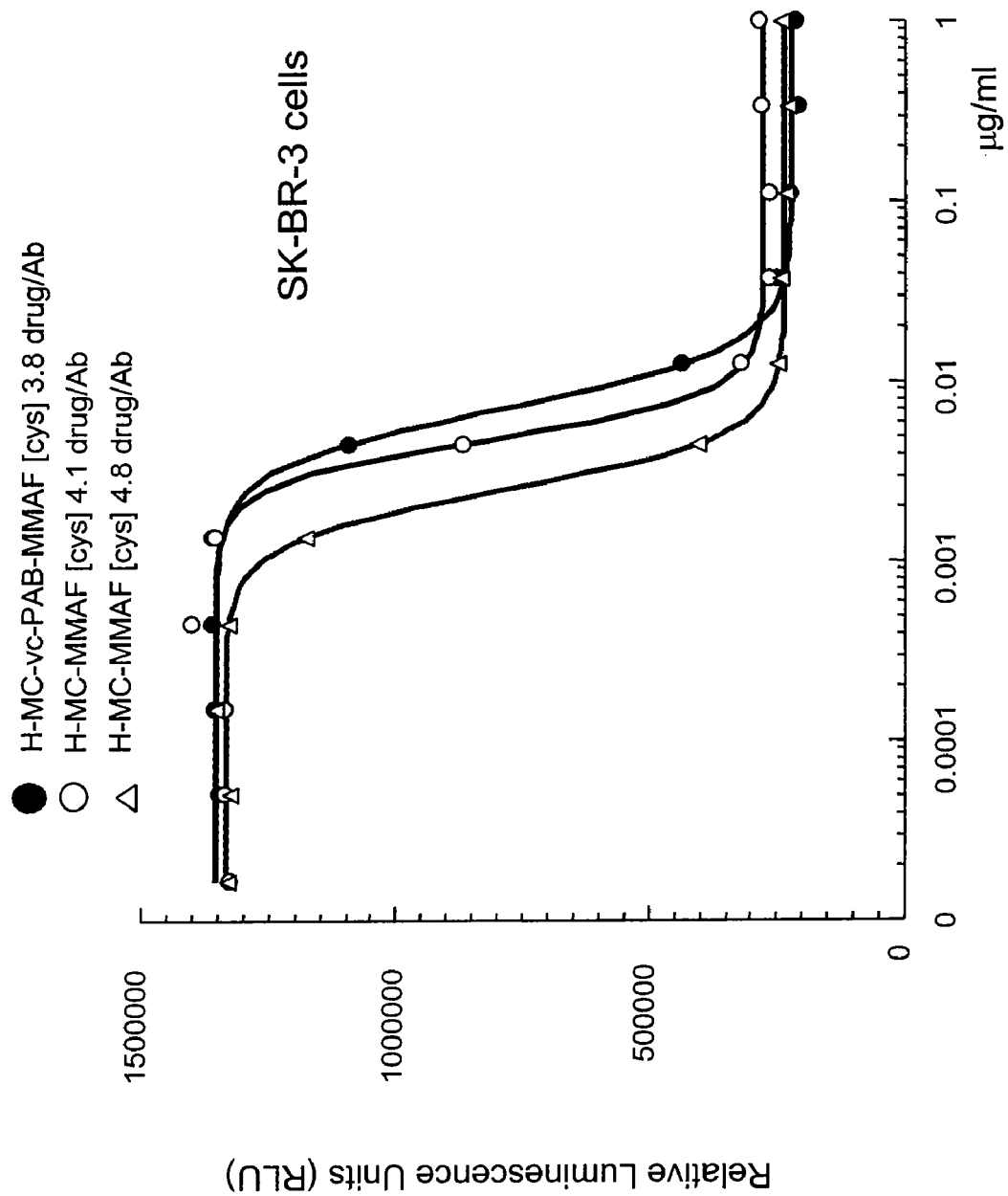
FIG. 7 shows an in vitro, cell proliferation assay with SK-BR-3 cells treated with antibody drug conjugates (ADC): -●- Trastuzumab-MC-vc-PAB-MMAF, 3.8 MMAF/Ab, -○- Trastuzumab-MC-MMAF, 4.1 MMAF/Ab, and -Δ- Trastuzumab-MC-MMAF, 4.8 MMAF/Ab, measured in Relative Fluorescence Units (RLU) versus µg/ml concentration of ADC. H=Trastuzumab where H is linked via a cysteine [cys].
Figure 11:
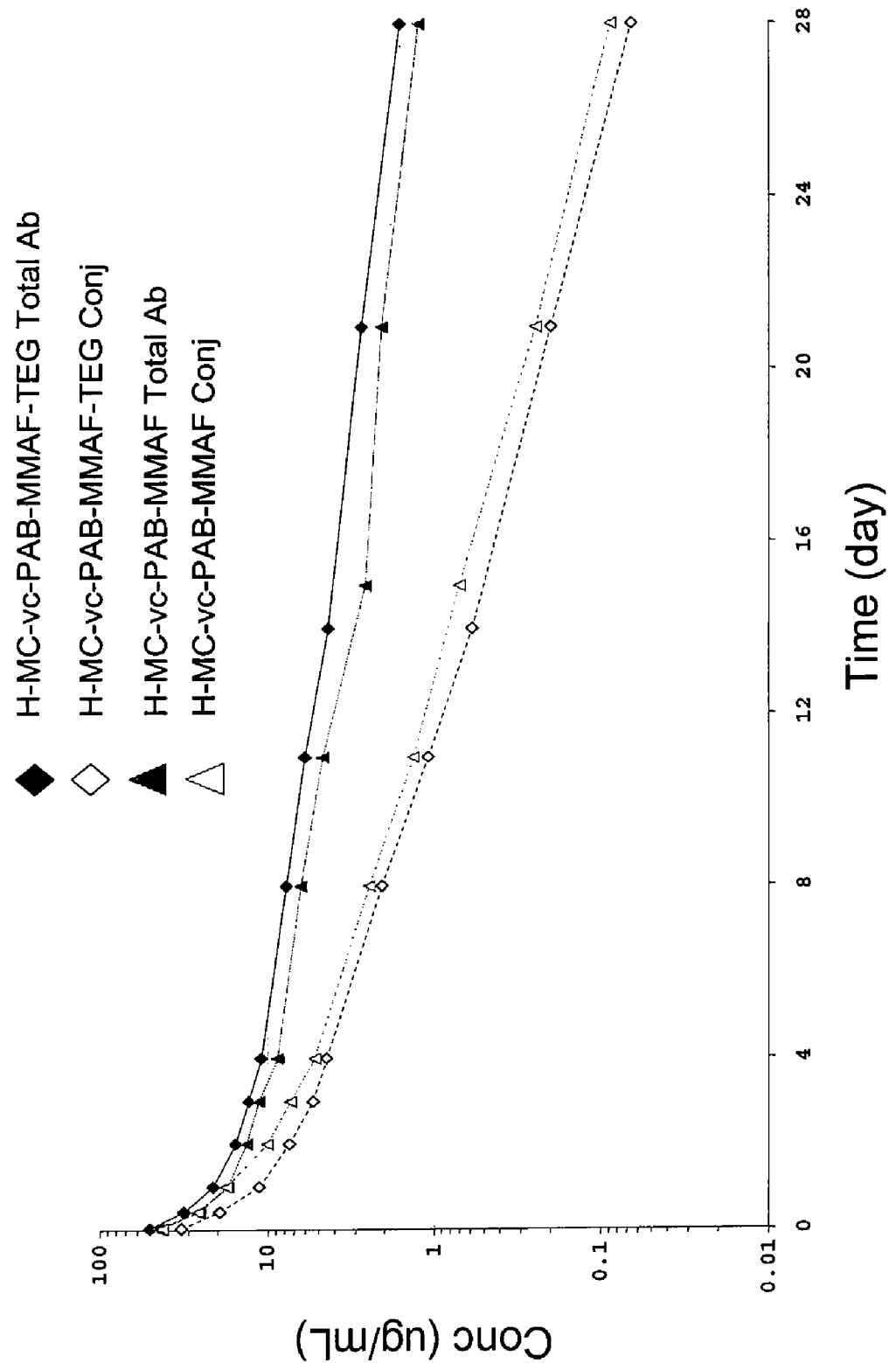
FIG. 11 shows a plasma concentration clearance study after administration of H-MC-vc-PAB-MMAF-TEG and H-MC-vc-PAB-MMAF to Sprague-Dawley rats: The administered dose was 2 mg of ADC per kg of rat. Concentrations of total antibody and ADC were measured over time. (H=Trastuzumab).

(17) HER2 (ErbB2, Genbank accession no. M11730, Coussens L., et al. Science (1985) 230(4730):1132-1139); Yamamoto T., et al. Nature 319, 230-234, 1986; Semba K., et al. Proc. Natl. Acad. Sci. USA. 82, 6497-6501, 1985; Swiercz J. M., et al. J. Cell Biol. 165, 869-880, 2004; Kuhns J. J., et al. J. Biol. Chem. 274, 36422-36427, 1999; Cho H.-S., et al. Nature 421, 756-760, 2003; Ehsani A., et al. (1993) Genomics 15, 426-429; WO2004048938 (Example 2); WO2004027049 (FIG. 11); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4);

Accession: P04626; EMBL; M11767; AAA35808.1. EMBL; M11761;

AAA35808.1.

1255 aa (SEQ ID NO: 17)
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV

(18) NCA (CEACAM6, Genbank accession no. M18728); Barnett T., et al Genomics 3, 59-66, 1988; Tawaragi Y., et al. Biochem. Biophys. Res. Commun. 150, 89-96, 1988; Strausberg R. L., et al. Proc. Natl. Acad. Sci. USA. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2);

Accession: P40199; Q14920; EMBL; M29541; AAA59915.1. EMBL; M18728;

344 aa (SEQ ID NO: 18)
MGPPSAPPCRLHVPWKEVLLTASLLTFWNPPTTAKLTIESTPFNVAEGKE

VLLLAHNLPQNRIGYSWYKGERVDGNSLIVGYVIGTQQATPGPAYSGRET

IYPNASLLIQNVTQNDTGFYTLQVIKSDLVNEEATGQFHVYPELPKPSIS

SNNSNPVEDKDAVAFTCEPEVQNTTYLWWVNGQSLPVSPRLQLSNGNMTL

TLLSVKRNDAGSYECEIQNPASANRSDPVTLNVLYGPDVPTISPSKANYR

PGENLNLSCHAASNPPAQYSWFINGTFQQSTQELFIPNITVNNSGSYMCQ

AHNSATGLNRTTVTMITVSGSAPVLSAVATVGITIGVLARVALI

Figure 8:
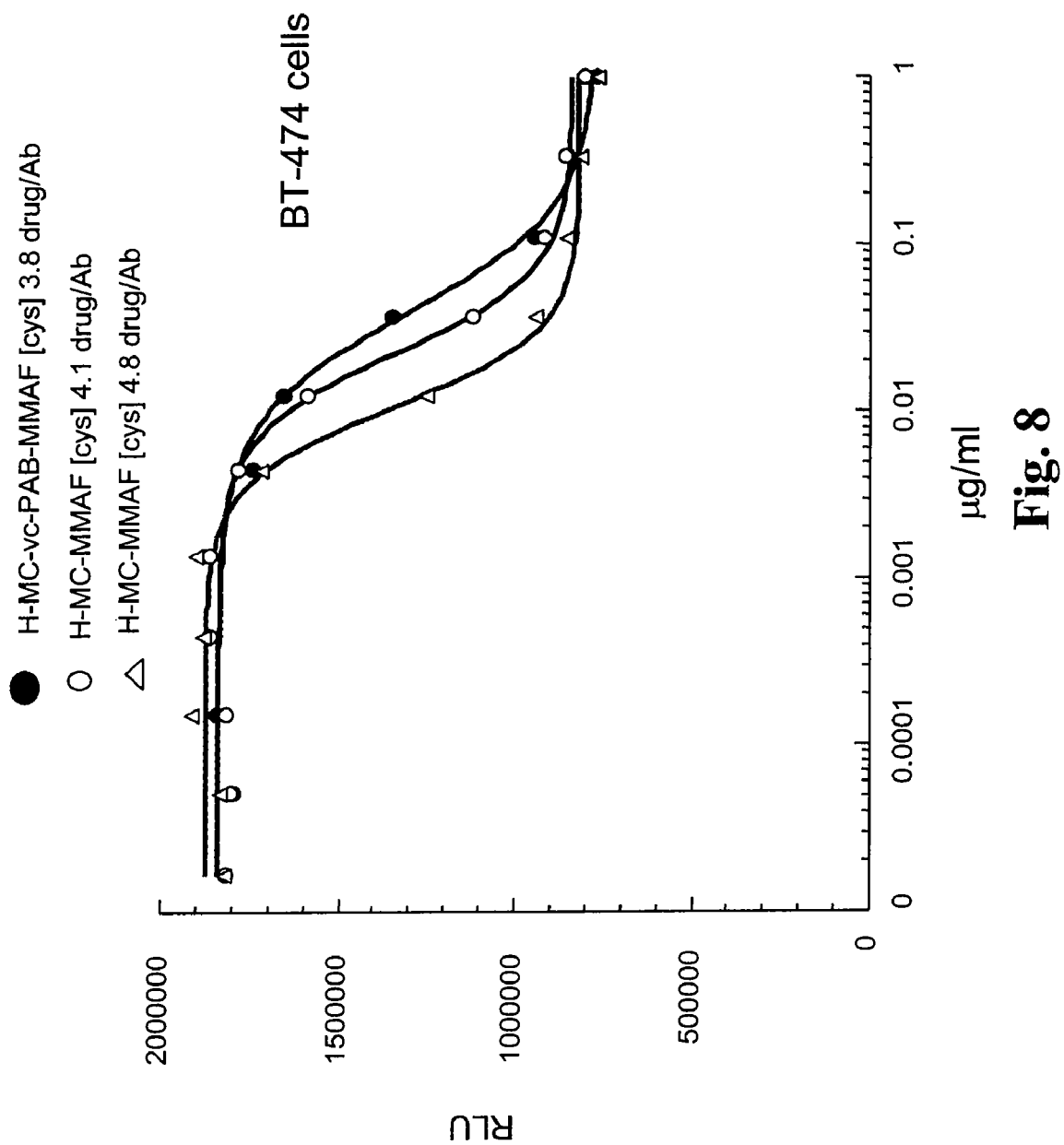
FIG. 8 shows an in vitro, cell proliferation assay with BT-474 cells treated with ADC: -●- Trastuzumab-MC-vc-PAB-MMAF, 3.8 MMAF/Ab, -○- Trastuzumab-MC-MMAF, 4.1 MMAF/Ab, and -Δ- Trastuzumab-MC-MMAF, 4.8 MMAF/Ab.

(19) MDP (DPEP1, Genbank accession no. BC017023, Proc. Natl. Acad. Sci. USA. 99 (26):16899-16903 (2002)); WO2003016475 (claim 1); WO200264798 (claim 33; Page 85-87); JP05003790 (FIG. 6-8); WO9946284 (FIG. 9);

Cross-references: MIM:179780; AAH17023.1; BC017023_1

411 aa (SEQ ID NO: 19)
MWSGWWLWPLVAVCTADFFRDEAERIMRDSPVIDGHNDLPWQLLDMFNNR

LQDERANLTTLAGTHTNIPKLRAGFVGGQFWSVYTPCDTQNKDAVRRTLE

QMDVVHRMCRMYPETFLYVTSSAGIRQAFREGKVASLIGVEGGHSIDSSL

GVLRALYQLGMRYLTLTHSCNTPWADNWLVDTGDSEPQSQGLSPFGQRVV

KELNRLGVLIDLAHVSVATMKATLQLSRAPVIFSHSSAYSVCASRRNVPD

DVLRLVKQTDSLVMVNFYNNYISCTNKANLSQVADHLDHIKEVAGARAVG

FGGDFDGVPRVPEGLEDVSKYPDLIAELLRRNWTEAEVKGALADNLLRVF

EAVEQASNLTQAPEEEPIPLDQLGGSCRTHYGYSSGASSLHRHWGLLLAS

LAPLVLCLSLL

(20) IL20Rα: (IL20Ra, ZCYTOR7, Genbank accession no. AF184971);

Clark H. F., et al. Genome Res. 13, 2265-2270, 2003; Mungall A. J., et al. Nature 425, 805-811, 2003; Blumberg H., et al. Cell 104, 9-19, 2001; Dumoutier L., et al. J. Immunol. 167, 3545-3549, 2001; Parrish-Novak J., et al. J. Biol. Chem. 277, 47517-47523, 2002; Pletnev S., et al. (2003) Biochemistry 42:12617-12624; Sheikh F., et al. (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1;Page 55-59);

Accession: Q9UHF4; Q6UWA9; Q96SH8; EMBL; AF184971; AAF01320.1.

553 aa (SEQ ID NO: 20)
MRAPGRPALRPLPLPPLLLLLLAAPWGRAVPCVSGGLPKPANITFLSINM

KNVLQWTPPEGLQGVKVTYTVQYFIYGQKKWLNKSECRNINRTYCDLSAE

TSDYEHQYYAKVKAIWGTKCSKWAESGRFYPFLETQIGPPEVALTTDEKS

ISVVLTAPEKWKRNPEDLPVSMQQIYSNLKYNVSVLNTKSNRTWSQCVTN

HTLVLTWLEPNTLYCVHVESFVPGPPRRAQPSEKQCARTLKDQSSEFKAK

IIFWYVLPISITVFLFSVMGYSIYRYIHVGKEKHPANLILIYGNEFDKRF

FVPAEKIVINFITLNISDDSKISHQDMSLLGKSSDVSSLNDPQPSGNLRP

PQEEEEVKHLGYASHLMEIFCDSEENTEGTSFTQQESLSRTIPPDKTVIE

YEYDVRTTDICAGPEEQELSLQEEVSTQGTLLESQAALAVLGPQTLQYSY

TPQLQDLDPLAQEHTDSEEGPEEEPSTTLVDWDPQTGRLCIPSLSSFDQD

SEGCEPSEGDGLGEEGLLSRLYEEPAPDRPPGENETYLMQFMEEWGLYVQ

MEN

(21) Brevican (BCAN, BEHAB, Genbank accession no. AF229053)

Gary S. C., et al. Gene 256, 139-147, 2000; Clark H. F., et al. Genome Res. 13, 2265-2270, 2003; Strausberg R. L., et al. Proc. Natl. Acad. Sci. USA. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);

911 aa (SEQ ID NO: 21)
MAQLFLPLLAALVLAQAPAALADVLEGDSSEDRAFRVRIAGDAPLQGVLG

GALTIPCHVHYLRPPPSRRAVLGSPRVKWTFLSRGREAEVLVARGVRVKV

NEAYRFRVALPAYPASLTDVSLALSELRPNDSGIYRCEVQHGIDDSSDAV

EVKVKGVVFLYREGSARYAFSFSGAQEACARIGAHIATPEQLYAAYLGGY

EQCDAGWLSDQTVRYPIQTPREACYGDMDGFPGVRNYGVVDPDDLYDVYC

YAEDLNGELFLGDPPEKLTLEEARAYCQERGAEIATTGQLYAAWDGGLDH

CSPGWLADGSVRYPIVTPSQRCGGGLPGVKTLFLFPNQTGFPNKHSRFNV

YCFRDSAQPSAIPEASNPASNPASDGLEAIVTVTETLEELQLPQEATESE

SRGAIYSIPIMEDGGGGSSTPEDPAEAPRTLLEFETQSMVPPTGFSEEEG

KALEEEEKYEDEEEKEEEEEEEVEDEALWAWPSELSSPGPEASLPTEPA

AQEKSLSQAPARAVLQPGASPLPDGESEASRPPRVHGPPTETLPTPRERN

LASPSPSTLVEAREVGEATGGPELSGVPRGESEETGSSEGAPSLLPATRA

PEGTRELEAPSEDNSGRTAPAGTSVQAQPVLPTDSASRGGVAVVPASGDC

VPSPCHNGGTCLEEEEGVRCLCLPGYGGDLCDVGLRFCNPGWDAFQGACY

KHFSTRRSWEEAETQCRMYGAHLASISTPEEQDFINNRYREYQWIGLNDR

TIEGDFLWSDGVPLLYENWNPGQPDSYFLSGENCVVMVWHDQGQWSDVPC

-continued
NYHLSYTCKMGLVSCGPPPELPLAQVFGRPRLRYEVDTVLRYRCREGLAQ

RNLPLIRCQENGRWEAPQISCVPRRPARALHPEEDPEGRQGRLLGRWKAL

LIPPSSPMPGP

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1;Page 42);

Cross-references: MIM:600997; NP_004433.2; NM_004442_1

987 aa (SEQ ID NO: 22)
MALRRLGAALLLLPLLAAVEETLMDSTTATAELGWMVHPPSGWEEVSGYD

ENMNTIRTYQVCNVFESSQNNWLRTKFIRRRGAHRIHVEMKFSVRDCSSI

PSVPGSCKETFNLYYYEADFDSATKTFPNWMENPWVKVDTIAADESFSQV

DLGGRVMKINTEVRSFGPVSRSGFYLAFQDYGGCMSLIAVRVFYRKCPRI

IQNGAIFQETLSGAESTSLVAARGSCIANAEEVDVPIKLYCNGDGEWLVP

IGRCMCKAGFEAVENGTVCRGCPSGTFKANQGDEACTHCPINSRTTSEGA

TNCVCRNGYYRADLDPLDMPCTTIPSAPQAVISSVNETSLMLEWTPPRDS

GGREDLVYNIICKSCGSGRGACTRCGDNVQYAPRQLGLTEPRIYISDLLA

HTQYTFEIQAVNGVTDQSPFSPQFASVNITTNQAAPSAVSIMHQVSRTVD

SITLSWSQPDQPNGVILDYELQYYEKELSEYNATAIKSPTNTVTVQGLKA

GAIYVFQVRARTVAGYGRYSGKMYFQTMTEAEYQTSIQEKLPLIIGSSAA

GLVFLIAVVVIAIVCNRRRGFERADSEYTDKLQHYTSGHMTPGMKIYIDP

FTYEDPNEAVREFAKEIDISCVKIEQVIGAGEFGEVCSGHLKLPGKREIF

VAIKTLKSGYTEKQRRDFLSEASIMGQFDHPNVIHLEGVVTKSTPVMIIT

EFMENGSLDSFLRQNDGQFTVIQLVGMLRGIAAGMKYLADMNYVHRDLAA

RNILVNSNLVCKVSDFGLSRFLEDDTSDPTYTSALGGKIPIRWTAPEAIQ

YRKFTSASDVWSYGIVMWEVMSYGERPYWDMTNQDVINAIEQDYRLPPPM

DCPSALHQLMLDCWQKDRNHRPKFGQIVNTLDKMIRNPNSLKAMAPLSSG

INLPLLDRTIPDYTSFNTVDEWLEAIKMGQYKESFANAGFTSFDVVSQMM

MEDILRVGVTLAGHQKKILNSIQVMRAQMNQIQSVEV

(23) ASLG659 (B7h, Genbank accession no. AX092328)

US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;

282 aa (SEQ ID NO: 23)
MASLGQILFWSIISIIIILAGAIALIIGFGISGRHSITVTTVASAGNIGE

DGILSCTFEPDIKLSDIVIQWLKEGVLGLVHEFKEGKDELSEQDEMFRGR

TAVFADQVIVGNASLRLKNVQLTDAGTYKCYIITSKGKKNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKASLCVSSFFAISWALLPLSPYLMLK

Figure 17:
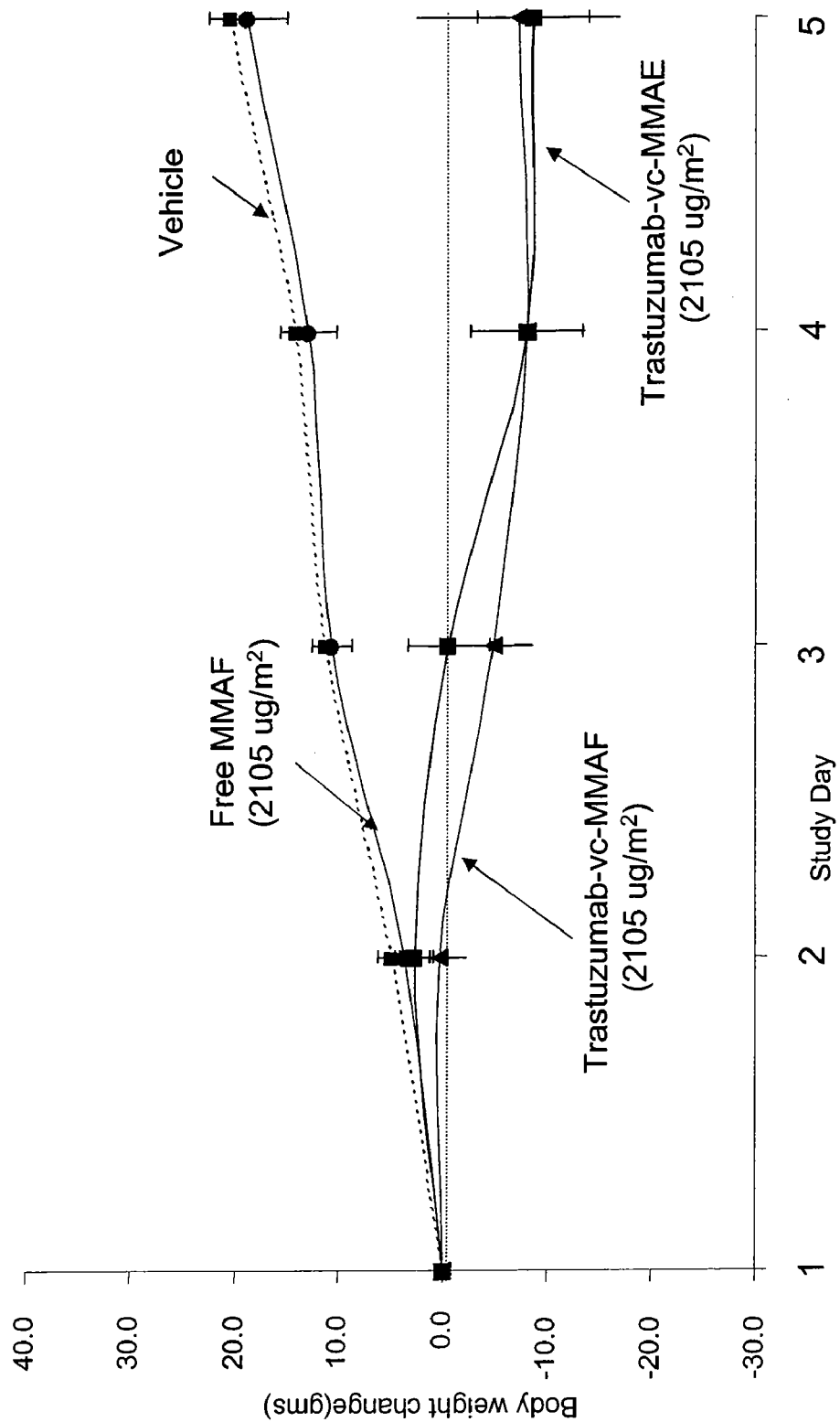
FIG. 17 shows the Group mean change, with error bars, in animal (rat) body weights (Mean±SD) after administration of Vehicle, trastuzumab-MC-val-cit-MMAF, trastuzumab-MC(Me)-val-cit-PAB-MMAF, trastuzumab-MC-MMAF and trastuzumab-MC-val-cit-PAB-MMAF.

(24) PSCA (Prostate stem cell antigen precursor, Genbank accession no. AJ297436) Reiter R. E., et al. Proc. Natl. Acad. Sci. USA. 95, 1735-1740, 1998; Gu Z., et al. Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B);

Accession: O43653; EMBL; AF043498; AAC39607.1.

123 aa (SEQ ID NO: 24)
MKAVLLALLMAGLALQPGTALLCYSCKAQVSNEDCLQVENCTQLGEQCWT

ARIRAVGLLTVISKGCSLNCVDDSQDYYVGKKNITCCDTDLCNASGAHAL

QPAAAILALLPALGLLLWGPGQL

(25) GEDA (Genbank accession No. AY260763);

AAP 14954 lipoma HMGIC fusion-partner-like protein/pid=AAP 14954.1-*Homo sapiens* Species: *Homo sapiens* (human)

WO2003054152 (claim 20); WO2003000842 (claim 1); WO2003023013 (Example 3, claim 20); US2003194704 (claim 45);

Cross-references: GI:30102449; AAP14954.1; AY260763_1

236 aa (SEQ ID NO: 25)
MPGAAAAAAAAAAMLPAQEAAKLYHTNYVRNSRAIGVLWAIFTICFAIV

NVVCFIQPYWIGDGVDTPQAGYFGLFHYCIGNGFSRELTCRGSFTDFSTL

PSGAFKAASFFIGLSMMLIIACIICFTLFFFCNTATVYKICAWMQLTSAA

CLVLGCMIFPDGWDSDEVKRMCGEKTDKYTLGACSVRWAYILAIIGILDA

LILSFLAFVLGNRQDSLMAEELKAENKVLLSQYSLE

(26) BAFF-R (B cell-activating factor receptor, BLyS receptor 3, BR3, Genbank accession No. NP_443177.1);

NP_443177 BAFF receptor/pid=NP_443177.1—*Homo sapiens*

Figure 6A:
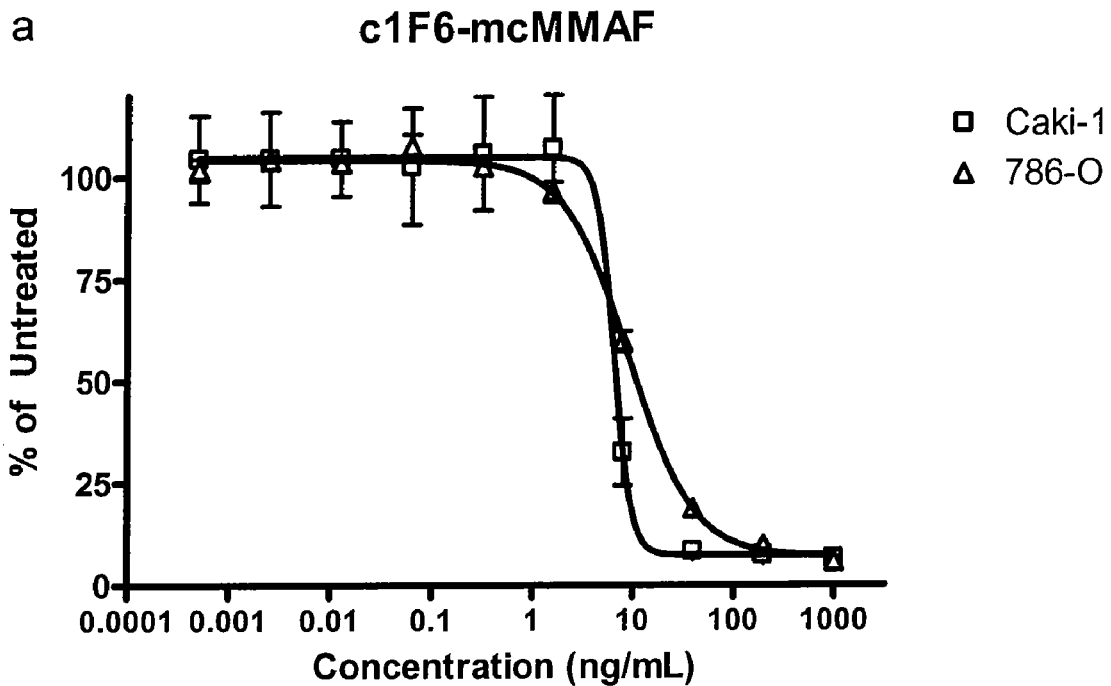
FIGS. 6a and 6b show in vitro activity of c1F6-antibody-drug conjugates against $CD70^+$ renal cell carcinoma cell lines.
Figure 6B:
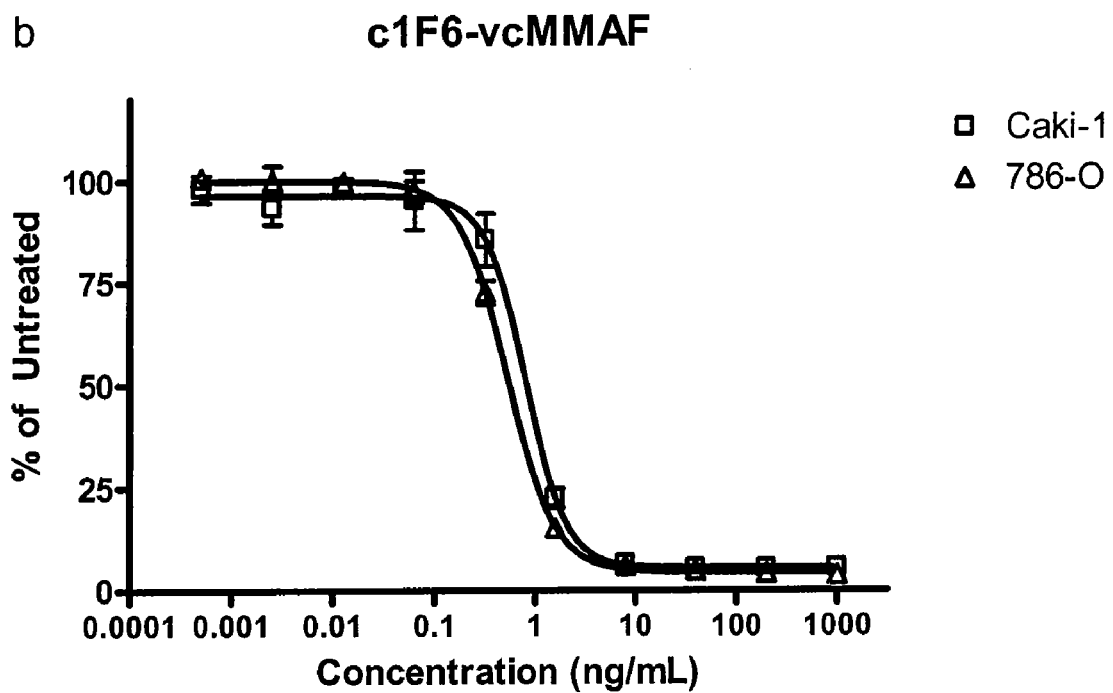

Thompson, J. S., et al. Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3);

Cross-references: MIM:606269; NP__443177.1; NM__052945__1

184 aa (SEQ ID NO: 26)
MRRGPRSLRGRDAPAPTPCVPAECFDLLVRHCVACGLLRTPRPKPAGASS

PAPRTALQPQESVGAGAGEAALPLPGLLFGAPALLGLALVLALVLVGLVS

WRRRQRRLRGASSAEAPDGDKDAPEPLDKVIILSPGISDATAPAWPPPGE

DPGTTPPGHSVPVPATELGSTELVTTKTAGPEQQ

(27) CD22 (B-cell receptor CD22-B isoform, Genbank accession No. NP-001762.1); Stamenkovic, I. and Seed, B., Nature 345 (6270), 74-77 (1990); US2003157113; US2003118592; WO2003062401 (claim 9); WO2003072036 (claim 1; FIG. 1); WO200278524 (Example 2);

Cross-references: MIM:107266; NP__001762.1; NM__001771__1

847 aa (SEQ ID NO: 27)
MHLLGPWLLLLVLEYLAFSDSSKWVFEHPETLYAWEGACVWIPCTYRALD

GDLESFILFHNPEYNKNTSKFDGTRLYESTKDGKVPSEQKRVQFLGDKNK

NCTLSIHPVHLNDSGQLGLRMESKTEKWMERIHLNVSERPFPPHIQLPPE

IQESQEVTLTCLLNFSCYGYPIQLQWLLEGVPMRQAAVTSTSLTIKSVFT

RSELKFSPQWSHHGKIVTCQLQDADGKFLSNDTVQLNVKHTPKLEIKVTP

SDAIVREGDSVTMTCEVSSSNPEYTTVSWLKDGTSLKKQNTFTLNLREVT

KDQSGKYCCQVSNDVGPGRSEEVFLQVQYAPEPSTVQILHSPAVEGSQVE

FLCMSLANPLPTNYTWYHNGKEMQGRTEEKVHIPKILPWHAGTYSCVAEN

ILGTGQRGPGAELDVQYPPKKVTTVIQNPMPIREGDTVTLSCNYNSSNPS

VTRYEWKPHGAWEEPSLGVLKIQNVGWDNTTIACARCNSWCSWASPVALN

VQYAPRDVRVRKIKPLSEIHSGNSVSLQCDFSSSHPKEVQFFWEKNGRLL

GKESQLNFDSISPEDAGSYSCWVNNSIGQTASKAWTLEVLYAPRRLRVSM

SPGDQVMEGKSATLTCESDANPPVSHYTWFDWNNQSLPHHSQKLRLEPVK

VQHSGAYWCQGTNSVGKGRSPLSTLTVYYSPETIGRRVAVGLGSCLAILI

LAICGLKLQRRWKRTQSQQGLQENSSGQSFFVRNKKVRRAPLSEGPHSLG

CYNPMMEDGISYTTLRFPEMNIPRTGDAESSEMQRPPRTCDDTVTYSALH

KRQVGDYENVIPDFPEDEGIHYSELIQFGVGERPQAQENVDYVILKH

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation) PROTEIN SEQUENCE Full mpggpgv . . . dvqlekp (SEQ ID NO:28) (1 . . . 226; 226 aa), pI: 4.84, MW: 25028 TM: 2 [P] Gene Chromosome: 19q13.2, Genbank accession No. NP__001774.1; WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al. (1992) J. Immunol. 148(5):1526-1531; Mueller et al. (1992) Eur. J. Biochem. 22:1621-1625; Hashimoto et al. (1994) Immunogenetics 40(4):287-295; Preud'homme et al. (1992) Clin. Exp. Immunol. 90(1):141-146; Yu et al. (1992) J. Immunol. 148(2) 633-637; Sakaguchi et al. (1988) EMBO J. 7(11):3457-3464;

226 aa (SEQ ID NO: 28)
MPGGPGVLQALPATIFLLFLLSAVYLGPGCQALWMHKVPASLMVSLGEDA

HFQCPHNSSNNANVTWWRVLHGNYTWPPEFLGPGEDPNGTLIIQNVNKSH

GGIYVCRVQEGNESYQQSCGTYLRVRQPPPRPFLDMGEGTKNRIITAEGI

ILLFCAVVPGTLLLFRKRWQNEKLGLDAGDEYEDENLYEGLNLDDCSMYE

DISRGLQGTYQDVGSLNIGDVQLEKP

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) PROTEIN SEQUENCE Full mnypltl . . . atslttf (SEQ ID NO:29) (1 . . . 372; 372 aa), pI: 8.54 MW: 41959 TM: 7 [P] Gene Chromosome: 11q23.3, Genbank accession No. NP__001707.1;

372 aa (SEQ ID NO: 29)
MNYPLTLEMDLENLEDLFWELDRLDNYNDTSLVENHLCPATEGPLMASFK

AVFVPVAYSLIFLLGVIGNVLVLVILERHRQTRSSTETFLFHLAVADLLL

VFILPFAVAEGSVGWVLGTFLCKTVIALHKVNFYCSSLLLACIAVDRYLA

IVHAVHAYRHRRLLSIHITCGTIWLVGFLLALPEILFAKVSQGHHNNSLP

RCTFSQENQAETHAWFTSRFLYHVAGFLLPMLVMGWCYVGVVHRLRQAQR

RPQRQKAVRVAILVTSIFFLCWSPYHIVIFLDTLARLKAVDNTCKLNGSL

PVAITMCEFLGLAHCCLNPMLYTFAGVKFRSDLSRLLTKLGCTGPASLCQ

LFPSWRRSSLSESENATSLTTF

(30) HLA-DOB (Beta subunit of MHC class II molecule (Ia antigen) that binds peptides and presents them to CD4+ T lymphocytes) PROTEIN SEQUENCE Full mgsgwvp . . . vllpqsc (SEQ ID NO:30) (1 . . . 273; 273 aa, pI: 6.56 MW: 30820 TM: 1 [P] Gene Chromosome: 6p21.3, Genbank accession No. NP__002111.1; Tonnelle et al. (1985) EMBO J. 4(11):2839-2847; Jonsson et al. (1989) Immunogenetics 29(6):411-413; Beck et al. (1992) J. Mol. Biol. 228:433-441; Strausberg et al. (2002) Proc. Natl. Acad. Sci. USA 99:16899-16903; Servenius et al. (1987) J. Biol. Chem. 262:8759-8766; Beck et al. (1996) J. Mol. Biol. 255:1-13; Naruse et al. (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al. (1989) Immunogenetics 30(1):66-68; Larhammar et al. (1985) J. Biol. Chem. 260(26):14111-14119;

273 aa (SEQ ID NO: 30)
MGSGWVPWVVALLVNLTRLDSSMTQGTDSPEDFVIQAKADCYFTNGTEKV

QFVVRFIFNLEEYVRFDSDVGMFVALTKLGQPDAEQWNSRLDLLERSRQA

VDGVCRHNYRLGAPFTVGRKVQPEVTVYPERTPLLHQHNLLHCSVTGFYP

GDIKIKWFLNGQEERAGVMSTGPIRNGDWTFQTVVMLEMTPELGHVYTCL

VDHSSLLSPVSVEWRAQSEYSWRKMLSGIAAFLLGLIFLLVGIVIQLRAQ

KGYVRTQMSGNEVSRAVLLPQSC

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) PROTEIN SEQUENCE Full mgqagck . . . lephrst (SEQ ID NO:31) (1 . . . 422; 422 aa), pI: 7.63, MW: 47206 TM: 1 [P] Gene Chromosome: 17p13.3, Genbank accession No. NP_002552.2; Le et al. (1997) FEBS Lett. 418(1-2):195-199; WO2004047749; WO2003072035 (claim 10); Touchman et al. (2000) Genome Res. 10:165-173; WO200222660 (claim 20); WO2003093444 (claim 1); WO2003087768 (claim 1); WO2003029277 (page 82);

422 aa (SEQ ID NO: 31)
MGQAGCKGLCLSLFDYKTEKYVIAKNKKVGLLYRLLQASILAYLVVWVFL

IKKGYQDVDTSLQSAVITKVKGVAFTNTSDLGQRIWDVADYVIPAQGENV

FFVVTNLIVTPNQRQNVCAENEGIPDGACSKDSDCHAGEAVTAGNGVKTG

RCLRRENLARGTCEIFAWCPLETSSRPEEPFLKEAEDFTIFIKNHIRFPK

FNFSKSNVMDVKDRSFLKSCHFGPKNHYCPIFRLGSVIRWAGSDFQDIAL

EGGVIGINIEWNCDLDKAASECHPHYSFSRLDNKLSKSVSSGYNFRFARY

YRDAAGVEFRTLMKAYGIRFDVMVNGKGAFFCDLVLIYLIKKREFYRDKK

YEEVRGLEDSSQEAEDEASGLGLSEQLTSGPGLLGMPEQQELQEPPEAKR

GSSSQKGNGSVCPQLLEPHRST

(32) CD72 (B-cell differentiation antigen CD72, Lyb-2) PROTEIN SEQUENCE Full maeaity . . . tafrfpd (SEQ ID NO:32) (1 . . . 359; 359 aa), pI: 8.66, MW: 40225 TM: 1 [P] Gene Chromosome: 9p13.3, Genbank accession No. NP_001773.1; WO2004042346 (claim 65); WO2003026493 (pages 51-52, 57-58); WO200075655 (pages 105-106); Von Hoegen et al. (1990) J. Immunol. 144 (12):4870-4877; Strausberg et al. (2002) Proc. Natl. Acad. Sci. USA 99:16899-16903;

359 aa (SEQ ID NO: 32)
MAEAITYADLRFVKAPLKKSISSRLGQDPGADDDGEITYENVQVPAVLGV

PSSLASSVLGDKAAVKSEQPTASWRAVTSPAVGRILPCRTTCLRYLLLGL

LLTCLLLGVTAICLGVRYLQVSQQLQQTNRVLEVTNSSLRQQLRLKITQL

GQSAEDLQGSRRELAQSQEALQVEQRAHQAAEGQLQACQADRQKTKETLQ

SEEQQRRALEQKLSNMENRLKPFFTCGSADTCCPSGWIMHQKSCFYISLT

SKNWQESQKQCETLSSKLATFSEIYPQSHSYYFLNSLLPNGGSGNSYWTG

LSSNKDWKLTDDTQRTRTYAQSSKCNKVHKTWSWWTLESESCRSSLPYIC

EMTAFRFPD

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis) PROTEIN SEQUENCE Full mafdvsc . . . rwkyqhi (SEQ ID NO:33) (1 . . . 661; 661 aa), pI: 6.20, MW: 74147 TM: 1 [P] Gene Chromosome: 5q12, Genbank accession No. NP_005573.1; US2002193567; WO9707198 (claim 11, pages 39-42); Miura et al. (1996) Genomics 38(3):299-304; Miura et al. (1998) Blood 92:2815-2822; WO2003083047; WO9744452

661 aa (SEQ ID NO: 33)
MAFDVSCFFWVVLFSAGCKVITSWDQMCIEKEANKTYNCENLGLSEIPDT

LPNTTEFLEFSFNFLPTIHNRTFSRLMNLTFLDLTRCQINWIHEDTFQSH

HQLSTLVLTGNPLIFMAETSLNGPKSLKHLFLIQTGISNLEFIPVHNLEN

LESLYLGSNHISSIKFPKDFPARNLKVLDFQNNAIHYISREDMRSLEQAI

NLSLNFNGNNVKGIELGAFDSTVFQSLNFGGTPNLSVIFNGLQNSTTQSL

WLGTFEDIDDEDISSAMLKGLCEMSVESLNLQEHRFSDISSTTFQCFTQL

QELDLTATHLKGLPSGMKGLNLLKKLVLSVNHFDQLCQISAANFPSLTHL

YIRGNVKKLHLGVGCLEKLGNLQTLDLSHNDIEASDCCSLQLKNLSHLQT

LNLSHNEPLGLQSQAFKECPQLELLDLAFTRLHINAPQSPFQNLHFLQVL

NLTYCFLDTSNQHLLAGLPVLRHLNLKGNHFQDGTITKTNLLQTVGSLEV

LILSSCGLLSIDQQAFHSLGKMSHVDLSHNSLTCDSIDSLSHLKGIYLNL

AANSINIISPRLLPILSQQSTINLSHNPLDCTCSNIHFLTWYKENLHKLE

GSEETTCANPPSLRGVKLSDVKLSCGITAIGIFFLIVFLLLLAILLFFAV

KYLLRWKYQHI

(34) FCRH1 (Fc receptor-like protein 1, a putative receptor for the immunoglobulin Fc domain that contains C2 type Ig-like and ITAM domains, may have a role in B-lymphocyte differentiation) PROTEIN SEQUENCE Full mlprlll . . . vdyedam (SEQ ID NO:34) (1 . . . 429; 429 aa), pI: 5.28, MW: 46925 TM: 1 [P] Gene Chromosome: 1q21-1q22, Genbank accession No. NP_443170.1; WO2003077836; WO200138490 (claim 6, FIGS. 18E-1-18-E-2); Davis et al. (2001) Proc. Natl. Acad. Sci. USA 98(17):9772-9777; WO2003089624 (claim 8); EP1347046 (claim 1); WO2003089624 (claim 7);

429 aa (SEQ ID NO: 34)
MLPRLLLLICAPLCEPAELFLIASPSHPTEGSPVTLTCKMPFLQSSDAQF

QFCFFRDTRALGPGWSSSPKLQIAAMWKEDTGSYWCEAQTMASKVLRSRR

SQINVHRVPVADVSLETQPPGGQVMEGDRLVLICSVAMGTGDITFLWYKG

AVGLNLQSKTQRSLTAEYEIPSVRESDAEQYYCVAENGYGPSPSGLVSIT

VRIPVSRPILMLRAPRAQAAVEDVLELHCEALRGSPPILYWFYHEDITLG

SRSAPSGGGASFNLSLTEEHSGNYSCEANNGLGAQRSEAVTLNFTVPTGA

-continued

```
RSNHLTSGVIEGLLSTLGPATVALLFCYGLKRKIGRRSARDPLRSLPSPL

PQEFTYLNSPTPGQLQPIYENVNVVSGDEVYSLAYYNQPEQESVAAETLG

THMEDKVSLDIYSRLRKANITDVDYEDAM
```

(35) IRTA2 (Immunoglobulin superfamily receptor translocation associated 2, a putative immunoreceptor with possible roles in B cell development and lymphomagenesis; deregulation of the gene by translocation occurs in some B cell malignancies) PROTEIN SEQUENCE Full mllwvil . . . assaphr (SEQ ID NO:35) (1 . . . 977; 977 aa), pI: 6.88 MW: 106468 TM: 1 [P] Gene Chromosome: 1q21, Genbank accession No. NP__112571.1; WO2003024392 (claim 2, FIG. 97); Nakayama et al. (2000) Biochem. Biophys. Res. Commun. 277(1):124-127; WO2003077836; WO200138490 (claim 3, FIGS. 18B-1-18B-2);

977 aa

```
                                              (SEQ ID NO: 35)
MLLWVILLVLAPVSGQFARTPRPIIFLQPPWTTVFQGERVTLTCKGFRFY

SPQKTKWYHRYLGKEILRETPDNILEVQESGEYRCQAQGSPLSSPVHLDF

SSASLILQAPLSVFEGDSVVLRCRAKAEVTLNNTIYKNDNVLAFLNKRTD

FHIPHACLKDNGAYRCTGYKESCCPVSSNTVKIQVQEPFTRPVLRASSFQ

PISGNPVTLTCETQLSLERSDVPLRFRFFRDDQTLGLGWSLSPNFQITAM

WSKDSGFYWCKAATMPHSVISDSPRSWIQVQIPASHPVLTLSPEKALNFE

GTKVTLHCETQEDSLRTLYRFYHEGVPLRHKSVRCERGASISFSLTTENS

GNYYCTADNGLGAKPSKAVSLSVTVPVSHPVLNLSSPEDLIFEGAKVTLH

CEAQRGSLPILYQFHHEDAALERRSANSAGGVAISFSLTAEHSGNYYCTA

DNGFGPQRSKAVSLSITVPVSHPVLTLSSAEALTFEGATVTLHCEVQRGS

PQILYQFYHEDMPLWSSSTPSVGRVSFSFSLTEGHSGNYYCTADNGFGPQ

RSEVVSLFVTVPVSRPILTLRVPRAQAVVGDLLELHCEAPRGSPPILYWF

YHEDVTLGSSSAPSGGEASFNLSLTAEHSGNYSCEANNGLVAQHSDTISL

SVIVPVSRPILTFRAPRAQAVVGDLLELHCEALRGSSPILYWFYHEDVTL

GKISAPSGGGASFNLSLTTEHSGIYSCEADNGPEAQRSEMVTLKVAVPVS

RPVLTLRAPGTHAAVGDLLELHCEALRGSPLILYRFFHEDVTLGNRSSPS

GGASLNLSLTAEHSGNYSCEADNGLGAQRSETVTLYITGLTANRSGPFAT

GVAGGLLSIAGLAAGALLLYCWLSRKAGRKPASDPARSPPDSDSQEPTYH

NVPAWEELQPVYTNANPRGENVVYSEVRIIQEKKKHAVASDPRHLRNKGS

PIIYSEVKVASTPVSGSLFLASSAPHR
```

See also: WO04/045516 (3 Jun. 2004); WO03/000113 (3 Jan. 2003); WO02/016429 (28 Feb. 2002); WO02/16581 (28 Feb. 2002); WO03/024392 (27 Mar. 2003); WO04/016225 (26 Feb. 2004); WO01/40309 (7 Jun. 2001), and U.S. Provisional patent application Ser. No. 60/520,842 "COMPOSITIONS AND METHODS FOR THE TREATMENT OF TUMOR OF HEMATOPOIETIC ORIGIN", filed 17 Nov. 2003; all of which are incorporated herein by reference in their entirety.

In an embodiment, the Ligand-Linker-Drug Conjugate has Formula IIIa, where the Ligand is an antibody Ab including one that binds at least one of CD30, CD40, CD70, Lewis Y antigen, w=0, y=0, and D has Formula Ib. Exemplary Conjugates of Formula IIIa include where $R^{17}$ is —$(CH_2)_5$—. Also included are such Conjugates of Formula IIIa in which D has the structure of Compound 2 in Example 3 and esters thereof. Also included are such Conjugates of Formula IIIa containing about 3 to about 8, in one aspect, about 3 to about 5 Drug moieties D, that is, Conjugates of Formula IIIa wherein p is a value in the range about 3-8, for example about 3-5. Conjugates containing combinations of the structural features noted in this paragraph are also contemplated as within the scope of the compounds of the invention.

In another embodiment, the Ligand-Linker-Drug Conjugate has Formula IIIa, where Ligand is an Antibody Ab that binds one of CD30, CD40, CD70, Lewis Y antigen, w=1, y=0, and D has Formula Ib. Included are such Conjugates of Formula IIIa in which $R^{17}$ is —$(CH_2)_5$—. Also included are such Conjugates of Formula IIIa in which W is -Val-Cit-, and/or where D has the structure of Compound 2 in Example 3 and esters thereof. Also included are such Conjugates of Formula IIIa containing about 3 to about 8, preferably about 3 to about 5 Drug moieties D, that is, Conjugates of Formula Ia wherein p is a value in the range of about 3-8, preferably about 3-5. Conjugates containing combinations of the structural features noted in this paragraph are also exemplary.

In an embodiment, the Ligand-Linker-Drug Conjugate has Formula IIIa, where the Ligand is an Antibody Ab that binds one of CD30, CD40, CD70, Lewis Y antigen, w=1, y=1, and D has Formula Ib. Included are Conjugates of Formula IIIa in which $R^{17}$ is —$(CH_2)_5$—. Also included are such Conjugates of Formula IIIa where: W is -Val-Cit-; Y has Formula X; D has the structure of Compound 2 in Example 3 and esters thereof, p is about 3 to about 8, preferably about 3 to about 5 Drug moieties D. Conjugates containing combinations of the structural features noted in this paragraph are also contemplated within the scope of the compounds of the invention.

A further embodiment is an antibody drug conjugate (ADC), or a pharmaceutically acceptable salt or solvate thereof, wherein Ab is an antibody that binds one of the tumor-associated antigens (1)-(35) noted above (the "TAA Compound").

Another embodiment is the TAA Compound or pharmaceutically acceptable salt or solvate thereof that is in isolated and purified form.

Another embodiment is a method for killing or inhibiting the multiplication of a tumor cell or cancer cell comprising administering to a patient, for example a human with a hyperproliferative disorder, an amount of the TAA Compound or a pharmaceutically acceptable salt or solvate thereof, said amount being effective to kill or inhibit the multiplication of a tumor cell or cancer cell.

Another embodiment is a method for treating cancer comprising administering to a patient, for example a human with a hyperproliferative disorder, an amount of the TAA Compound or a pharmaceutically acceptable salt or solvate thereof, said amount being effective to treat cancer, alone or together with an effective amount of an additional anticancer agent.

Another embodiment is a method for treating an autoimmune disease, comprising administering to a patient, for example a human with a hyperproliferative disorder, an amount of the TAA Compound or a pharmaceutically acceptable salt or solvate thereof, said amount being effective to treat an autoimmune disease.

The antibodies suitable for use in the invention can be produced by any method known in the art for the synthesis of antibodies, in particular, by chemical synthesis or by recombinant expression, and are preferably produced by recombinant expression techniques.

4.5.1 Production of Recombinant Antibodies

Antibodies of the invention can be produced using any method known in the art to be useful for the synthesis of antibodies, in particular, by chemical synthesis or by recombinant expression.

Recombinant expression of antibodies, or fragment, derivative or analog thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides, e.g., by PCR.

Alternatively, a nucleic acid molecule encoding an antibody can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by, e.g., PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin), antibodies specific for a particular antigen can be generated by any method known in the art, for example, by immunizing a patient, or suitable animal model such as a rabbit or mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody can be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid sequence encoding at least the variable domain of the antibody is obtained, it can be introduced into a vector containing the nucleotide sequence encoding the constant regions of the antibody (see, e.g., International Publication No. WO 86/05807; WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis and in vitro site directed mutagenesis (Hutchinson et al., 1978, J. Biol. Chem. 253:6551).

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038-1041).

Antibody fragments that recognize specific epitopes can be generated by known techniques. For example, such fragments include, but are not limited to the $F(ab')_2$ fragments that can be produced by pepsin digestion of the antibody molecule and the Fab fragments that can be generated by reducing the disulfide bridges of the $F(ab')_2$ fragments.

Once a nucleic acid sequence encoding an antibody has been obtained, the vector for the production of the antibody can be produced by recombinant DNA technology using techniques well known in the art. Methods that are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

An expression vector comprising the nucleotide sequence of an antibody or the nucleotide sequence of an antibody can be transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

The host cells used to express the recombinant antibody can be either bacterial cells such as Escherichia coli, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al, 198, Gene 45:101; Cockett et al., 1990, BioTechnology 8:2).

A variety of host-expression vector systems can be utilized to express the immunoglobulin antibodies. Such host-expression systems represent vehicles by which the coding sequences of the antibody can be produced and subsequently purified, but also represent cells that can, when transformed or transfected with the appropriate nucleotide coding sequences, express an antibody immunoglobulin molecule in situ. These include, but are not limited to, microorganisms such as bacteria (e.g., E. coli and B. subtilis) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX Vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) or the analogous virus from *Drosophila Melanogaster* is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (e.g., see Logan & Shenk, 1984, *Proc. Natl. Acad. Sci. USA* 81:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, *Methods in Enzymol.* 153:51-544).

In addition, a host cell strain can be chosen to modulate the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERY, BH, Hela, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody. Such engineered cell lines can be particularly useful in screening and evaluation of tumor antigens that interact directly or indirectly with the antibody.

A number of selection systems can be used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes can be employed in tk–, hgprt– or aprt– cells, respectively. Also, antimetabolite resistance can be used as the basis of selection for the following genes: DHFR, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260: 926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, Current Protocols in Molecular Biology, John Wiley & Sons, NY; Kriegler, 1990, *Gene Transfer and Expression, A Laboratory Manual*, Stockton Press, NY; and in Chapters 12 and 13, Dracopoli et al.

(eds), 1994, Current Protocols in Human Genetics, John Wiley & Sons, NY.; Colberre-Garapin et al., 1981, *J. Mol. Biol.* 150:1).

The expression levels of an antibody can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257).

The host cell can be co-transfected with two expression vectors, the first vector encoding a heavy chain derived polypeptide and the second vector encoding a light chain derived polypeptide. The two vectors can contain identical selectable markers that enable equal expression of heavy and light chain polypeptides. Alternatively, a single vector can be used to encode both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains can comprise cDNA or genomic DNA.

Once the antibody has been recombinantly expressed, it can be purified using any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

In yet another exemplary embodiment, the antibody is a monoclonal antibody.

In any case, the hybrid antibodies have a dual specificity, preferably with one or more binding sites specific for the hapten of choice or one or more binding sites specific for a target antigen, for example, an antigen associated with a tumor, an autoimmune disease, an infectious organism, or other disease state.

4.5.2 Production of Antibodies

The production of antibodies will be illustrated with reference to anti-CD30 antibodies but it will be apparent for those skilled in the art that antibodies to other members of the TNF receptor family can be produced and modified in a similar manner. The use of CD30 for the production of antibodies is exemplary only and not intended to be limiting.

The CD30 antigen to be used for production of antibodies may be, e.g., a soluble form of the extracellular domain of CD30 or a portion thereof, containing the desired epitope. Alternatively, cells expressing CD30 at their cell surface (e.g., L540 (Hodgkin's lymphoma derived cell line with a T cell phenotype) and L428 (Hodgkin's lymphoma derived cell line with a B cell phenotype)) can be used to generate antibodies. Other forms of CD30 useful for generating antibodies will be apparent to those skilled in the art.

In another exemplary embodiment, the ErbB2 antigen to be used for production of antibodies may be, e.g., a soluble form of the extracellular domain of ErbB2 or a portion thereof, containing the desired epitope. Alternatively, cells expressing ErbB2 at their cell surface (e.g., NIH-3T3 cells transformed to overexpress ErbB2; or a carcinoma cell line such as SK-BR-3 cells, see Stancovski et al. *Proc. Natl. Acad. Sci. USA* 88:8691-8695 (1991)) can be used to generate antibodies. Other forms of ErbB2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al. (1984) Proc. Natl. Acad. Sci. USA 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

A humanized antibody may have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522-525 (1986); Riechmann et al., Nature, 332:323-327 (1988); Verhoeyen et al., Science 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

In another embodiment, the antibodies may be humanized with retention of high affinity for the antigen and other favorable biological properties. Humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody are contemplated. For example, the humanized antibody may be an antibody fragment, such as a Fab. Alternatively, the humanized antibody may be an intact antibody, such as an intact IgG1 antibody.

The Examples describe production of an exemplary humanized anti-ErbB2 antibody. The humanized antibody may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest,* 5th Ed. Public Health Service, National Institutes of Health, Bethesda, Md. (1991). In one embodiment, the humanized antibody comprises FR substitutions at two or all of positions 69H, 71H and 73H. Another Example describes preparation of purified trastuzumab antibody from the HERCEPTIN® formulation.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275). Human anti-CD30 antibodies are described in U.S. patent application Ser. No. 10/338,366.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the CD30 protein. Alternatively, an anti-CD30 arm may be combined with an arm which binds to a Fc receptors for IgG (FcγR), such as FcγRI (CD64), FcγRII (CD32) and FcγRIII (CD16) so as to focus cellular defense mechanisms to the CD30-expressing cell. Bispecific antibodies may also be used to localize cytotoxic agents to cells which express CD30.

Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991). According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (V$_H$) connected to a light-chain variable domain (V$_L$) by a linker which is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibodies are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are favored locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al. J. Exp Med. 176:1191-1195 (1992) and Shopes, B. J. Immunol. 148:2918-2922 (1992). Homodimeric antibodies with enhanced antitumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(viii) Glycosylation Variants

Antibodies in the ADC of the invention may be glycosylated at conserved positions in their constant regions (Jefferis and Lund, (1997) Chem. Immunol. 65:111-128; Wright and Morrison, (1997) TibTECH 15:26-32). The oligosaccharide side chains of the immunoglobulins affect the protein's function (Boyd et al., (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner, (1996) Current Opin. Biotech. 7:409-416). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., (1995) Nature Med. 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., (1996) Mol. Immunol. 32:1311-1318), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of $\beta(1,4)$-N-acetyl-glucosaminyltransferase III (GnTIII), a glycosyltransferase catalyzing formation of bisecting GlcNAc, was reported to have improved ADCC activity (Umana et al. (1999) Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence variants) or preparation by oligonucleotide-mediated (or site-directed) mutagenesis, PCR mutagenesis, and cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., (1997) J. Biol. Chem. 272:9062-9070. In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261; 5,278,299). Glycosylation, or certain types of glycosylation, can be enzymatically removed from the glycoprotein, for example using endoglycosidase H (Endo H). In addition, the recombinant host cell can be genetically engineered, e.g., make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

4.5.2a Screening for Antibody-Drug Conjugates (ADC)

Transgenic animals and cell lines are particularly useful in screening antibody drug conjugates (ADC) that have potential as prophylactic or therapeutic treatments of diseases or disorders involving overexpression of proteins including Lewis Y, CD30, CD40, and CD70. Transgenic animals and cell lines are particularly useful in screening antibody drug conjugates (ADC) that have potential as prophylactic or therapeutic treatments of diseases or disorders involving overexpression of HER2 (U.S. Pat. No. 6,632,979). Screening for a useful ADC may involve administering candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. Candidate ADC may be screened serially and individually, or in parallel under medium or high-throughput screening format. The rate at which ADC may be screened for utility for prophylactic or therapeutic treatments of diseases or disorders is limited only by the rate of synthesis or screening methodology, including detecting/measuring/analysis of data.

One embodiment is a screening method comprising (a) transplanting cells from a stable renal cell cancer cell line into a non-human animal, (b) administering an ADC drug candidate to the non-human animal and (c) determining the ability of the candidate to inhibit the formation of tumors from the transplanted cell line.

Another embodiment is a screening method comprising (a) contacting cells from a stable Hodgkin's disease cell line with an ADC drug candidate and (b) evaluating the ability of the ADC candidate to block ligand activation of CD40.

Another embodiment is a screening method comprising (a) contacting cells from a stable Hodgkin's disease cell line with an ADC drug candidate and (b) evaluating the ability of the ADC candidate to induce cell death. In one embodiment the ability of the ADC candidate to induce apoptosis is evaluated.

One embodiment is a screening method comprising (a) transplanting cells from a stable cancer cell line into a non-human animal, (b) administering an ADC drug candidate to the non-human animal and (c) determining the ability of the candidate to inhibit the formation of tumors from the transplanted cell line. The invention also concerns a method of screening ADC candidates for the treatment of a disease or disorder characterized by the overexpression of HER2 comprising (a) contacting cells from a stable breast cancer cell line with a drug candidate and (b) evaluating the ability of the ADC candidate to inhibit the growth of the stable cell line.

Another embodiment is a screening method comprising (a) contacting cells from a stable cancer cell line with an ADC drug candidate and (b) evaluating the ability of the ADC candidate to block ligand activation of HER2. In one embodiment the ability of the ADC candidate to block heregulin binding is evaluated. In another embodiment the ability of the ADC candidate to block ligand-stimulated tyrosine phosphorylation is evaluated.

Another embodiment is a screening method comprising (a) contacting cells from a stable cancer cell line with an ADC drug candidate and (b) evaluating the ability of the ADC candidate to induce cell death. In one embodiment the ability of the ADC candidate to induce apoptosis is evaluated.

Another embodiment is a screening method comprising (a) administering an ADC drug candidate to a transgenic non-human mammal that overexpresses in its mammary gland cells a native human HER2 protein or a fragment thereof, wherein such transgenic mammal has stably integrated into its genome a nucleic acid sequence encoding a native human HER2 protein or a fragment thereof having the biological activity of native human HER2, operably linked to transcriptional regulatory sequences directing its expression to the mammary gland, and develops a mammary tumor not responding or poorly responding to anti-HER2 antibody treatment, or to a non-human mammal bearing a tumor transplanted from said transgenic non-human mammal; and (b) evaluating the effect of the ADC candidate on the target disease or disorder. Without limitations, the disease or disorder may be a HER2-overexpressing cancer, such as breast, ovarian, stomach, endometrial, salivary gland, lung, kidney, colon, thyroid, pancreatic and bladder cancer. The cancer preferably is breast cancer which expressed HER2 in at least about 500,000 copies per cell, more preferably at least about 2,000,000 copies per cell. ADC drug candidates may, for example, be evaluated for their ability to induce cell death and/or apoptosis, using assay methods well known in the art and described hereinafter.

In one embodiment, candidate ADC are screened by being administered to the transgenic animal over a range of doses, and evaluating the animal's physiological response to the compounds over time. Administration may be oral, or by suitable injection, depending on the chemical nature of the compound being evaluated. In some cases, it may be appropriate to administer the compound in conjunction with cofactors that would enhance the efficacy of the compound. If cell lines derived from the subject transgenic animals are used to screen for compounds useful in treating various disorders, the test compounds are added to the cell culture medium at an appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

Thus, provided herein are assays for identifying ADC which specifically target and bind a target protein, the presence of which is correlated with abnormal cellular function, and in the pathogenesis of cellular proliferation and/or differentiation that is causally related to the development of tumors.

To identify an ADC which blocks ligand activation of an ErbB (e.g., ErbB2) receptor, the ability of the compound to block ErbB ligand binding to cells expressing the ErbB (ErbB2) receptor (e.g., in conjugation with another ErbB receptor with which the ErbB receptor of interest forms an ErbB hetero-oligomer) may be determined. For example, cells isolated from the transgenic animal overexpressing HER2 and transfected to express another ErbB receptor (with which HER2 forms hetero-oligomer) may be incubated, i.e. culturing, with the ADC and then exposed to labeled ErbB ligand. The ability of the compound to block ligand binding to the ErbB receptor in the ErbB hetero-oligomer may then be evaluated.

For example, inhibition of heregulin (HRG) binding to breast tumor cell lines, overexpressing HER2 and established from the transgenic non-human mammals (e.g., mice) herein, by the candidate ADC may be performed using monolayer cultures on ice in a 24-well-plate format. Anti-ErbB2 monoclonal antibodies may be added to each well and incubated for 30 minutes. $^{125}$I-labeled rHRGβ1$_{177-224}$ (25,000 cpm) may then be added, and the incubation may be continued for 4 to 16 hours. Dose response curves may be prepared and an IC$_{50}$ value (cytotoxic activity) may be calculated for the compound of interest.

Alternatively, or additionally, the ability of an ADC to block ErbB ligand-stimulated tyrosine phosphorylation of an ErbB receptor present in an ErbB hetero-oligomer may be assessed. For example, cell lines established from the transgenic animals herein may be incubated with a test ADC and then assayed for ErbB ligand-dependent tyrosine phosphorylation activity using an anti-phosphotyrosine monoclonal antibody (which is optionally conjugated with a detectable label). The kinase receptor activation assay described in U.S. Pat. No. 5,766,863 is also available for determining ErbB receptor activation and blocking of that activity by the compound.

In one embodiment, one may screen for ADC which inhibit HRG stimulation of p180 tyrosine phosphorylation in MCF7 cells essentially as described below. For example, a cell line established from a HER2-transgenic animal may be plated in 24-well plates and the compound may be added to each well and incubated for 30 minutes at room temperature; then rHRGβ1$_{177-244}$ may be added to each well to a final concentration of 0.2 nM, and the incubation may be continued for about 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at M$_r$-180,000 may be quantified by reflectance densitometry. An alternate method to evaluate inhibition of receptor phosphorylation is the KIRA (kinase receptor activation) assay of Sadick et al. (1998) Jour. of Pharm. and Biomed. Anal. Some of the well established monoclonal antibodies against HER2 that are known to inhibit HRG stimulation of p180 tyrosine phosphorylation can be used as positive control in this assay. A dose-response curve for inhibition of HRG stimulation of p180 tyrosine phosphorylation as determined by reflectance densitometry may be prepared and an IC$_{50}$ for the compound of interest may be calculated.

One may also assess the growth inhibitory effects of a test ADC on cell lines derived from a HER2-transgenic animal, e.g., essentially as described in Schaefer et al. (1997) Oncogene 15:1385-1394. According to this assay, the cells may be treated with a test compound at various concentrations for 4 days and stained with crystal violet or the redox dye Alamar Blue. Incubation with the compound may show a growth inhibitory effect on this cell line similar to that displayed by monoclonal antibody 2C4 on MDA-MB-175 cells (Schaefer et al., supra). In a further embodiment, exogenous HRG will not significantly reverse this inhibition.

To identify growth inhibitory compounds that specifically target an antigen of interest, one may screen for compounds which inhibit the growth of cancer cells overexpressing antigen of interest derived from transgenic animals, the assay described in U.S. Pat. No. 5,677,171 can be performed. According to this assay, cancer cells overexpressing the antigen of interest are grown in a 1:1 mixture of F12 and DMEM medium supplemented with 10% fetal bovine serum, glutamine and penicillin streptomycin. The cells are plated at 20,000 cells in a 35 mm cell culture dish (2 mls/35 mm dish) and the test compound is added at various concentrations. After six days, the number of cells, compared to untreated cells is counted using an electronic COULTER™ cell counter. Those compounds which inhibit cell growth by about 20-100% or about 50-100% may be selected as growth inhibitory compounds.

To select for compounds which induce cell death, loss of membrane integrity as indicated by, e.g., PI, trypan blue or 7AAD uptake may be assessed relative to control. The PI uptake assay uses cells isolated from the tumor tissue of interest of a transgenic animal. According to this assay, the cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. The cells are seeded at a density of $3\times10^6$ per dish in 100×20 mm dishes and allowed to attach overnight. The medium is then removed and replaced with fresh medium alone or medium containing various concentrations of the compound. The cells are incubated for a 3-day time period. Following each treatment, monolayers are washed with PBS and detached by trypsinization. Cells are then centrifuged at 1200 rpm for 5 minutes at 4° C., the pellet resuspended in 3 ml cold Ca$^{2+}$ binding buffer (10 mM Hepes, pH 7.4, 140 mM NaCl, 2.5 mM CaCl$_2$) and aliquoted into 35 mm strainer-capped 12×75 mm tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson). Those compounds which induce statistically significant levels of cell death as determined by PI uptake may be selected as cell death-inducing compounds.

In order to select for compounds which induce apoptosis, an annexin binding assay using cells established from the tumor tissue of interest of the transgenic animal is performed. The cells are cultured and seeded in dishes as discussed in the preceding paragraph. The medium is then removed and replaced with fresh medium alone or medium containing 10 μg/ml of the antibody drug conjugate (ADC). Following a three-day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g., annexin V-FITC) (1 μg/ml). Samples may be analyzed using a FACSCAN™ flow cytometer and FACSCONVERT™ CellQuest software (Becton Dickinson). Those compounds which induce statistically significant levels of annexin binding relative to control are selected as apoptosis-inducing compounds.

4.5.3 In Vitro Cell Proliferation Assays

Generally, the cytotoxic or cytostatic activity of an antibody drug conjugate (ADC) is measured by: exposing mammalian cells having receptor proteins to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody drug conjugates was measured by a cell proliferation assay (Example 18, FIGS. 7-10). The CellTiter-Glo® Luminescent Cell Viability Assay is a commercially available (Promega Corp., Madison, Wis.), homogeneous assay method based on the recombinant expression of *Coleoptera* luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al. (1993) J. Immunol. Meth. 160:81-88, U.S. Pat. No. 6,602,677). The CellTiter-Glo® Assay was conducted in 96 well format, making it amenable to automated high-throughput screening (HTS) (Cree et al. (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

Figure 24:
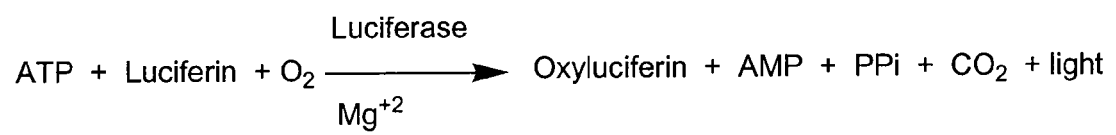
FIG. 24 shows a scheme of the CellTiter-Glo® Assay.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used (FIG. 24). Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g., 96 or 384 well format. Data can be recorded by luminometer or CCD camera imaging device. The luminescence output is presented as relative light units (RLU), measured over time.

The anti-proliferative effects of antibody drug conjugates were measured by the cell proliferation, in vitro cell killing assay above against four different breast tumor cell lines (FIGS. 7-10). $IC_{50}$ values were established for SK-BR-3 and BT-474 which are known to over express HER2 receptor protein. Table 2a shows the potency ($IC_{50}$) measurements of exemplary antibody drug conjugates in the cell proliferation assay against SK-BR-3 cells. Table 2b shows the potency ($IC_{50}$) measurements of exemplary antibody drug conjugates in the cell proliferation assay against BT-474 cells.

Antibody drug conjugates: Trastuzumab-MC-vc-PAB-MMAF, 3.8 MMAF/Ab; Trastuzumab-MC-(N-Me)vc-PAB-MMAF, 3.9 MMAF/Ab; Trastuzumab-MC-MMAF, 4.1 MMAF/Ab; Trastuzumab-MC-vc-PAB-MMAE, 4.1 MMAE/Ab; Trastuzumab-MC-vc-PAB-MMAE, 3.3 MMAE/Ab; and Trastuzumab-MC-vc-PAB-MMAF, 3.7 MMAF/Ab did not inhibit the proliferation of MCF-7 cells (FIG. 9).

Antibody drug conjugates: Trastuzumab-MC-vc-PAB-MMAE, 4.1 MMAE/Ab; Trastuzumab-MC-vc-PAB-MMAE, 3.3 MMAE/Ab; Trastuzumab-MC-vc-PAB-MMAF, 3.7 MMAF/Ab; Trastuzumab-MC-vc-PAB-MMAF, 3.8 MMAF/Ab; Trastuzumab-MC-(N-Me)vc-PAB-MMAF, 3.9 MMAF/Ab; and Trastuzumab-MC-MMAF, 4.1 MMAF/Ab did not inhibit the proliferation of MDA-MB-468 cells (FIG. 10).

MCF-7 and MDA-MB-468 cells do not overexpress HER2 receptor protein. The anti-HER2 antibody drug conjugates of the invention therefore show selectivity for inhibition of cells which express HER2.

TABLE 2a

SK-BR-3 cells

| Antibody Drug Conjugate<br>H = trastuzumab linked via a cysteine [cys]<br>except where noted | $IC_{50}$ (μg ADC/ml) |
|---|---|
| H-MC-MMAF, 4.1 MMAF/Ab | 0.008 |
| H-MC-MMAF, 4.8 MMAF/Ab | 0.002 |
| H-MC-vc-PAB-MMAE, | 0.007 |
| H-MC-vc-PAB-MMAE | 0.015 |
| H-MC-vc-PAB-MMAF, 3.8 MMAF/Ab | 0.0035-0.01 |
| H-MC-vc-PAB-MMAF, 4.4 MMAF/Ab | 0.006-0.007 |
| H-MC-vc-PAB-MMAF, 4.8 MMAF/Ab | 0.006 |
| H-MC-(N-Me)vc-PAB-MMAF, 3.9 MMAF/Ab | 0.0035 |
| H-MC-MMAF, 4.1 MMAF/Ab | 0.0035 |
| H-MC-vc-PAB-MMAE, 4.1 MMAE/Ab | 0.010 |
| H-MC-vc-PAB-MMAE, 3.8 MMAF/Ab | 0.007 |
| H-MC-vc-PAB-MMAE, 4.1 MMAE/Ab | 0.015 |
| H-MC-vc-PAB-MMAE, 3.7 MMAF/Ab. | 0.010 |
| H-MC-vc-PAB-MMAE, 7.5 MMAE/Ab | 0.0025 |
| H-MC-MMAE, 8.8 MMAE/Ab | 0.018 |
| H-MC-MMAE, 4.6 MMAE/Ab | 0.05 |
| H-MC-(L)val-(L)cit-PAB-MMAE, 8.7 MMAE/Ab | 0.0003 |
| H-MC-(D)val-(D)cit-PAB-MMAE, 8.2 MMAE/Ab | 0.02 |
| H-MC-(D)val-(L)cit-PAB-MMAE, 8.4 MMAE/Ab | 0.0015 |
| H-MC-(D)val-(L)cit-PAB-MMAE, 3.2 MMAE/Ab | 0.003 |
| H-Trastuzumab | 0.083 |
| H-vc-MMAE, linked via a lysine [lys] | 0.002 |

TABLE 2a-continued

SK-BR-3 cells

| Antibody Drug Conjugate<br>H = trastuzumab linked via a cysteine [cys]<br>except where noted | $IC_{50}$ (μg ADC/ml) |
|---|---|
| H-phe-lys-MMAE, linked via a lysine [lys] | 0.0015 |
| 4D5-Fc8-MC-vc-PAB-MMAF, 4.4 MMAF/Ab | 0.004 |
| Hg-MC-vc-PAB-MMAF, 4.1 MMAF/Ab | 0.01 |
| 7C2-MC-vc-PAB-MMAF, 4.0 MMAF/Ab | 0.01 |
| 4D5 Fab-MC-vc-PAB-MMAF, 1.5 MMAF/Ab | 0.02 |
| Anti-TF Fab-MC-vc-PAB-MMAE* | — |

TABLE 2b

BT474 cells

| Antibody Drug Conjugate<br>H = trastuzumab linked via a cysteine [cys] | $IC_{50}$ (μg ADC/ml) |
|---|---|
| H-MC-MMAF, 4.1 MMAF/Ab | 0.008 |
| H-MC-MMAF, 4.8 MMAF/Ab | 0.002 |
| H-MC-vc-PAB-MMAE, 4.1 MMAE/Ab | 0.015 |
| H-MC-vc-PAB-MMAF, 3.8 MMAF/Ab | 0.02-0.05 |
| H-MC-vc-PAB-MMAF, 4.4 MMAF/Ab | 0.01 |
| H-MC-vc-PAB-MMAF, 4.8 MMAF/Ab | 0.01 |
| H-MC-vc-PAB-MMAE, 3.3 MMAE/Ab | 0.02 |
| H-MC-vc-PAB-MMAF, 3.7 MMAF/Ab. | 0.02 |
| H-MC-vc-PAB-MMAF, 3.8 MMAF/Ab | 0.015 |
| H-MC-(N-Me)vc-PAB-MMAF, 3.9 MMAF/Ab | 0.010 |
| H-MC-MMAF, 4.1 MMAF/Ab | 0.00015 |
| H-MC-vc-PAB-MMAE, 7.5 MMAE/Ab | 0.0025 |
| H-MC-MMAE, 8.8 MMAE/Ab | 0.04 |
| H-MC-MMAE, 4.6 MMAE/Ab | 0.07 |
| 4D5-Fc8-MC-vc-PAB-MMAF, 4.4 MMAF/Ab | 0.008 |
| Hg-MC-vc-PAB-MMAF, 4.1 MMAF/Ab | 0.01 |
| 7C2-MC-vc-PAB-MMAF, 4.0 MMAF/Ab | 0.015 |
| 4D5 Fab-MC-vc-PAB-MMAF, 1.5 MMAF/Ab | 0.04 |
| Anti-TF Fab-MC-vc-PAB-MMAE* | — |

H = trastuzumab
7C2 = anti-HER2 murine antibody which binds a different epitope than trastuzumab.
Fc8 = mutant that does not bind to FcRn
Hg = "Hingeless" full-length humanized 4D5, with heavy chain hinge cysteines mutated to serines. Expressed in *E. coli* (therefore non-glycosylated.)
Anti-TF Fab = anti-tissue factor antibody fragment
*activity against MDA-MB-468 cells In a surprising and unexpected discovery, the in vitro cell proliferation activity results of the ADC in Tables 2a and 2b show generally that ADC with a low average number of drug moieties per antibody showed efficacy, e.g., $IC_{50}$<0.1 μg ADC/ml. The results suggest that at least for trastuzumab ADC, the optimal ratio of drug moieties per antibody may be less than 8, and may be about 2 to about 5.

4.5.4 In Vivo Plasma Clearance and Stability

Pharmacokinetic plasma clearance and stability of ADC were investigated in rats and cynomolgus monkeys. Plasma concentration was measured over time. Table 2c shows pharmacokinetic data of antibody drug conjugates and other dosed samples in rats. Rats are a non-specific model for ErbB receptor antibodies, since the rat is not known to express HER2 receptor proteins.

TABLE 2c

Pharmacokinetics in Rats
H = trastuzumab linked via a cysteine [cys] except where noted
2 mg/kg dose except where noted

| Sample<br>dose mg/kg | AUCinf day *<br>μg/mL | CL<br>mL/day/kg | Cmax<br>μg/mL | T ½<br>Term.<br>days | % Conj. |
|---|---|---|---|---|---|
| H-MC-vc-PAB-MMAE (Total Ab) | 78.6 | 26.3 | 39.5 | 5.80 | 40.6 |
| H-MC-vc-PAB-MMAE (Conj.) | 31.1 | 64.4 | 33.2 | 3.00 | |
| H-MC-vc-PAB-MMAF (Total Ab) | 170 | 12.0 | 47.9 | 8.4 | 50.0 |
| H-MC-vc-PAB-MMAF (Conj.) | 83.9 | 24.0 | 44.7 | 4.01 | |
| H-MC-MMAE (Total Ab) | 279 | 18.9 | 79.6 | 7.65 | 33 |
| H-MC-MMAE (Conj.)<br>5 mg/kg | 90.6 | 62.9 | 62.9 | 4.46 | |
| H-MC-MMAF (Total Ab) | 299 | 6.74 | 49.1 | 11.6 | 37 |
| H-MC-MMAF (Conj.) | 110 | 18.26 | 50.2 | 4.54 | |
| H-MC-vc-MMAF, wo/PAB, (Total Ab) | 306 | 6.6 | 78.7 | 11.9 | 19.6 |
| H-MC-vc-MMAF, wo/PAB, (Conj.) | 59.9 | 33.4 | 82.8 | 2.1 | |
| H-Me-vc-PAB-MMAF (Total Ab) | 186 | 10.8 | 46.9 | 8.3 | 45.3 |
| H-Me-vc-PAB-MMAF (Conj.) | 84.0 | 23.8 | 49.6 | 4.3 | |
| H-Me-vc-PAB-MMAE (Total Ab) | 135 | 15.0 | 44.9 | 11.2 | 23.8 |
| H-Me-vc-PAB-MMAE (Conj.) | 31.9 | 63.8 | 45.2 | 3.0 | |
| H-MC-vc-MMAF, wo/PAB, (Total Ab) | 306 | 6.6 | 78.7 | 11.9 | 19.6 |
| H-MC-vc-MMAF, wo/PAB, (Conj.) | 59.9 | 33.4 | 82.8 | 2.1 | |

TABLE 2c-continued

Pharmacokinetics in Rats
H = trastuzumab linked via a cysteine [cys] except where noted
2 mg/kg dose except where noted

| Sample<br>dose mg/kg | AUCinf day *<br>µg/mL | CL<br>mL/day/kg | Cmax<br>µg/mL | T½<br>Term.<br>days | % Conj. |
|---|---|---|---|---|---|
| H-MC-(D)val-(L)cit-PAB-MMAE (Total Ab) | 107 | 19.2 | 30.6 | 9.6 | 38.1 |
| H-MC-(D)val-(L)cit-PAB-MMAE (Conj.) | 40 | 50.4 | 33.7 | 3.98 | |
| H-MC-(Me)-vc-PAB-MMAE, Total Ab | 135.1 | 15.0 | 44.9 | 11.2 | 23.8 |
| H-MC-(Me)-vc-PAB-MMAE, Conj. | 31.9 | 63.8 | 45.2 | 2.96 | |
| H-MC-(D)val-(D)cit-PAB-MMAE, Total Ab | 88.2 | 22.8 | 33.8 | 10.5 | 38.3 |
| H-MC-(D)val-(D)cit-PAB-MMAE, Conj. | 33.6 | 59.8 | 36.0 | 4.43 | |
| H-MC-vc-PAB-MMAE, Total Ab | 78.6 | 26.3 | 39.5 | 5.8 | 40.6 |
| H-MC-vc-PAB-MMAE, Conj. | 31.1 | 64.4 | 33.2 | 3.00 | |
| H linked to MC by lysine [lys] MMAF 200 µg/kg | 0.99 | 204 | 280 | 0.224 | — |
| MMAE 206 µg/kg | 3.71 | 62.6 | 649 | 0.743 | — |
| HER F(ab')$_2$-MC-vc-MMAE, Total Ab | 9.3 | 217 | 34.4 | 0.35 | 95 |
| HER F(ab')$_2$-MC-vc-MMAE, Conj. | 8.8 | 227 | 36.9 | 0.29 | |
| 4D5-H-Fab-MC-vc-MMAF, Total Ab | 43.8 | 46.2 | 38.5 | 1.49 | 68 |
| 4D5-H-Fab-MC-vc-MMAF, Conj. | 29.9 | 68.1 | 34.1 | 1.12 | |
| 4D5-H-Fab-MC-vc-MMAE, Total Ab | 71.5 | 70.3 | 108 | 1.18 | 59 |
| 4D5-H-Fab-MC-vc-MMAE, Conj. | 42.2 | 118.9 | 114 | 0.74 | |
| 4D5-H-Fab | 93.4 | 53.9 | 133 | 1.08 | — |
| H-MC-vc-PAB-MMAF, Total Ab | 170 | 12.03 | 47.9 | 8.44 | 49.5 |
| H-MC-vc-PAB-MMAF, Conj. | 83.9 | 23.96 | 44.7 | 4.01 | |
| H-MC-vc-PAB-MMAF-DMAEA, Total Ab | 211 | 9.8 | 39.8 | 8.53 | 34.3 |
| H-MC-vc-PAB-MMAF-DMAEA, Conj. | 71.5 | 28.2 | 38.8 | 3.64 | |
| H-MC-vc-PAB-MMAF-TEG, Total Ab | 209 | 9.75 | 53.2 | 8.32 | 29.7 |
| H-MC-vc-PAB-MMAF-TEG, Conj. | 63.4 | 31.8 | 34.9 | 4.36 | |

AUC inf is the area under the plasma concentration-time curve from time of dosing to infinity and is a measure of the total exposure to the measured entity (drug, ADC). CL is defined as the volume of plasma cleared of the measured entity in unit time and is expressed by normalizing to body weight. T1/2 term is the half-life of the drug in the body measured during its elimination phase. The % Conj. term is the relative amount of ADC compared to total antibody detected, by separate ELISA immunoaffinity tests ("Analytical Methods for Biotechnology Products", Ferraiolo et al, p85-98 in Pharmacokinetics of Drugs (1994) P. G. Welling and L. P. Balant, Eds., Handbook of Experimental Pharmacology, Vol. 110, Springer-Verlag. The % Conj. calculation is simply AUCinf of ADC÷AUCinf total Ab, and is a general indicator of linker stability, although other factors and mechanisms may be in effect.

FIG. 11 shows a graph of a plasma concentration clearance study after administration of the antibody drug conjugates: H-MC-vc-PAB-MMAF-TEG and H-MC-vc-PAB-MMAF to Sprague-Dawley rats. Concentrations of total antibody and ADC were measured over time.

FIG. 12 shows a graph of a two stage plasma concentration clearance study where ADC was administered at different dosages and concentrations of total antibody and ADC were measured over time.

In Vivo Efficacy

The in vivo efficacy of the ADC of the invention was measured by a high expressing HER2 transgenic explant mouse model. An allograft was propagated from the Of5 mmtv transgenic mouse which does not respond to, or responds poorly to, HERCEPTIN® therapy. Subjects were treated once with ADC and monitored over 3-6 weeks to measure the time to tumor doubling, log cell kill, and tumor shrinkage. Follow up dose-response and multi-dose experiments were conducted.

Tumors arise readily in transgenic mice that express a mutationally activated form of neu, the rat homolog of HER2, but the HER2 that is overexpressed in breast cancers is not mutated and tumor formation is much less robust in transgenic mice that overexpress nonmutated HER2 (Webster et al. (1994) Semin. Cancer Biol. 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al. (1999) J. Biol. Chem. 274: 24335-24341). Additionally, a chimeric intron was added to the 5' end, which should also enhance the level of expression as reported earlier (Neuberger and Williams (1988) Nucleic Acids Res. 16: 6713; Buchman and Berg (1988) Mol. Cell. Biol. 8:4395; Brinster et al. (1988) Proc. Natl. Acad. Sci. USA 85:836). The chimeric intron was derived from a Promega vector, pCI-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al. (1997) Breast Cancer Res. and Treatment 45:149-158).

TABLE 2d

Tumor measurements in allograft mouse model - MMTV-HER2 Fo5 Mammary Tumor, athymic nude mice
single dose at day 1 (T = 0) except where noted
H = trastuzumab linked via a cysteine [cys] except where noted

| Sample Drugs per antibody | Dose | Ti | PR | CR | Tumor doubling time (days) | Mean log cell kill |
|---|---|---|---|---|---|---|
| Vehicle | | | | | 2-5 | 0 |
| H-MC-vc-PAB-MMAE 8.7 MMAE/Ab | 1250 μg/m² | 5/5 | 4/7 | 0/7 | 18 | 1.5 |
| H-MC-vc-PAB-MMAF 3.8 MMAF/Ab | 555 μg/m² | 2/5 | 2/7 | 5/7 | 69 | 6.6 |
| H-MC(Me)-vc-PAB-MMAF | | | | | >50 | 6.4 |
| H-MC-MMAF 4.8 MMAF/Ab | 9.2 mg/kg Ab 550 μg/m² at 0, 7, 14 and 21 days | 7/7 | 6/7 | 0/7 | 63 | 9 |
| H-MC-MMAF 4.8 MMAF/Ab | 14 mg/kg Ab 840 μg/m² at 0, 7, 14 and 21 days | 5/5 | 5/7 | 2/7 | >63 | |
| H-MC-vc-PAB-MMAF 5.9 MMAF/Ab | 3.5 mg/kg Ab 300 μg/m² at 0, 21, and 42 days | 5/6 | 1/7 | 3/7 | >36 | |
| H-MC-vc-PAB-MMAF 5.9 MMAF/Ab | 4.9 mg/kg Ab 425 μg/m² at 0, 21, and 42 days | 4/7 | 2/7 | 5/7 | >90 | |
| H-MC-vc-PAB-MMAF 5.9 MMAF/Ab | 6.4 mg/kg Ab 550 μg/m² at 0, 21, and 42 days | 3/6 | 1/7 | 6/7 | >90 | |
| H-(L)val-(L)cit-MMAE 8.7 MMAE/Ab | 10 mg/kg | 7/7 | 1/7 | 0/7 | 15.2 | 1.1 |
| H-MC-MMAE 4.6 MMAE/Ab | 10 mg/kg | 7/7 | 0/7 | 0/7 | 4 | 0.1 |
| H-(D)val-(D)cit-MMAE 4.2 MMAE/Ab | 10 mg/kg | 7/7 | 0/7 | 0/7 | 3 | |
| H-(D)val-(L)cit-MMAE 3.2 MMAE/Ab | 13 mg/kg | 7/7 | 0/7 | 0/7 | 9 | 0.6 |
| H-MC(Me)-vc-MMAE 3.0 MMAE/Ab | 13 mg/kg | 7/7 | 3/7 | 0/7 | 17 | 1.2 |
| H-(L)val-(D)cit-MMAE 3.5 MMAE/Ab | 12 mg/kg | 7/7 | 0/7 | 0/7 | 5 | 0.2 |
| H-vc-MMAE 8.7 MMAE/Ab | 10 mg/kg | 7/7 | | | 17 | |
| H-cys-vc-MMAF 3.8 MMAF/Ab | 1 mg/kg | 7/7 | | | 3 | |
| H-cys-vc-MMAF 3.8 MMAF/Ab | 3 mg/kg | 7/7 | | | >17 | |
| H-cys-vc-MMAF 3.8 MMAF/Ab | 10 mg/kg | 4/7 | 4/7 | 3/7 | >17 | |

TABLE 2d-continued

Tumor measurements in allograft mouse model - MMTV-HER2 Fo5
Mammary Tumor, athymic nude mice
single dose at day 1 (T = 0) except where noted
H = trastuzumab linked via a cysteine [cys] except where noted

| Sample Drugs per antibody | Dose | Ti | PR | CR | Tumor doubling time (days) | Mean log cell kill |
|---|---|---|---|---|---|---|
| H-MC-vc-MMAF-TEG 4 MMAF/Ab | 10 mg/kg | 3/6 | 1/7 | 6/7 | 81 | 7.8 |
| H-MC-vc-MMAF-TEG 4 MMAF/Ab | 10 mg/kg q3 wk × 3 | 0/5 | 0/7 | 7/7 | 81 | 7.9 |
| H-vc-MMAF (lot 1) | 10 mg/kg | 4/6 | 2/8 | 5/8 | | |
| H-vc-MMAF (lot 2) | 10 mg/kg | 7/8 | 1/8 | 1/8 | | |
| H-MC-MMAF | 10 mg/kg 550 μg/m² | 8/8 | 1/8 | 0/8 | 18 | |
| H-(Me)-vc-MMAF | 10 mg/kg | 3/7 | 2/8 | 5/8 | | |
| H-vc-MMAE 7.5 MMAE/Ab | 3.7 mg/kg at 0, 7, 14, 21, 28 days | 6/6 | 0/7 | 1/7 | 17 | 2.3 |
| H-vc-MMAE 7.5 MMAE/Ab | 7.5 mg/kg at 0, 7, 14, 21, 28 days | 5/7 | 3/7 | 3/7 | 69 | 10 |
| anti IL8-vc-MMAE 7.5 MMAE/Ab | 7.5 mg/kg at 0, 7, 14, 21, 28 days | 7/7 | 0/7 | 0/7 | 5 | 0.5 |
| anti IL8-vc-MMAE 7.5 MMAE/Ab | 3.7 mg/kg at 0, 7, 14, 21, 28 days | 6/6 | 0/7 | 0/7 | 3 | 0.2 |
| H-fk-MMAE 7.5 MMAE/Ab | 7.5 mg/kg at 0, 7, 14, 21, 28 days | 7/7 | 1/7 | 0/7 | 31 | 4.4 |
| H-fk-MMAE 7.5 MMAE/Ab | 3.7 mg/kg at 0, 7, 14, 21, 28 days | 7/7 | 0/7 | 0/7 | 8.3 | 0.9 |
| anti IL8-fk-MMAE 7.5 MMAE/Ab | 7.5 mg/kg at 0, 7, 14, 21, 28 days | 7/7 | 0/7 | 0/7 | 6 | 0.5 |
| anti IL8-fk-MMAE 7.5 MMAE/Ab | 3.7 mg/kg at 0, 7, 14, 21, 28 days | 7/7 | 0/7 | 0/7 | 3 | 0.1 |
| Trastuzumab | 7.5 mg/kg at 0, 7, 14, 21, 28 days | 7/7 | 0/7 | 0/7 | 5 | 0.4 |
| H-vc-MMAE 8.7 MMAE/Ab | 10 mg/kg 1250 μg/m² | 6/6 | 3/6 | 0/6 | 15 | 1.3 |
| H-vc-MMAE | 10 mg/kg 1250 μg/m² at 0, 7, and 14 days | 7/7 | 5/7 | | >19 | |
| H-vc-MMAE | 3 mg/kg at 0, 7, and 14 days | 7/7 | | | 8 | |
| H-vc-MMAE | 1 mg/kg at 0, 7, and 14 days | 7/7 | | | 7 | |
| H-vc-MMAF | 10 mg/kg | 8/8 | 5/8 | | >21 | |
| H-vc-MMAF | 10 mg/kg at 0, 7, and 14 days | 4/7 | 4/7 | 3/7 | >21 | |
| H-vc-MMAF | 3 mg/kg at 0, 7, and 14 days | 7/7 | | | 6 | |
| H-vc-MMAF | 1 mg/kg at 0, 7, and 14 days | 8/8 | | | 4 | |
| Trastuzumab | 10 mg/kg at 0 and 7 days | 8/8 | | | 3 | |
| Hg-MC-vc-PAB-MMAF 4.1 MMAF/Ab | 10 mg/kg at 0 days | 6/7 | 3/8 | 5/8 | 56 | 5.1 |
| Fc8-MC-vc-PAB-MMAF 4.4 MMAF/Ab | 10 mg/kg at 0 days | 7/7 | 6/8 | 0/8 | 25 | 2.1 |
| 7C2-MC-vc-PAB-MMAF 4 MMAF/Ab | 10 mg/kg at 0 days | 5/6 | 6/8 | 1/8 | 41 | 3.7 |

TABLE 2d-continued

Tumor measurements in allograft mouse model - MMTV-HER2 Fo5
Mammary Tumor, athymic nude mice
single dose at day 1 (T = 0) except where noted
H = trastuzumab linked via a cysteine [cys] except where noted

| Sample Drugs per antibody | Dose | Ti | PR | CR | Tumor doubling time (days) | Mean log cell kill |
|---|---|---|---|---|---|---|
| H-MC-vc-PAB-MMAF 5.9 MMAF/Ab | 10 mg/kg at 0 days | 3/8 | 3/8 | 5/8 | 62 | 5.7 |
| 2H9-MC-vc-PAB-MMAE | | 9/9 | | | >14 days | |
| 2H9-MC-vc-PAB-MMAF | | 9/9 | | | >14 days | |
| 11D10-vc-PAB-MMAE | | 9/9 | | | >14 days | |
| 11D10-vc-PAB-MMAF | | 9/9 | | | 11 days | |

7C2 = anti-HER2 murine antibody which binds a different epitope than trastuzumab.
Fc8 = mutant that does not bind to FcRn
Hg = "Hingeless" full-length humanized 4D5, with heavy chain hinge cysteines mutated to serines. Expressed in *E. coli* (therefore non-glycosylated.)
2H9 = Anti-EphB2R
11D10 = Anti-O772P The term Ti is the number of animals in the study group with tumor at T=0÷total animals in group. The term PR is the number of animals attaining partial remission of tumor÷animals with tumor at T=0 in group. The term CR is the number of animals attaining complete remission of tumor÷animals with tumor at T=0 in group. The term Log cell kill is the time in days for the tumor volume to double–the time in days for the control tumor volume to double divided by 3.32×time for tumor volume to double in control animals (dosed with Vehicle). The log-cell-kill calculation takes into account tumor growth delay resulting from treatment and tumor volume doubling time of the control group. Anti-tumor activity of ADC is classified with log-cell-kill values of:

| | |
|---|---|
| ++++ | ≧3.4 (highly active) |
| +++ = | 2.5-3.4 |
| ++ = | 1.7-2.4 |
| + = | 1.0-1.6 |
| inactive = | 0 |

Figure 13:
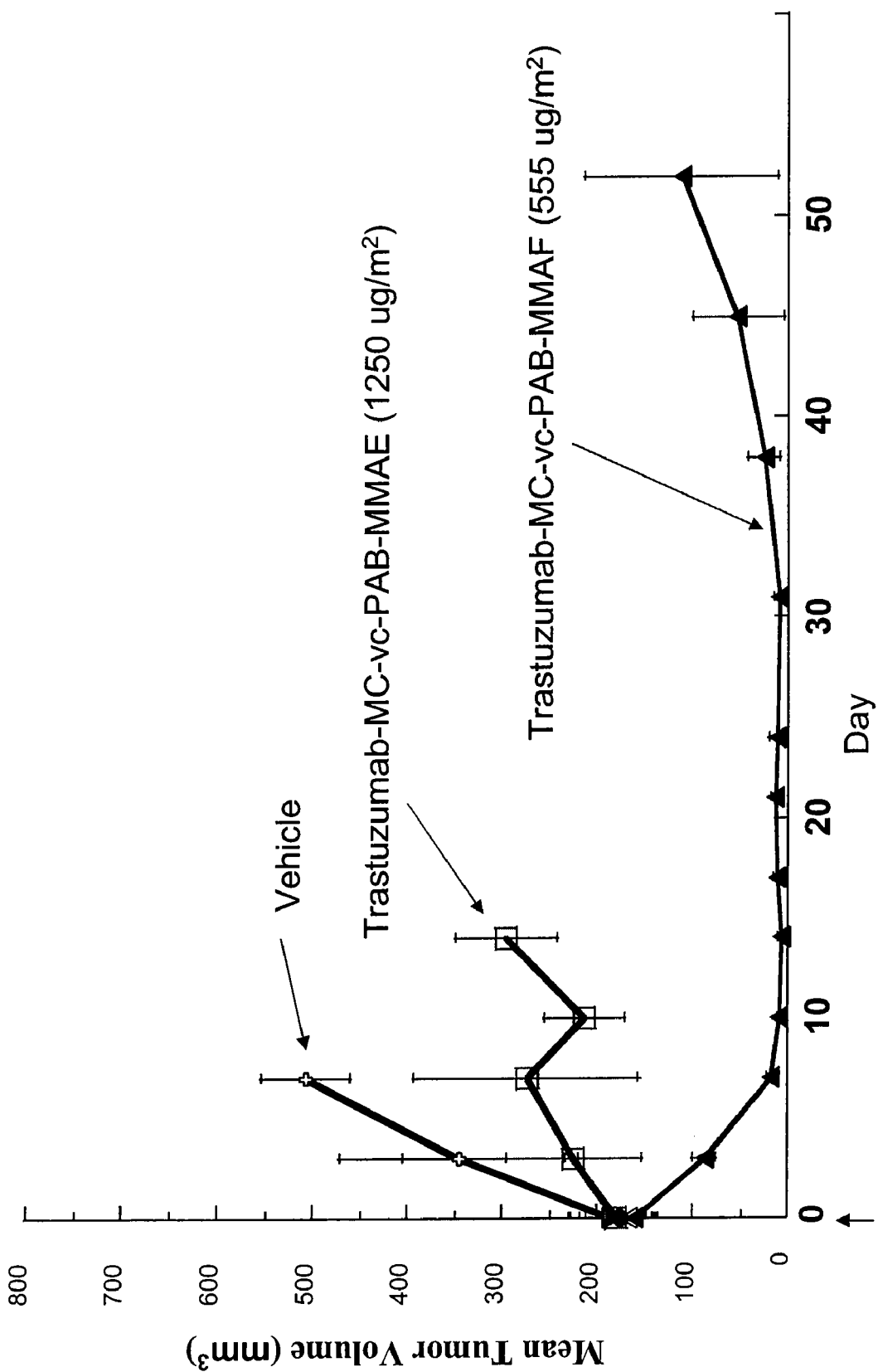
FIG. 13 shows the mean tumor volume change over time in athymic nude mice with MMTV-HER2 Of5 Mammary tumor allografts dosed on Day 0 with: Vehicle, Trastuzumab-MC-vc-PAB-MMAE (1250 µg/m$^2$) and Trastuzumab-MC-vc-PAB-MMAF (555 µg/m$^2$). (H=Trastuzumab).
Figure 14:
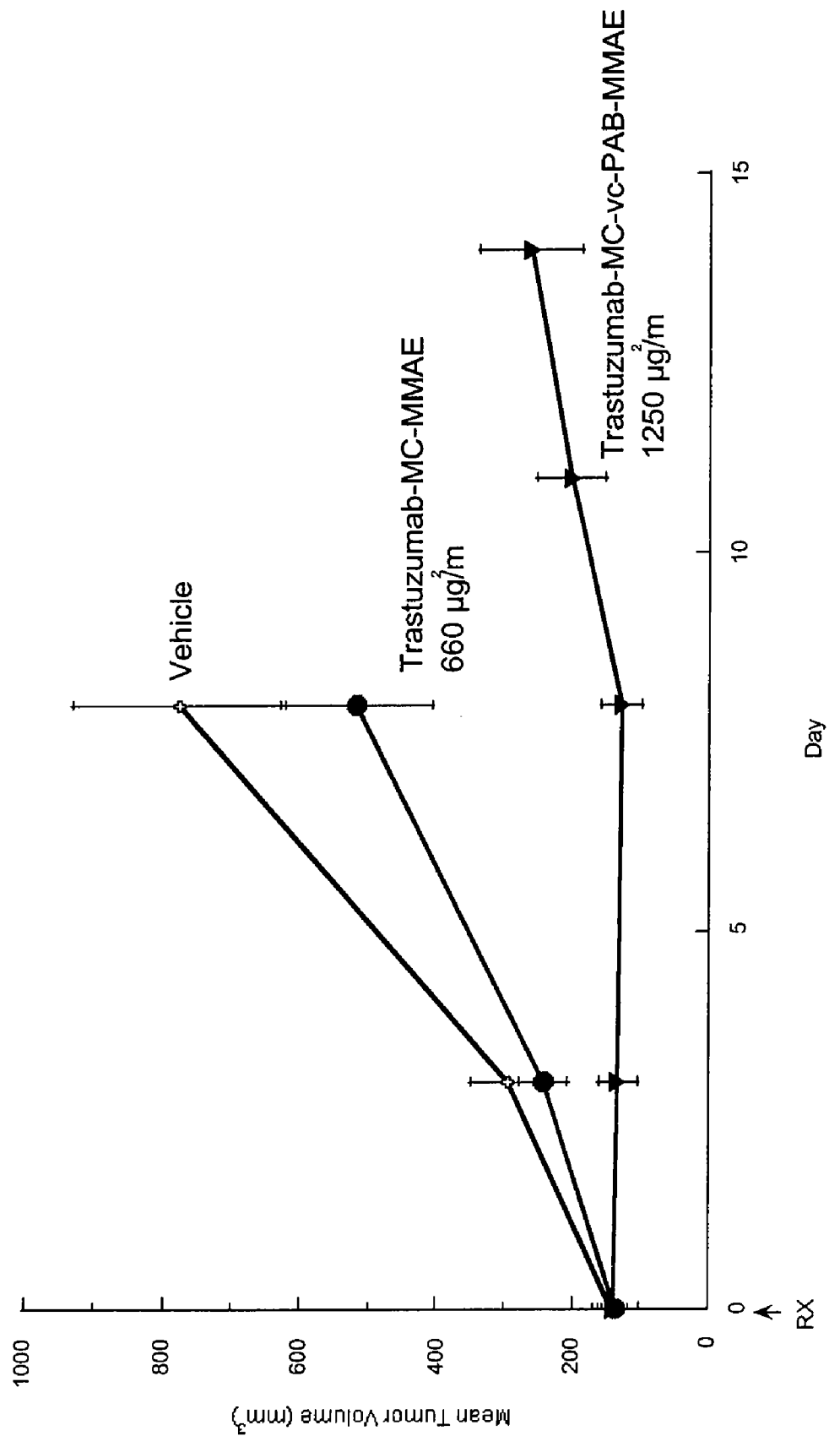
FIG. 14 shows the mean tumor volume change over time in athymic nude mice with MMTV-HER2 Of5 Mammary tumor allografts dosed on Day 0 with 10 mg/kg (660 µg/m$^2$) of Trastuzumab-MC-MMAE and 1250 µg/m$^2$ Trastuzumab-MC-vc-PAB-MMAE.
Figure 15:
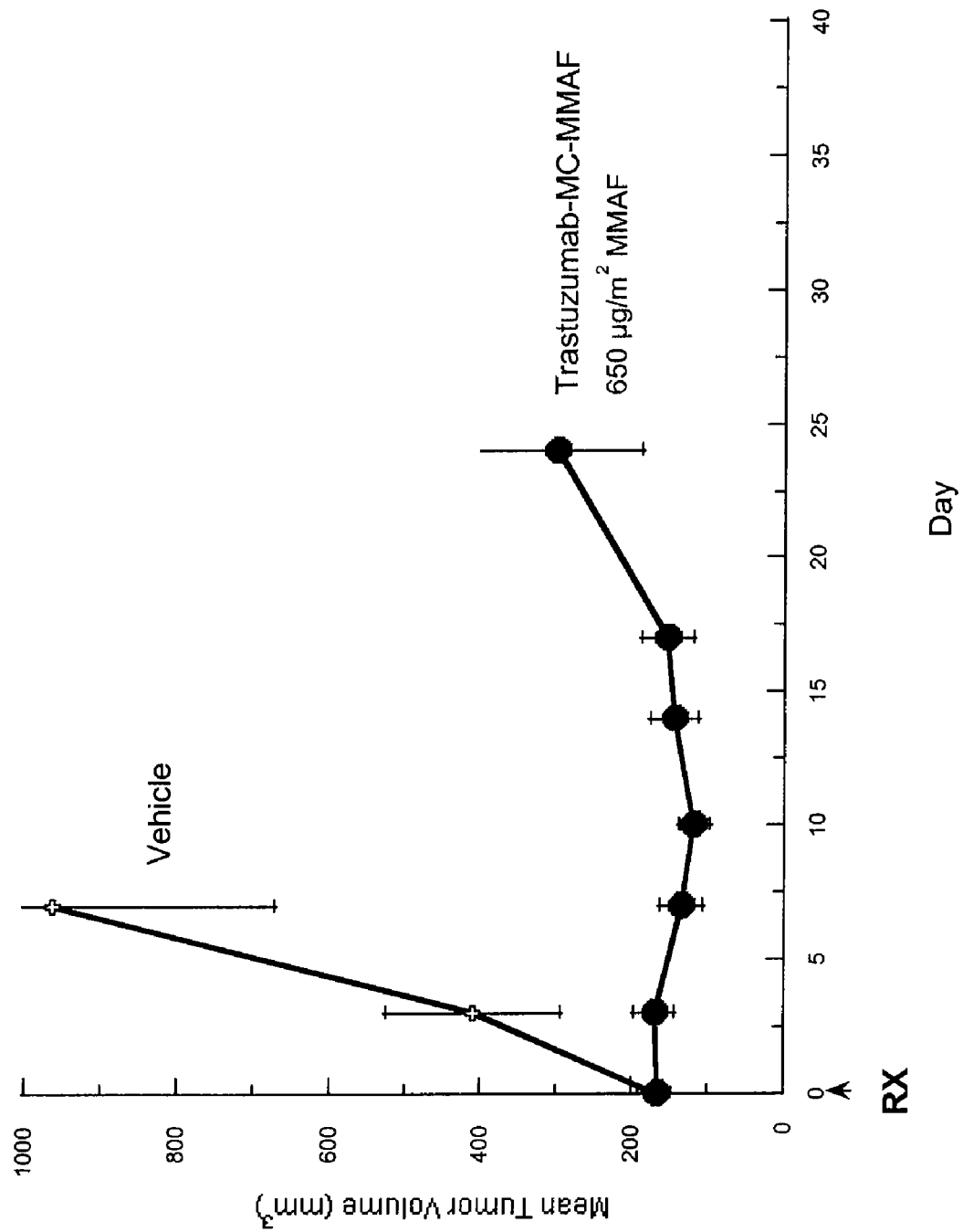
FIG. 15 shows the mean tumor volume change over time in athymic nude mice with MMTV-HER2 Of5 Mammary tumor allografts dosed on Day 0 with Vehicle and 650 µg/m$^2$ trastuzumab-MC-MMAF.

FIG. 13 shows the mean tumor volume change over time in athymic nude mice with MMTV-HER2Of5 Mammary tumor allografts dosed on Day 0 with: Vehicle, Trastuzumab-MC-vc-PAB-MMAE (1250 µg/m$^2$) and Trastuzumab-MC-vc-PAB-MMAF (555 µg/m$^2$). (H=Trastuzumab). The growth of tumors was retarded by treatment with ADC as compared to control (Vehicle) level of growth. FIG. 14 shows the mean tumor volume change over time in athymic nude mice with MMTV-HER2 Fo5 Mammary tumor allografts dosed on Day 0 with 10 mg/kg (660 µg/m$^2$) of Trastuzumab-MC-MMAE and 1250 µg/m$^2$ Trastuzumab-MC-vc-PAB-MMAE. FIG. 15 shows the mean tumor volume change over time in athymic nude mice with MMTV-HER2 Fo5 Mammary tumor allografts dosed with 650 µg/m$^2$ Trastuzumab-MC-MMAF. Table 2d and FIGS. 13-15 show that the ADC have strong anti-tumor activity in the allograft of a HER2 positive tumor (Fo5) that originally arose in an MMTV-HER2 transgenic mouse. The antibody alone (e.g., Trastuzumab) does not have significant anti-tumor activity in this model (Erickson et al. U.S. Pat. No. 6,632,979). As illustrated in FIGS. 13-15, the growth of the tumors was retarded by treatment with ADC as compared to control (Vehicle) level of growth.

Figure 16:
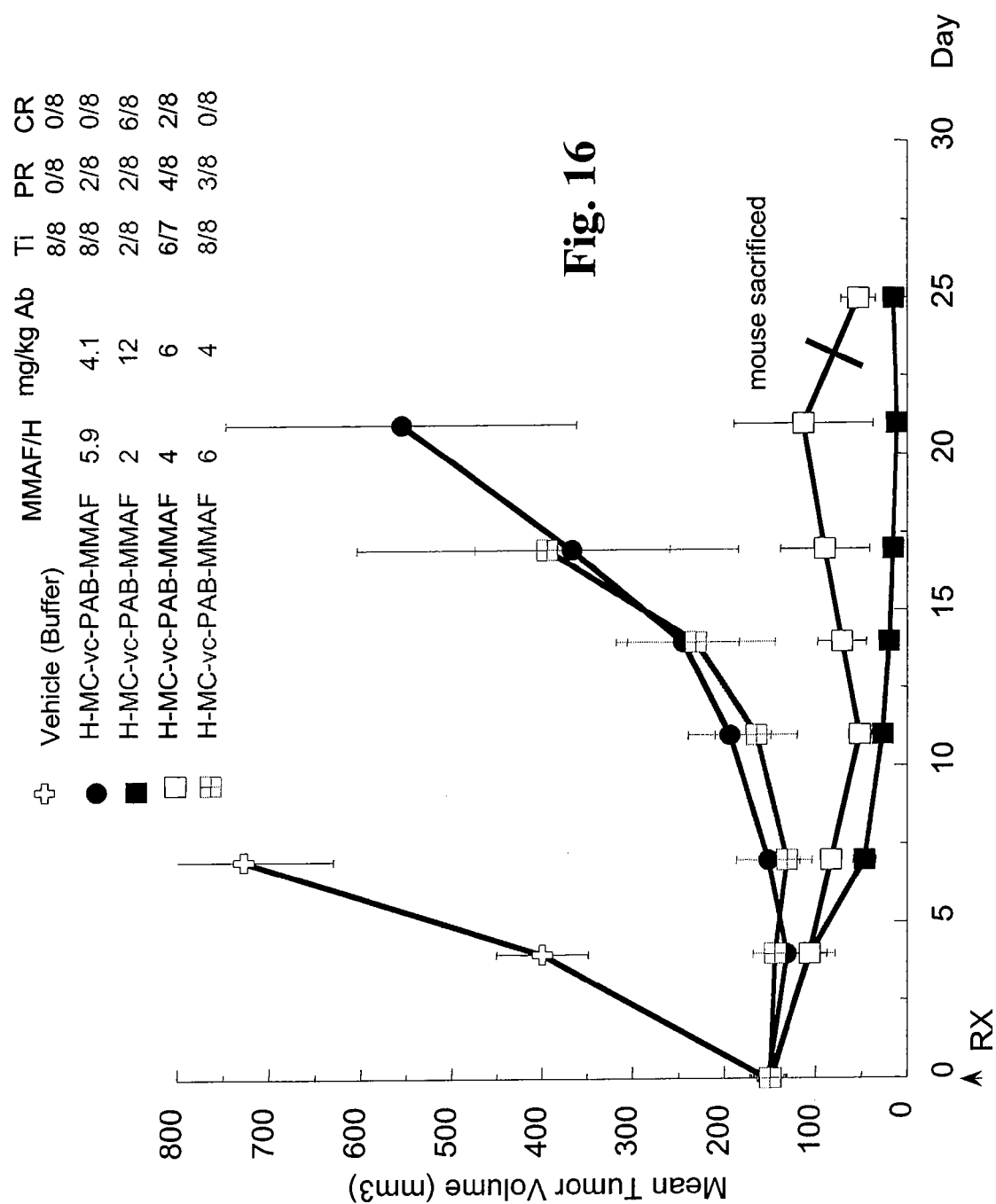
FIG. 16 shows the mean tumor volume change over time in athymic nude mice with MMTV-HER2 Of5 Mammary tumor allografts dosed on Day 0 with Vehicle and 350 µg/m$^2$ of four trastuzumab-MC-MMAF conjugates where the MMAF/trastuzumab (H) ratio is 2, 4, 5.9 and 6.

In a surprising and unexpected discovery, the in vivo anti-tumor activity results of the ADC in Table 2d show generally that ADC with a low average number of drug moieties per antibody showed efficacy, e.g., tumor doubling time>15 days and mean log cell kill>1.0. FIG. 16 shows that for the antibody drug conjugate, trastuzumab-MC-vc-PAB-MMAF, the mean tumor volume diminished and did not progress where the MMAF:trastuzumab ratio was 2 and 4, whereas tumor progressed at a ratio of 5.9 and 6, but at a rate lower than Vehicle (buffer). The rate of tumor progression in this mouse xenograft model was about the same, i.e. 3 days, for Vehicle and trastuzumab. The results suggest that at least for trastuzumab ADC, the optimal ratio of drug moieties per antibody may be less than about 8, and may be about 2 to about 4.

4.5.5 Rodent Toxicity

Antibody drug conjugates and an ADC-minus control, "Vehicle", were evaluated in an acute toxicity rat model. Toxicity of ADC was investigated by treatment of male and female Sprague-Dawley rats with the ADC and subsequent inspection and analysis of the effects on various organs. Gross observations included changes in body weights and signs of lesions and bleeding. Clinical pathology parameters (serum chemistry and hematology), histopathology, and necropsy were conducted on dosed animals.

Figure 18:
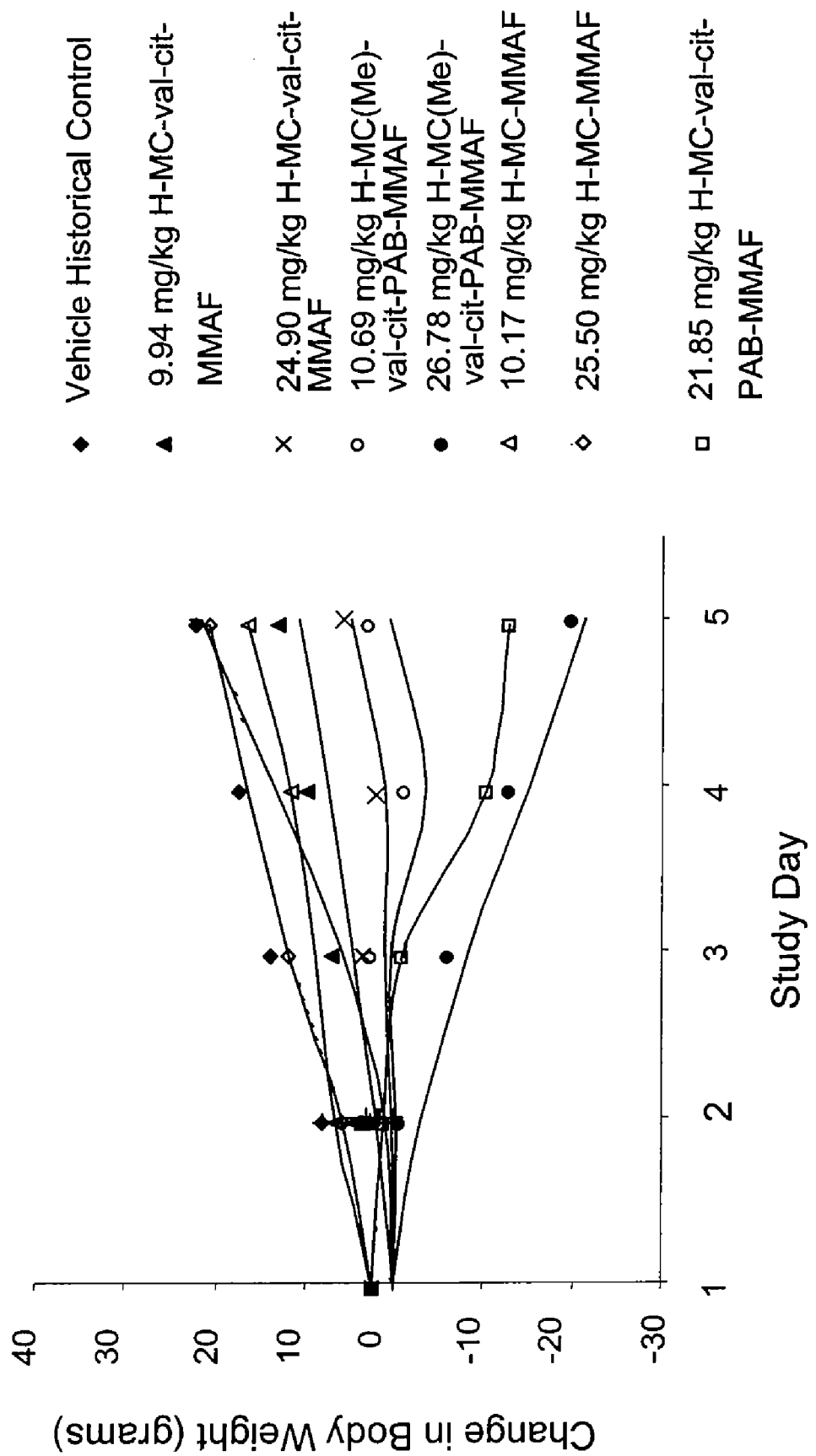
FIG. 18 shows the Group mean change in animal (rat) body weights (Mean±SD) after administration of 9.94 mg/kg H-MC-vc-MMAF, 24.90 mg/kg H-MC-vc-MMAF, 10.69 mg/kg H-MC(Me)-vc-PAB-MMAF, 26.78 mg/kg H-MC(Me)-vc-PAB-MMAF, 10.17 mg/kg H-MC-MMAF, 25.50 mg/kg H-MC-MMAF, and 21.85 mg/kg H-MC-vc-PAB-MMAF. H=trastuzumab. The MC linker is attached via a cysteine of trastuzumab for each conjugate.
Figure 19:
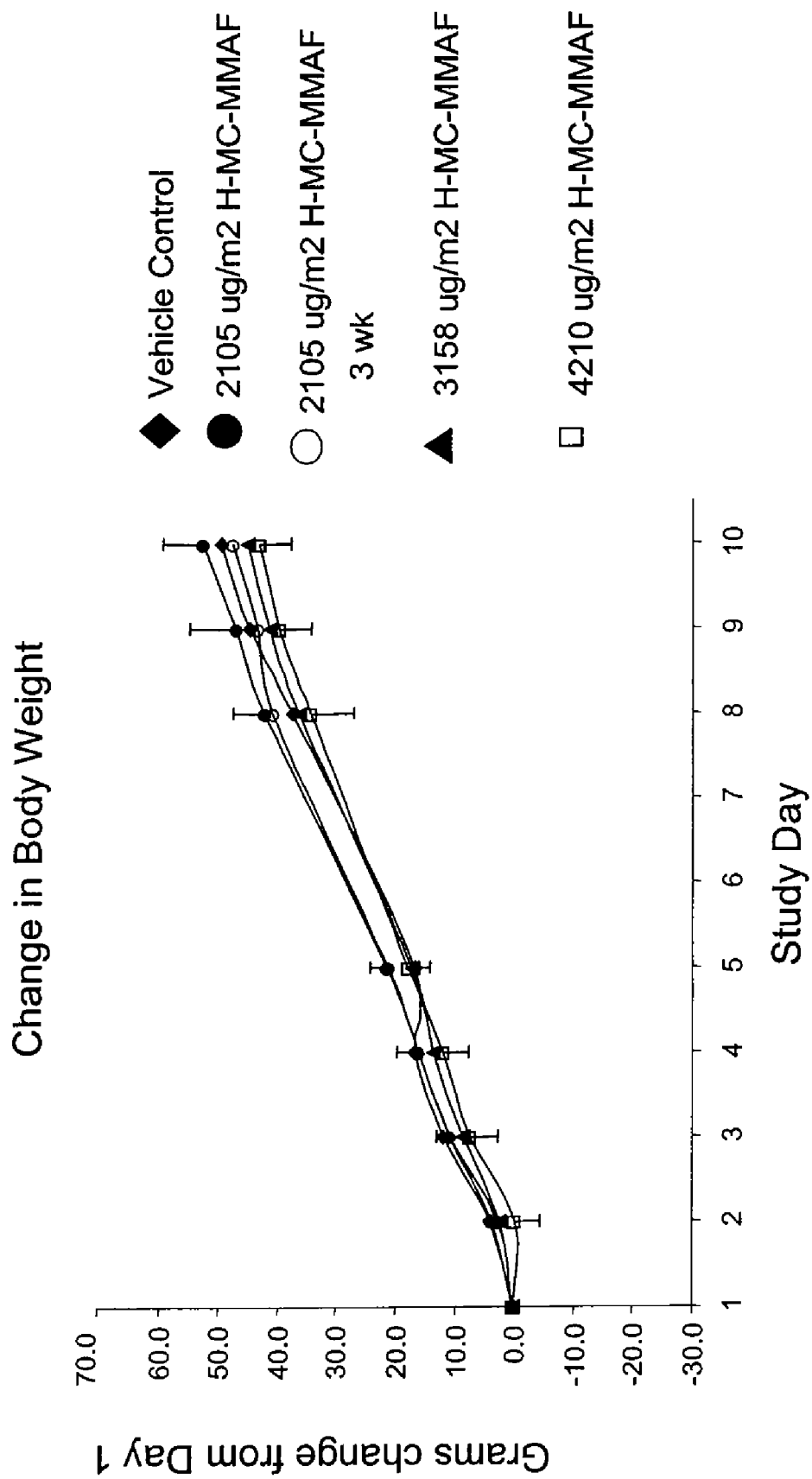
FIG. 19 shows the Group mean change, with error bars, in Sprague Dawley rat body weights (Mean±SD) after administration of trastuzumab (H)-MC-MMAF at doses of 2105, 3158, and 4210 µg/m$^2$. The MC linker is attached via a cysteine of trastuzumab for each conjugate.

It is considered that weight loss, or weight change relative to animals dosed only with Vehicle, in animals after dosing with ADC is a gross and general indicator of systemic or localized toxicity. FIGS. 17-19 show the effects of various ADC and control (Vehicle) after dosing on rat body weight.

Hepatotoxicity was measured by elevated liver enzymes, increased numbers of mitotic and apoptotic figures and hepatocyte necrosis. Hematolymphoid toxicity was observed by depletion of leukocytes, primarily granuloctyes (neutrophils), and/or platelets, and lymphoid organ involvement, i.e. atrophy or apoptotic activity. Toxicity was also noted by gastrointestinal tract lesions such as increased numbers of mitotic and apoptotic figures and degenerative enterocolitis.

Enzymes indicative of liver injury that were studied include:
AST (aspartate aminotransferase)
Localization: cytoplasmic; liver, heart, skeletal muscle, kidney
Liver:Plasma ratio of 7000:1
T1/2: 17 hrs ALT (alanine aminotransferase)
Localization: cytoplasmic; liver, kidney, heart, skeletal muscle
Liver:Plasma ratio of 3000:1
T1/2: 42 hrs; diurnal variation
GGT (g-glutamyl transferase)
Localization: plasma membrane of cells with high secretory or absorptive capacity; liver, kidney, intestine
Poor predictor of liver injury; commonly elevated in bile duct disorders The toxicity profiles of trastuzumab-MC-val-cit-MMAF, trastuzumab-MC(Me)-val-cit-PAB-MMAF, trastuzumab-MC-MMAF and trastuzumab-MC-val-cit-PAB-MMAF were studied in female Sprague-Dawley rats (Example 19). The humanized trastuzumab antibody does not bind appreciably to rat tissue, and any toxicity would be considered non-specific. Variants at dose levels of 840 and 2105 ug/m$^2$ MMAF were compared to trastuzumab-MC-val-cit-PAB-MMAF at 2105 ug/m$^2$.

Animals in groups 1, 2, 3, 4, 6, and 7 (Vehicle, 9.94 & 24.90 mg/kg trastuzumab-MC-val-cit-MMAF, 10.69 mg/kg trastuzumab-MC(Me)-val-cit-PAB-MMAF, and 10.17 & 25.50 mg/kg trastuzumab-MC-MMAF, respectively) gained weight during the study. Animals in groups 5 and 8 (26.78 mg/kg trastuzumab-MC(Me)-val-cit-PAB-MMAF and 21.85 mg/kg trastuzumab-MC-val-cit-PAB-MMAF, respectively) lost weight during the study. On Study Day 5, the change in body weights of animals in groups 2, 6 and 7 were not significantly different from group 1 animals. The change in body weights of animals in groups 3, 4, 5 and 8 were statistically different from group 1 animals (Example 19).

Rats treated with trastuzumab-MC-MMAF (groups 6 and 7) were indistinguishable from vehicle-treated control animals at both dose levels; i.e. this conjugate showed a superior safety profile in this model. Rats treated with trastuzumab-MC-val-cit-MMAF (without the self-immolative PAB moiety; groups 2 and 3) showed dose-dependent changes typical for MMAF conjugates; the extent of the changes was less compared with a full length MC-val-cit-PAB-MMAF conjugate (group 8). The platelet counts on day 5 were at approximately 30% of baseline values in animals of group 3 (high dose trastuzumab-MC-val-cit-MMAF) compared with 15% in animals of group 8 (high dose trastuzumab-MC-val-cit-PAB-MMAF). Elevation of liver enzymes AST and ALT, of bilirubin and the extent of thrombocytopenia was most evident in animals treated with trastuzumab-MC(Me)-val-cit-PAB-MMAF (groups 4 and 5) in a dose-dependent fashion; animals of group 5 (high dose group) showed on day 5 levels of ALT of approximately 10× the baseline value and platelets were reduced by approximately 90% at the time of necropsy.

Female Sprague Dawley Rats were also dosed at high levels (Example 19, High Dose study: Groups 2, 3, 4) with trastuzumab-MC-MMAF, and Vehicle control (Group 1). Mild toxicity signals were observed, including a dose-dependent elevation of liver enzymes ALT, AST and GGT. On day 5 animals in the highest dose group showed a 2-fold elevation of ALT and a 5-fold elevation of AST; GGT is also elevated (6 U/L). Enzyme levels show a trend towards normalization on day 12. There was a mild granulocytosis in all three dose groups on day 5, the platelet count remained essentially unchanged in all animals. Morphological changes were mild; animals treated at the 4210 μg/m$^2$ dose level (Group 2) showed unremarkable histology of liver, spleen, thymus, intestines and bone marrow. Mildly increased apoptotic and mitotic activity was observed in thymus and liver, respectively in animals treated at the 5500 μg/m$^2$ dose level (Group 3). The bone marrow was normocellular, but showed evidence of granulocytic hyperplasia, which is consistent with the absolute granulocytosis observed in the peripheral blood counts in these animals. Animals at the highest dose in group 4 showed qualitatively the same features; the mitotic activity in the liver appears somewhat increased compared to animals in Group 3. Also, extramedullary hematopoiesis was seen in spleen and liver.

EphB2R is a type 1 TM tyrosine kinase receptor with close homology between mouse and human, and is over-expressed in colorectal cancer cells. 2H9 is an antibody against EphB2R. The naked antibody has no effect on tumor growth, but 2H9-val-cit-MMAE killed EphB2R expressing cells and showed efficacy in a mouse xenograft model using CXF1103 human colon tumors (Mao et al (2004) Cancer Res. 64:781-788). 2H9 and 7C2 are both mouse IgG1 anti-HER2 antibodies. The toxicity profiles of 2H9-MC-val-cit-PAB-MMAF (3.7 MMAF/Ab), 7C2-MC-val-cit-PAB-MMAF (4 MMAF/Ab), and trastuzumab-MC-val-cit-PAB-MMAF (5.9 MMAF/Ab) were compared. The differences in the structure of each immunoconjugate or the drug portion of the immunoconjugate may affect the pharmacokinetics and ultimately the safety profile. The humanized trastuzumab antibody does not bind appreciably to rat tissue, and any toxicity would be considered non-specific.

Cynomolgus Monkey Toxicity/Safety

Similar to the rat toxicity/safety study, cynomolgus monkeys were treated with ADC followed by liver enzyme measurements, and inspection and analysis of the effects on various organs. Gross observations included changes in body weights and signs of lesions and bleeding. Clinical pathology parameters (serum chemistry and hematology), histopathology, and necropsy were conducted on dosed animals (Example 19).

The antibody drug conjugate, H-MC-vc-PAB-MMAE (H=trastuzumab linked through cysteine) showed no evidence of liver toxicity at any of the dose levels tested. Peripheral blood granulocytes showed depletion after a single dose of 1100 mg/m$^2$ with complete recovery 14 days post-dose. The antibody drug conjugate H-MC-vc-PAB-MMAF showed elevation of liver enzymes at 550 (transient) and 880 mg/m$^2$ dose level, no evidence of granulocytopenia, and a dose-dependent, transient (groups 2 & 3) decline of platelets.

4.6 Synthesis of the Compounds of the Invention

The Exemplary Compounds and Exemplary Conjugates can be made using the synthetic procedures outlined below in FIGS. 25-36. As described in more detail below, the Exemplary Compounds or Exemplary Conjugates can be conveniently prepared using a Linker having a reactive site for binding to the Drug and Ligand. In one aspect, a Linker has a reactive site which has an electrophilic group that is reactive to a nucleophilic group present on a Ligand, such as but not limited to an antibody. Useful nucleophilic groups on an antibody include but are not limited to, sulfhydryl, hydroxyl and amino groups. The heteroatom of the nucleophilic group of an antibody is reactive to an electrophilic group on a Linker and forms a covalent bond to a Linker unit. Useful electrophilic groups include, but are not limited to, maleimide and haloacetamide groups. The electrophilic group provides a convenient site for antibody attachment.

In another embodiment, a Linker has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Carboxylic acid functional groups and chloroformate functional groups are also useful reactive sites for a Linker because they can react with secondary amino groups of a Drug to form an amide linkage. Also useful as a reactive site is a carbonate functional group on a Linker, such as but not limited to p-nitrophenyl carbonate, which can react with an amino group of a Drug, such as but not limited to N-methyl valine, to form a carbamate linkage. Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

Figure 28:
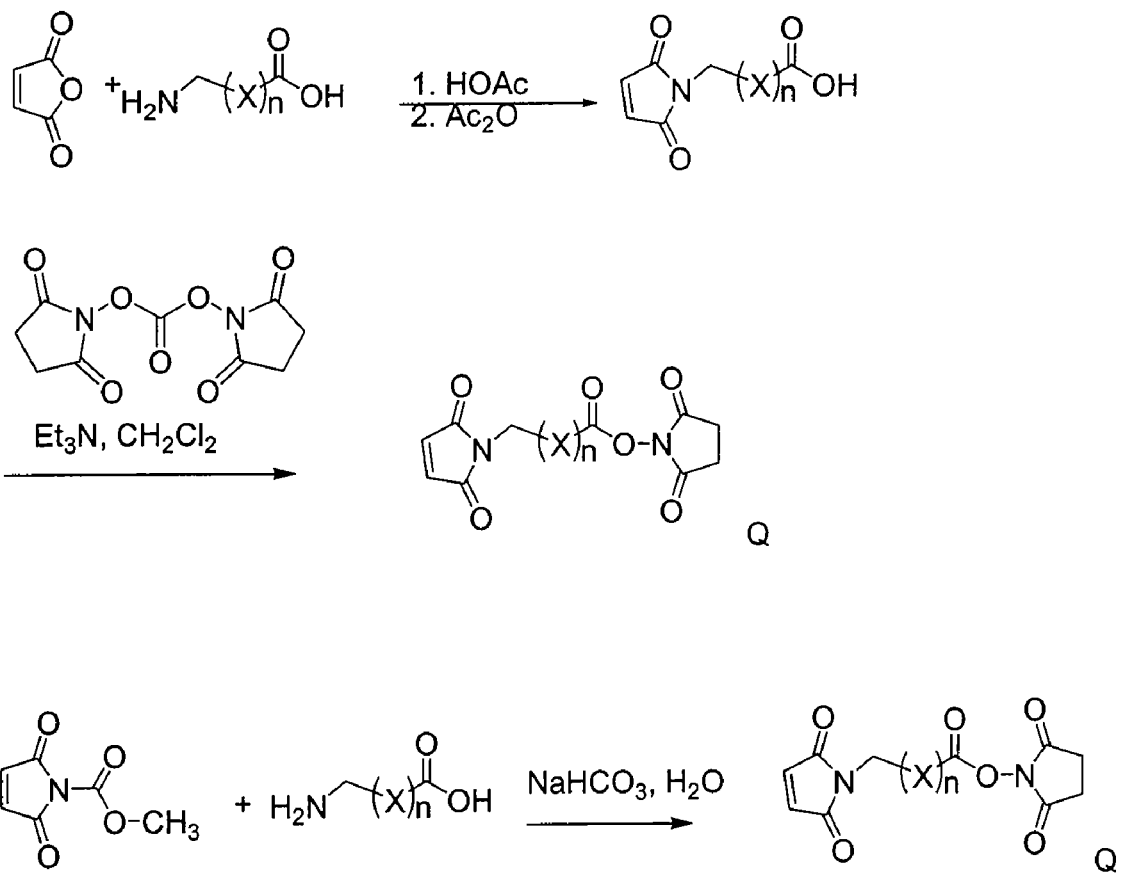
FIG. 28 shows the synthesis of useful linkers.
Figure 31:
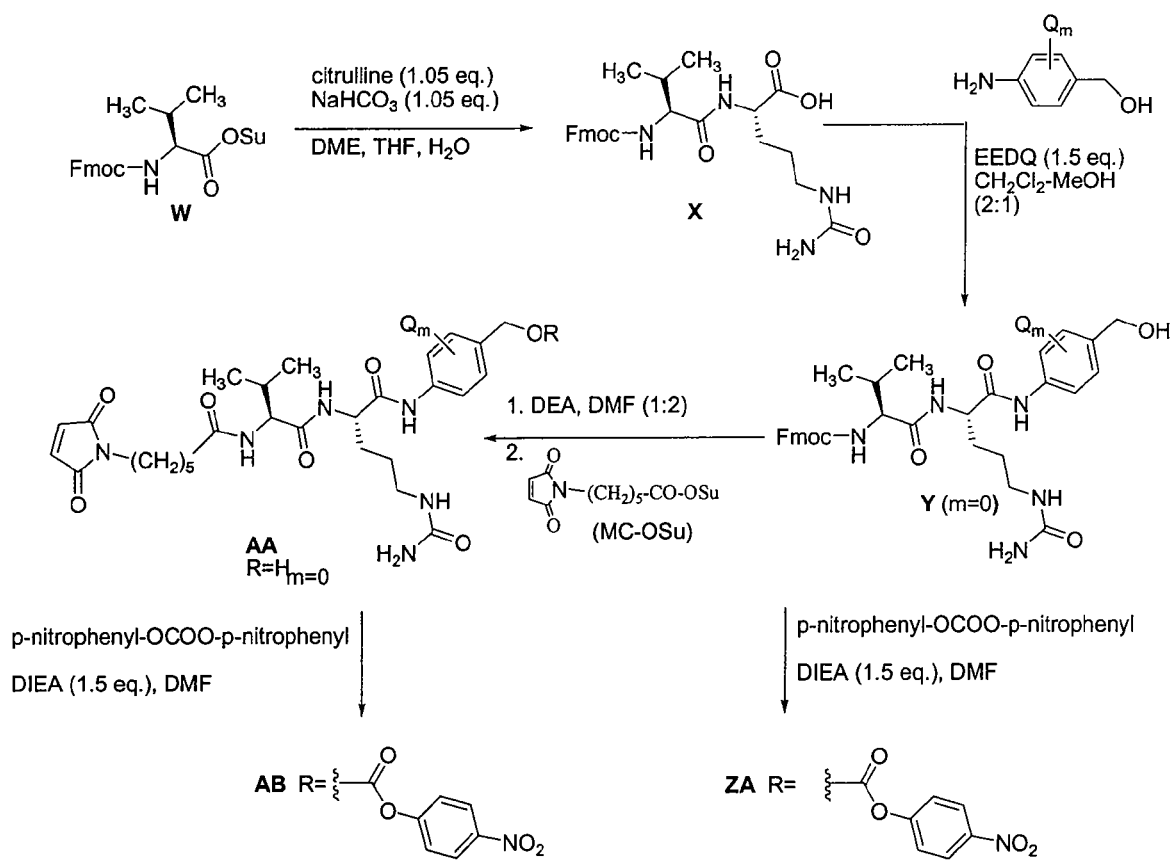
FIG. 31 shows the synthesis of a val-cit dipeptide Linker having a maleimide Stretcher and optionally a p-aminobenzyl self-immolative Spacer.
Figure 32:
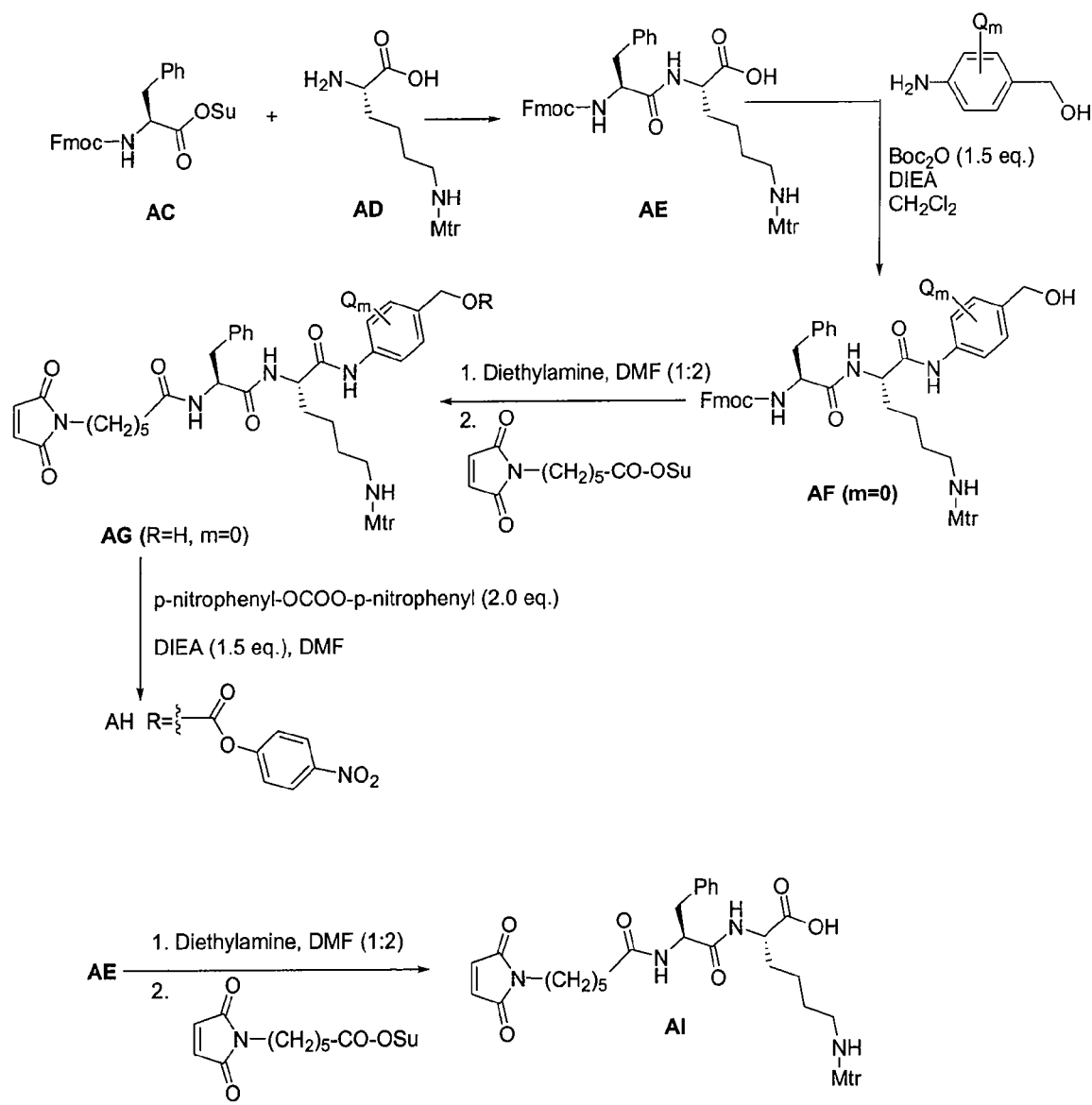
FIG. 32 shows the synthesis of a phe-lys(Mtr) dipeptide Linker unit having a maleimide Stretcher unit and a p-aminobenzyl self-immolative Spacer unit.
Figure 33:
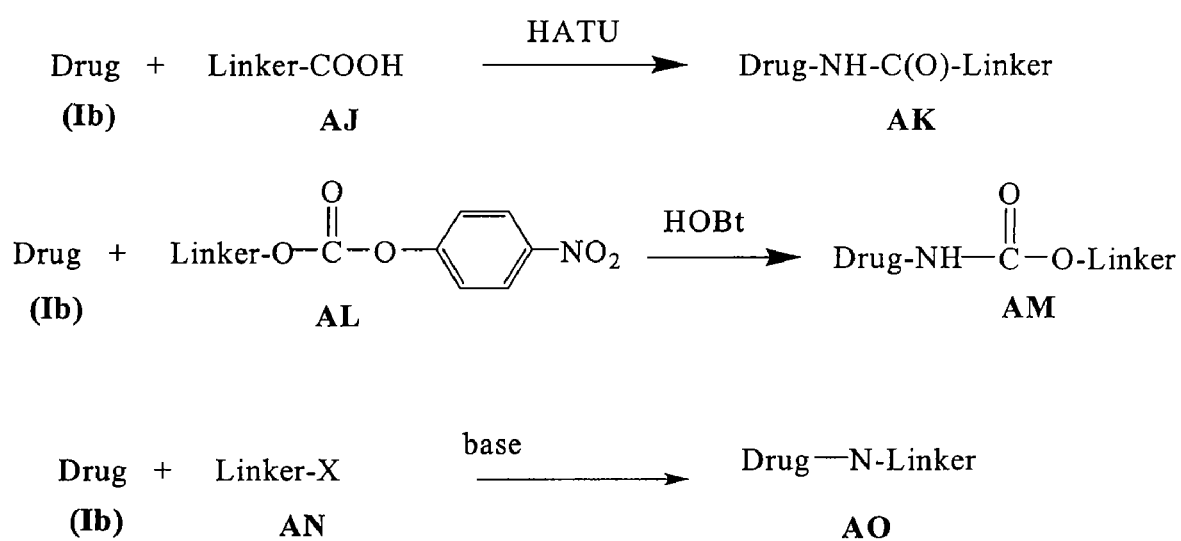
FIG. 33 shows the synthesis of a Drug-Linker Compound that contains an amide or carbamate group, linking the Drug unit to the Linker unit.
Figure 34:
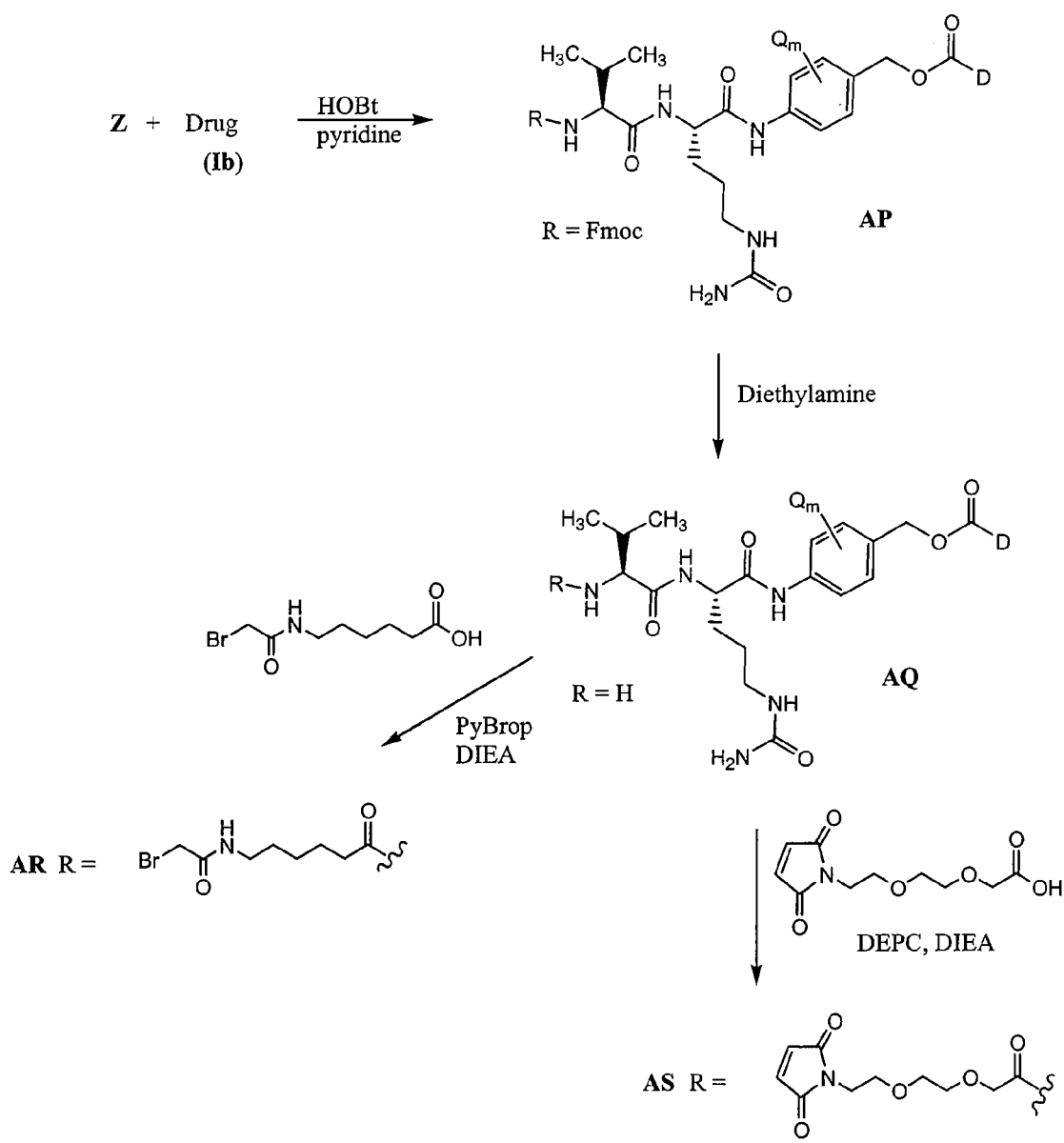
FIG. 34 shows illustrative methods useful for linking a Drug to a Ligand to form a Drug-Linker Compound.
Figure 35:
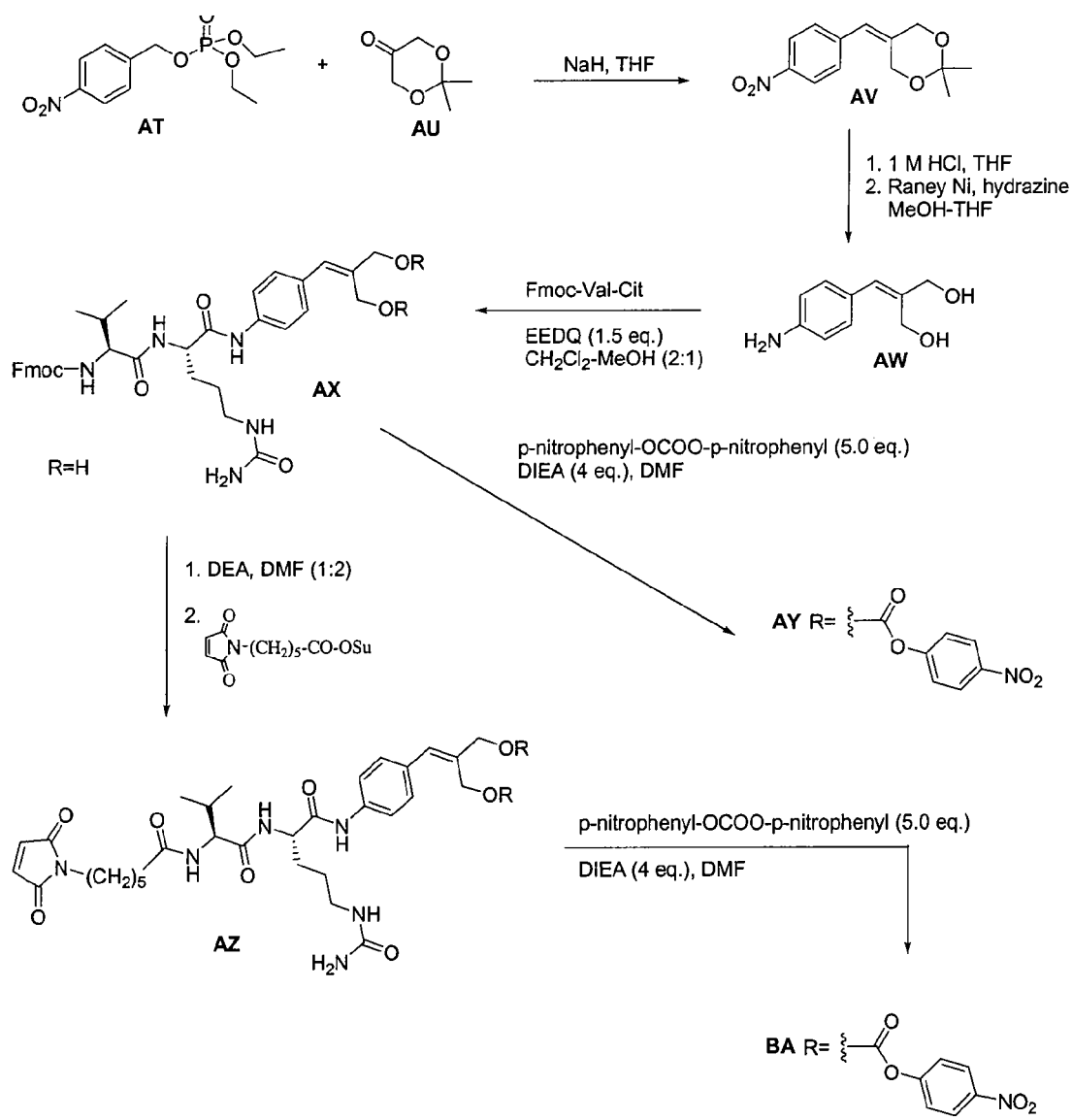
FIG. 35 shows the synthesis of a val-cit dipeptide linker having a maleimide Stretcher unit and a bis(4-hydroxymethyl)styrene (BHMS) unit.
Figure 36:
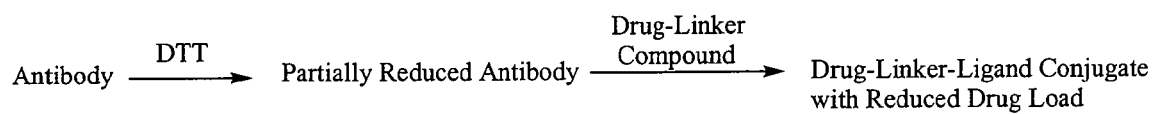
FIG. 36 shows methodology useful for making Drug-Linker-Ligand conjugates having about 2 to about 4 drugs per antibody.

The synthesis of an illustrative Stretcher having an electrophilic maleimide group is illustrated below in FIGS. 28 and 29. General synthetic methods useful for the synthesis of a Linker are described in FIG. 30. FIG. 31 shows the construction of a Linker unit having a val-cit group, an electrophilic maleimide group and a PAB self-immolative Spacer group. FIG. 32 depicts the synthesis of a Linker having a phe-lys group, an electrophilic maleimide group, with and without the PAB self-immolative Spacer group. FIG. 33 presents a general outline for the synthesis of a Drug-Linker Compound, while FIG. 34 presents an alternate route for preparing a Drug-Linker Compound. FIG. 35 depicts the synthesis of a branched linker containing a BHMS group. FIG. 36 outlines the attachment of an antibody to a Drug-Linker Compound to form a Drug-Linker-Antibody Conjugate, and FIG. 34 illustrates the synthesis of Drug-Linker-Antibody Conjugates having, for example but not limited to, 2 or 4 drugs per Antibody.

As described in more detail below, the Exemplary Conjugates are conveniently prepared using a Linker having two or more Reactive Sites for binding to the Drug and a Ligand. In one aspect, a Linker has a Reactive site which has an electrophilic group that is reactive to a nucleophilic group present on a Ligand, such as an antibody. Useful nucleophilic groups on an antibody include but are not limited to, sulfhydryl, hydroxyl and amino groups. The heteroatom of the nucleophilic group of an antibody is reactive to an electrophilic group on a Linker and forms a covalent bond to a Linker unit. Useful electrophilic groups include, but are not limited to, maleimide and haloacetamide groups. The electrophilic group provides a convenient site for antibody attachment.

In another embodiment, a Linker has a Reactive site which has a nucleophilic group that is reactive to an electrophilic group present on a Ligand, such as an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

4.6.1 Drug Moiety Synthesis

Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

The auristatin/dolastatin drug moieties may be prepared according to the general methods of: U.S. Pat. No. 5,635,483; U.S. Pat. No. 5,780,588; Pettit et al. (1989) J. Am. Chem. Soc. 111:5463-5465; Pettit et al. (1998) Anti-Cancer Drug Design 13:243-277; and Pettit et al. (1996) J. Chem. Soc. Perkin Trans. 1 5:859-863.

Figure 26:
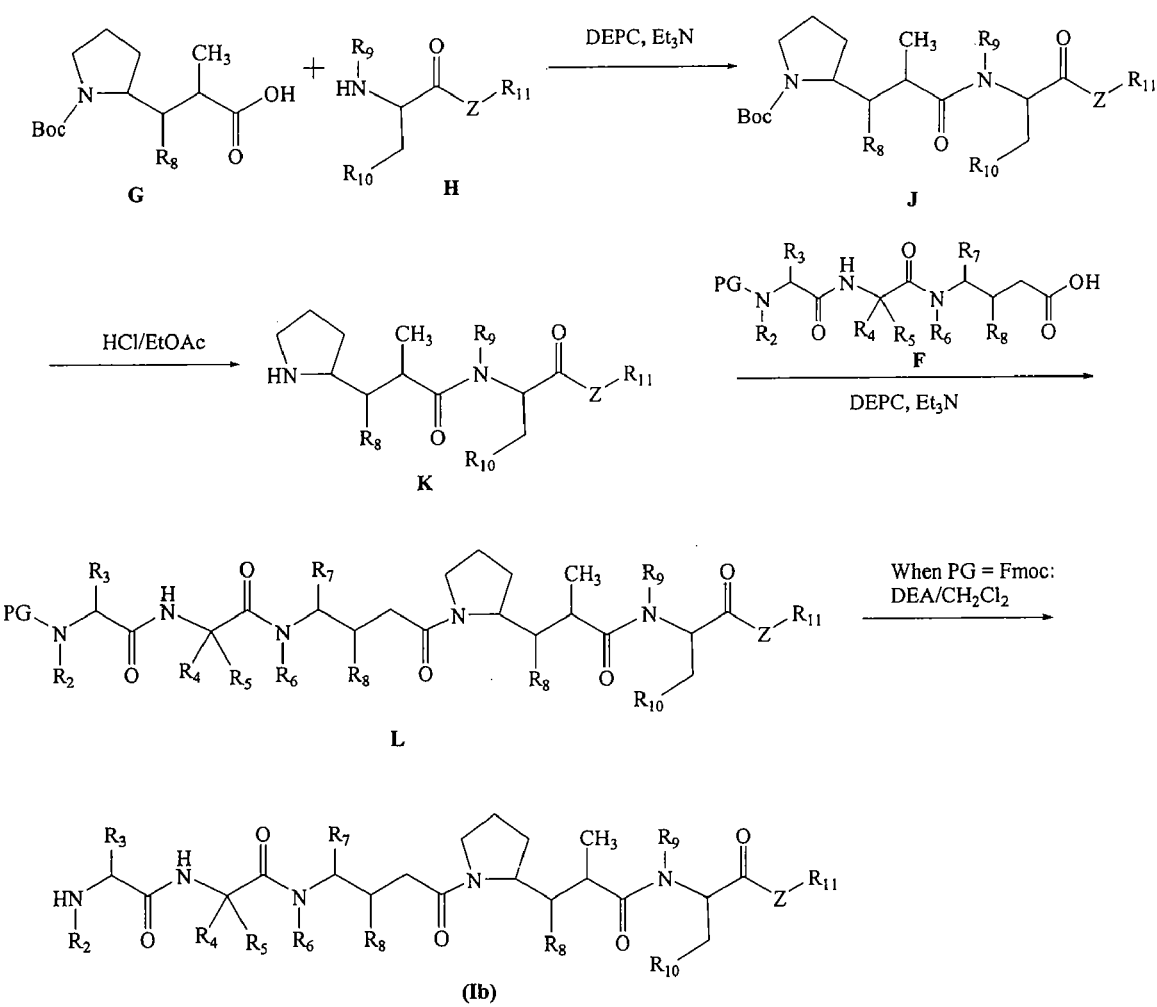
FIG. 26 shows the synthesis of an N-terminal tripeptide unit F which is a useful intermediate for the synthesis of the drug compounds of Formula Ib.
Figure 27:
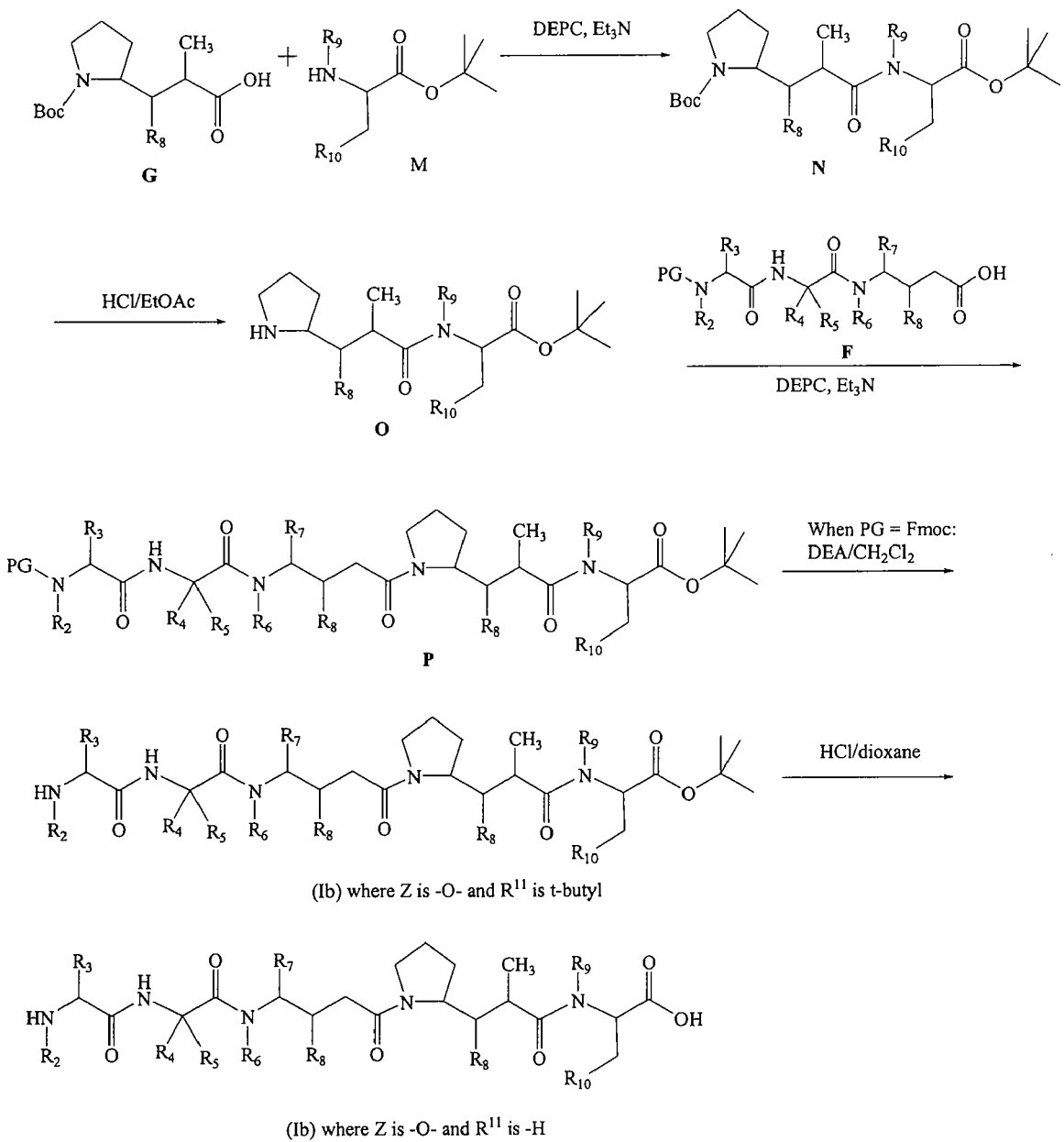
FIG. 27 shows the synthesis of an N-terminal tripeptide unit F which is a useful intermediate for the synthesis of the drug compounds of Formula Ib.

In one embodiment, a Drug is prepared by combining about a stoichiometric equivalent of a dipeptide and a tripeptide, preferably in a one-pot reaction under suitable condensation conditions. This approach is illustrated in FIGS. 25-27, below.

Figure 25:
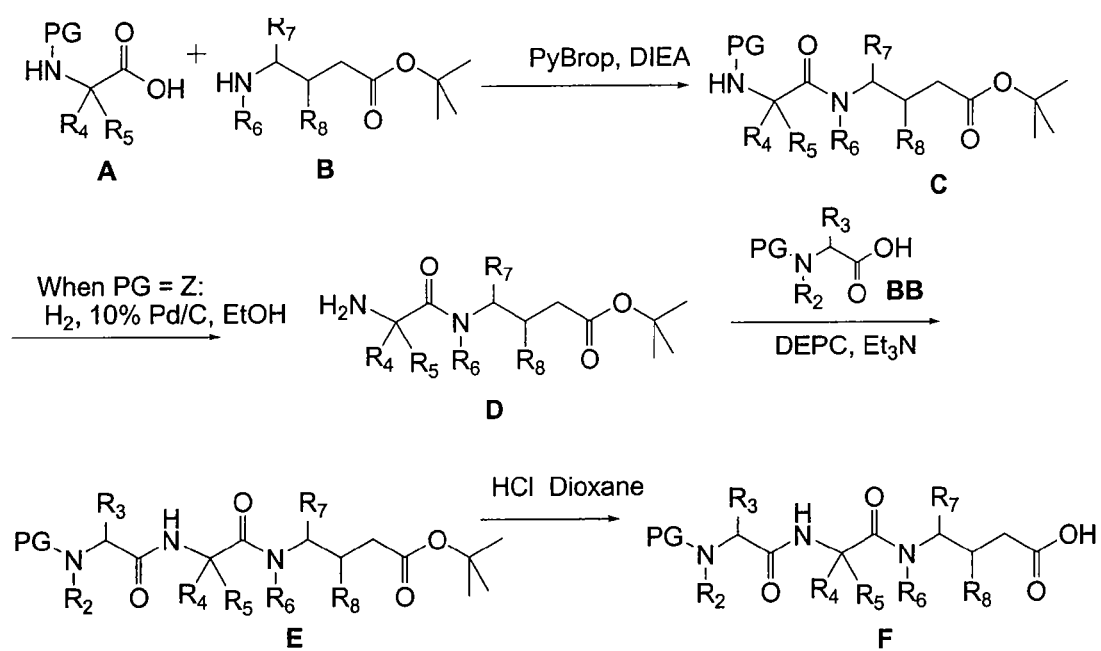
FIG. 25 shows the synthesis of an N-terminal tripeptide unit F which is a useful intermediate for the synthesis of the drug compounds of Formula Ib.

FIG. 25 illustrates the synthesis of an N-terminal tripeptide unit F which is a useful intermediate for the synthesis of the drug compounds of Formula Ib.

As illustrated in FIG. 25, a protected amino acid A (where PG represents an amine protecting group, $R^4$ is selected from hydrogen, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle, alkyl-($C_3$-$C_8$ heterocycle) wherein $R^5$ is selected from H and methyl; or $R^4$ and $R^5$ join, have the formula —$(CR^aR^b)_n$— wherein $R^a$ and $R^b$ are independently selected from hydrogen, $C_1$-$C_8$ alkyl and $C_3$-$C_8$ carbocycle and n is selected from 2, 3, 4, 5 and 6, and form a ring with the carbon atom to which they are attached) is coupled to t-butyl ester B (where $R^6$ is selected from —H and —$C_1$-$C_8$ alkyl; and $R^7$ is selected from hydrogen, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle and alkyl-($C_3$-$C_8$ heterocycle)) under suitable coupling conditions, e.g., in the presence of PyBrop and diisopropylethylamine, or using DCC (see, for example, Miyazaki, K. et. al. *Chem. Pharm. Bull.* 1995, 43(10), 1706-1718).

Suitable protecting groups PG, and suitable synthetic methods to protect an amino group with a protecting group are well known in the art. See, e.g., Greene, T. W. and Wuts, P. G. M., Protective Groups in Organic Synthesis, 2nd Edition, 1991, John Wiley & Sons. Exemplary protected amino acids A are PG-Ile and, particularly, PG-Val, while other suitable protected amino acids include, without limitation: PG-cyclohexylglycine, PG-cyclohexylalanine, PG-aminocyclopropane-1-carboxylic acid, PG-aminoisobutyric acid, PG-phenylalanine, PG-phenylglycine, and PG-tert-butylglycine. Z is an exemplary protecting group. Fmoc is another exemplary protecting group. An exemplary t-butyl ester B is dolaisoleuine t-butyl ester.

The dipeptide C can be purified, e.g., using chromatography, and subsequently deprotected, e.g., using $H_2$ and 10% Pd—C in ethanol when PG is benzyloxycarbonyl, or using diethylamine for removal of an Fmoc protecting group. The resulting amine D readily forms a peptide bond with an amino acid BB (wherein $R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached; and $R^3$ is selected from hydrogen, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle and alkyl-($C_3$-$C_8$ heterocycle)). N,N-Dialkyl amino acids are exemplary amino acids for BB, such as commercially available N,N-dimethyl valine. Other N,N-dialkyl amino acids can be prepared by reductive bis-alkylation using known procedures (see, e.g., Bowman, R. E, Stroud, H. H *J. Chem. Soc.*, 1950, 1342-1340). Fmoc-Me-L-Val and Fmoc-Me-L-glycine are two exemplary amino acids BB useful for the synthesis of N-monoalkyl derivatives. The amine D and the amino acid BB react to provide the tripeptide E using coupling reagent DEPC with triethylamine as the base. The C-terminus protecting group of E is subsequently deprotected using HCl to provide the tripeptide compound of formula F.

Illustrative DEPC coupling methodology and the PyBrop coupling methodology shown in FIG. 25 are outlined below in General Procedure A and General Procedure B, respectively. Illustrative methodology for the deprotection of a Z-protected amine via catalytic hydrogenation is outlined below in General Procedure C.

General Procedure A: Peptide synthesis using DEPC. The N-protected or N,N-disubstituted amino acid or peptide D (1.0 eq.) and an amine BB (1.1 eq.) are diluted with an aprotic organic solvent, such as dichloromethane (0.1 to 0.5 M). An organic base such as triethylamine or diisopropylethylamine (1.5 eq.) is then added, followed by DEPC (1.1 eq.). The resulting solution is stirred, preferably under argon, for up to 12 hours while being monitored by HPLC or TLC. The solvent is removed in vacuo at room temperature, and the crude product is purified using, for example, HPLC or flash column chromatography (silica gel column). Relevant fractions are combined and concentrated in vacuo to afford tripeptide E which is dried under vacuum overnight.

General procedure B: Peptide synthesis using PyBrop. The amino acid B (1.0 eq.), optionally having a carboxyl protecting group, is diluted with an aprotic organic solvent such as dichloromethane or DME to provide a solution of a concentration between 0.5 and 1.0 mM, then diisopropylethylamine (1.5 eq.) is added. Fmoc-, or Z-protected amino acid A (1.1 eq.) is added as a solid in one portion, then PyBrop (1.2 eq.) is added to the resulting mixture. The reaction is monitored by TLC or HPLC, followed by a workup procedure similar to that described in General Procedure A.

General procedure C: Z-removal via catalytic hydrogenation. Z-protected amino acid or peptide C is diluted with ethanol to provide a solution of a concentration between 0.5 and 1.0 mM in a suitable vessel, such as a thick-walled round bottom flask. 10% palladium on carbon is added (5-10% w/w) and the reaction mixture is placed under a hydrogen atmosphere. Reaction progress is monitored using HPLC and is generally complete within 1-2 h. The reaction mixture is filtered through a pre-washed pad of celite and the celite is again washed with a polar organic solvent, such as methanol after filtration. The eluent solution is concentrated in vacuo to afford a residue which is diluted with an organic solvent, preferably toluene. The organic solvent is then removed in vacuo to afford the deprotected amine C.

FIG. 26 shows a method useful for making a C-terminal dipeptide of formula K and a method for coupling the dipeptide of formula K with the tripeptide of formula F to make drug compounds of Formula Ib.

The dipeptide K can be readily prepared by condensation of the modified amino acid Boc-Dolaproine G (see, for example, Pettit, G. R., et al. Synthesis, 1996, 719-725), with an amine of formula H using condensing agents well known for peptide chemistry, such as, for example, DEPC in the presence of triethylamine, as shown in FIG. 25.

The dipeptide of formula K can then be coupled with a tripeptide of formula F using General Procedure D to make the Fmoc-protected drug compounds of formula L which can be subsequently deprotected using General Procedure E in order to provide the drug compounds of formula (Ib).

General procedure D: Drug synthesis. A mixture of dipeptide K (1.0 eq.) and tripeptide F (1 eq.) is diluted with an aprotic organic solvent, such as dichloromethane, to form a 0.1M solution, then a strong acid, such as trifluoroacetic acid (½ v/v) is added and the resulting mixture is stirred under a nitrogen atmosphere for two hours at 0° C. The reaction can be monitored using TLC or, preferably, HPLC. The solvent is removed in vacuo and the resulting residue is azeotropically dried twice, preferably using toluene. The resulting residue is dried under high vacuum for 12 h and then diluted with and aprotic organic solvent, such as dichloromethane. An organic base such as triethylamine or diisopropylethylamine (1.5 eq.) is then added, followed by either PyBrop (1.2 eq.) or DEPC (1.2 eq.) depending on the chemical functionality on the residue. The reaction mixture is monitored by either TLC or HPLC and upon completion, the reaction is subjected to a workup procedure similar or identical to that described in General Procedure A.

General procedure E: Fmoc-removal using diethylamine. An Fmoc-protected Drug L is diluted with an aprotic organic solvent such as dichloromethane and to the resulting solution is added diethylamine (½ v/v). Reaction progress is monitored by TLC or HPLC and is typically complete within 2 h. The reaction mixture is concentrated in vacuo and the resulting residue is azeotropically dried, preferably using toluene, then dried under high vacuum to afford Drug Ib having a deprotected amino group.

FIG. 27 shows a method useful for making MMAF derivatives of Formula (Ib).

The dipeptide O can be readily prepared by condensation of the modified amino acid Boc-Dolaproine G (see, for example, Pettit, G. R., et al. *Synthesis,* 1996, 719-725), with a protected amino acid of formula M using condensing agents well known for peptide chemistry, such as, for example, DEPC in the presence of triethylamine, as shown in FIGS. 25 and 26.

The dipeptide of formula O can then be coupled with a tripeptide of formula F using General Procedure D to make the Fmoc-protected MMAF compounds of formula P which can be subsequently deprotected using General Procedure E in order to provide the MMAF drug compounds of formula (Ib).

Thus, the above methods are useful for making Drugs that can be used in the present invention.

4.6.2 Drug Linker Synthesis

To prepare a Drug-Linker Compound of the present invention, the Drug is reacted with a reactive site on the Linker. In general, the Linker can have the structure:

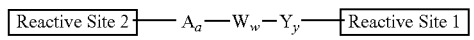

when both a Spacer unit (—Y—) and a Stretcher unit (-A-) are present. Alternately, the Linker can have the structure:

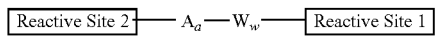

when the Spacer unit (—Y—) is absent.
The Linker can also have the structure:

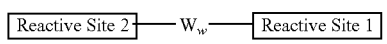

when both the Stretcher unit (-A-) and the Spacer unit (—Y—) are absent.
The Linker can also have the structure:

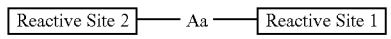

when both the Amino Acid unit (W) and the Spacer Unit (Y) are absent.

In general, a suitable Linker has an Amino Acid unit linked to an optional Stretcher Unit and an optional Spacer Unit. Reactive Site 1 is present at the terminus of the Spacer and Reactive site 2 is present at the terminus of the Stretcher. If a Spacer unit is not present, then Reactive site 1 is present at the C-terminus of the Amino Acid unit.

In an exemplary embodiment of the invention, Reactive Site No. 1 is reactive to a nitrogen atom of the Drug, and Reactive Site No. 2 is reactive to a sulfhydryl group on the Ligand. Reactive Sites 1 and 2 can be reactive to different functional groups.

In one aspect of the invention, Reactive Site No. 1 is

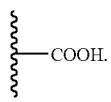

In another aspect of the invention, Reactive Site No. 1 is

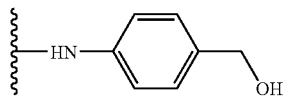

In still another aspect of the invention, Reactive Site No. 1 is a p-nitrophenyl carbonate having the formula

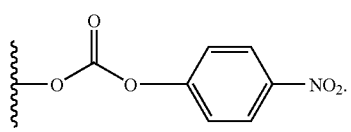

In one aspect of the invention, Reactive Site No. 2 is a thiol-accepting group. Suitable thiol-accepting groups include haloacetamide groups having the formula

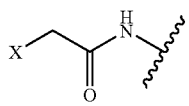

wherein X represents a leaving group, preferably O-mesyl, O-tosyl, —Cl, —Br, or —I; or a maleimide group having the formula

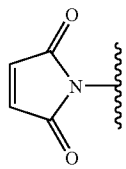

Useful Linkers can be obtained via commercial sources, such as Molecular Biosciences Inc. (Boulder, Colo.), or prepared as summarized in FIGS. 28-30. In FIG. 28 X is —CH$_2$— or —CH$_2$OCH$_2$—; and n is an integer ranging either from 0-10 when X is —CH$_2$—; or 1-10 when X is —CH$_2$OCH$_2$—.

Figure 29:
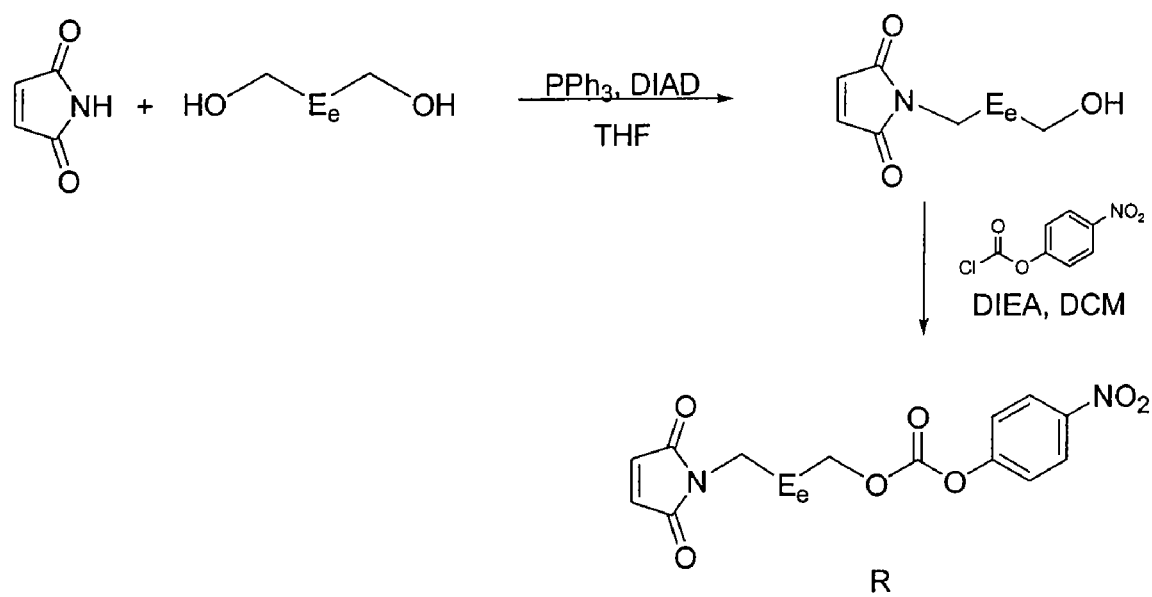
FIG. 29 shows the synthesis of useful linkers.

The method shown in FIG. 29 combines maleimide with a glycol under Mitsunobu conditions to make a polyethylene glycol maleimide Stretcher (see for example, Walker, M. A. *J. Org. Chem.* 1995, 60, 5352-5), followed by installation of a p-nitrophenyl carbonate Reactive Site group.

In FIG. 29 E is —CH$_2$— or —CH$_2$OCH$_2$—; and e is an integer ranging from 0-8;

Alternatively, PEG-maleimide and PEG-haloacetamide stretchers can be prepared as described by Frisch, et al., *Bioconjugate Chem.* 1996, 7, 180-186.

Figure 30:
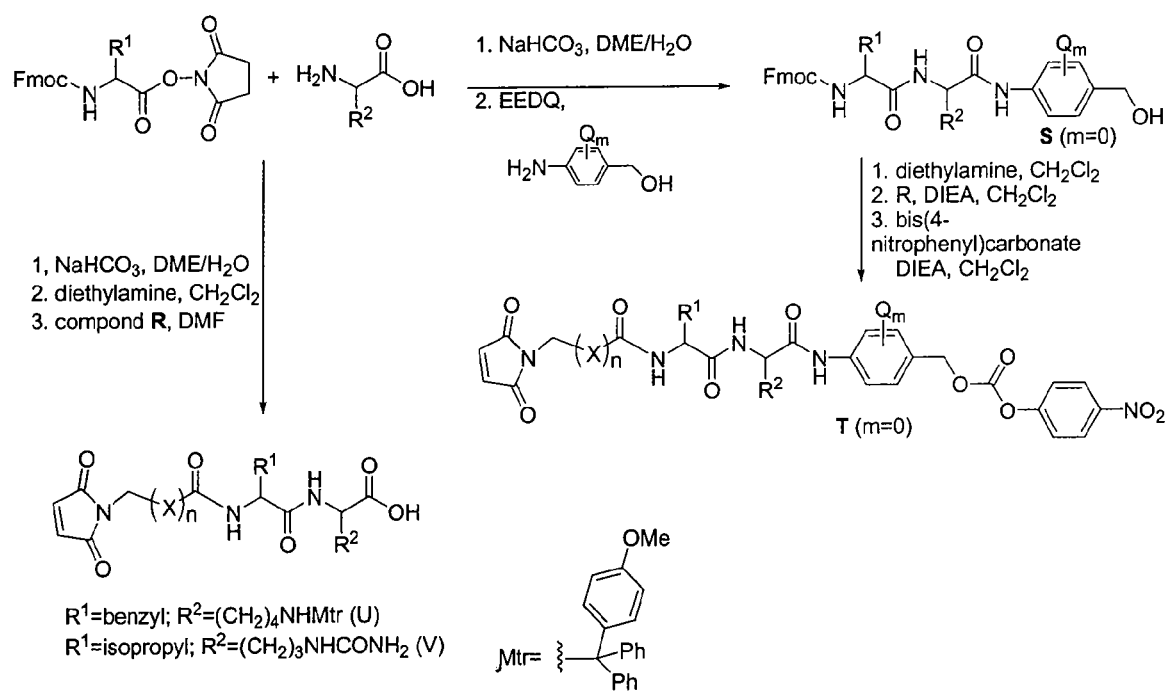
FIG. 30 shows a general synthesis of an illustrative Linker unit containing a maleimide Stretcher group and optionally a p-aminobenzyl ether self-immolative Spacer.

FIG. 30 illustrates a general synthesis of an illustrative Linker unit containing a maleimide Stretcher group and optionally a p-aminobenzyl ether self-immolative Spacer.

In FIG. 30 Q is —C$_1$-C$_8$ alkyl, —O—(C$_1$-C$_8$ alkyl), -halogen, -nitro or -cyano; m is an integer ranging from 0-4; and n is an integer ranging from 0-10.

Useful Stretchers may be incorporated into a Linker using the commercially available intermediates from Molecular Biosciences (Boulder, Colo.) described below by utilizing known techniques of organic synthesis.

Stretchers of formula (IIa) can be introduced into a Linker by reacting the following intermediates with the N-terminus of an Amino Acid unit as depicted in FIGS. 31 and 32:

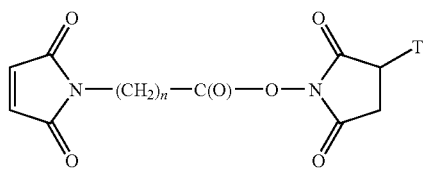

where n is an integer ranging from 1-10 and T is —H or —SO$_3$Na;

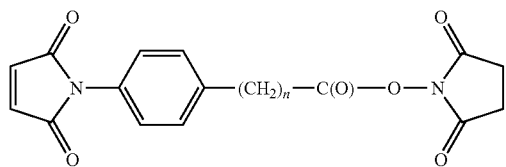

where n is an integer ranging from 0-3;

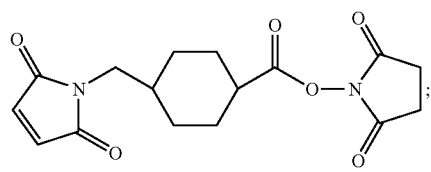

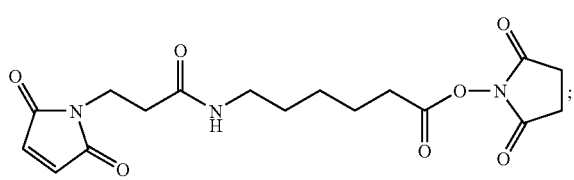

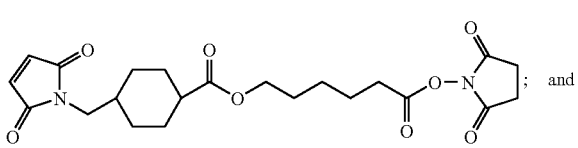

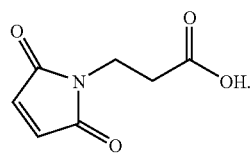

Stretcher units of formula (IIIb) can be introduced into a Linker by reacting the following intermediates with the N-terminus of an Amino Acid unit:

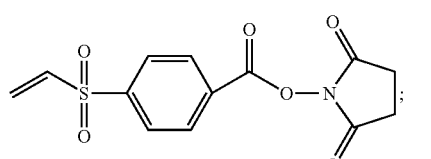

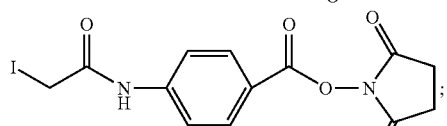

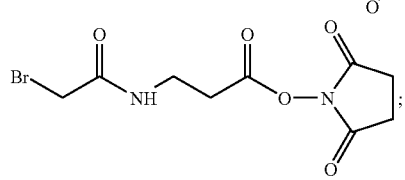

-continued

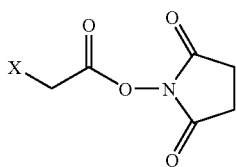

where X is —Br or —I; and

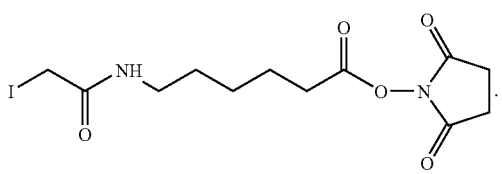

Stretcher units of formula (IV) can be introduced into a Linker by reacting the following intermediates with the N-terminus of an Amino Acid unit:

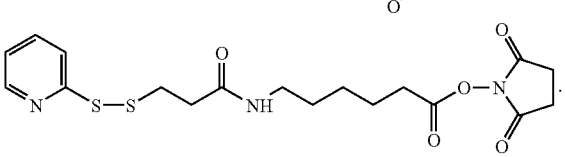

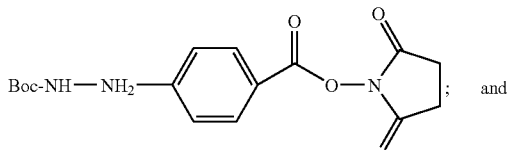

Stretcher units of formula (Va) can be introduced into a Linker by reacting the following intermediates with the N-terminus of an Amino Acid unit:

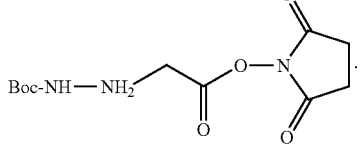

Other useful Stretchers may be synthesized according to known procedures. Aminooxy Stretchers of the formula shown below can be prepared by treating alkyl halides with N-Boc-hydroxylamine according to procedures described in Jones, D. S. et al., *Tetrahedron Letters,* 2000, 41(10), 1531-1533; and Gilon, C. et al., *Tetrahedron,* 1967, 23(11), 4441-4447.

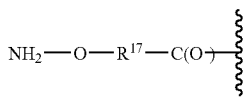

wherein —R$^{17}$— is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_r$—, —(CH$_2$CH$_2$O)$_r$—CH$_2$—; and r is an integer ranging from 1-10;

Isothiocyanate Stretchers of the formula shown below may be prepared from isothiocyanatocarboxylic acid chlorides as described in *Angew. Chem.*, 1975, 87(14):517.

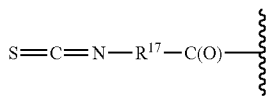

wherein —R$^{17}$— is as described herein.

FIG. 31 shows a method for obtaining of a val-cit dipeptide Linker having a maleimide Stretcher and optionally a p-aminobenzyl self-immolative Spacer.

In FIG. 31 Q is —C$_1$-C$_8$ alkyl, —O—(C$_1$-C$_8$ alkyl), -halogen, -nitro or -cyano; and m is an integer ranging from 0-4.

FIG. 32 illustrates the synthesis of a phe-lys(Mtr) dipeptide Linker unit having a maleimide Stretcher unit and a p-aminobenzyl self-immolative Spacer unit. Starting material AD (lys(Mtr)) is commercially available (Bachem, Torrance, Calif.) or can be prepared according to Dubowchik, et al. *Tetrahedron Letters* (1997) 38:5257-60.

In FIG. 32 Q is —C$_1$-C$_8$ alkyl, —O—(C$_1$-C$_8$ alkyl), -halogen, -nitro or -cyano; and m is an integer ranging from 0-4.

As shown in FIG. 33, a Linker can be reacted with an amino group of a Drug Compound of Formula (Ib) to form a Drug-Linker Compound that contains an amide or carbamate group, linking the Drug unit to the Linker unit. When Reactive Site No. 1 is a carboxylic acid group, as in Linker AJ, the coupling reaction can be performed using HATU or PyBrop and an appropriate amine base, resulting in a Drug-Linker Compound AK, containing an amide bond between the Drug unit and the Linker unit. When Reactive Site No. 1 is a carbonate, as in Linker AL, the Linker can be coupled to the Drug using HOBt in a mixture of DMF/pyridine to provide a Drug-Linker Compound AM, containing a carbamate bond between the Drug unit and the Linker unit Alternately, when Reactive Site No. 1 is a good leaving group, such as in Linker AN, the Linker can be coupled with an amine group of a Drug via a nucleophilic substitution process to provide a Drug-Linker Compound having an amine linkage (AO) between the Drug unit and the Linker unit.

Illustrative methods useful for linking a Drug to a Ligand to form a Drug-Linker Compound are depicted in FIG. 33 and are outlined in General Procedures G-H.

General Procedure G: Amide formation using HATU. A Drug (Ib) (1.0 eq.) and an N-protected Linker containing a carboxylic acid Reactive site (1.0 eq.) are diluted with a suitable organic solvent, such as dichloromethane, and the resulting solution is treated with HATU (1.5 eq.) and an organic base, preferably pyridine (1.5 eq.). The reaction mixture is allowed to stir under an inert atmosphere, preferably argon, for 6 h, during which time the reaction mixture is monitored using HPLC. The reaction mixture is concentrated and the resulting residue is purified using HPLC to yield the amide of formula AK.

Procedure H: Carbamate formation using HOBt. A mixture of a Linker AL having a p-nitrophenyl carbonate Reactive site (1.1 eq.) and Drug (Ib) (1.0 eq.) are diluted with an aprotic organic solvent, such as DMF, to provide a solution having a concentration of 50-100 mM, and the resulting solution is treated with HOBt (2.0 eq.) and placed under an inert atmosphere, preferably argon. The reaction mixture is allowed to stir for 15 min, then an organic base, such as pyridine (¼ v/v), is added and the reaction progress is monitored using HPLC. The Linker is typically consumed within 16 h. The reaction mixture is then concentrated in vacuo and the resulting residue is purified using, for example, HPLC to yield the carbamate AM.

An alternate method of preparing Drug-Linker Compounds is outlined in FIG. 34. Using the method of FIG. 34, the Drug is attached to a partial Linker unit (ZA, for example), which does not have a Stretcher unit attached. This provides intermediate AP, which has an Amino Acid unit having an Fmoc-protected N-terminus. The Fmoc group is then removed and the resulting amine intermediate AQ is then attached to a Stretcher unit via a coupling reaction catalyzed using PyBrop or DEPC. The construction of Drug-Linker Compounds containing either a bromoacetamide Stretcher AR or a PEG maleimide Stretcher AS is illustrated in FIG. 34.

In FIG. 34 Q is —C$_1$-C$_8$ alkyl, —O—(C$_1$-C$_8$ alkyl), -halogen, -nitro or -cyano; and m is an integer ranging from 0-4.

Methodology useful for the preparation of a Linker unit containing a branched spacer is shown in FIG. 35.

FIG. 35 illustrates the synthesis of a val-cit dipeptide linker having a maleimide Stretcher unit and a bis(4-hydroxymethyl)styrene (BHMS) unit. The synthesis of the BHMS intermediate (AW) has been improved from previous literature procedures (see International Publication No, WO 9813059 to Firestone et al., and Crozet, M. P.; Archaimbault, G.; Vanelle, P.; Nouguier, R. *Tetrahedron Lett.* (1985) 26:5133-5134) and utilizes as starting materials, commercially available diethyl (4-nitrobenzyl)phosphonate (AT) and commercially available 2,2-dimethyl-1,3-dioxan-5-one (AU). Linkers AY and BA can be prepared from intermediate AW using the methodology described in FIG. 29.

4.6.3 Dendritic Linkers

The linker may be a dendritic type linker for covalent attachment of more than one drug moiety through a branching, multifunctional linker moiety to a Ligand, such as but not limited to an antibody (Sun et al. (2002) Bioorganic & Medicinal Chemistry Letters 12:2213-2215; Sun et al. (2003) Bioorganic & Medicinal Chemistry 11:1761-1768). Dendritic linkers can increase the molar ratio of drug to antibody, i.e. loading, which is related to the potency of the Drug-Linker-Ligand Conjugate. Thus, where a cysteine engineered antibody bears only one reactive cytsteine thiol group, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

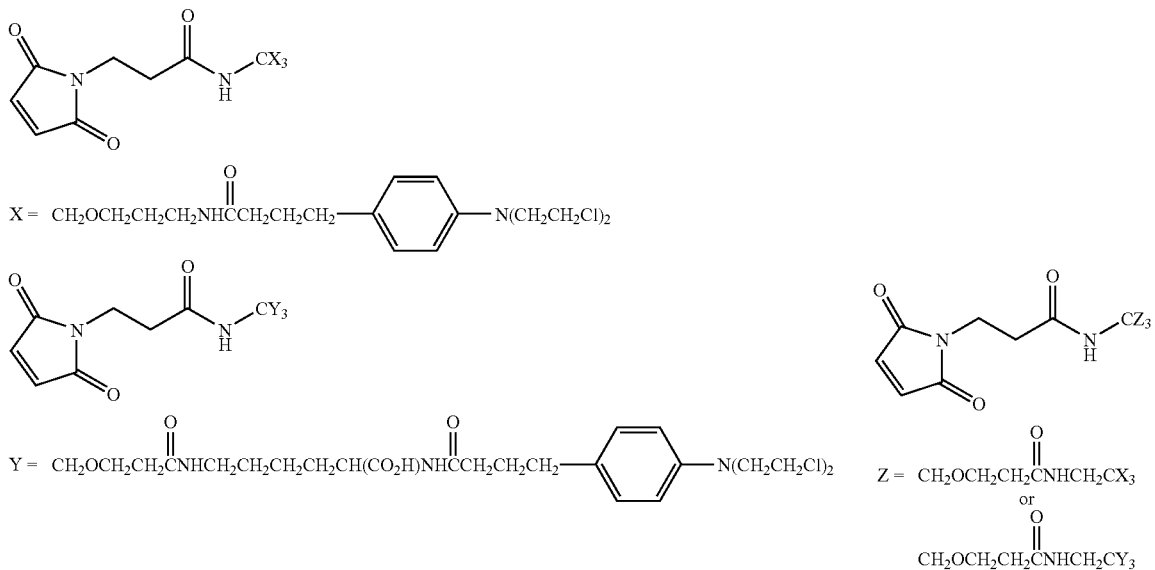

4.6.4 Conjugation of Drug Moieties to Antibodies

FIG. 36 illustrates methodology useful for making Drug-Linker-Ligand conjugates having about 2 to about 4 drugs per antibody. An antibody is treated with a reducing agent, such as dithiothreitol (DTT) to reduce some or all of the cysteine disulfide residues to form highly nucleophilic cysteine thiol groups (—CH$_2$SH). The partially reduced antibody thus reacts with drug-linker compounds, or linker reagents, with electrophilic functional groups such as maleimide or α-halo carbonyl, according to the conjugation method at page 766 of Klussman, et al. (2004), Bioconjugate Chemistry 15(4):765-773.

For example, an antibody, e.g., AC10, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker, e.g., MC-val-cit-PAB-MMAE in DMSO, dissolved in acetonitrile and water at known concentration, is added to the chilled reduced antibody in PBS. After about one hour, an excess of maleimide is added to quench the reaction and cap any unreacted antibody thiol groups. The reaction mixture is concentrated by centrifugal ultrafiltration and the ADC, e.g., AC10-MC-vc-PAB-MMAE, is purified and desalted by elution through G25 resin in PBS, filtered through 0.2 µm filters under sterile conditions, and frozen for storage.

A variety of antibody drug conjugates (ADC) were prepared, with a variety of linkers, and the drug moieties, MMAE and MMAF. The following table is an exemplary group of ADC which were prepared following the protocol of Example 27, and characterized by HPLC and drug loading assay.

| Target (antigen) | ADC | isolated amount (mg) | drug/Ab ratio |
|---|---|---|---|
| 0772P | 16E12-MC-vc-PAB-MMAE | 1.75 | 4 |
| 0772P | 11D10-MC-vc-PAB-MMAE | 46.8 | 4.4 |
| 0772P | 11D10-MC-vc-PAB-MMAF | 54.5 | 3.8 |
| Brevican | Brevican-MC-MMAF | 2 | 6 |
| Brevican | Brevican-MC-vc-MMAE | 2 | 6 |
| Brevican | Brevican-MC-vc-PAB-MMAF | 1.4 | 6 |
| CD21 | CD21-MC-vc-PAB-MMAE | 38.1 | 4.3 |
| CD21 | CD21-MC-vc-PAB-MMAF | 43 | 4.1 |
| CRIPTO | 11F4-MC-vc-PAB-MMAF | 6 | 4.8 |
| CRIPTO | 25G8-MC-vc-PAB-MMAF | 7.4 | 4.7 |
| E16 | 12G12-MC-vc-PAB-MMAE | 2.3 | 4.6 |
| E16 | 3B5-MC-vc-PAB-MMAE | 2.9 | 4.6 |
| E16 | 12B9-MC-vc-PAB-MMAE | 1.4 | 3.8 |
| E16 | 12B9-MC-vc-PAB-MMAE | 5.1 | 4 |
| E16 | 12G12-MC-vc-PAB-MMAF | 3 | 4.6 |
| E16 | 3B5-MC-vc-PAB-MMAE | 4.8 | 4.1 |
| E16 | 3B5-MC-vc-PAB-MMAF | 24.7 | 4.4 |
| EphB2R | 2H9-MC-vc-PAB-MMAE | 29.9 | 7.1 |
| EphB2R | 2H9-MC-fk-PAB-MMAE | 25 | 7.5 |
| EphB2R | 2H9-MC-vc-PAB-MMAE | 175 | 4.1 |
| EphB2R | 2H9-MC-vc-PAB-MMAF | 150 | 3.8 |
| EphB2R | 2H9-MC-vc-PAB-MMAF | 120 | 3.7 |
| EphB2R | 2H9-MC-vc-PAB-MMAE | 10.7 | 4.4 |
| IL-20Ra | IL20Ra-fk-MMAE | 26 | 6.7 |
| IL-20Ra | IL20Ra-vc-MMAE | 27 | 7.3 |
| EphB2 | IL8-MC-vc-PAB-MMAE | 251 | 3.7 |
| MDP | MDP-vc-MMAE | 32 | |
| MPF | 19C3-vc-MMAE | 1.44 | 6.5 |
| MPF | 7D9-vc-MMAE | 4.3 | 3.8 |
| MPF | 19C3-vc-MMAE | 7.9 | 3 |
| MPF | 7D9-MC-vc-PAB-MMAF | 5 | 4.3 |
| Napi3b | 10H1-vc-MMAE | 4.5 | 4.6 |
| Napi3b | 4C9-vc-MMAE | 3.0 | 5.4 |
| Napi3b | 10H1-vc-MMAE | 4.5 | 4.8 |
| Napi3b | 10H1-vc-MMAF | 6.5 | 4 |
| NCA | 3E6-MC-fk-PAB-MMAE | 49.6 | 5.4 |
| NCA | 3E6-MC-vc-PAB-MMAE | 56.2 | 6.4 |
| PSCA | PSCA-fk-MMAE | 51.7 | 8.9 |
| PSCA | PSCA-vc-MMAE | 61.1 | 8.6 |
| Napi3b | 10H1-MC-vc-PAB-MMAE | 75 | 4.2 |
| Napi3b | 10H1-MC-vc-PAB-MMAF | 95 | 4.4 |
| Napi3b | 10H1-MC-MMAF | 92 | 4 |
| EphB2R | 2H9-MC-vc-PAB-MMAE | 79 | 5 |

-continued

| Target (antigen) | ADC | isolated amount (mg) | drug/Ab ratio |
|---|---|---|---|
| EphB2R | 2H9-MC-MMAF | 92 | 4.9 |
| O772P | 11D10(Fc chimera)-MC-vc-PAB-MMAE | 79 | 4.3 |
| O772P | 11D10(Fc chimera)-MC-vc-PAB-MMAF | 70 | 4.5 |
| O772P | 11D10(Fc chimera)-MC-MMAF | 23 | 4.5 |
| Brevican | 6D2-MC-vc-PAB-MMAF | 0.3 | 4.5 |
| Brevican | 6D2-MC-MMAF | 0.36 | 4.5 |
| EphB2R | 2H9(Fc chimera)-MC-vc-PAB-MMAE | 1983 | 4.3 |
| E16 | 12B9-MC-vc-PAB-MMAE | 14.1 | 4.6 |
| E16 | 12B9-MC-vc-PAB-MMAF | 16.4 | 4.5 |
| E16 | 12G12-MC-vc-PAB-MMAE | 10.5 | 4.1 |
| E16 | 12G12-MC-vc-PAB-MMAF | 10.2 | 3.8 |
| E16 | 3B5-MC-vc-PAB-MMAE | 58.6 | 3.8 |
| E16 | 3B5-MC-vc-PAB-MMAF | 8 | 3.1 |
| O772P | 11D10(Fc chimera)-MC-vc-PAB-MMAE | 340 | 3.9 |
| Steap1 | (Steap1-92)-MC-vc-PAB-MMAE | 3.5 | 4 |
| Steap1 | (Steap1-92)-MC-vc-PAB-MMAF | 4.7 | 4 |
| Steap1 | (Steap1-120)-MC-vc-PAB-MMAE | 2 | 4 |
| Steap1 | (Steap1-120)-MC-vc-PAB-MMAF | 2.3 | 4 |
| E16 | 3B5-MC-vc-PAB-MMAF | 52.2 | 4.5 |

4.7 Compositions and Methods of Administration

In other embodiments, described is a composition including an effective amount of an Exemplary Compound and/or Exemplary Conjugate and a pharmaceutically acceptable carrier or vehicle. For convenience, the Drug units and Drug-Linker Compounds can be referred to as Exemplary Compounds, while Drug-Ligand Conjugates and Drug-Linker-Ligand Conjugates can be referred to as Exemplary Conjugates. The compositions are suitable for veterinary or human administration.

The present compositions can be in any form that allows for the composition to be administered to a patient. For example, the composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In one aspect, the compositions are administered parenterally. In yet another aspect, the Exemplary Compounds and/or the Exemplary Conjugates or compositions are administered intravenously.

Pharmaceutical compositions can be formulated so as to allow an Exemplary Compound and/or Exemplary Conjugate to be bioavailable upon administration of the composition to a patient. Compositions can take the form of one or more dosage units, where for example, a tablet can be a single dosage unit, and a container of an Exemplary Compound and/or Exemplary Conjugate in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Exemplary Compound or Exemplary Conjugate, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Exemplary Compound and/or Exemplary Conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of an Exemplary Compound and/or Exemplary Conjugate such that a suitable dosage will be obtained. Typically, this amount is at least about 0.01% of an Exemplary Compound and/or Exemplary Conjugate by weight of the composition. When intended for oral administration, this amount can be varied to range from about 0.1% to about 80% by weight of the composition. In one aspect, oral compositions can comprise from about 4% to about 50% of the Exemplary Compound and/or Exemplary Conjugate by weight of the composition. In yet another aspect, present compositions are prepared so that a parenteral dosage unit contains from about 0.01% to about 2% by weight of the Exemplary Compound and/or Exemplary Conjugate.

For intravenous administration, the composition can comprise from about 0.01 to about 100 mg of an Exemplary Compound and/or Exemplary Conjugate per kg of the animal's body weight. In one aspect, the composition can include from about 1 to about 100 mg of an Exemplary Compound and/or Exemplary Conjugate per kg of the animal's body weight. In another aspect, the amount administered will be in the range from about 0.1 to about 25 mg/kg of body weight of the Exemplary Compound and/or Exemplary Conjugate.

Generally, the dosage of an Exemplary Compound and/or Exemplary Conjugate administered to a patient is typically about 0.01 mg/kg to about 2000 mg/kg of the animal's body weight. In one aspect, the dosage administered to a patient is between about 0.01 mg/kg to about 10 mg/kg of the animal's body weight, in another aspect, the dosage administered to a patient is between about 0.1 mg/kg and about 250 mg/kg of the animal's body weight, in yet another aspect, the dosage administered to a patient is between about 0.1 mg/kg and about 20 mg/kg of the animal's body weight, in yet another aspect the dosage administered is between about 0.1 mg/kg to about 10 mg/kg of the animal's body weight, and in yet another aspect, the dosage administered is between about 1 mg/kg to about 10 mg/kg of the animal's body weight.

The Exemplary Compounds and/or Exemplary Conjugate or compositions can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer an Exemplary Compound and/or Exemplary Conjugate or composition. In certain embodiments, more than one Exemplary Compound and/or Exemplary Conjugate or composition is administered to a patient.

In specific embodiments, it can be desirable to administer one or more Exemplary Compounds and/or Exemplary Conjugate or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more Exemplary Compounds and/or Exemplary Conjugate or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In yet another embodiment, the Exemplary Compounds and/or Exemplary Conjugate or compositions can be delivered in a controlled release system, such as but not limited to, a pump or various polymeric materials can be used. In yet another embodiment, a controlled-release system can be placed in proximity of the target of the Exemplary Compounds and/or Exemplary Conjugate or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which an Exemplary Compound and/or Exemplary Conjugate is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the Exemplary Compound and/or Exemplary Conjugate or compositions and pharmaceutically acceptable carriers are sterile. Water is an exemplary carrier when the Exemplary Compounds and/or Exemplary Conjugates are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

In an embodiment, the Exemplary Compounds and/or Exemplary Conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where an Exemplary Compound and/or Exemplary Conjugate is to be administered by infusion, it can be dispensed, for example, with an infusion bottle containing sterile pharmaceutical grade water or saline. Where the Exemplary Compound and/or Exemplary Conjugate is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The compositions can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of an Exemplary Compound and/or Exemplary Conjugate of from about 0.05% to about 50% w/v (weight per unit volume of composition), in another aspect, from 0.1% to 10% w/v.

The composition can be intended for rectal administration, in the form, e.g., of a suppository which will melt in the rectum and release the Exemplary Compound and/or Exemplary Conjugate.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients.

Whether in solid, liquid or gaseous form, the present compositions can include a pharmacological agent used in the treatment of cancer, an autoimmune disease or an infectious disease.

4.8 Therapeutic Uses of the Exemplary Conjugates

The Exemplary Compounds and/or Exemplary Conjugates are useful for treating cancer, an autoimmune disease or an infectious disease in a patient.

4.8.1 Treatment of Cancer

The Exemplary Compounds and/or Exemplary Conjugates are useful for inhibiting the multiplication of a tumor cell or cancer cell, causing apoptosis in a tumor or cancer cell, or for treating cancer in a patient. The Exemplary Compounds and/or Exemplary Conjugates can be used accordingly in a variety of settings for the treatment of animal cancers. The Drug-Linker-Ligand Conjugates can be used to deliver a Drug or Drug unit to a tumor cell or cancer cell. Without being bound by theory, in one embodiment, the Ligand unit of an Exemplary Conjugate binds to or associates with a cancer-cell or a tumor-cell-associated antigen, and the Exemplary Conjugate can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the Linker unit are hydrolytically cleaved by one or more tumor-cell or cancer-cell-associated proteases, resulting in release of a Drug or a Drug-Linker Compound. The released Drug or Drug-Linker Compound is then free to migrate within the cell and induce cytotoxic or cytostatic activities. In an alternative embodiment, the Drug or Drug unit is cleaved from the Exemplary Conjugate outside the tumor cell or cancer cell, and the Drug or Drug-Linker Compound subsequently penetrates the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, Exemplary Conjugates having a BR96 Ligand unit can be useful for treating antigen positive carcinomas including those of the lung, breast, colon, ovaries, and pancreas. Exemplary Conjugates having an Anti-CD30 or an anti-CD40 Ligand unit can be useful for treating hematologic malignancies.

Other particular types of cancers that can be treated with Exemplary Conjugates include, but are not limited to, those disclosed in Table 3.

TABLE 3

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer

TABLE 3-continued esophogeal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
blood-borne cancers, including but not limited to:

acute lymphoblastic leukemia "ALL"
acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma
acute and chronic leukemias:

lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera The Exemplary Conjugates provide conjugation-specific tumor or cancer targeting, thus reducing general toxicity of these compounds. The Linker units stabilize the Exemplary Conjugates in blood, yet are cleavable by tumor-specific proteases within the cell, liberating a Drug.

4.8.2 Multi-Modality Therapy for Cancer

Cancers, including, but not limited to, a tumor, metastasis, or other disease or disorder characterized by uncontrolled cell growth, can be treated or prevented by administration of an Exemplary Conjugate and/or an Exemplary Compound.

In other embodiments, methods for treating or preventing cancer are provided, including administering to a patient in need thereof an effective amount of an Exemplary Conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Exemplary Conjugates can be administered to a patient that has also undergone surgery as treatment for the cancer.

In one embodiment, the additional method of treatment is radiation therapy.

In a specific embodiment, the Exemplary Conjugate is administered concurrently with the chemotherapeutic agent or with radiation therapy. In another specific embodiment, the chemotherapeutic agent or radiation therapy is administered prior or subsequent to administration of an Exemplary Conjugates, in one aspect at least an hour, five hours, 12 hours, a day, a week, a month, in further aspects several months (e.g., up to three months), prior or subsequent to administration of an Exemplary Conjugate.

A chemotherapeutic agent can be administered over a series of sessions. Any one or a combination of the chemotherapeutic agents listed in Table 4 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with an Exemplary Compound and/or Exemplary Conjugate are provided as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Exemplary Compounds and/or Exemplary Conjugates can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of an Exemplary Compound and/or Exemplary Conjugate with or without accompanying high dose radiation therapy, and the stem cell graft is infused back into the animal. Supportive care is then provided while bone marrow function is restored and the animal recovers.

4.8.3 Multi-Drug Therapy for Cancer

Methods for treating cancer including administering to a patient in need thereof an effective amount of an Exemplary Conjugate and another therapeutic agent that is an anti-cancer agent are disclosed. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel. In one aspect, the anti-cancer agent includes, but is not limited to, a drug listed in Table 4.

TABLE 4

| | |
|---|---|
| Alkylating agents | |
| Nitrogen mustards: | cyclophosphamide |
| | ifosfamide |
| | trofosfamide |
| | chlorambucil |
| | melphalan |
| Nitrosoureas: | carmustine (BCNU) |
| | lomustine (CCNU) |
| Alkylsulphonates | busulfan |
| | treosulfan |
| Triazenes: | decarbazine |
| Platinum containing compounds: | cisplatin |
| | carboplatin |
| Plant Alkaloids | |
| Vinca alkaloids: | vincristine |
| | vinblastine |
| | vindesine |
| | vinorelbine |
| Taxoids: | paclitaxel |
| | docetaxol |
| DNA Topoisomerase Inhibitors | |
| Epipodophyllins: | etoposide |
| | teniposide |
| | topotecan |
| | 9-aminocamptothecin |
| | camptothecin |
| | crisnatol |
| mitomycins: | mitomycin C |
| Anti-metabolites | |
| Anti-folates: | |
| DHFR inhibitors: | methotrexate |
| | trimetrexate |
| IMP dehydrogenase Inhibitors: | mycophenolic acid |
| | tiazofurin |
| | ribavirin |
| | EICAR |
| Ribonucleotide reductase Inhibitors: | hydroxyurea |
| | deferoxamine |
| Pyrimidine analogs: | |
| Uracil analogs | 5-Fluorouracil |
| | floxuridine |
| | doxifluridine |
| | ratitrexed |
| Cytosine analogs | cytarabine (ara C) |
| | cytosine arabinoside |
| | fludarabine |
| Purine analogs: | mercaptopurine |
| | thioguanine |
| Hormonal therapies: | |
| Receptor antagonists: | |
| Anti-estrogen | tamoxifen |
| | raloxifene |
| | megestrol |

TABLE 4-continued

| | |
|---|---|
| LHRH agonists: | goscrclin |
| | leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodynamic therapies: | vertoporfin (BPD-MA) |
| | phthalocyanine |
| | photosensitizer Pc4 |
| | demethoxy-hypocrellin A |
| | (2BA-2-DMHA) |
| Cytokines: | Interferon-α |
| | Interferon-γ |
| | tumor necrosis factor |
| Others: | Gemcitabine |
| | Velcade |
| | Revamid |
| | Thalamid |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | dactinomycin |
| Bleomycins: | bleomycin A2 |
| | bleomycin B2 |
| | peplomycin |
| Anthracyclines: | daunorubicin |
| | Doxorubicin (adriamycin) |
| | idarubicin |
| | epirubicin |
| | pirarubicin |
| | zorubicin |
| | mtoxantrone |
| MDR inhibitors: | verapamil |
| $Ca^{2+}$ATPase inhibitors: | thapsigargin |

4.8.4 Treatment of Autoimmune Diseases

The Exemplary Conjugates are useful for killing or inhibiting the replication of a cell that produces an autoimmune disease or for treating an autoimmune disease. The Exemplary Conjugates can be used accordingly in a variety of settings for the treatment of an autoimmune disease in a patient. The Drug-Linker-Ligand Conjugates can be used to deliver a Drug to a target cell. Without being bound by theory, in one embodiment, the Drug-Linker-Ligand Conjugate associates with an antigen on the surface of a target cell, and the Exemplary Conjugate is then taken up inside a target-cell through receptor-mediated endocytosis. Once inside the cell, one or more specific peptide sequences within the Linker unit are enzymatically or hydrolytically cleaved, resulting in release of a Drug. The released Drug is then free to migrate in the cytosol and induce cytotoxic or cytostatic activities. In an alternative embodiment, the Drug is cleaved from the Exemplary Conjugate outside the target cell, and the Drug subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand binds to activated lymphocytes that are associated with the autoimmune disease state.

In a further embodiment, the Exemplary Conjugates kill or inhibit the multiplication of cells that produce an autoimmune antibody associated with a particular autoimmune disease.

Particular types of autoimmune diseases that can be treated with the Exemplary Conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 5.

TABLE 5

Active Chronic Hepatitis
Addison's Disease
Allergic Alveolitis
Allergic Reaction
Allergic Rhinitis
Alport's Syndrome
Anaphlaxis
Ankylosing Spondylitis
Anti-phosholipid Syndrome
Arthritis
Ascariasis
Aspergillosis
Atopic Allergy
Atropic Dermatitis
Atropic Rhinitis
Behcet's Disease
Bird-Fancier's Lung
Bronchial Asthma
Caplan's Syndrome
Cardiomyopathy
Celiac Disease
Chagas' Disease
Chronic Glomerulonephritis
Cogan's Syndrome
Cold Agglutinin Disease
Congenital Rubella Infection
CREST Syndrome
Crohn's Disease
Cryoglobulinemia
Cushing's Syndrome
Dermatomyositis
Discoid Lupus
Dressler's Syndrome
Eaton-Lambert Syndrome
Echovirus Infection
Encephalomyelitis
Endocrine opthalmopathy
Epstein-Barr Virus Infection
Equine Heaves
Erythematosis
Evan's Syndrome
Felty's Syndrome
Fibromyalgia
Fuch's Cyclitis
Gastric Atrophy
Gastrointestinal Allergy
Giant Cell Arteritis
Glomerulonephritis
Goodpasture's Syndrome
Graft v. Host Disease
Graves' Disease
Guillain-Barre Disease
Hashimoto's Thyroiditis
Hemolytic Anemia
Henoch-Schonlein Purpura
Idiopathic Adrenal Atrophy
Idiopathic Pulmonary Fibritis
IgA Nephropathy
Inflammatory Bowel Diseases
Insulin-dependent Diabetes Mellitus
Juvenile Arthritis
Juvenile Diabetes Mellitus (Type I)
Lambert-Eaton Syndrome
Laminitis
Lichen Planus
Lupoid Hepatitis TABLE 5-continued Lupus
Lymphopenia
Meniere's Disease
Mixed Connective Tissue Disease
Multiple Sclerosis
Myasthenia Gravis
Pernicious Anemia
Polyglandular Syndromes
Presenile Dementia
Primary Agammaglobulinemia
Primary Biliary Cirrhosis
Psoriasis
Psoriatic Arthritis
Raynauds Phenomenon
Recurrent Abortion
Reiter's Syndrome
Rheumatic Fever
Rheumatoid Arthritis
Sampter's Syndrome
Schistosomiasis
Schmidt's Syndrome
Scleroderma
Shulman's Syndrome
Sjorgen's Syndrome
Stiff-Man Syndrome
Sympathetic Ophthalmia
Systemic Lupus Erythematosis
Takayasu's Arteritis
Temporal Arteritis
Thyroiditis
Thrombocytopenia
Thyrotoxicosis
Toxic Epidermal Necrolysis
Type B Insulin Resistance
Type I Diabetes Mellitus
Ulcerative Colitis
Uveitis
Vitiligo
Waldenstrom's Macroglobulemia
Wegener's Granulomatosis 4.8.5 Multi-Drug Therapy of Autoimmune Diseases Methods for treating an autoimmune disease are also disclosed including administering to a patient in need thereof an effective amount of an Exemplary Conjugate and another therapeutic agent known for the treatment of an autoimmune disease. In one embodiment, the anti-autoimmune disease agent includes, but is not limited to, agents listed in Table 6.

TABLE 6 cyclosporine
cyclosporine A
mycophenylate mofetil
sirolimus
tacrolimus
enanercept
prednisone
azathioprine
methotrexate cyclophosphamide
prednisone
aminocaproic acid
chloroquine
hydroxychloroquine
hydrocortisone
dexamethasone
chlorambucil
DHEA
danazol
bromocriptine
meloxicam
infliximab 4.8.6 Treatment of Infectious Diseases The Exemplary Conjugates are useful for killing or inhibiting the multiplication of a cell that produces an infectious disease or for treating an infectious disease. The Exemplary Conjugates can be used accordingly in a variety of settings for the treatment of an infectious disease in a patient. The Drug-Linker-Ligand Conjugates can be used to deliver a Drug to a target cell. In one embodiment, the Ligand unit binds to the infectious disease cell.

In one embodiment, the Conjugates kill or inhibit the multiplication of cells that produce a particular infectious disease.

Particular types of infectious diseases that can be treated with the Exemplary Conjugates include, but are not limited to, those disclosed in Table 7.

TABLE 7

Bacterial Diseases:

Diphtheria
Pertussis
Occult Bacteremia
Urinary Tract Infection
Gastroenteritis
Cellulitis
Epiglottitis
Tracheitis
Adenoid Hypertrophy
Retropharyngeal Abcess
Impetigo
Ecthyma
Pneumonia
Endocarditis
Septic Arthritis
Pneumococcal
Peritonitis
Bactermia
Meningitis
Acute Purulent Meningitis
Urethritis
Cervicitis
Proctitis
Pharyngitis
Salpingitis
Epididymitis
Gonorrhea
Syphilis
Listeriosis
Anthrax
Nocardiosis
Salmonella
Typhoid Fever
Dysentery
Conjunctivitis
Sinusitis
Brucellosis
Tullaremia
Cholera
Bubonic Plague
Tetanus
Necrotizing Enteritis
Actinomycosis
Mixed Anaerobic Infections
Syphilis
Relapsing Fever
Leptospirosis
Lyme Disease
Rat Bite Fever
Tuberculosis
Lymphadenitis
Leprosy
Chlamydia
Chlamydial Pneumonia
Trachoma
Inclusion Conjunctivitis TABLE 7-continued Systemic Fungal Diseases:

Histoplamosis
Coccidiodomycosis
Blastomycosis
Sporotrichosis
Cryptococcsis
Systemic Candidiasis
Aspergillosis
Mucormycosis
Mycetoma
Chromomycosis
Rickettsial Diseases:

Typhus
Rocky Mountain Spotted Fever
Ehrlichiosis
Eastern Tick-Borne Rickettsioses
Rickettsialpox
Q Fever
Bartonellosis
Parasitic Diseases:

Malaria
Babesiosis
African Sleeping Sickness
Chagas' Disease
Leishmaniasis
Dum-Dum Fever
Toxoplasmosis
Meningoencephalitis
Keratitis
Entamebiasis
Giardiasis
Cryptosporidiasis
Isosporiasis
Cyclosporiasis
Microsporidiosis
Ascariasis
Whipworm Infection
Hookworm Infection
Threadworm Infection
Ocular Larva Migrans
Trichinosis
Guinea Worm Disease
Lymphatic Filariasis
Loiasis
River Blindness
Canine Heartworm Infection
Schistosomiasis
Swimmer's Itch
Oriental Lung Fluke
Oriental Liver Fluke
Fascioliasis
Fasciolopsiasis
Opisthorchiasis
Tapeworm Infections
Hydatid Disease
Alveolar Hydatid Disease
Viral Diseases:

Measles
Subacute sclerosing panencephalitis
Common Cold
Mumps
Rubella
Roseola
Fifth Disease
Chickenpox
Respiratory syncytial virus infection
Croup
Bronchiolitis
Infectious Mononucleosis
Poliomyelitis
Herpangina
Hand-Foot-and-Mouth Disease
Bornholm Disease
Genital Herpes
Genital Warts

TABLE 7-continued

Aseptic Meningitis
Myocarditis
Pericarditis
Gastroenteritis
Acquired Immunodeficiency Syndrome (AIDS)
Human Immunodeficiency Virus (HIV)
Reye's Syndrome
Kawasaki Syndrome
Influenza
Bronchitis
Viral "Walking" Pneumonia
Acute Febrile Respiratory Disease
Acute pharyngoconjunctival fever
Epidemic keratoconjunctivitis
Herpes Simplex Virus 1 (HSV-1)
Herpes Simplex Virus 2 (HSV-2)
Shingles
Cytomegalic Inclusion Disease
Rabies
Progressive Multifocal Leukoencephalopathy
Kuru
Fatal Familial Insomnia
Creutzfeldt-Jakob Disease
Gerstmann-Straussler-Scheinker Disease
Tropical Spastic Paraparesis
Western Equine Encephalitis
California Encephalitis
St. Louis Encephalitis
Yellow Fever
Dengue
Lymphocytic choriomeningitis
Lassa Fever
Hemorrhagic Fever
Hantvirus Pulmonary Syndrome
Marburg Virus Infections
Ebola Virus Infections
Smallpox

4.8.7 Multi-Drug Therapy of Infectious Diseases

Methods for treating an infectious disease are disclosed including administering to a patient in need thereof an Exemplary Conjugate and another therapeutic agent that is an anti-infectious disease agent. In one embodiment, the anti-infectious disease agent is, but not limited to, agents listed in Table 8.

TABLE 8

β-Lactam Antibiotics:

Penicillin G
Penicillin V
Cloxacilliin
Dicloxacillin
Methicillin
Nafcillin
Oxacillin
Ampicillin
Amoxicillin
Bacampicillin
Azlocillin
Carbenicillin
Mezlocillin
Piperacillin
Ticarcillin
Aminoglycosides:

Amikacin
Gentamicin
Kanamycin
Neomycin
Netilmicin
Streptomycin
Tobramycin

TABLE 8-continued

Macrolides:

Azithromycin
Clarithromycin
Erythromycin
Lincomycin
Clindamycin
Tetracyclines:

Demeclocycline
Doxycycline
Minocycline
Oxytetracycline
Tetracycline
Quinolones:

Cinoxacin
Nalidixic Acid
Fluoroquinolones:

Ciprofloxacin
Enoxacin
Grepafloxacin
Levofloxacin
Lomefloxacin
Norfloxacin
Ofloxacin
Sparfloxacin
Trovafloxicin
Polypeptides:

Bacitracin
Colistin
Polymyxin B
Sulfonamides:

Sulfisoxazole
Sulfamethoxazole
Sulfadiazine
Sulfamethizole
Sulfacetamide
Miscellaneous Antibacterial Agents:

Trimethoprim
Sulfamethazole
Chloramphenicol
Vancomycin
Metronidazole
Quinupristin
Dalfopristin
Rifampin
Spectinomycin
Nitrofurantoin
Antiviral Agents:
General Antiviral Agents:

Idoxuradine
Vidarabine
Trifluridine
Acyclovir
Famcicyclovir
Pencicyclovir
Valacyclovir
Gancicyclovir
Foscarnet
Ribavirin
Amantadine
Rimantadine
Cidofovir
Antisense Oligonucleotides
Immunoglobulins
Inteferons

TABLE 8-continued

Drugs for HIV infection:

Tenofovir
Emtricitabine
Zidovudine
Didanosine
Zalcitabine
Stavudine
Lamivudine
Nevirapine
Delavirdine
Saquinavir
Ritonavir
Indinavir
Nelfinavir

5. EXAMPLES

Example 1

Preparation of Compound AB

Fmoc-val-cit-PAB-OH (14.61 g, 24.3 mmol, 1.0 eq., U.S. Pat. No. 6,214,345 to Firestone et al) was diluted with DMF (120 mL, 0.2 M) and to this solution was added a diethylamine (60 mL). The reaction was monitored by HPLC and found to be complete in 2 h. The reaction mixture was concentrated and the resulting residue was precipitated using ethyl acetate (ca. 100 mL) under sonication over for 10 min. Ether (200 mL) was added and the precipitate was further sonicated for 5 min. The solution was allowed to stand for 30 min. without stirring and was then filtered and dried under high vacuum to provide Val-cit-PAB-OH, which was used in the next step without further purification. Yield: 8.84 g (96%). Val-cit-PAB-OH (8.0 g, 21 mmol) was diluted with DMF (110 mL) and the resulting solution was treated with MC-OSu (Willner et al., (1993) Bioconjugate Chem. 4:521; 6.5 g, 21 mmol, 1.0 eq.). Reaction was complete according to HPLC after 2 h. The reaction mixture was concentrated and the resulting oil was precipitated using ethyl acetate (50 mL). After sonicating for 15 min, ether (400 mL) was added and the mixture was sonicated further until all large particles were broken up. The solution was then filtered and the solid dried to provide an off-white solid intermediate. Yield: 11.63 g (96%); ES-MS m/z 757.9 [M–H]

Fmoc-val-cit-PAB-OH (14.61 g, 24.3 mmol, 1.0 eq., U.S. Pat. No. 6,214,345 to Firestone et al.) was diluted with DMF (120 mL, 0.2 M) and to this solution was added a diethylamine (60 mL). The reaction was monitored by HPLC and found to be complete in 2 h. The reaction mixture was concentrated and the resulting residue was precipitated using ethyl acetate (ca. 100 mL) under sonication over for 10 min. Ether (200 mL) was added and the precipitate was further sonicated for 5 min. The solution was allowed to stand for 30 min. without stirring and was then filtered and dried under high vacuum to provide Val-cit-PAB-OH, which was used in the next step without further purification. Yield: 8.84 g (96%). Val-cit-PAB-OH (8.0 g, 21 mmol) was diluted with DMF (110 mL) and the resulting solution was treated with MC-OSu (Willner et al., (1993) Bioconjugate Chem. 4:521; 6.5 g, 21 mmol, 1.0 eq.). Reaction was complete according to HPLC after 2 h. The reaction mixture was concentrated and the

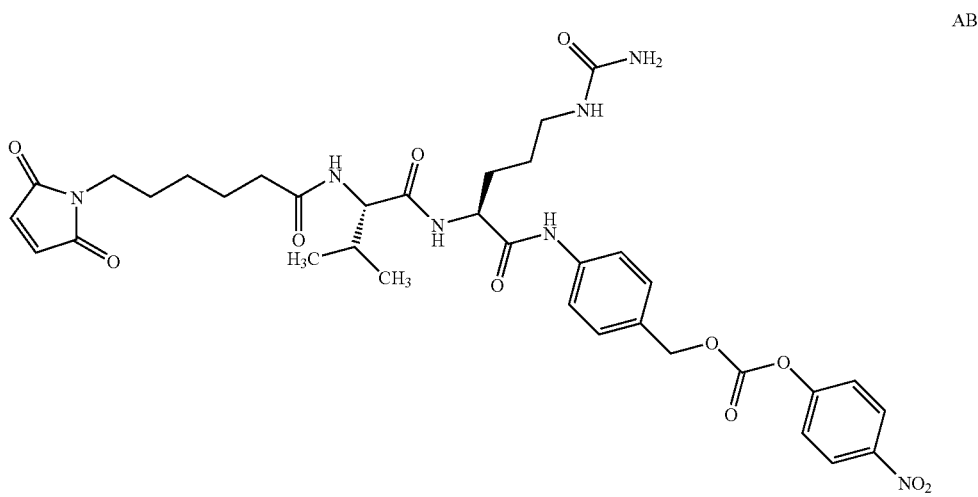

AB resulting oil was precipitated using ethyl acetate (50 mL). After sonicating for 15 min, ether (400 mL) was added and the mixture was sonicated further until all large particles were broken up. The solution was then filtered and the solid dried to provide an off-white solid intermediate. Yield: 11.63 g (96%); ES-MS m/z 757.9 [M–H].

The off-white solid intermediate (8.0 g, 14.0 mmol) was diluted with DMF (120 mL, 0.12 M) and to the resulting solution was added bis(4-nitrophenyl)carbonate (8.5 g, 28.0 mmol, 2.0 eq.) and DIEA (3.66 mL, 21.0 mmol, 1.5 eq.). The reaction was complete in 1 h according to HPLC. The reaction mixture was concentrated to provide an oil that was precipitated with EtOAc, and then triturated with EtOAc (ca. 25 mL). The solute was further precipitated with ether (ca. 200 mL) and triturated for 15 min. The solid was filtered and dried under high vacuum to provide Compound AB which was 93% pure according to HPLC and used in the next step without further purification. Yield: 9.7 g (94%).

Example 2

Preparation of Compound 1

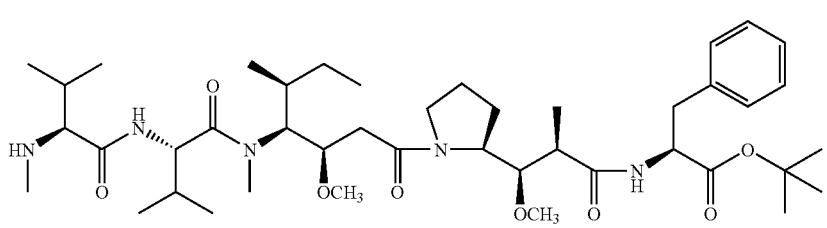

Phenylalanine t-butyl ester HCl salt (868 mg, 3 mmol), N-Boc-Dolaproine (668 mg, 1 eq.), DEPC (820 mL, 1.5 eq.), and DIEA (1.2 mL) were diluted with dichloromethane (3 mL). After 2 hours (h) at room temperature (about 28 degrees Celsius), the reaction mixture was diluted with dichloromethane (20 mL), washed successively with saturated aqueous (aq.) NaHCO$_3$ (2×10 mL), saturated aq. NaCl (2×10 mL). The organic layer was separated and concentrated. The resulting residue was re-suspended in ethyl acetate and was purified via flash chromatography in ethyl acetate. The relevant fractions were combined and concentrated to provide the dipeptide as a white solid: 684 mg (46%). ES-MS m/z 491.3 [M+H]$^+$.

For selective Boc cleavage in the presence of t-butyl ester, the above dipeptide (500 mg, 1.28 mmol) was diluted with dioxane (2 mL). 4M HCl/dioxane (960 µL, 3 eq.) was added, and the reaction mixture was stirred overnight at room temperature. Almost complete Boc deprotection was observed by RP-HPLC with minimal amount of t-butyl ester cleavage. The mixture was cooled down on an ice bath, and triethylamine (500 µL) was added. After 10 min., the mixture was removed from the cooling bath, diluted with dichloromethane (20 mL), washed successively with saturated aq. NaHCO$_3$ (2×10 mL), saturated aq. NaCl (2×10 mL). The organic layer was concentrated to give a yellow foam: 287 mg (57%). The intermediate was used without further purification.

The tripeptide Fmoc-Meval-val-dil-O-t-Bu (prepared as described in WO 02/088172, entitled "Pentapeptide Compounds and Uses Related Thereto"; 0.73 mmol) was treated with TFA (3 mL), dichloromethane (3 mL) for 2 h at room temperature. The mixture was concentrated to dryness, the residue was co-evaporated with toluene (3×20 mL), and dried in vacuum overnight. The residue was diluted with dichloromethane (5 mL) and added to the deprotected dipeptide (287 mg, 0.73 mmol), followed by DIEA (550 µL, 4 eq.), DEPC (201 µL, 1.1 eq.). After 2 h at room temperature the reaction mixture was diluted with ethyl acetate (50 mL), washed successively with 10% aq. citric acid (2×20 mL), saturated aq. NaHCO$_3$ (2×10 mL), saturated aq. NaCl (10 mL). The organic layer was separated and concentrated. The resulting residue was re-suspended in ethyl acetate and was purified via flash chromatography in ethyl acetate. The relevant fractions were combined and concentrated to provide Fmoc-Meval-val-dil-dap-phe-O-t-Bu as a white solid: 533 mg (71%). R$_f$ 0.4 (EtOAc). ES-MS m/z 1010.6 [M+H]$^+$.

The product (200 mg, 0.2 mmol) was diluted with dichloromethane (3 mL), diethylamine (1 mL). The reaction mixture was stirred overnight at room temperature. Solvents were removed to provide an oil that was purified by flash silica gel chromatography in a step gradient 0-10% MeOH in dichloromethane to provide Compound 1 as a white solid: 137 mg (87%). R$_f$ 0.3 (10% MeOH/CH$_2$Cl$_2$). ES-MS m/z 788.6 [M+H]$^+$.

Example 3

Preparation of Compound 2

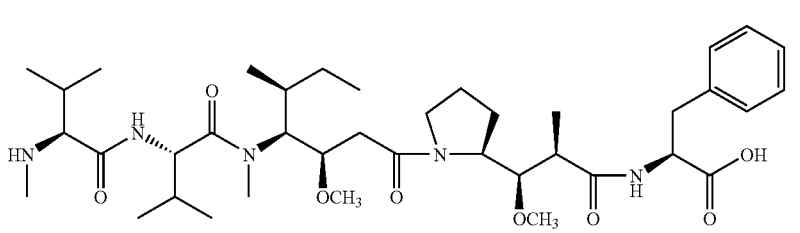

Compound 2 was prepared from compound 1 (30 mg, 0.038 mmol) by treatment with 4M HCl/dioxane (4 ml) for 7 h at room temperature. The solvent was removed, and the residue was dried in a vacuum overnight to give provide Compound 2 as a hydroscopic white solid: 35 mg (120% calculated for HCl salt). ES-MS m/z 732.56 [M+H]$^+$.

Example 4

Preparation of Compound 3

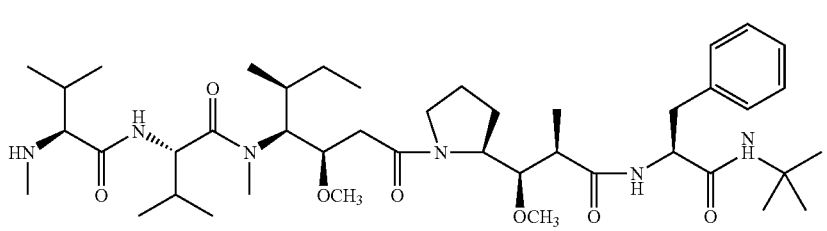

Fmoc-Meval-val-dil-dap-phe-O-t-Bu (Example 2, 50 mg) was treated with 4M HCl/dioxane (4 ml) for 16 h at room temperature. The solvent was removed, and the residue was dried in vacuum overnight to give 50 mg of a hydroscopic white solid intermediate The white solid intermediate (20 mg, 0.02 mmol) was diluted with dichloromethane (1 mL); DEPC (5 μL, 0.03 mmol, 1.5 eq.) was added followed by DIEA (11 μL, 0.06 mmol, 3 eq.), and t-butylamine (3.2 μL, 0.03 mmol, 1.5 eq.). After 2 h at room temperature, the reaction was found to be uncompleted by RP-HPLC. More DEPC (10 μL) and t-butylamine (5 μL) were added and the reaction was stirred for additional 4 h. Reaction mixture was diluted with dichloromethane (15 mL), washed successively with water (5 mL), 0.1 M aq. HCl (10 mL), saturated aq. NaCl (10 mL). The organic layer was separated and concentrated. The resulting residue was diluted with dichloromethane and purified via flash chromatography in a step gradient 0-5% MeOH in dichloromethane. The relevant fractions were combined and concentrated to provide the Fmoc protected intermediate as a white solid: 7.3 mg (36%). $R_f$ 0.75 (10% MeOH/CH$_2$Cl$_2$).

Fmoc protected intermediate was diluted with dichloromethane (0.5 mL) and treated with diethylamine (0.5 mL) for 3 h at room temperature. The reaction mixture was concentrated to dryness. The product was isolated by flash silica gel chromatography in a step gradient 0-10% MeOH in dichloromethane to provide Compound 3 as a white solid: 4 mg (70%). $R_f$ 0.2 (10% MeOH/CH$_2$Cl$_2$). ES-MS m/z 787 [M+H]$^+$, 809 [M+Na]$^+$.

Example 5

Preparation of Compound 4

Boc-L-Phenylalanine (265 mg, 1 mmol, 1 eq.) and triethyleneglycol monomethyl ether (164 μL, 1 mmol, 1 eq.) were diluted with dichloromethane (5 mL). Then, DCC (412 mg, 2 mmol, 2 eq.) was added, followed by DMAP (10 mg). The reaction mixture was stirred overnight at room temperature. The precipitate was filtered off. The solvent was removed in a vacuum, the residue was diluted with ethyl acetate, and purified by silica gel flash chromatography in ethyl acetate. The product containing fractions were pulled, concentrated, and dried in vacuum to give a white solid: 377 mg (91%). $R_f$ 0.5 (EtOAc). ES-MS m/z 434 [M+Na]$^+$.

Removal of Boc protecting group was performed by treatment of the above material in dioxane (10 mL) with 4M HCl/dioxane (6 mL) for 6 h at room temperature. The solvent was removed in a vacuum, the residue was dried in a vacuum to give a white solid.

The HCl salt of Phenylalanine-triethyleneglycol monomethyl ether ester (236 mg, 0.458 mmol, 1 eq.) and N-Boc-Dolaproine (158 mg, 0.55 mmol, 1.2 eq.) were diluted with dichloromethane (3 mL). DEPC (125 μL, 1.5 eq.) and added to the mixture followed by DIEA (250 μL, 3 eq.). After 2 h at room temperature the reaction mixture was diluted with ethyl acetate (30 mL), washed successively with saturated aq. NaHCO$_3$ (2×10 mL), 10% aq. citric acid (2×10 mL), saturated aq. NaCl (10 mL). The organic layer was separated and concentrated. The resulting residue was re-suspended in ethyl acetate and was purified via flash chromatography on silica gel in ethyl acetate. The relevant fractions were combined and concentrated to provide a white foam intermediate: 131 mg (50%). $R_f$ 0.25 (EtOAc). ES-MS m/z 581.3 [M+H]$^+$.

Boc deprotection was done in dichloromethane (2 mL), TFA (0.5 mL) at room temperature for 2 h. Solvent was removed in vacuum, and the residue was co-evaporated with toluene (3×25 mL), then dried in vacuum to give 138 mg of dipeptide TFA salt.

Fmoc-Meval-val-dil-OH (Example 2, 147 mg, 0.23 mmol, 1 eq.), and dipeptide TFA salt (138 mg) were diluted with dichloromethane (2 mL). To the mixture DEPC (63 μL, 1.5 eq.) was added, followed by DIEA (160 μL, 4 eq.). After 2 h

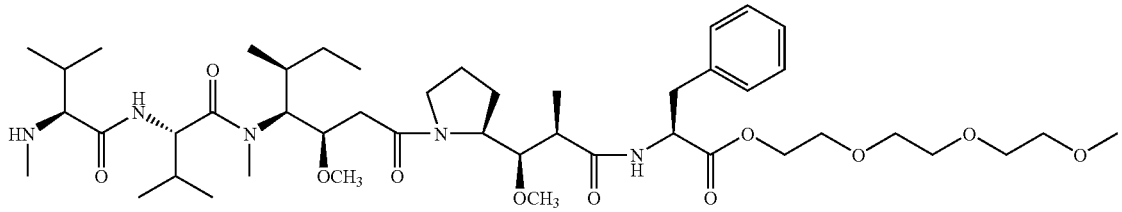

at room temperature the reaction mixture was diluted with dichloromethane (30 mL), washed successively with 10% aq. citric acid (2×20 mL), saturated aq. NaCl (20 mL). The organic layer was separated and concentrated. The resulting residue was re-suspended in dichloromethane and was purified via flash chromatography on silica gel in a step gradient 0-5% MeOH in dichloromethane. The relevant fractions were combined and concentrated to provide white foam: 205 mg (81%). $R_f$ 0.4 (10% MeOH/CH$_2$Cl$_2$). ES-MS m/z 1100.6 [M+H]$^+$, 1122.4 [M+Na]$^+$.

Fmoc protecting group was removed by treatment with diethylamine (2 mL) in dichloromethane (6 mL). After 6 h at room temperature solvent was removed in vacuum, product was isolated by flash chromatography on silica gel in a step gradient 0-10% MeOH in dichloromethane. The relevant fractions were combined and concentrated. After evaporation from dichloromethane/hexane, 1:1, Compound 4 was obtained as a white foam: 133 mg (80%). $R_f$ 0.15 (10% MeOH/CH$_2$Cl$_2$). ES-MS m/z 878.6 [M+H]$^+$.

Example 6

Preparation of Compound 5

HPLC in 1 h. The mixture was concentrated to an oil and purified by SiO$_2$ chromatography (300×25 mm column) and eluting with 100% EtOAc. The product was isolated as a white foamy solid. Yield: 0.65 g (87%). ES-MS m/z 968.35 [M+H]$^+$, 991.34 [M+Na]$^+$; UV $\lambda_{max}$ 215, 265 nm.

The Fmoc-protected peptide (0.14 g, 0.14 mmol) in methylene chloride (5 mL) was treated with diethylamine (2 mL) and the contents stood at room temperature for 2 h. The reaction, complete by HPLC, was concentrated to an oil, taken up in 2 mL of DMSO and injected into a preparative-HPLC (C$_{12}$-RP column, 5μ, 100 Å, linear gradient of MeCN in water (containing 0.1% TFA) 10 to 100% in 40 min followed by 20 min at 100%, at a flow rate of 25 mL/min). Fractions containing the product were evaporated to afford a white powder for the trifluoroacetate salt. Yield: 0.126 g

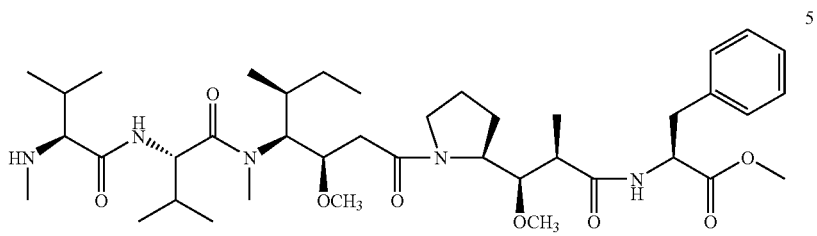

Fmoc-Meval-val-dil-OH (Example 2, 0.50 g, 0.78 mmol) and dap-phe-OMe.HCl (0.3 g, 0.78 mmol, prepared according to Pettit, G. R., et al. *Anti-Cancer Drug Design* 1998, 13, 243-277) were dissolved in CH$_2$Cl$_2$ (10 mL) followed by the addition of diisopropylethylamine (0.30 mL, 1.71 mmol, 2.2 eq.). DEPC (0.20 mL, 1.17, 1.5 eq.) was added and the contents stood over Ar. Reaction was complete according to (98%). $R_f$ 0.28 (100% EtOAc); ES-MS m/z 746.59 [M+H]$^+$, 768.51 [M+Na]$^+$; UV $\lambda_{max}$ 215 nm.

Example 7

Preparation of Compound 6

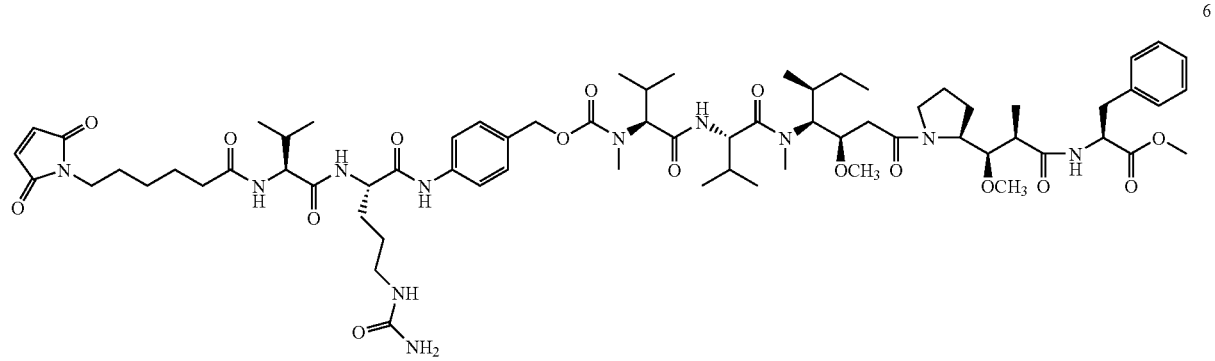

The trifluoroacetate salt of Compound 5 (0.11 g, 0.13 mmol), Compound AB (0.103 g, 0.14 mmol, 1.1 eq.) and HOBt (3.4 mg, 26 μmol, 0.2 eq.) were suspended in DMF/pyridine (2 mL/0.5 mL, respectively). Diisopropylethylamine (22.5 μL, 0.13 mmol, 1.0 eq.) was added and the yellow solution stirred while under argon. After 3 h, an additional 1.0 eq. of DIEA was added. 24 hours later, 0.5 eq. of the activated linker was included in the reaction mixture. After 40 h total, the reaction was complete. The contents were evaporated, taken up in DMSO and injected into a prep-HPLC ($C_{12}$-RP column, 5μ, 100 Å, linear gradient of MeCN in water (containing 0.1% TFA) 10 to 100% in 40 min followed by 20 min at 100%, at a flow rate of 50 mL/min). The desired fractions were evaporated to give the product as a yellow oil. Methylene chloride (ca. 2 mL) and excess ether were added to provide Compound 6 as a white precipitate that was filtered and dried. Yield: 90 mg (52%). ES-MS m/z 1344.32 $[M+H]^+$, 1366.29 $[M+Na]^+$; UV $\lambda_{max}$ 215, 248 nm.

Example 8
Preparation of Compound 7

Compound 4 (133 mg, 0.15 mmol, 1 eq.), Compound AB, (123 mg, 0.167 mmol, 1.1 eq.), and HOBt (4 mg, 0.2 eq.) were diluted with DMF (1.5 mL). After 2 min, pyridine (5 mL) was added and the reaction was monitored using RP-HPLC. The reaction was shown to be complete within 18 h. The reaction mixture was diluted with dichloromethane (20 mL), washed successively with 10% aq. citric acid (2×10 mL), water (10 mL), saturated aq. NaCl (10 mL). The organic layer was separated and concentrated. The resulting residue was re-suspended in dichloromethane and was purified via flash chromatography on silica gel in a step gradient 0-10% MeOH in dichloromethane. The relevant fractions were combined and concentrated to provide Compound 7 as a white foam: 46 mg (21%). $R_f$ 0.15 (10% MeOH/$CH_2Cl_2$). ES-MS m/z 1476.94 $[M+H]^+$.

Example 9
Preparation of MC-Val-Cit-PAB-MMAF t-butyl Ester 8

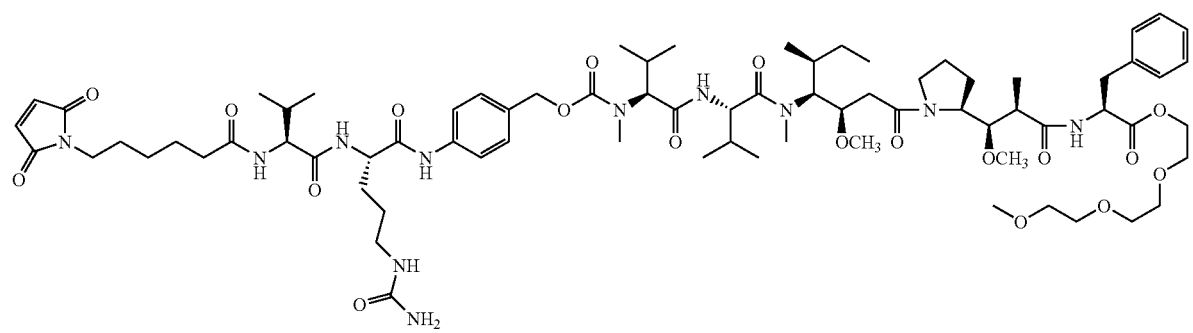

7

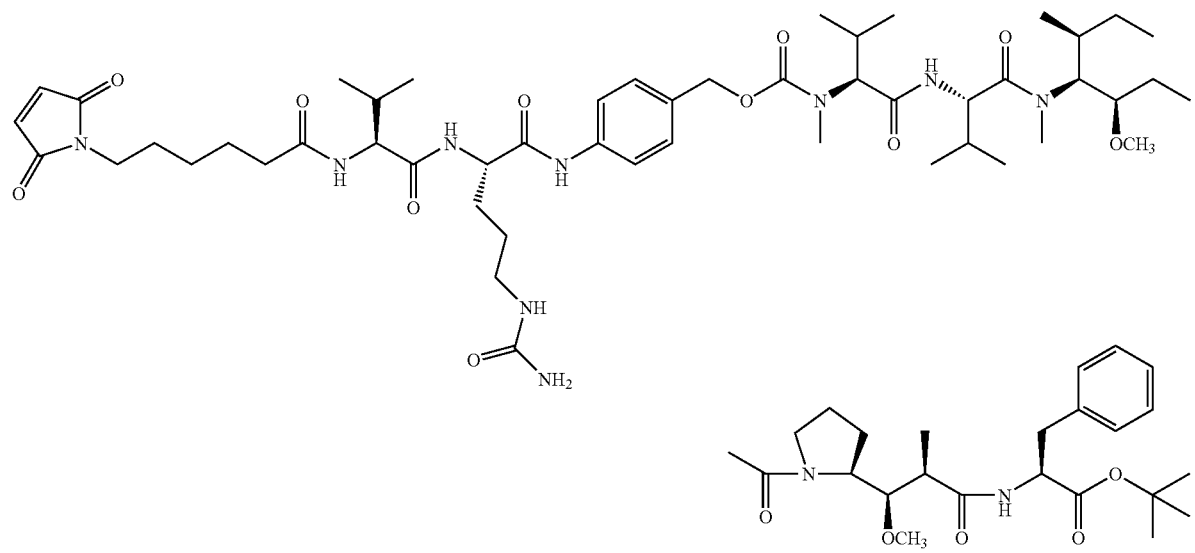

8

Compound 1 (83 mg, 0.11 mmol), Compound AB (85 mg, 0.12 mmol, 1.1 eq.), and HOBt (2.8 mg, 21 μmol, 0.2 eq.) were taken up in dry DMF (1.5 mL) and pyridine (0.3 mL) while under argon. After 30 h, the reaction was found to be essentially complete by HPLC. The mixture was evaporated, taken up in a minimal amount of DMSO and purified by prep-HPLC ($C_{12}$-RP column, 5μ, 100 Å, linear gradient of MeCN in water (containing 0.1% TFA) 10 to 100% in 40 min followed by 20 min at 100%, at a flow rate of 25 mL/min) to provide Compound 8 as a white solid. Yield: 103 mg (71%). ES-MS m/z 1387.06 [M+H]$^+$, 1409.04 [M+Na]$^+$; UV $\lambda_{max}$ 205, 248 nm.

Example 10

Preparation of MC-val-cit-PAB-MMAF 9

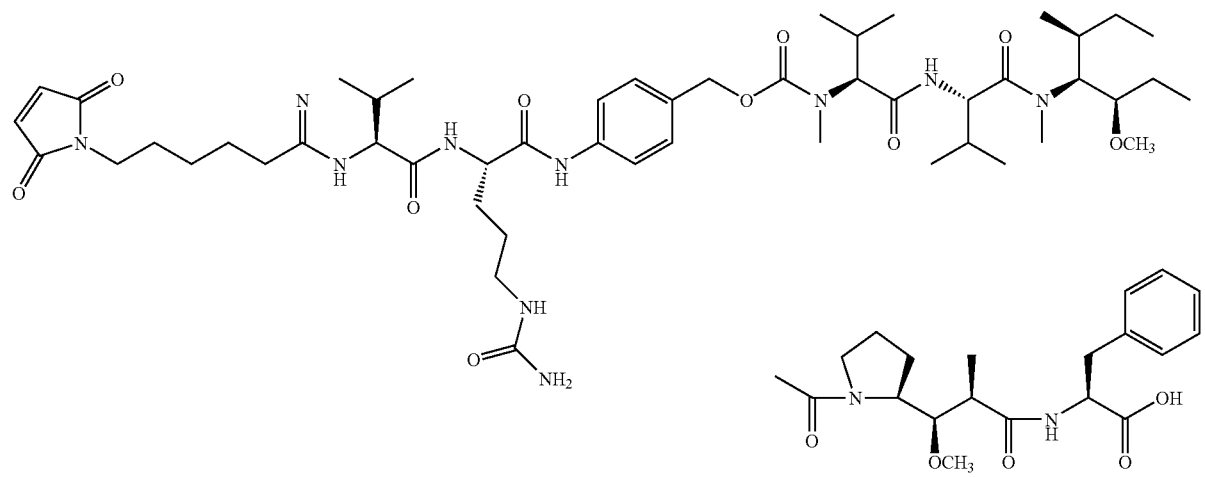

Compound 8 (45 mg, 32 μmol) was suspended in methylene chloride (6 mL) followed by the addition of TFA (3 mL). The resulting solution stood for 2 h. The reaction mixture was concentrated in vacuo and purified by prep-HPLC ($C_{12}$-RP column, 5μ, 100 Å, linear gradient of MeCN in water (containing 0.1% TFA) 10 to 100% in 40 min followed by 20 min at 100%, at a flow rate of 25 mL/min). The desired fractions were concentrated to provide maleimidocaproyl-valine-citrulline-p-hydroxymethylaminobenzene-MMAF (MC-val-cit-PAB-MMAF) 9 as an off-white solid. Yield: 11 mg (25%). ES-MS m/z 1330.29 [M+H]$^+$, 1352.24 [M+Na]$^+$; UV $\lambda_{max}$ 205, 248 nm.

Example 11

Preparation of MC-val-cit-PAB-MMAF tert-butyl Amide 10

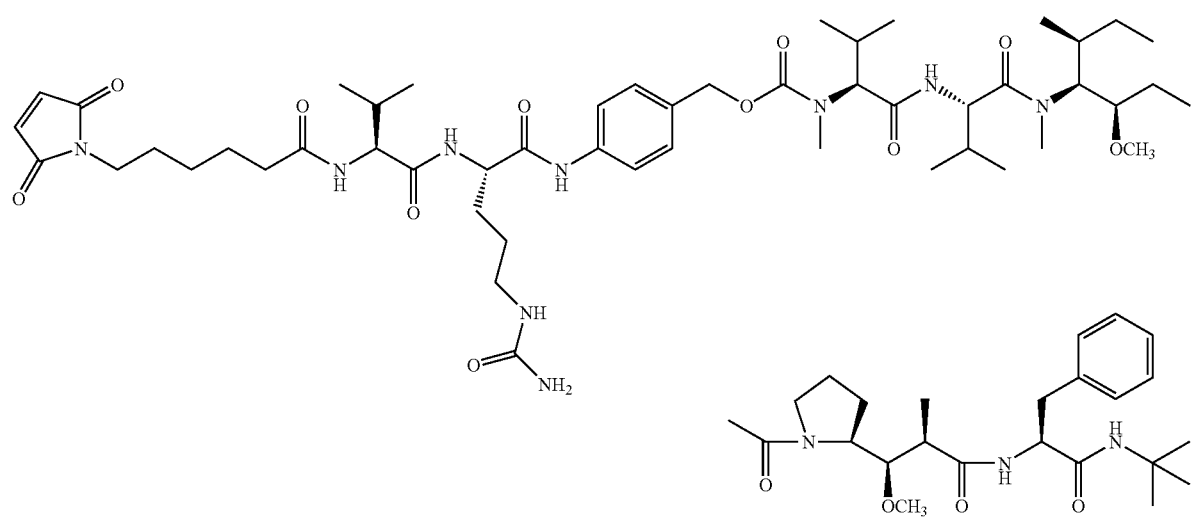

Compound 3 (217 mg, 0.276 mmol, 1.0 eq.), Compound AB (204 mg, 0.276 mmol, 1.0 eq.), and HOBt (11 mg, 0.0828 mmol, 0.3 eq.) were diluted with pyridine/DMF (6 mL). To this mixture was added DIEA (0.048 mL), and the mixture was stirred ca. 16 hr. Volatile organics were evaporated in vacuo. The crude residue was purified by Chromatotron® (radial thin-layer chromatography) with a step gradient (0-5-10% methanol in DCM) to provide MC-val-cit-PAB-MMAF tert-butyl amide 10. Yield: 172 mg (45%); ES-MS m/z 1386.33 [M+H]$^+$, 1408.36 [M+Na]$^+$; UV $\lambda_{max}$ 215, 248 nm.

Example 12

Preparation of AC10-MC-MMAE by Conjugation of AC10 and MC-MMAE

AC10, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, maleimidocaproyl-monomethyl auristatin E, i.e. MC-MMAE, dissolved in DMSO, is diluted in acetonitrile and water at known concentration, and added to the chilled reduced antibody AC10 in PBS. After about one hour, an excess of maleimide is added to quench the reaction and cap any unreacted antibody thiol groups. The reaction mixture is concentrated by centrifugal ultrafiltration and AC 10-MC-MMAE is purified and desalted by elution through G25 resin in PBS, filtered through 0.2 μm filters under sterile conditions, and frozen for storage.

Example 13

Preparation of AC10-MC-MMAF by Conjugation of AC10 and MC-MMAF

AC10-MC-MMAF was prepared by conjugation of AC10 and MC-MMAF following the procedure of Example 12.

Example 14

Preparation of AC10-MC-val-cit-PAB-MMAE by Conjugation of AC10 and MC-val-cit-PAB-MMAE AC10-MC-val-cit-PAB-MMAE was prepared by conjugation of AC10 and MC-val-cit-PAB-MMAE following the procedure of Example 12.

Example 15

Preparation of AC10-M-val-cit-PAB-MMAF by Conjugation of AC10 and MC-val-cit-PAB-MMAF (9)

AC10-MC-val-cit-PAB-MMAF was prepared by conjugation of AC10 and MC-val-cit-PAB-MMAF (9) following the procedure of Example 12.

Example 16

Determination of Cytotoxicity of Selected Compounds

Cytotoxic activity of MMAF and Compounds 1-5 was evaluated on the Lewis Y positive cell lines OVCAR-3, H3396 breast carcinoma, L2987 lung carcinoma and LS174t colon carcinoma Lewis Y positive cell lines can be assayed for cytotoxicity. To evaluate the cytotoxicity of Compounds 1-5, cells can be seeded at approximately 5-10,000 per well in 150 μl of culture medium then treated with graded doses of Compounds 1-5 in quadruplicates at the initiation of assay. Cytotoxicity assays are usually carried out for 96 hours after addition of test compounds. Fifty μl of resazurin dye may be added to each well during the last 4 to 6 hours of the incubation to assess viable cells at the end of culture. Dye reduction can be determined by fluorescence spectrometry using the excitation and emission wavelengths of 535 nm and 590 nm, respectively. For analysis, the extent of resazurin reduction by the treated cells can be compared to that of the untreated control cells.

For 1 h exposure assays cells can be pulsed with the drug for 1 h and then washed; the cytotoxic effect can be determined after 96 h of incubation.

Example 17

In Vitro Cytotoxicity Cata for Selected Compounds

Table 10 shows cytotoxic effect of cAC10 Conjugates of Compounds 7-10, assayed as described in General Procedure I on a CD30+ cell line Karpas 299. Data of two separate experiments are presented. The cAC10 conjugates of Compounds 7 and 9 were found to be slightly more active than cAC10-val-cit-MMAE.

TABLE 10

| Conjugate | IC$_{50}$ (ng/mL) |
|---|---|
| cAC10-val-cit-MMAE | 6 |
| cAC10-7 | 1.0 |
| cAC10-8 | 15 |
| cAC10-9 | 0.5 |
| cAC10-10 | 20 |

In other experiments, BR96-val-cit-MMAF was at least 250 fold more potent than the free MMAF.

General Procedure I—Cytotoxicity determination. To evaluate the cytotoxicity of Exemplary Conjugates 7-10, cells were seeded at approximately 5-10,000 per well in 150 μl of culture medium then treated with graded doses of Exemplary Conjugates 7-10 in quadruplicates at the initiation of assay. Cytotoxicity assays were carried out for 96 hours after addition of test compounds. Fifty μl of the resazurin dye was added to each well during the last 4 to 6 hours of the incubation to assess viable cells at the end of culture. Dye reduction was determined by fluorescence spectrometry using the excitation and emission wavelengths of 535 nm and 590 nm, respectively. For analysis, the extent of resazurin reduction by the treated cells was compared to that of the untreated control cells.

Example 18

In Vitro Cell Proliferation Assay

Efficacy of ADC can be Measured by a Cell Proliferation Assay Employing the following protocol (Promega Corp. Technical Bulletin TB288; Mendoza et al., (2002) Cancer Res. 62:5485-5488):

1. An aliquot of 100 μl of cell culture containing about 10$^4$ cells (SKBR-3, BT474, MCF7 or MDA-MB-468) in medium was deposited in each well of a 96-well, opaque-walled plate.

2. Control wells were prepared containing medium and without cells.

3. ADC was added to the experimental wells and incubated for 3-5 days.

4. The plates were equilibrated to room temperature for approximately 30 minutes.

5. A volume of CellTiter-Glo Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Example 19

Plasma Clearance in Rat

Plasma clearance pharmacokinetics of antibody drug conjugates and total antibody was studied in Sprague-Dawley rats (Charles River Laboratories, 250-275 gms each). Animals were dosed by bolus tail vein injection (IV Push). Approximately 300 µl whole blood was collected through jugular cannula, or by tail stick, into lithium/heparin anticoagulant vessels at each timepoint: 0 (predose), 10, and 30 minutes; 1, 2, 4, 8, 24 and 36 hours; and 2, 3, 4, 7, 14, 21, 28 days post dose. Total antibody was measured by ELISA-ECD/GxhuFc-HRP. Antibody drug conjugate was measured by ELISA-MMAE/MMAF/ECD-Bio/SA-HRP.

Example 20

Plasma Clearance in Monkey

Plasma clearance pharmacokinetics of antibody drug conjugates and total antibody can be studied in cynomolgus monkeys. FIG. 12 shows a two-stage plasma concentration clearance study after administration of H-MC-vc-MMAE to Cynomolgus monkeys at different doses: 0.5, 1.5, 2.5, and 3.0 mg/kg, administered at day 1 and day 21. Concentrations of total antibody and ADC were measured over time. (H=Trastuzumab).

Example 21

Tumor Volume In Vivo Efficacy in Transgenic Explant Mice

Animals suitable for transgenic experiments can be obtained from standard commercial sources such as Taconic (Germantown, N.Y.). Many strains are suitable, but FVB female mice are preferred because of their higher susceptibility to tumor formation. FVB males can be used for mating and vasectomized CD.1 studs can be used to stimulate pseudopregnancy. Vasectomized mice can be obtained from any commercial supplier. Founders can be bred with either FVB mice or with 129/BL6×FVB p53 heterozygous mice. The mice with heterozygosity at p53 allele can be used to potentially increase tumor formation. Some F1 tumors are of mixed strain. Founder tumors can be FVB only.

Animals having tumors (allograft propagated from Of5 mmtv transgenic mice) can be treated with a single or multiple dose by IV injection of ADC. Tumor volume can be assessed at various time points after injection.

Example 22

Synthesis of MC-MMAF Via t-butyl Ester

Figure 37:
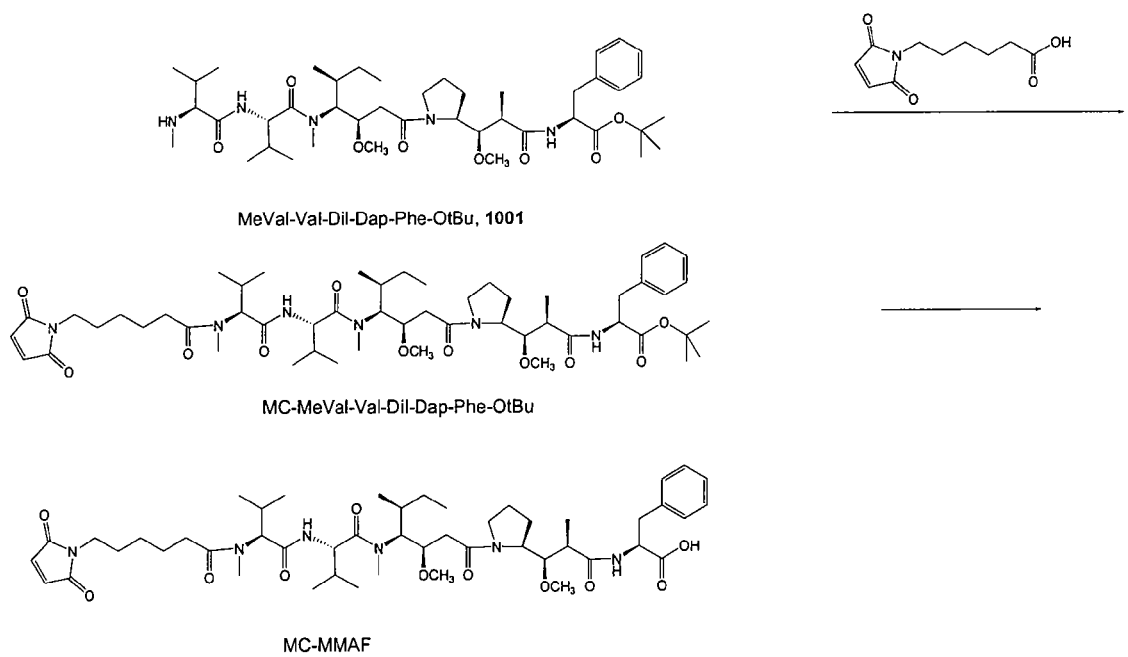
FIG. 37 shows the synthesis of MC-MMAF via t-butyl ester.

MeVal-Val-Dil-Dap-Phe-OtBu (compound 1, 128.6 mg, 0.163 mmol) was suspended in $CH_2Cl_2$ (0.500 mL). 6-Maleimidocaproic acid (68.9 mg, 0.326 mmol) and 1,3-diisopropylcarbodiimide (0.0505 mL, 0.326 mmol) were added followed by pyridine (0.500 mL). Reaction mixture was allowed to stir for 1.0 hr. HPLC analysis indicated complete consumption of starting compound 1. Volatile organics were evaporated under reduced pressure. Product was isolated via flash column chromatography, using a step gradient from 0 to 5% Methanol in $CH_2Cl_2$. A total of 96 mg of pure MC-MeVal-Val-Dil-Dap-Phe-OtBu (12) (60% yield) was recovered. ES-MS m/z 981.26 $[M+H]^+$; 1003.47 $[M+Na]^+$; 979.65 $[M-H]^-$ See FIG. 37.

MC-MeVal-Val-Dil-Dap-Phe-OtBu (Compound 12, 74 mg, 0.0754 mmol) was suspended in $CH_2Cl_2$ (2.0 mL) and TFA (1 mL) at room temperature. After 2.5 hr, HPLC analysis indicated complete consumption of starting material. Volatile organics were evaporated under reduced pressure, and the product was isolated via preparatory RP-HPLC, using a Phenomenex $C_{12}$ Synergi Max-RP 80 Å Column (250×21.20 mm). Eluent: linear gradient 10% to 90% MeCN/0.05% TFA (aq) over 30 minutes, then isocratic 90% MeCN/0.05% TFA (aq) for an additional 20 minutes. ES-MS m/z 925.33 $[M+H]^+$; 947.30 $[M+Na]^+$; 923.45 $[M-H]^-$.

Example 23a

Synthesis of MC-MMAF (11) Via Dimethoxybenzyl Ester

Figure 38:
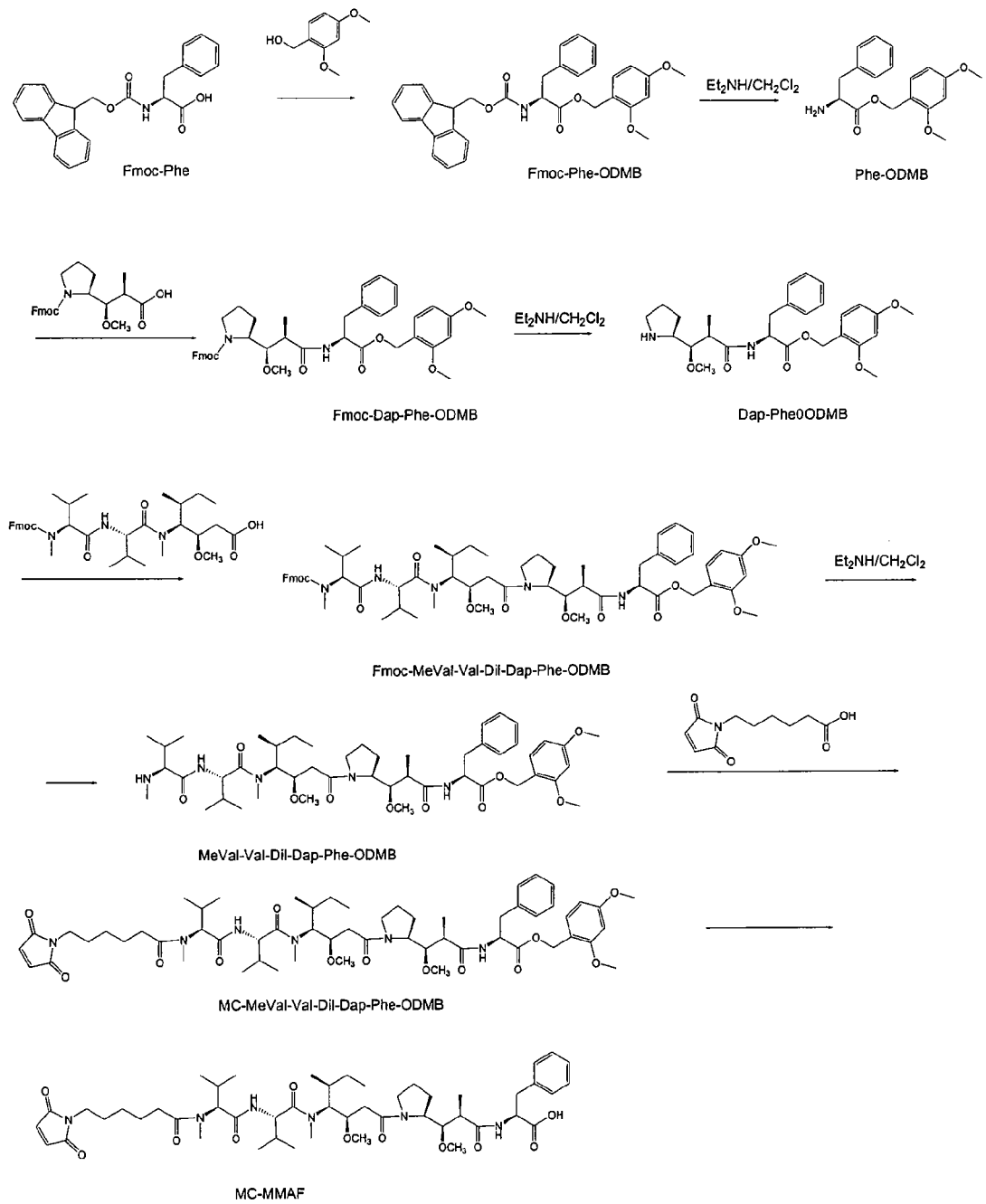
FIG. 38 shows the synthesis of MC-MMAF (11) via dimethoxybenzyl ester.

Preparation of Fmoc-L-Phenylalanine-2,4-dimethoxybenzyl ester (Fmoc-Phe-ODMB) See FIG. 38.

A 3-neck, 5-L round-bottom flask was charged with Fmoc-L-Phenylalanine (200 g, 516 mmol Bachem), 2,4-dimethoxybenzyl alcohol (95.4 g, 567 mmol, Aldrich), and $CH_2Cl_2$ (2.0 L). N,N-dimethylformamide t-butyl acetal (155 mL, 586 mmol, Fluka) was added to the resulting suspension over 20 min under $N_2$, which resulted in a clear solution. The reaction was then stirred at room temperature overnight, after which time TLC analysis (0.42, Heptane/EtOAc=2:1) indicated that the reaction was complete. The reaction mixture was concentrated under reduced pressure to give a light yellow oil, which was redissolved in $CH_2Cl_2$ (200 mL) and purified through a short plug of silica gel (25 cm×25 cm, $CH_2Cl_2$) to give a colorless foam (250 g). MeCN (1 L) was added into the resulting foam, which totally dissolved the batch. It was then concentrated to dryness and redissolved in MeCN (1 L) and the resulting suspension was stirred for 1 h, filtered and the filter cake was rinsed with MeCN (2×200 mL) to give Fmoc-L-phenylalanine-2,4-dimethoxybenzyl ester as a white solid (113.58 g, 41%, 95.5% AUC by HPLC analysis). Data: HPLC.

Preparation L-Phenylalanine-2,4-dimethoxybenzyl ester (Phe-ODMB)

A 500-mL round-bottom flask was charged with Fmoc-L-phenylalanine-2,4-dimethoxybenzyl ester (26.00 g, 48.3 mmol), $CH_2Cl_2$ (150 mL) and diethylamine (75 mL, Acros). Mixture was stirred at room temperature and the completion monitored by HPLC. After 4 h, the mixture was concentrated (bath temp <30° C.). The residue was resuspended in $CH_2Cl_2$ (200 mL) and concentrated. This was repeated once. To the residue was added MeOH (20 mL), which caused the formation of a gel. This residue was diluted with $CH_2Cl_2$ (200 mL), concentrated and the cloudy oil left under vacuum overnight. The residue was suspended in $CH_2Cl_2$ (100 mL), then toluene (120 mL) was added. The mixture was concentrated and the residue left under vacuum overnight.

Data: HPLC, $^1H$ NMR.

Preparation of Fmoc-Dolaproine (Fmoc-Dap)

Boc-Dolaproine (58.8 g, 0.205 mol) was suspended in 4 N HCl in 1,4-dioxane (256 mL, 1.02 mol, Aldrich). After stirring for 1.5 hours, TLC analysis indicated the reaction was complete (10% MeOH/$CH_2Cl_2$) and the mixture was concentrated to near-dryness. Additional 1,4-dioxane was charged (50 mL) and the mixture was concentrated to dryness and dried under vacuum overnight. The resulting white solid was dissolved in $H_2O$ (400 mL) and transferred to a 3-L, three-neck, round-bottom flask with a mechanical stirrer and temperature probe. N,N-diisopropylethylamine (214.3 mL, 1.23 mol, Acros) was added over one minute, causing an exotherm from 20.5 to 28.2° C. (internal). The mixture was cooled in an ice bath and 1,4-dioxane was added (400 mL). A solution of Fmoc-OSu (89.90 g, 0.267 mol, Advanced ChemTech) in 1,4-dioxane (400 mL) was added from an addition funnel over 15 minutes, maintaining the reaction temperature below 9° C. The mixture was allowed to warm to room temperature and stir for 19 hours, after which the mixture was concentrated by rotary evaporation to an aqueous slurry (390 g). The suspension was diluted with $H_2O$ (750 mL) and $Et_2O$ (750 mL), causing a copious white precipitate to form. The layers were separated, keeping the solids with the organic layer. The aqueous layer was acidified using conc. HCl (30 mL) and extracted with EtOAc (3×500 mL). The combined extracts were dried over $MgSO_4$, filtered and concentrated to give 59.25 g of a yellow oil A. The $Et_2O$ extract was extracted once with sat. $NaHCO_3$ (200 mL), keeping the solids with the aqueous layer. The aqueous suspension was acidified using conc. HCl (50 mL) and extracted with $Et_2O$ (50 mL) keeping the solids with the organic layer. The organic layer was filtered and concentrated to give 32.33 g of a yellow oil B. The two oils (A and B) were combined and purified by flash chromatography on silica gel eluting with $CH_2Cl_2$ (3.5 L), then 3% MeOH/$CH_2Cl_2$ (9 L) to give 68.23 g of Fmoc-dolaproine as a white foam (81%, 97.5% purity by HPLC (AUC)).

Preparation of Fmoc-Dap-Phe-ODMB

Crude Phe-ODMB (48.3 mmol) was suspended in anhydrous DMF (105 mL, Acros) for 5 minutes and Fmoc-Dap (19.80 g, 48.3 mmol) was added. The mixture was cooled in an ice bath and TBTU (17.08 g, 53.20 mmol, Matrix Innovations) was added. N,N-diisopropylethylamine (25.3 mL, 145.0 mmol, Acros) was added via syringe over 3 min. After 1 h, the ice bath was removed and the mixture was allowed to warm over 30 min. The mixture was poured into water (1 L) and extracted with ethyl acetate (300 mL). After separation, the aqueous layer was re-extracted with ethyl acetate (2×150 mL). The combined organic layers were washed with brine (150 mL), dried (MgSO4) and filtered (filter paper) to remove the insolubles (inorganics and some dibenzofulvene). After concentration, the residue (41 g) was adsorbed on silica (41 g) and purified by chromatography (22 cm×8 cm column; 65% Heptane/EtOAc (2.5 L); 33% Heptane/EtOAc (3.8 L), to give 29.4 g of product as a white foam (86%, 92% purity by HPLC).

Data: HPLC, $^1H$ NMR, TLC (1:1 EtOAc/Heptane $R_f$=0.33, red in vanillin stain).

Preparation of Dap-Phe-ODMB

A 1-L round bottom flask was charged with Fmoc-Dap-Phe-ODMB (27.66 g), $CH_2Cl_2$ (122 mL) and diethylamine (61 mL, Acros). The solution was stirred at room temperature and the completion monitored by HPLC. After 7 h, the mixture was concentrated (bath temp. <30° C.). The residue was suspended in $CH_2Cl_2$ (300 mL) and concentrated. This was repeated twice. To the residue was added MeOH (20 mL) and $CH_2Cl_2$ (300 mL), and the solution was concentrated. The residue was suspended in $CH_2Cl_2$ (100 mL) and toluene (400 mL), concentrated, and the residue left under vacuum overnight to give a cream-like residue.

Data: HPLC, $^1H$ NMR, MS.

Preparation of Fmoc-Meval-Val-Dil-Dap-Phe-ODMB

Crude Dap-Phe-ODMB (39.1 mmol) was suspended in anhydrous DMF (135 mL, Acros) for 5 minutes and Fmoc-MeVal-Val-Dil-OH (24.94 g, 39.1 mmol, see Example 2 for preparation) was added. The mixture was cooled in an ice bath and TBTU (13.81 g, 43.0 mmol, Matrix Innovations) was added. N,N-Diisopropylethylamine (20.5 mL, 117.3 mmol, Acros) was added via syringe over 2 minutes. After 1 hour, the ice bath was removed and the mixture was allowed to warm over 30 min. The mixture was poured into water (1.5 L) and diluted with ethyl acetate (480 mL). After standing for 15 minutes, the layers were separated and the aqueous layer was extracted with ethyl acetate (300 mL). The combined organic layers were washed with brine (200 mL), dried ($MgSO_4$) and filtered (filter paper) to remove insolubles (inorganics and some dibenzofulvene). After concentration, the residue (49 g) was scraped from the flask and adsorbed on silica (49 g) and purified by chromatography (15 cm×10 cm dia column; 2:1 EtOAc/Heptane (3 L), EtOAc (5 L); 250 mL fractions) to give 31.84 g of Fmoc-MeVal-Val-Dil-Dap-Phe-ODMB as a white foam (73%, 93% purity by HPLC (AUC)).

Data: HPLC, TLC (2:1 EtOAc/heptane, $R_f$=0.21, red in vanillin stain).

Preparation of Meval-Val-Dil-Dap-Phe-ODMB

A 1-L, round-bottom flask was charged with Fmoc-MeVal-Val-Dil-Dap-Phe-ODMB (28.50 g), $CH_2Cl_2$ (80 mL) and diethylamine (40 mL). Mixture was stirred at room temperature overnight and then was concentrated under reduced pressure. The residue was adsorbed on silica (30 g) and purified by flash chromatography (15 cm×8 cm dia column; 2% MeOH/DCM (2 L), 3% MeOH/DCM (1 L), 6% MeOH/DCM (4 L); 250 mL fractions) to give 15.88 g of MeVal-Val-Dil-Dap-Phe-ODMB as a white foam (69%, 96% purity by HPLC (AUC)).

Data: HPLC, TLC (6% MeOH/DCM, $R_f$=0.24, red in vanillin stain).

Preparation of Mc-Meval-Val-Dil-Dap-Phe-ODMB

A 50-mL, round-bottom flask was charged with MeVal-Val-Dil-Dap-Phe-ODMB (750 mg, 0.85 mmol), anhydrous DMF (4 mL), maleimidocaproic acid (180 mg, 0.85 mmol), and TBTU (300 mg, 0.93 mmol, Matrix Innovations) at room temperature. N,N-Diisopropylethylamine (450 µL, 2.57 mmol) was added via syringe. After 1.5 hours, the mixture was poured in water (50 mL) and diluted with ethyl acetate (30 mL). NaCl was added to improve the separation. After separation of the layers, the aqueous layer was extracted with ethyl acetate (25 mL). The combined organic layers were dried (MgSO4), filtered and concentrated. The resulting oil (1 g) was purified by flash chromatography [100 mL silica; 25% Heptane/EtOAc (100 mL), 10% Heptane/EtOAc (200 mL), EtOAc (1.5 L)] to give MC-MeVal-Val-Dil-Dap-Phe-ODMB (13) as a white foam (521 mg, 57%, 94% purity by HPLC (AUC)).

Data: 1H NMR, HPLC.

Preparation of MC-MeVal-Val-Dil-Dap-Phe-OH (MC-MMAF) (11)

A 50-mL, round-bottom flask was charged with MC-MeVal-Val-Dil-Dap-Phe-ODMB (Compound 13, 428 mg, 0.39 mmol) and dissolved in 2.5% TFA/CH$_2$Cl$_2$ (20 mL). The solution turned pink-purple over 2 min. The completion was monitored by HPLC and TLC (6% MeOH/DCM, KMnO$_4$ stain). After 40 min, three drops of water were added and the cloudy pink-purple mixture was concentrated to give 521 mg of a pink residue. Purification by chromatography (15% IPA/DCM) gave 270 mg of MC-MMAF (73%, 92% purity by HPLC) as a white solid.

Example 23b

Synthesis of Analog of mc-MMAF

Figure 39:
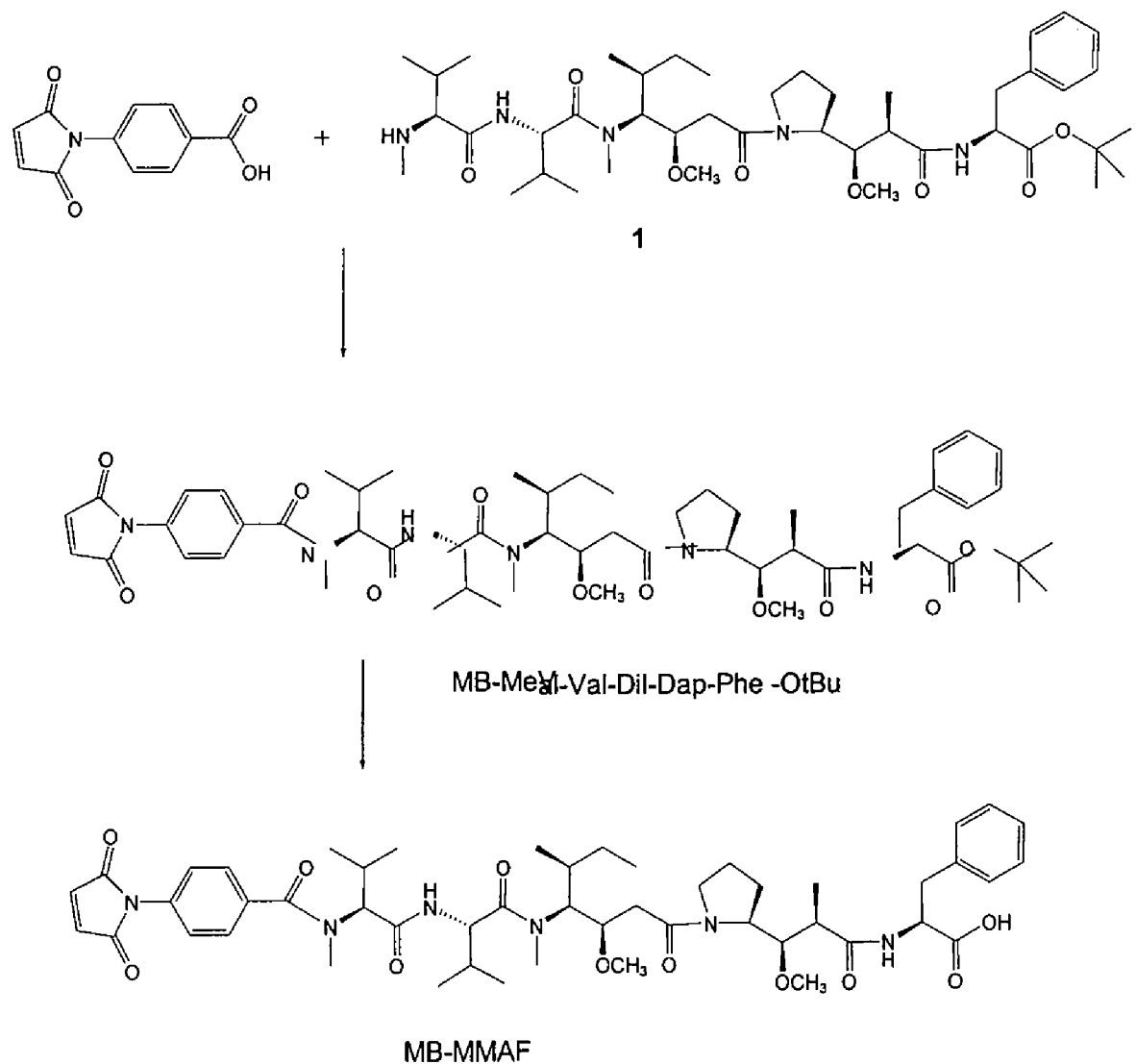
FIG. 39 shows the synthesis of analog of mc-MMAF.

MeVal-Val-Dil-Dap-Phe-OtBu (compound 1, 35 mg, 0.044 mmol) was suspended in DMF (0.250 mL). 4-(2,5-Dioxo-2,5-dihydro-pyrrol-1-yl)-benzoic acid (11 mg, 0.049 mmol) and HATU (17 mg, 0.044 mmol) were added followed by DIEA (0.031 mL, 0.17 mmol) See FIG. 39. This reaction mixture was allowed to stir for 2.0 hr. HPLC analysis indicated complete consumption of starting compound 1.

Product was isolated via preparatory RP-HPLC, using a Phenomenex C$_{12}$ Synergi Max-RP 80 Å Column (250×21.20 mm). Eluent: linear gradient 10% to 80% MeCN/0.05% TFA (aq) over 8 minutes, then isocratic 80% MeCN/0.05% TFA (aq) for an additional 12 minutes. A total of 20 mg of pure product (14) was isolated (0.02 mmol, 46% yield). ES-MS m/z 987.85 [M+H]$^+$; 1019.41 [M+Na]$^+$; 985.54 [M−H]$^−$.

MB-MeVal-Val-Dil-Dap-Phe-OtBu (Compound 14, 38 mg, 0.0385 mmol) was suspended in CH$_2$Cl$_2$ (1 mL) and TFA (1 mL). Mixture was stirred for 2.0 hr, and then volatile organics were evaporated under reduced pressure. Product was purified by preparatory RP-HPLC, using a Phenomenex C$_{12}$ Synergi Max-RP 80A Column (250×21.20 mm). Eluent: linear gradient 10% to 80% MeCN/0.05% TFA (aq) over 8 minutes, then isocratic 80% MeCN/0.05% TFA (aq) for an additional 12 minutes. A total of 14.4 mg of MB-MMAF product was isolated (0.015 mmol, 40% yield). ES-MS m/z 930.96 [M+H]$^+$ 952.98 [M+Na]$^+$; 929.37 [M−H]$^−$.

Example 23c

Preparation of MC-MeVal-Cit-PAB-MMAF (16)

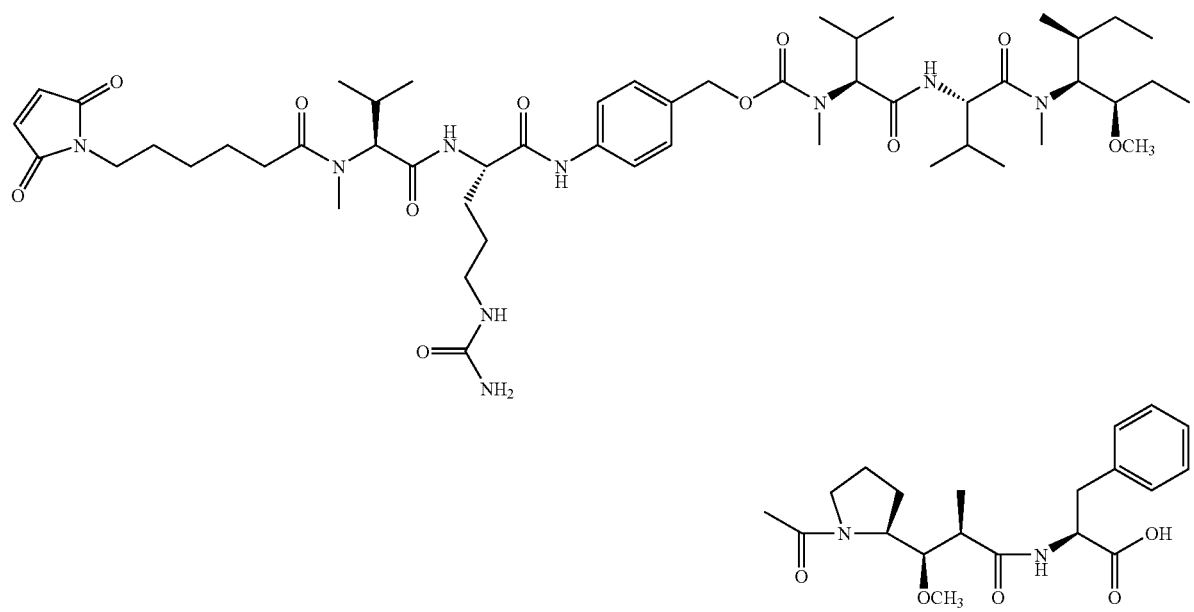

To a room temperature suspension of Fmoc-MeVal-OH (3.03 g, 8.57 mmol) and N,N'-disuccimidyl carbonate (3.29 g, 12.86 mmol) in CH$_2$Cl$_2$ (80 mL) was added DIEA (4.48 mL, 25.71 mmol). This reaction mixture was allowed to stir for 3.0 hr, and then poured into a separation funnel where the organic mixture was extracted with 0.1 M HCl (aq). The crude organic residue was concentrated under reduced pressure, and the product was isolated by flash column chromatography on silica gel using a 20-100% ethyl acetate/hexanes linear gradient. A total of 2.18 g of pure Fmoc-MeVal-OSu (4.80 mmoles, 56% yield) was recovered.

To a room temperature suspension of Fmoc-MeVal-OSu (2.18 g, 4.84 mmol) in DME (13 mL) and THF (6.5 mL) was added a solution of L-citrulline (0.85 g, 4.84 mmol) and NaHCO$_3$ (0.41 g, 4.84 mmol) in H$_2$O (13 mL). The suspension was allowed to stir at room temperature for 16 hr, then it was extracted into tert-BuOH/CHCl$_3$/H$_2$O, acidified to pH=2-3 with 1 M HCl. The organic phase was separated, dried and concentrated under reduced pressure. The residue was triturated with diethyl ether resulting in 2.01 g of Fmoc-MeVal-Cit-COOH which was used without further purification.

The crude Fmoc-MeVal-Cit-COOH was suspended in 2:1 CH$_2$Cl$_2$/MeOH (100 mL), and to it was added p-aminobenzyl alcohol (0.97 g, 7.9 mmol) and EEDQ (1.95 g, 7.9 mmol). This suspension was allowed to stir for 125 hr, then the volatile organics were removed under reduced pressure, and the residue was purified by flash column chromatography on silica gel using a 10% MeOH/CH$_2$Cl$_2$. Pure Fmoc-MeVal-Cit-PAB-OH (0.55 g, 0.896 mmol, 18.5% yield) was recovered. ES-MS m/z 616.48 [M+H]$^+$.

To a suspension of Fmoc-MeVal-Cit-PAB-OH (0.55 g, 0.896 mmol) in CH$_2$Cl$_2$ (40 mL) was added STRATO-SPHERES™ (piperizine-resin-bound) (>5 mmol/g, 150 mg). After being stirred at room temperature for 16 hr the mixture was filtered through celite (pre-washed with MeOH), and concentrated under reduced pressure. Residue was triturated with diethyl ether and hexanes. Resulting solid material, MeVal-Cit-PAB-OH, was suspended in CH$_2$Cl$_2$ (20 mL), and to it was added MC-OSu (0.28 g, 0.896 mmol), DIEA (0.17 mL, 0.99 mmol), and DMF (15 mL). This suspension was stirred for 16 hr, but HPLC analysis of the reaction mixture indicated incomplete reaction, so the suspension was concentrated under reduced pressure to a volume of 6 mL, then a 10% NaHCO$_3$ (aq) solution was added and the suspension stirred for an additional 16 hr. Solvent was removed under reduced pressure, and the residue was purified by flash column chromatography on silica gel using a 0-10% MeOH/CH$_2$Cl$_2$ gradient, resulting in 42 mg (0.072 mmol, 8% yield) of MC-MeVal-Cit-PAB-OH.

To a suspension of MC-MeVal-Cit-PAB-OH (2.37 g, 4.04 mmol) and bis(nitrophenyl)carbonate (2.59 g, 8.52 mmol) in CH$_2$Cl$_2$ (10 mL) was added DIEA (1.06 mL, 6.06 mmol). This suspension was stirred for 5.5 hr, concentrated under reduced pressure and purified by trituration with diethyl ether. MC-MeVal-Cit-PAB-OCO-pNP (147 mg, 0.196 mmol) was suspended in a 1:5 pyridine/DMF solution (3 mL), and to it was added HOBt (5 mg, 0.039 mmol), DIEA (0.17 mL, 0.978 mmol) and MMAF (compound 2, 150 mg, 0.205 mmol). This reaction mixture was stirred for 16 hr at room temperature, and then purified by preparatory RP-HPLC (×3), using a Phenomenex C$_{12}$ Synergi Max-RP 80 Å Column (250×21.20 mm). Eluent: linear gradient 10% to 90% MeCN/0.05% TFA (aq) over 30 minutes, then isocratic 90% MeCN/0.05% TFA (aq) for an additional 20 minutes. MC-MeVal-Cit-PAB-MMAF (16) was obtained as a yellowish solid (24.5 mg, 0.0182, 0.45% yield). ES-MS m/z 1344.95 [M+H]$^+$; 1366.94 [M+Na]$^+$.

Example 23c

Preparation of Succinimide Ester of suberyl-Val-Cit-PAB-MMAF (17)

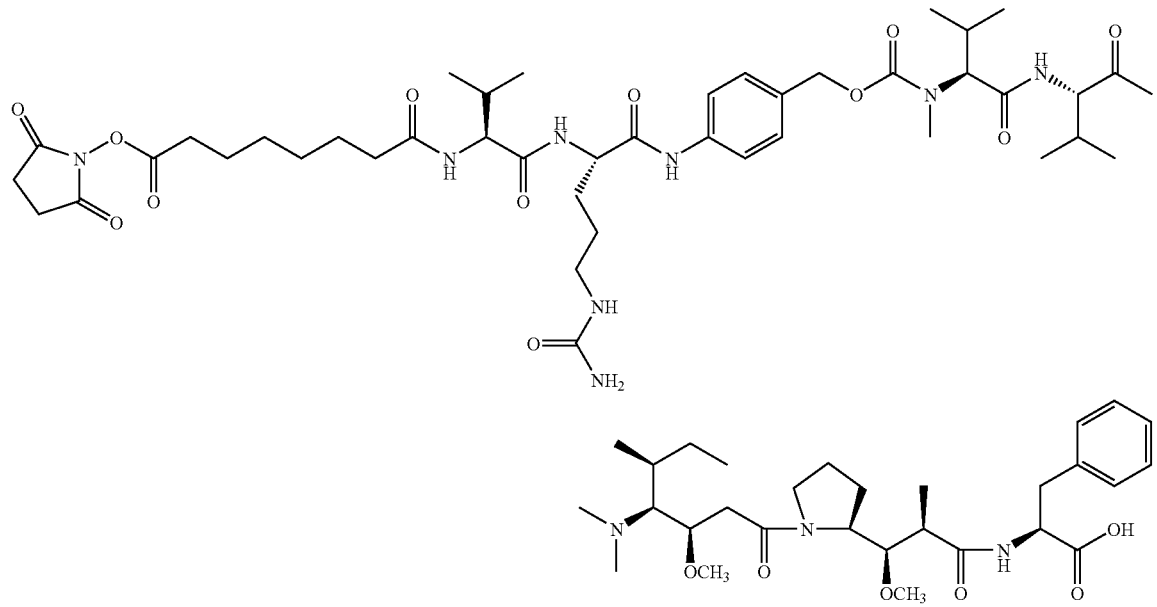

Compound 17

Compound 1 (300 mg, 0.38 mmol), Fmoc-Val-Cit-PAB-pNP (436 mg, 0.57 mmol, 1.5 eq.) were suspended in anhydrous pyridine, 5 mL. HOBt (10 mg, 0.076 mmol, 0.2 eq.) was added followed by DIEA (199 µl, 1.14 mmol, 3 eq.). Reaction mixture was sonicated for 10 min, and then stirred overnight at room temperature. Pyridine was removed under reduced pressure, residue was re-suspended in CH$_2$Cl$_2$. Mixture was separated by silica gel flash chromatography in a step gradient of MeOH, from 0 to 10%, in CH$_2$Cl$_2$. Product containing fractions were pulled, concentrated, dried in vacuum overnight to give 317 mg (59% yield) of Fmoc-Val-Cit-PAB-MMAF-OtBu. ES-MS m/z 1415.8 [M+H]$^+$.

Fmoc-Val-Cit-PAB-MMAF-OtBu (100 mg) was stirred in 20% TFA/CH$_2$Cl$_2$ (10 mL), for 2 hrs. Mixture was diluted with CH$_2$Cl$_2$ (50 mL). Organic layer was washed successively with water (2×30 mL) and brine (1×30 mL). Organic phase was concentrated, loaded onto pad of silica gel in 10% MeOH/CH$_2$Cl$_2$. Product was eluted with 30% MeOH/CH$_2$Cl$_2$. After drying in vacuum overnight, Fmoc-Val-Cit-PAB-MMAF was obtained as a white solid, 38 mg, 40% yield. ES-MS m/z 1357.7 [M−H]$^-$.

Fmoc-Val-Cit-PAB-MMAF, 67 mg, was suspended in CH$_2$Cl$_2$ (2 mL) diethylamine (2 mL) and DMF (2 mL). Mixture was stirred for 2 hrs at room temperature. Solvent was removed under reduced pressure. Residue was co-evaporated with pyridine (2 mL), then with toluene (2×5 mL), dried in vacuum. Val-Cit-PAB-MMAF was obtained as brownish oil, and used without further purification.

All Val-Cit-PAB-MMAF prepared from 67 mg of Fmoc-Val-Cit-PAB-MMAF, was suspended in pyridine (2 mL), and added to a solution of disuccinimidyl suberate (74 mg, 0.2 mmol, 4 eq.), in pyridine (1 mL). Reaction mixture was stirred at room temperature. After 3 hrs ether (20 mL) was added. Precipitate was collected, washed with additional amount of ether. Reddish solid was suspended in 30% MeOH/CH$_2$Cl$_2$, filtered trough a pad of silica gel with 30% MeOH/CH$_2$Cl$_2$ as an eluent. Compound 17 was obtained as white solid, 20 mg (29% yield). ES-MS m/z 1388.5 [M−H]$^−$ Example 24

In Vivo Efficacy of mcMMAF Antibody-Drug Conjugates

Efficacy of cAC10-mcMMAF in Karpas-299 ALCL xenografts: To evaluate the in vivo efficacy of cAC10-mcMMAF with an average of 4 drug moieties per antibody (cAC10-mcF4), Karpas-299 human ALCL cells were implanted subcutaneously into immunodeficient C.B-17 SCID mice (5×10$^6$ cells per mouse). Tumor volumes were calculated using the formula (0.5×L×W$^2$) where L and W are the longer and shorter of two bidirectional measurements. When the average tumor volume in the study animals reached approximately 100 mm$^3$ (range 48-162) the mice were divided into 3 groups (5 mice per group) and were either left untreated or were given a single intravenous injection through the tail vein of either 1 or 2 mg/kg cAC10-mcF4 (FIG. 1). The tumors in the untreated mice grew rapidly to an average volume of >1,000 mm$^3$ within 7 days of the start of therapy. In contrast, all of the cAC10-mcF4 treated tumor showed rapid regression with 3/5 in the 1 mg/kg group and 5/5 in the 2 mg/kg group obtaining complete tumor response. While the tumor in one of the complete responders in the 2 mg/kg group did recur approximately 4 weeks later, there were no detectable tumors in the remaining 4/5 responders in this group and in the 3 complete responders in the 1 mg/kg group at 10 weeks post therapy.

Figure 3A:
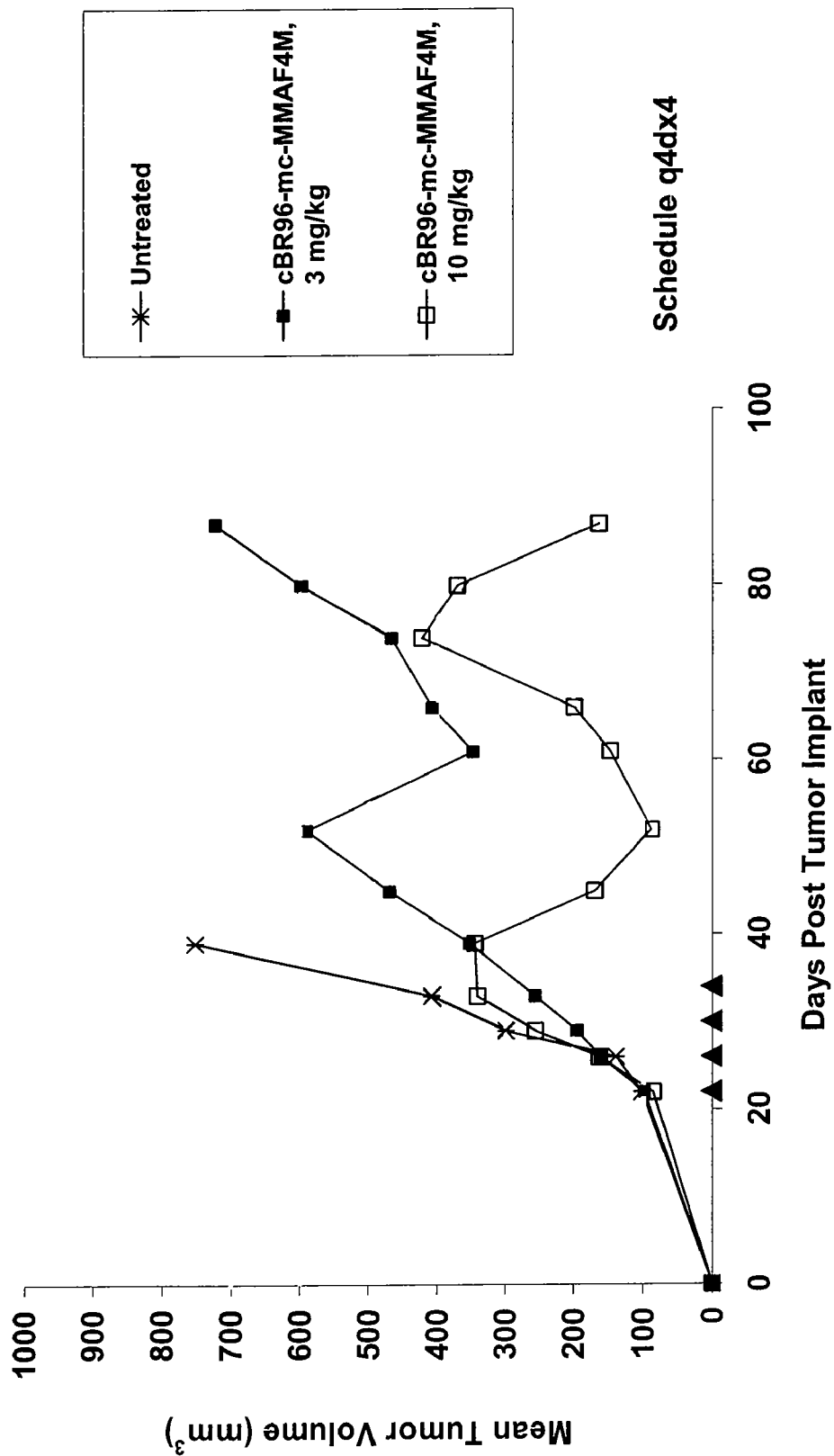

Efficacy of cBR96-mcMMAF in L2987 NSCLC xenografts: cBR96 is a chimeric antibody that recognizes the Le$^Y$ antigen. To evaluate the in vivo efficacy of cBR96-mcMMAF with 4 drugs per antibody (cBR96-mcF4) L2987 non-small cell lung cancer (NSCLC) tumor fragments were implanted into athymic nude mice. When the tumors averaged approximately 100 mm$^3$ the mice were divided into 3 groups: untreated and 2 therapy groups. For therapy, as shown in FIG. 3a, mice were administered cBR96-mcF4 at either 3 or 10 mg/kg/injection every 4 days for a total of 4 injections (q4dx4). As shown in FIG. 3b, mice were administered cBR96-mcF4 or a non-binding control conjugate, cAC10-mcF4, at 10 mg/kg/injection every 4 days for a total of 4 injections (q4dx4). As shown in FIGS. 3a and 3b, BR96-mcF4 produced pronounced tumor growth delay compared to the controls.

FIG. 2 shows an in vivo, single dose, efficacy assay of cAC10-mcMMAF in subcutaneous L540CY. For this study there were 4 mice in the untreated group and 10 in each of the treatment groups.

Example 25

In Vitro Efficacy of MC-MMAF Antibody-Drug Conjugates

Activity of cAC10-antibody-drug conjugates against CD30$^+$ cell lines. FIGS. 4a and 16b show dose-response curves from a representative experiment where cultures of Karpas 299 (anaplastic large cell lymphoma) and L428 (Hodgkin's Lymphoma) were incubated with serially diluted cAC10-mcMMAF (FIG. 4a) or cAC10-vcMMAF (FIG. 4b) for 96 hours. The cultures were labeled for 4 hours with 50 µM resazurin [7-hydroxy-3H-phenoxazin-3-one 10-oxide] and the fluorescence measured. The data were reduced in GraphPad Prism version 4.00 using the 4-parameter dose-response curve fit procedure. IC$_{50}$ values are defined as the concentration where growth is reduced 50% compared with untreated control cultures. Each concentration was tested in quadruplicate.

Figure 5A:
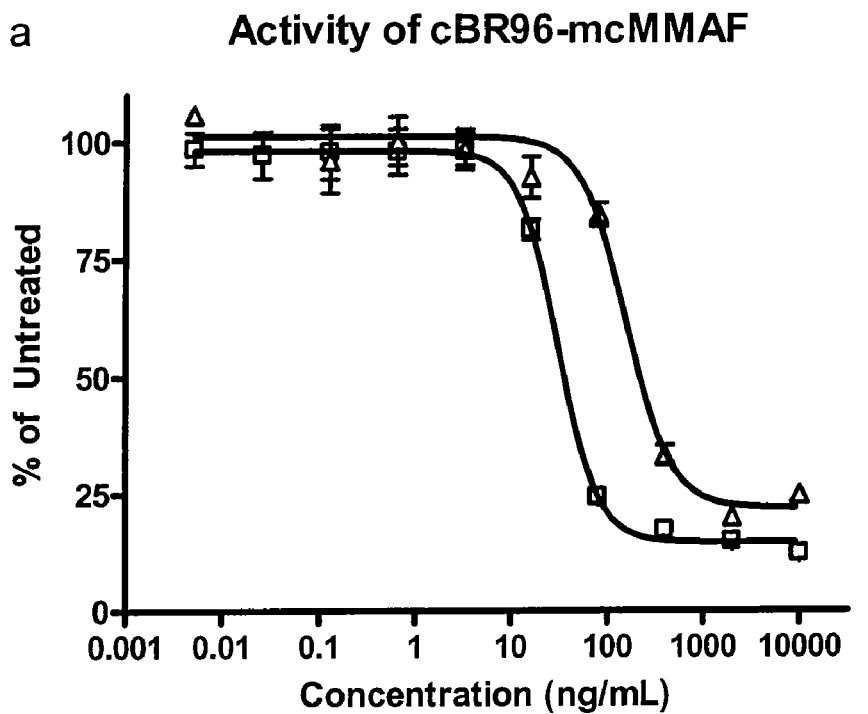
FIGS. 5a and 5b show in vitro activity of cBR96-antibody-drug conjugates against $Le^{y+}$ cell lines.
Figure 5B:
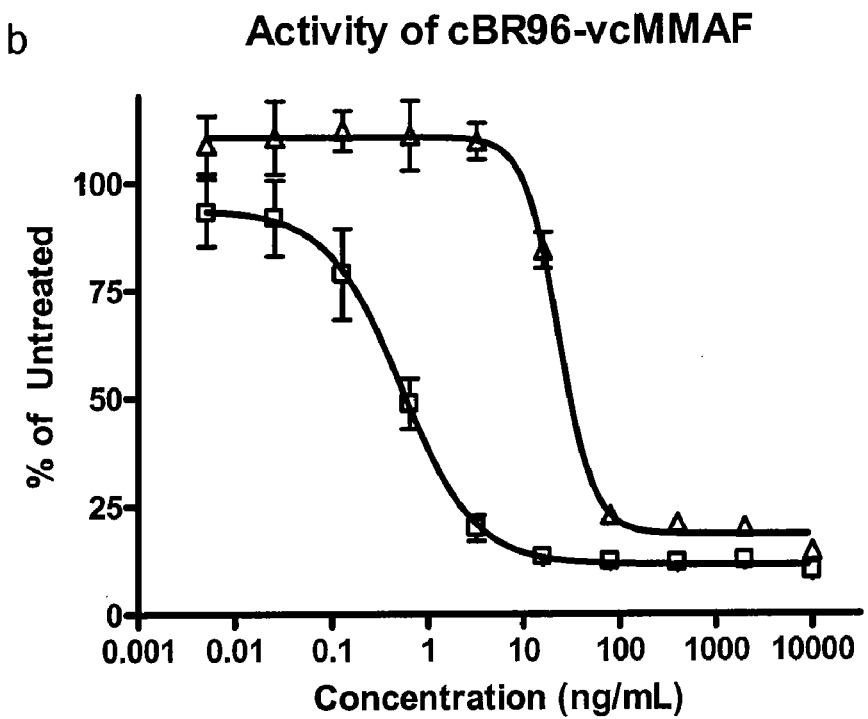

Activity of cBR96-antibody-drug conjugates against Le$^{y+}$ cell lines. FIGS. 5a and 5b show dose-response curves from a representative experiment where cultures of H3396 (breast carcinoma) and L2987 (non small cell lung carcinoma) were incubated with serially diluted cBR96-mcMMAF (FIG. 5a) or -vcMMAF (FIG. 5b) for 96 hours. The cultures were labeled for 4 hours with 50 µM resazurin and the fluorescence measured. The data were reduced in GraphPad Prism version 4.00 using the 4-parameter dose-response curve fit procedure. IC$_{50}$ values are defined as the concentration where growth is reduced 50% compared with untreated control cultures. Each concentration is tested in quadruplicate.

Activity of c1F6-antibody-drug conjugates against CD 70$^+$ renal cell carcinoma cell lines. FIGS. 6a and 6b show dose-response curves from a representative experiment where cultures of Caki-1 and 786-0 cells were incubated with serially diluted c1F6-mcMMAF (FIG. 6a) or -vcMMAF (FIG. 6b) for 96 hours. The cultures were labeled for 4 hours with 50 µM resazurin and the fluorescence measured. The data were reduced in GraphPad Prism version 4.00 using the 4-parameter dose-response curve fit procedure. IC$_{50}$ values are defined as the concentration where growth is reduced 50% compared with untreated control cultures. Each concentration is tested in quadruplicate.

Example 26

Purification of Trastuzumab

One vial containing 440 mg HERCEPTIN® (huMAb4D5-8, rhuMAb HER2, U.S. Pat. No. 5,821,337) antibody) was dissolved in 50 mL MES buffer (25 mM MES, 50 mM NaCl, pH 5.6) and loaded on a cation exchange column (Sepharose S, 15 cm×1.7 cm) that had been equilibrated in the same buffer. The column was then washed with the same buffer (5 column volumes). Trastuzumab was eluted by raising the NaCl concentration of the buffer to 200 mM. Fractions containing the antibody were pooled, diluted to 10 mg/mL, and dialyzed into a buffer containing 50 mm potassium phosphate, 50 mM NaCl, 2 mM EDTA, pH 6.5.

Example 27

Preparation of Trastuzumab-MC-MMAE by Conjugation of Trastuzumab and MC-MMAE

Trastuzumab, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, maleimidocaproyl-monomethyl auristatin E (MMAE), i.e. MC-MMAE, dissolved in DMSO, is diluted in acetonitrile and water at known concentration, and added to the chilled reduced antibody trastuzumab in PBS. After about one hour, an excess of maleimide is added to quench the reaction and cap any unreacted antibody thiol groups. The reaction mixture is concentrated by centrifugal ultrafiltration and trastuzumab-MC-MMAE is purified and desalted by elution through G25 resin in PBS, filtered through 0.2 μm filters under sterile conditions, and frozen for storage.

Example 28

Preparation of Trastuzumab-MC-MMAF by Conjugation of Trastuzumab and MC-MMAF

Trastuzumab-MC-MMAF was prepared by conjugation of trastuzumab and MC-MMAF following the procedure of Example 27.

Example 29

Preparation of Trastuzumab-MC-val-cit-PAB-MMAE by Conjugation of Trastuzumab and MC-val-cit-PAB-MMAE Trastuzumab-MC-val-cit-PAB-MMAE was prepared by conjugation of trastuzumab and MC-val-cit-PAB-MMAE following the procedure of Example 27.

Example 30

Preparation of Trastuzumab-MC-val-cit-PAB-MMAF by Conjugation of Trastuzumab and MC-val-cit-PAB-MMAF 9

Trastuzumab-MC-val-cit-PAB-MMAF was prepared by conjugation of trastuzumab and MC-val-cit-PAB-MMAF 9 following the procedure of Example 27.

Example 31

Rat Toxicity

The acute toxicity profile of free drugs and ADC was evaluated in adolescent Sprague-Dawley rats (75-125 gms each, Charles River Laboratories (Hollister, Calif.). Animals were injected on day 1, complete chemistry and hematology profiles were obtained at baseline, day 3 and day 5 and a complete necropsy was performed on day 5. Liver enzyme measurements was done on all animals and routine histology as performed on three random animals for each group for the following tissues: sternum, liver, kidney, thymus, spleen, large and small intestine. The experimental groups were as follows:

| Group | Administered | mg/kg | μg MMAF/$m^2$ | MMAF/MAb | N/Sex |
|---|---|---|---|---|---|
| 1 | Vehicle | 0 | 0 | 0 | 2/F |
| 2 | trastuzumab-MC-val-cit-MMAF | 9.94 | 840 | 4.2 | 6/F |
| 3 | trastuzumab-MC-val-cit-MMAF | 24.90 | 2105 | 4.2 | 6/F |
| 4 | trastuzumab-MC(Me)-val-cit-PAB-MMAF | 10.69 | 840 | 3.9 | 6/F |
| 5 | trastuzumab-MC(Me)-val-cit-PAB-MMAF | 26.78 | 2105 | 3.9 | 6/F |
| 6 | trastuzumab-MC-MMAF | 10.17 | 840 | 4.1 | 6/F |
| 7 | trastuzumab-MC-MMAF | 25.50 | 2105 | 4.1 | 6/F |
| 8 | trastuzumab-MC-val-cit-PAB-MMAF | 21.85 | 2105 | 4.8 | 6/F |

For trastuzumab-MC-val-cit-MMAF, trastuzumab-MC(Me)-val-cit-PAB-MMAF, trastuzumab-MC-MMAF and trastuzumab-MC-val-cit-PAB-MMAF, the μg MMAF/$m^2$ was calculated using 731.5 as the MW of MMAF and 145167 as the MW of Herceptin.

The body surface area was calculated as follows: [{(body weight in grams to 0.667 power)×11.8}/10000]. (Guidance for Industry and Reviewers, 2002).

The dose solutions were administered by a single intravenous bolus tail-vein injection on Study Day 1 at a dose volume of 10 mL/kg. Body weights of the animals were measured pre-dose on Study Day 1 and daily thereafter. Whole blood was collected into EDTA containing tubes for hematology analysis. Whole blood was collected into serum separator tubes for clinical chemistry analysis. Blood samples were collected pre-dose on Study Day 4, Study Day 3 and Study Day 5. Whole blood was also collected into sodium heparin containing tubes at necropsy and the plasma was frozen at −70° C. for possible later analysis. The following tissues were collected and placed in neutral buffered formalin at necropsy: liver, kidneys, heart, thymus, spleen, brain, sternum and sections of the GI tract, including stomach, large and small intestine. Sternum, small intestine, large intestine, liver, thymus, spleen and kidney were examined.

Liver associated serum enzyme levels at each timepoint were compared to a range (5th and 95th percentile) from normal female Sprague-Dawley rats. White blood cell and platelet counts at each timepoint were compared to a range (5th and 95th percentile) from normal female Sprague-Dawley rats.

High dose study in normal female Sprague-Dawley rats:

| | |
|---|---|
| Group 1: | Vehicle |
| Group 2: | trastuzumab-MC-MMAF, 52.24 mg/kg, 4210 μg/$m^2$ |
| Group 3: | trastuzumab-MC-MMAF, 68.25 mg/kg, 5500 μg/$m^2$ |
| Group 4: | trastuzumab-MC-MMAF, 86.00 mg/kg, 6930 μg/$m^2$ |

Tissues from 11 animals were submitted for routine histology. These animals had been part of an acute dose-ranging toxicity study using a trastuzumab-MC-MMAF immunoconjugate. Animals were followed for 12 days following dosing.

Example 32

Cynomolgus Monkey Toxicity/Safety

Three groups of four (2 male, 2 female) naive *Macaca fascicularis* (cynomolgus monkey) were studied for trastuzumab-MC-vc-PAB-MMAE and trastuzumab-MC-vc-PAB-MMAF. Intravenous administration was conducted at days 1 and 22 of the studies.

| Sample | Group | Dose |
|---|---|---|
| Vehicle | 1 1M/1F | day 1 day 22 |
| H-MC-vc-PAB-MMAE | 2 2M/2F | 180 µg/m² (0.5 mg/kg) at day 1 1100 µg/m² (3.0 mg/kg) at day 22 |
| H-MC-vc-PAB-MMAE | 3 2M/2F | 550 µg/m² (1.5 mg/kg) at day 8 550 µg/m² (1.5 mg/kg) at day 29 |
| H-MC-vc-PAB-MMAE | 4 2M/2F | 880 µg/m² (2.5 mg/kg) at day 15 880 µg/m² (2.5 mg/kg) at day 36 |

| Sample | Group | Dose |
|---|---|---|
| Vehicle | 1 1M/1F | day 1 day 22 |
| H-MC-vc-PAB-MMAF | 2 2M/2F | 180 µg/m² (0.5 mg/kg) at day 1 1100 µg/m² (3.0 mg/kg) at day 22 |
| H-MC-vc-PAB-MMAF | 3 2M/2F | 550 µg/m² (1.5 mg/kg) at day 1 550 µg/m² (1.5 mg/kg) at day 22 |
| H-MC-vc-PAB-MMAF | 4 2M/2F | 880 µg/m² (2.5 mg/kg) at day 1 880 µg/m² (2.5 mg/kg) at day 22 |

H = trastuzumab

Dosing is expressed in surface area of an animal so as to be relevant to other species, i.e. dosage at µg/m² is independent of species and thus comparable between species. Formulations of ADC contained PBS, 5.4 mM sodium phosphate, 4.2 mM potassium phosphate, 140 mM sodium chloride, pH 6.5.

Blood was collected for hematology analysis predose, and at 5 min., 6 hr, 10 hr, and 1, 3, 5, 7, 14, 21 days after each dose. Erythrocyte (RBC) and platelet (PLT) counts were measured by the light scattering method. Leukocyte (WBC) count was measured by the peroxidase/basophil method. Reticulocyte count was measured by the light scattering method with cationic dye. Cell counts were measured on an Advia 120 apparatus. ALT (alanine aminotransferase) and AST (aspartate aminotransferase) were measured in U/L by UV/NADH; IFCC methodology on an Olympus AU400 apparatus, and using Total Ab ELISA-ECD/GxhuFc-HRP. Conj. Ab ELISA-MMAE/MMAF//ECD-Bio/SA-HRP tests.

Example 33

Production, Characterization and Humanization of Anti-ErbB2 Monoclonal Antibody 4D5

The murine monoclonal antibody 4D5 which specifically binds the extracellular domain of ErbB2 was produced as described in Fendly et al. (1990) Cancer Research 50:1550-1558. Briefly, NIH 3T3/HER2-3$_{400}$ cells (expressing approximately 1×10⁵ ErbB2 molecules/cell) produced as described in Hudziak et al *Proc. Natl. Acad. Sci. (USA)* 84:7158-7163 (1987) were harvested with phosphate buffered saline (PBS) containing 25 mM EDTA and used to immunize BALB/c mice. The mice were given injections i.p. of 10⁷ cells in 0.5 ml PBS on weeks 0, 2, 5 and 7. The mice with antisera that immunoprecipitated ³²P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation.

Epitope Mapping and Characterization

The ErbB2 epitope bound by monoclonal antibody 4D5 was determined by competitive binding analysis (Fendly et al. *Cancer Research* 50:1550-1558 (1990)). Cross-blocking studies were done by direct fluorescence on intact cells using the PANDEX™ Screen Machine to quantitate fluorescence. The monoclonal antibody was conjugated with fluorescein isothiocyanate (FITC), using established procedures (Wofsy et al. *Selected Methods in Cellular Immunology*, p. 287, Mishel and Schiigi (eds.) San Francisco: W.J. Freeman Co. (1980)). Confluent monolayers of NIH 3T3/HER2-3$_{400}$ cells were trypsinized, washed once, and resuspended at 1.75×10⁶ cell/ml in cold PBS containing 0.5% bovine serum albumin (BSA) and 0.1% NaN$_3$. A final concentration of 1% latex particles (IDC, Portland, Oreg.) was added to reduce clogging of the PANDEX™ plate membranes. Cells in suspension, 20 µl, and 20 µl of purified monoclonal antibodies (100 µg/ml to 0.1 µg/ml) were added to the PANDEX™ plate wells and incubated on ice for 30 minutes. A predetermined dilution of the FITC-labeled monoclonal antibody in 20 µl was added to each well, incubated for 30 minutes, washed, and the fluorescence was quantitated by the PANDEX™. Monoclonal antibodies were considered to share an epitope if each blocked binding of the other by 50% or greater in comparison to an irrelevant monoclonal antibody control. In this experiment, monoclonal antibody 4D5 was assigned epitope I (amino acid residues from about 529 to about 625, inclusive within the ErbB2 extracellular domain.

The growth inhibitory characteristics of monoclonal antibody 4D5 were evaluated using the breast tumor cell line, SK-BR-3 (see Hudziak et al. (1989) *Molec. Cell. Biol.* 9(3): 1165-1172). Briefly, SK-BR-3 cells were detached by using 0.25% (vol/vol) trypsin and suspended in complete medium at a density of 4×10⁵ cells per ml. Aliquots of 100 µl (4×10⁴ cells) were plated into 96-well microdilution plates, the cells were allowed to adhere, and 100 µl of media alone or media containing monoclonal antibody (final concentration 5 µg/ml) was then added. After 72 hours, plates were washed twice with PBS (pH 7.5), stained with crystal violet (0.5% in methanol), and analyzed for relative cell proliferation as described in Sugarman et al. (1985) *Science* 230:943-945. Monoclonal antibody 4D5 inhibited SK-BR-3 relative cell proliferation by about 56%.

Monoclonal antibody 4D5 was also evaluated for its ability to inhibit HRG-stimulated tyrosine phosphorylation of proteins in the $M_r$, 180,000 range from whole-cell lysates of MCF7 cells (Lewis et al. (1996) *Cancer Research* 56:1457-1465). MCF7 cells are reported to express all known ErbB receptors, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis. However, these cells are ideal for HRG tyrosine phosphorylation assays because under the assay conditions used, in the absence of exogenously added HRG, they exhibit low to undetectable levels of tyrosine phosphorylation proteins in the $M_r$, 180,000 range.

MCF7 cells were plated in 24-well plates and monoclonal antibodies to ErbB2 were added to each well and incubated for 30 minutes at room temperature; then rHRGβ1$_{177-244}$ was added to each well to a final concentration of 0.2 nM, and the incubation was continued for 8 minutes. Media was carefully aspirated from each well, and reactions were stopped by the addition of 100 μl of SDS sample buffer (5% SDS, 25 mM DTT, and 25 mM Tris-HCl, pH 6.8). Each sample (25 μl) was electrophoresed on a 4-12% gradient gel (Novex) and then electrophoretically transferred to polyvinylidene difluoride membrane. Antiphosphotyrosine (4G10, from UBI, used at 1 μg/ml) immunoblots were developed, and the intensity of the predominant reactive band at $M_r$ 80,000 was quantified by reflectance densitometry, as described previously (Holmes et al. (1992) *Science* 256:1205-1210; Sliwkowski et al. *J. Biol. Chem.* 269:14661-14665 (1994)).

Monoclonal antibody 4D5 significantly inhibited the generation of a HRG-induced tyrosine phosphorylation signal at $M_r$ 180,000. In the absence of HRG, but was unable to stimulate tyrosine phosphorylation of proteins in the $M_r$ 180,000 range. Also, this antibody does not cross-react with EGFR (Fendly et al. *Cancer Research* 50:1550-1558 (1990)), ErbB3, or ErbB4. Monoclonal antibody 4D5 was able to block HRG stimulation of tyrosine phosphorylation by 50%.

The growth inhibitory effect of monoclonal antibody 4D5 on MDA-MB-175 and SK-BR-3 cells in the presence or absence of exogenous rHRGβ1 was assessed (Schaefer et al. *Oncogene* 15:1385-1394 (1997)). ErbB2 levels in MDA-MB-175 cells are 4-6 times higher than the level found in normal breast epithelial cells and the ErbB2-ErbB4 receptor is constitutively tyrosine phosphorylated in MDA-MB-175 cells. Monoclonal antibody 4D5 was able to inhibit cell proliferation of MDA-MB-175 cells, both in the presence and absence of exogenous HRG. Inhibition of cell proliferation by 4D5 is dependent on the ErbB2 expression level (Lewis et al. *Cancer Immunol. Immunother.* 37:255-263 (1993)). A maximum inhibition of 66% in SK-BR-3 cells could be detected. However this effect could be overcome by exogenous HRG.

The murine monoclonal antibody 4D5 was humanized, using a "gene conversion mutagenesis" strategy, as described in U.S. Pat. No. 5,821,337, the entire disclosure of which is hereby expressly incorporated by reference. The humanized monoclonal antibody 4D5 used in the following experiments is designated huMAb4D5-8. This antibody is of IgG1 isotype.

REFERENCES CITED

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety and for all purposes to the same extent as if each individual publication or patent or patent application was specifically and individually indicated to be incorporated by reference in its entirety for all purposes.

What is claimed is:

1. A method for treating cancer comprising administering to a patient in need thereof an effective amount of an antibody-drug conjugate compound having formula Ic:

Ab–(A$_a$-W$_w$-Y$_y$-D)$_p$     Ic or a pharmaceutically acceptable salt thereof, wherein:
Ab is an antibody which binds to one or more tumor-associated antigens (1) to (35):

(1) BMPR1B (bone morphogenetic protein receptor-type IB);
(2) E16 (LAT1, SLC7A5);
(3) STEAP1 (six transmembrane epithelial antigen of prostate);
(4) 0772P (CA125, MUC16);
(5) MPF (MPF, MSLN, SMR, megakaryocyte potentiating factor, mesothelin);
(6) Napi3b (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs.73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) Ephb2R;
(23) ASLG659;
(24) PSCA;
(25) GEDA;
(26) BAFF-R (B cell activating factor receptor, BLyS receptor 3, BR3);
(27) CD22 (B-cell receptor CD22-B isoform);
(28) CD79a (CD79A, CD79α, immunoglobulin-associated alpha);
(29) CXCR5 (Burkitt's lymphoma receptor 1);
(30) HLA-DOB (Beta subunit of MHC class II molecule Ia antigen);
(31) P2X5 (Purinergic receptor P2X ligand-gated ion channel 5);
(32) CD72 (B-cell differentiation antigen CD72, Lyb-2);
(33) LY64 (Lymphocyte antigen 64, RP105);
(34) FCRH1 (Fc receptor-like protein 1); and
(35) IRTA2 (Immunoglobulin superfamily receptor translocation associated 2),
A is a Stretcher unit,
a is 0 or 1,
each W is independently an Amino Acid unit,
w is an integer ranging from 0 to 12, Y is a Spacer unit, and
y is 0, 1 or 2,
p ranges from 1 to 20, and
D is a drug moiety selected of Formula $D_E$:

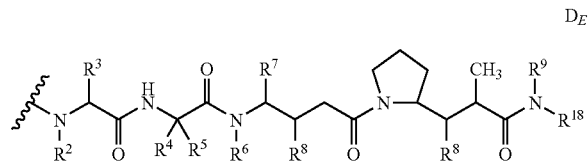

the wavy line of $D_E$ indicates the covalent attachment site to A, W, or Y, and independently at each location:

$R^2$ is selected from the group consisting of H and $C_1$-$C_8$ alkyl;

$R^3$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from the group consisting of H and methyl;

or $R^4$ and $R^5$ jointly form a carbocyclic ring and have the formula —$(CR^aR^b)_n$—; $R^a$ and $R^b$ are independently selected from the group consisting of H, $C_1$-$C_8$ alkyl and $C_3$-$C_8$ carbocycle and n is selected from the group consisting of 2, 3, 4, 5 and 6;

$R^6$ is selected from the group consisting of H and $C_1$-$C_8$ alkyl;

$R^7$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from the group consisting of H, OH, $C_1$-$C_8$ alkyl, $C_3$-$C_8$ carbocycle and O—($C_1$-$C_8$ alkyl);

$R^9$ is selected from the group consisting of H and $C_1$-$C_8$ alkyl; and $R^{18}$ is selected from the group consisting of —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle).

2. The method of claim 1 further comprising administering an effective amount of an additional anticancer agent.

3. The method of claim 1 further comprising administering an effective amount of an immunosuppressant agent.

4. The method of claim 1 wherein the antibody-drug conjugate compound or pharmaceutically acceptable salt thereof specifically binds to a receptor encoded by an ErbB2 gene.

5. The method of claim 1 wherein the amount of antibody-drug conjugate compound or pharmaceutically acceptable salt thereof administered to the patient is in the range of about 0.1 to about 10 mg/kg of patient weight.

6. The method of claim 1 wherein the antibody-drug conjugate or pharmaceutically acceptable salt thereof is administered at about three week intervals.

7. The method of claim 1 wherein said antibody-drug conjugate compound or pharmaceutically acceptable salt thereof is administered parenterally.

8. The method of claim 7 wherein said antibody-drug conjugate compound or pharmaceutically acceptable salt thereof is formulated with a pharmaceutically acceptable parenteral vehicle.

9. The method of claim 1 wherein said antibody-drug conjugate compound or pharmaceutically acceptable salt thereof is formulated in a unit dosage injectable form.

10. The method of claim 1 wherein said antibody-drug conjugate compound or pharmaceutically acceptable salt thereof is administered intravenously.

11. The method of claim 1 further comprising the administration of a second antibody which binds a tumor-associated antigen selected from the group consisting of (1) to (35).

12. The method of claim 11 wherein said second antibody is conjugated with a cytotoxic agent.

13. The method of claim 1 wherein the antibody-drug conjugate compound or pharmaceutically acceptable salt thereof induces apoptosis.

14. The method of claim 1 wherein the cancer is selected from the group consisting of breast, ovarian, stomach, endometrial, salivary gland, lung, kidney, colon, colorectal, thyroid, pancreatic, prostate and bladder cancer.

15. The method of claim 1 wherein the antibody-drug conjugate or pharmaceutically acceptable salt thereof is formulated with a pharmaceutically acceptable diluent, carrier or excipient.

16. The method of claim 1 wherein the cancer is characterized by the overexpression of an ErbB2 receptor.

17. The method of claim 1 wherein the cancer does not respond, or responds poorly, to treatment with an anti-ErbB2 antibody.

18. The method of claim 1 wherein in the antibody-drug conjugate compound or pharmaceutically acceptable salt thereof, the antibody binds to tumor-associated antigen (1) BMPR1B (Bone morphogenetic protein receptor-type IB).

19. The method of claim 1 wherein in the antibody-drug conjugate compound or pharmaceutically acceptable salt thereof, the antibody binds to tumor-associated antigen (3) STEAP1 (Six transmembrane epithelial antigen of prostate).

20. The method of claim 1 wherein in the antibody-drug conjugate compound or pharmaceutically acceptable salt thereof, the antibody binds to tumor-associated antigen (4) 0772P (CA125, MUC16).

21. The method of claim 1 wherein in the antibody-drug conjugate compound or pharmaceutically acceptable salt thereof, the antibody binds to tumor-associated antigen (5) MPF (MPF, MSLN, SMR, megakaryocyte potentiating factor, mesothelin).

22. The method of claim 1 wherein in the antibody-drug conjugate compound or pharmaceutically acceptable salt thereof, the antibody binds to tumor-associated antigen (6) Napi3b (NAPI-3B, NPTIIb, SLC34A2, solute carrier family 34 (sodium phosphate), member 2, type II sodium-dependent phosphate transporter 3b).

23. The method of claim 1 wherein in the antibody-drug conjugate compound or pharmaceutically acceptable salt thereof, the antibody binds to tumor-associated antigen (7) Sema 5b (FLJ10372, KIAA1445, Mm.42015, SEMA5B, 5EMAG, Semaphorin 5b Hlog, sema domain, seven thrombospondin repeats (type 1 and type 1-like), transmembrane domain (TM) and short cytoplasmic domain, (semaphorin) 5B).

24. The method of claim 1 wherein in the antibody-drug conjugate compound or pharmaceutically acceptable salt thereof, the antibody binds to tumor-associated antigen (8) PSCA hlg (2700050C12Rik, C530008O16Rik, RIKEN cDNA 2700050C12, RIKEN cDNA 2700050C12 gene).

25. The method of claim 1 wherein in the antibody-drug conjugate compound or pharmaceutically acceptable salt thereof, the antibody binds to tumor-associated antigen (9) ETBR (Endothelin type B receptor).

26. The method of claim 1 wherein in the antibody-drug conjugate compound or pharmaceutically acceptable salt thereof, the antibody binds to tumor-associated antigen (11) STEAP2 (HGNC 8639, IPCA-1, PCANAP1, STAMP1, STEAP2, STMP, prostate, six transmembrane epithelial antigen of prostate 2).

27. The method of claim 1 wherein in the antibody-drug conjugate compound or pharmaceutically acceptable salt thereof, the antibody binds to tumor-associated antigen (13) CRIPTO (CR, CR1, CRGF, CRIPTO, TDGF1, Teratocarcinoma-derived growth factor).

28. The method of claim 1 wherein in the antibody-drug conjugate compound or pharmaceutically acceptable salt thereof, the antibody binds to tumor-associated antigen (15) CD79b (CD79B, CD79β, IGb (immunoglobulin-associated beta), B29).

29. The method of claim 1 wherein in the antibody-drug conjugate compound or pharmaceutically acceptable salt thereof, the antibody binds to tumor-associated antigen (17) HER2.

30. The method of claim 1 wherein in the antibody-drug conjugate compound or pharmaceutically acceptable salt thereof, the antibody binds to tumor-associated antigen (23) ASLG659.

31. The method of claim 1 wherein in the antibody-drug conjugate compound or pharmaceutically acceptable salt thereof, the antibody binds to tumor-associated antigen (27) CD22 (B-cell receptor CD22-B isoform).

32. The method of claim 1 wherein in the antibody-drug conjugate compound or pharmaceutically acceptable salt thereof, the antibody binds to tumor-associated antigen (28) CD79a (CD79A, CD79α, immunoglobulin-associated alpha).

33. The method of claim 1 wherein in the antibody-drug conjugate compound or pharmaceutically acceptable salt thereof, the antibody binds to tumor-associated antigen (30) HLA-DOB (Beta subunit of MHC class II molecule Ia antigen).

34. The method of claim 1 wherein in the antibody-drug conjugate compound or pharmaceutically acceptable salt thereof, the antibody binds to tumor-associated antigen (35) IRTA2 (Immunoglobulin superfamily receptor translocation associated 2).

35. The method of claim 1, wherein in the antibody-drug conjugate compound or pharmaceutically acceptable salt thereof, the antibody is attached to the drug moiety through a cysteine residue of the antibody.

36. The method of claim 1, wherein the antibody-drug conjugate compound having a formula selected from the group consisting of:

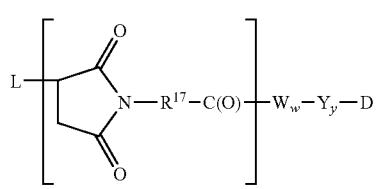

a)

or a pharmaceutically acceptable salt thereof; L is an antibody and $R^{17}$ is $C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —(CH$_2$CH$_2$O)$_r$—, —(CH$_2$CH$_2$O)$_r$—CH$_2$—; and r is an integer ranging from 1 to 10;

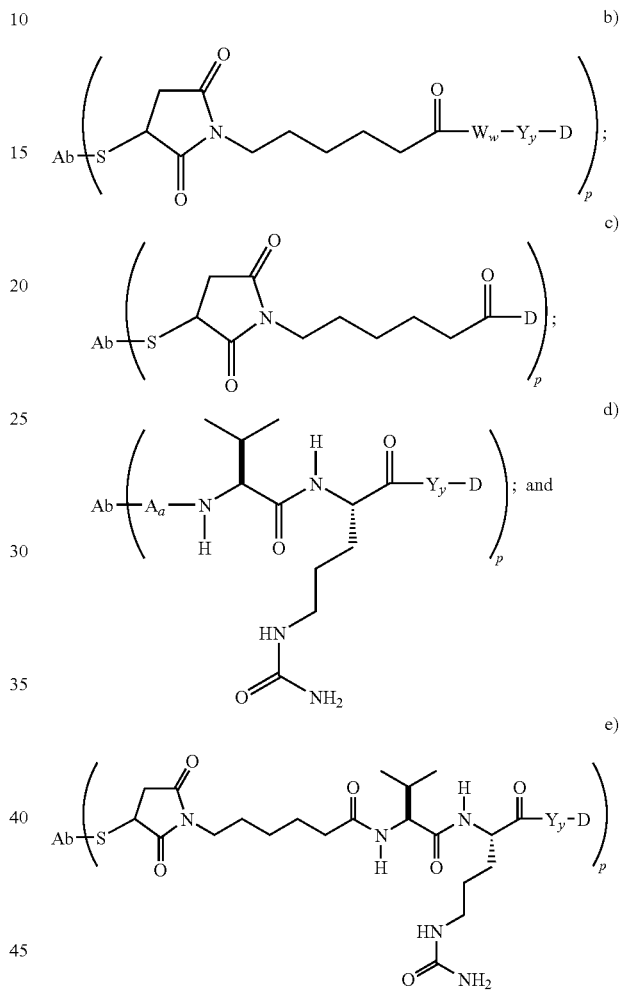

or pharmaceutically acceptable salt thereof.

37. The method of claim 36, wherein in the antibody-drug conjugate compound or pharmaceutically acceptable salt thereof, A is maleimidocaproyl and a is 1.

38. The method of claim 36, wherein in the antibody-drug conjugate compound or pharmaceutically acceptable salt thereof, W is valine-citrulline and w is 2.

39. The method of claim 36, wherein Y, with the nitrogen of the drug moiety to which it is attached, is a para-aminobenzyl carbamoyl group and y is 1.

40. The method of claim 1, wherein in the antibody-drug conjugate compound or pharmaceutically acceptable salt thereof, the antibody is a monoclonal antibody.

41. The method of claim 1, wherein in the antibody-drug conjugate compound or pharmaceutically acceptable salt thereof, the antibody is a humanized antibody.

42. The method of claim 1, wherein the antibody-drug conjugate compound has the formula:

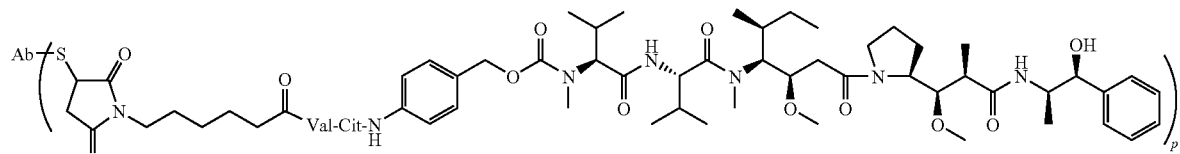

Ab-MC-vc-PAB-MMAE or a pharmaceutically acceptable salt thereof; wherein Ab is an antibody, Val is valine, and Cit is citrulline.

43. The method of claim 1, wherein in the antibody-drug conjugate compound or pharmaceutically acceptable salt thereof, the Stretcher unit has a formula selected from one of the group consisting of formulae IIIa, Mb, IV, Va, Vb, VIa, VIb, and VIc:

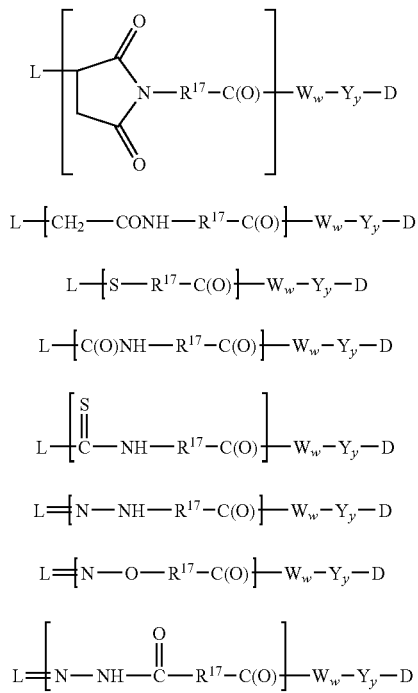

$R^{17}$ is selected from the group consisting of —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, and —($CH_2CH_2O)_r$—$CH_2$—; and r is an integer ranging from 1 to 10.

44. The method of claim 1, wherein in the antibody-drug conjugate compound or pharmaceutically acceptable salt thereof, the Spacer unit has a formula selected from one of the group consisting of formulae (X)-(XII):

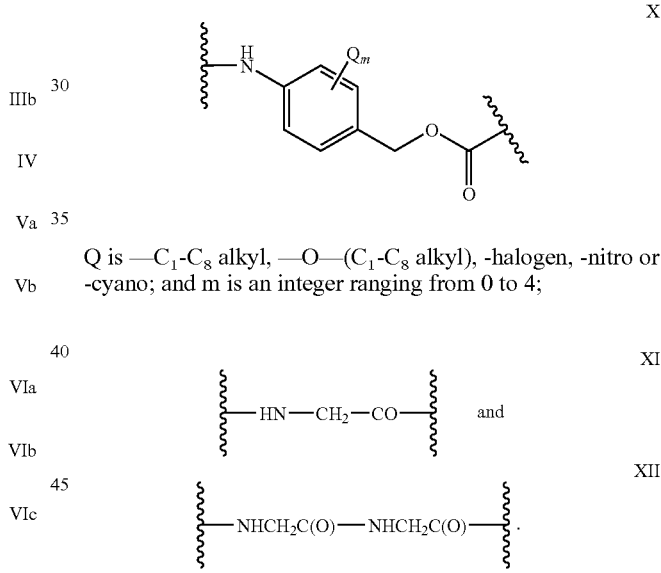

Q is —$C_1$-$C_8$ alkyl, —O—($C_1$-$C_8$ alkyl), -halogen, -nitro or -cyano; and m is an integer ranging from 0 to 4;

* * * * *